United States Patent
Nakache et al.

(10) Patent No.: US 10,851,064 B2
(45) Date of Patent: Dec. 1, 2020

(54) ACSS2 INHIBITORS AND METHODS OF USE THEREOF

(71) Applicant: METABOMED LTD., Yavne (IL)

(72) Inventors: Philippe Nakache, Ness Ziona (IL); Omri Erez, Rehovot (IL); Simone Botti, Rehovot (IL); Andreas Goutopoulos, Boston, MA (US)

(73) Assignee: METABOMED LTD., Yavne (IL)

( * ) Notice: Subject to any disclaimer, the term of this patent is extended or adjusted under 35 U.S.C. 154(b) by 0 days.

(21) Appl. No.: 16/411,168

(22) Filed: May 14, 2019

(65) Prior Publication Data

US 2019/0263758 A1 Aug. 29, 2019

Related U.S. Application Data

(63) Continuation-in-part of application No. PCT/IL2018/051232, filed on Nov. 15, 2018.
(Continued)

(51) Int. Cl.
| | |
|---|---|
| *C07D 231/22* | (2006.01) |
| *C07D 231/20* | (2006.01) |
| *C07D 401/04* | (2006.01) |
| *C07D 401/12* | (2006.01) |
| *C07D 403/12* | (2006.01) |
| *C07D 405/12* | (2006.01) |
| *C07D 409/04* | (2006.01) |
| *C07D 413/12* | (2006.01) |
| *C07D 417/12* | (2006.01) |
| *C07D 401/10* | (2006.01) |
| *C07D 413/14* | (2006.01) |
| *C07D 409/12* | (2006.01) |
| *C07D 413/10* | (2006.01) |
| *C07D 405/14* | (2006.01) |
| *C07D 405/04* | (2006.01) |

(Continued)

(52) U.S. Cl.
CPC ........ *C07D 231/22* (2013.01); *A61K 31/4152* (2013.01); *A61K 31/4155* (2013.01); *A61K 31/4184* (2013.01); *A61K 31/422* (2013.01); *A61K 31/427* (2013.01); *A61K 31/4439* (2013.01); *A61K 31/454* (2013.01); *A61K 31/497* (2013.01); *A61K 31/506* (2013.01); *A61K 45/06* (2013.01); *A61P 3/00* (2018.01); *A61P 25/00* (2018.01); *A61P 29/00* (2018.01); *A61P 31/12* (2018.01); *A61P 35/00* (2018.01); *A61P 37/02* (2018.01); *C07D 231/20* (2013.01); *C07D 231/26* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/12* (2013.01); *C07D 405/04* (2013.01); *C07D 405/10* (2013.01); *C07D 405/12* (2013.01); *C07D 405/14* (2013.01); *C07D 409/04* (2013.01); *C07D 409/12* (2013.01); *C07D 413/10* (2013.01); *C07D 413/12* (2013.01); *C07D 413/14* (2013.01); *C07D 417/12* (2013.01); *C07F 5/025* (2013.01)

(58) Field of Classification Search
CPC ............ A61K 2300/00; A61K 31/4152; A61K 31/4155; A61K 31/4178; A61K 31/4184; A61K 31/4196; A61K 31/422; A61K 31/427; A61K 31/4439; A61K 31/454; A61K 31/4709; A61K 31/497; A61K 31/506; A61K 31/69; A61K 45/06; A61P 25/00; A61P 29/00; A61P 31/12; A61P 35/00; A61P 37/02; A61P 3/00; C07D 231/20; C07D 231/22; C07D 231/26; C07D 401/04; C07D 401/10; C07D 401/12; C07D 401/14; C07D 403/04; C07D 403/10; C07D 403/12; C07D 405/04; C07D 405/10; C07D 405/12; C07D 405/14; C07D 409/04; C07D 409/12; C07D 413/10; C07D 413/12; C07D 413/14; C07D 417/12; C07F 5/025
See application file for complete search history.

(56) References Cited

U.S. PATENT DOCUMENTS

| | | | |
|---|---|---|---|
| 3,905,997 A | 9/1975 | Zinnes et al. | |
| 4,207,317 A | * 6/1980 | Walker ................. | C07D 231/22 514/184 |

FOREIGN PATENT DOCUMENTS

| | | |
|---|---|---|
| JP | H11291635 A | 10/1999 |
| WO | WO 03/013484 A2 | 2/2003 |

(Continued)

OTHER PUBLICATIONS

Santeusanio, et al, Divergent Approach to Thiazolylidene Derivatives: A Perspective on the Synthesis of a Heterocyclic Skeleton from β-Amidothioamides Reactivity, J. Org. Chem., 82, 9773-9778 (2017). (Year: 2017).*

(Continued)

*Primary Examiner* — Erich A Leeser

(74) *Attorney, Agent, or Firm* — Mark S. Cohen; Pearl Cohen Zedek Latzer Baratz LLP

(57) ABSTRACT

The present invention relates to novel ACSS2 inhibitors having activity as anti-cancer therapy, treatment of alcoholism, and viral infection (e.g., CMV), composition and methods of preparation thereof, and uses thereof for treating viral infection, alcoholism, alcoholic steatohepatitis (ASH), non-alcoholic steatohepatitis (NASH), obesity/weight gain, anxiety, depression, post-traumatic stress disorder, inflammatory/autoimmune conditions and cancer, including metastatic cancer, advanced cancer, and drug resistant cancer of various types.

8 Claims, 2 Drawing Sheets

Related U.S. Application Data

(60) Provisional application No. 62/586,195, filed on Nov. 15, 2017.

(51) Int. Cl.

| | | |
|---|---|---|
| C07D 403/10 | (2006.01) | |
| C07D 231/26 | (2006.01) | |
| C07D 401/14 | (2006.01) | |
| C07D 405/10 | (2006.01) | |
| C07D 403/04 | (2006.01) | |
| A61P 25/00 | (2006.01) | |
| A61P 29/00 | (2006.01) | |
| A61P 3/00 | (2006.01) | |
| A61P 37/02 | (2006.01) | |
| A61P 31/12 | (2006.01) | |
| A61P 35/00 | (2006.01) | |
| A61K 31/4152 | (2006.01) | |
| A61K 31/4155 | (2006.01) | |
| A61K 31/4184 | (2006.01) | |
| A61K 31/422 | (2006.01) | |
| A61K 31/427 | (2006.01) | |
| A61K 31/4439 | (2006.01) | |
| A61K 31/454 | (2006.01) | |
| A61K 31/497 | (2006.01) | |
| A61K 31/506 | (2006.01) | |
| A61K 45/06 | (2006.01) | |
| C07F 5/02 | (2006.01) | |

(56) References Cited

FOREIGN PATENT DOCUMENTS

| WO | WO 03/024448 A2 | 3/2003 |
|---|---|---|
| WO | WO 2007/026215 A1 | 3/2007 |
| WO | WO 2011/143425 A2 | 11/2011 |
| WO | WO 2013/159224 A1 | 10/2013 |
| WO | WO 2015/175845 A1 | 11/2015 |

OTHER PUBLICATIONS

Gaffer, et al, Synthesis and Antioxidant Activity of Some New Thiazolyl-Pyrazolone Derivatives, J. Heterocyclic Chem., 54, 331 (2017). (Year: 2017).*
Linchenko, et al, Cyclizations in the Reactions of Isocyanates with Compounds Containing Active Methylene Groups in the Presence of Triethylamine, Russian Chemical Bulletin, vol. 55, No. 5, pp. 873-878 (2006). (Year: 2006).*
Björnson et al. "Stratification of hepatocellular carcinoma patients based on acetate utilization" Cell reports. Dec. 1, 2015;13(9):2014-26.
Bulusu et al. "Acetate recapturing by nuclear acetyl-CoA synthetase 2 prevents loss of histone acetylation during oxygen and serum limitation" Cell reports. Jan. 17, 2017;18(3):647-58.
CAS Registry No. 1808705-10-3, CA Index Name: 1H-Pyrazole-4-carboxamide, 1-(4,6-dimethyl-2-pyrimidinyl)-4,5-dihydro-3-methyl-N-[2-(1- methylethyl)phenyl]-5-oxo-, Entered STN: Sep. 30, 2015.
CAS Registry No. 1791350-17-8, CA Index Name: 1H-Pyrazole-4-carboxamide, 1-(2,4-dimethylphenyl)-4,5-dihydro-3-methyl-N-[1-(1- methylethyl)-1H-pyrazol-5-yl]-5-oxo-, Entered STN: Jun. 30, 2015.
CAS Registry No. 1787906-31-3, CA Index Name: 1H-Pyrazole-4-carboxamide, 4,5-dihydro-3-methyl-N-[3-methyl-1-(phenylmethyl)-1H- pyrazol-5-yl]-5-oxo-1-phenyl-, Entered STN: Jun. 25, 2015.
CAS Registry No. 1444619-19-5, CA Index Name: 1H-Pyrazole-4-carboxamide, 1-(4-fluorophenyl)-4,5-dihydro-3-methyl-5-oxo-N-(tetrahydro-1,1-dioxido-3-thienyl)-, Entered STN: Jul. 16, 2013.
CAS Registry No. 1444612-86-5, CA Index Name: 1H-Pyrazole-4-carboxamide, 1-(3-chlorophenyl)-4,5-dihydro-3-methyl-5-oxo-N-tetrahydro-1,1-dioxido-3-thienyl)-, Entered STN: Jun. 16, 2013.
CAS Registry No. 1444608-50-7, CA Index Name: 1H-Pyrazole-4-carboxamide, 1-(2,4-dimethylphenyl)-4,5-dihydro-3-methyl-5-oxo-N- (tetrahydro-1,1-dioxido-3-thienyl)-, Entered STN: Jul. 16, 2013.
CAS Registry No. 1427938-63-3, CA Index Name: 1H-Pyrazole-4-carboxamide, 4,5-dihydro-3-methyl-5-oxo-N-2-pyridinyl-1-(tetrahydro-1,1- dioxido-3-thienyl)-, Entered STN: Apr. 11, 2013.
CAS Registry No. 1424277-15-5, CA Index Name: 1H-Pyrazole-4-carboxamide, 4,5-dihydro-3-methyl-5-oxo-1-(tetrahydro-1,1-dioxido-3- thienyl)-N-2-thiazolyl, Entered STN: Mar. 15, 2013.
CAS Registry No. 1424179-52-1, CA Index Name: 1H-Pyrazole-4-carboxamide,4,5-dihydro-3-methyl-5-oxo-1-(tetrahydro-1,1-dioxido-3- thienyl)-N-1,3,4-thiadiazol-2-yl, Entered STN: Mar. 15, 2013.
CAS Registry No. 1424083-43-1, CA Index Name: 1H-Pyrazole-4-carboxamide, 4,5-dihydro-3-methyl-5-oxo-N-3-pyridinyl-1-(tetrahydro-1,1- dioxido-3-thienyl), Entered STN: Mar. 15, 2013.
CAS Registry No. 1423725-39-6, CA Index Name: 1H-Pyrazole-4-carboxamide, N-1,3-benzodioxol-5-yl-4,5-dihydro-3-methyl-5-oxo-1- (tetrahydro-1,1-dioxido-3-thienyl)- Entered STN: Mar. 14, 2013.
CAS Registry No. 1423670-51-2, CA Index Name: 1H-Pyrazole-4-carboxamide, 4,5-dihydro-3-methyl-5-oxo-N-phenyl-1-(tetrahydro-1,1- dioxido-3-thienyl), Entered STN: Mar. 14, 2013.
CAS Registry No. 1423624-35-4, CA Index Name: 1H-Pyrazole-4-carboxamide, N-(2-chloro-3-pyridinyl)-4,5-dihydro-3-methyl-5-oxo-1- (tetrahydro-1,1-dioxido-3-thienyl)-, Entered STN: Mar. 14, 2013.
CAS Registry No. 1376380-77-6, CA Index Name: 1H-Pyrazole-4-carboxamide, N-[4-(3-fluorophenyl)-2-thiazolyl]-4,5-dihydro-3-methyl-5- oxo-1-(tetrahydro-1,1-dioxido-3-thienyl)-, Entered STN: Jun. 7, 2012.
CAS Registry No. 1375980-06-5, CA Index Name: 1H-Pyrazole-4-carboxamide, N-(6-ethyl-2-benzothiazolyl)-4,5-dihydro-3-methyl-5-oxo-1- (tetrahydro-1,1-dioxido-3-thienyl)-, Entered STN: Jun. 7, 2012.
CAS Registry No. 483276-32-0, CA Index Name: 1H-Pyrazole-4-carbothloamide, 1-[4-(4-chlorophenyl)-2-thiazolyl]-4,5-dihydro-5-oxo-N,3- diphenyl-, Entered STN: Jan. 30, 2003.
CAS Registry No. 483276-31-9, CA Index Name: 1H-Pyrazole-4-carboxamide, N-(4-chlorophenyl)-1-[4-(4-chlorophenyl)-2-thiazolyl]-4,5- dihydro-5-oxo-3-phenyl-, Entered STN: Jan. 30, 2003.
Chen et al. "Coordinate regulation of stress signaling and epigenetic events by Acss2 and HIF-2" in cancer cells. PloS one. Dec. 27, 2017;12(12):e0190241.
Chen et al. "The acetate/ACSS2 switch regulates HIF-2 stress signaling in the tumor cell microenvironment" PloS one. Feb. 17, 2015;10(2):e0116515.
Chen et al. "TM6SF2 E167K variant, a novel genetic susceptibility variant, contributing to nonalcoholic fatty liver disease" Journal of clinical and translational hepatology. Dec. 28, 2015;3(4):265.
Comerford et al. "Acetate dependence of tumors" Cell. Dec. 18, 2014;159(7):1591-602.
El-Desoky et al. "Utility of isothiocyanates in heterocyclic synthesis" Sulfur Letters. Jan. 1, 2002;25(5):199-205.
Gaffer et al. "Synthesis and antioxidant activity of some new thiazolyl-pyrazolone derivatives" Journal of Heterocyclic Chemistry. Jan. 2017;54(1):331-40.
Gao et al. "Acetate functions as an epigenetic metabolite to promote lipid synthesis under hypoxia. Nature communications" Jun. 30, 2016;7:11960.
Gräff et al. "Histone acetylation: molecular mnemonics on the chromatin" Nature Reviews Neuroscience. Feb. 2013;14(2):97.
Harriman et al. "Acetyl-CoA carboxylase inhibition by ND-630 reduces hepatic steatosis, improves insulin sensitivity, and modulates dyslipidemia in rats" Proceedings of the National Academy of Sciences. Mar. 29, 2016;113(13):E1796-805.
Hosios et al. "Acetate metabolism in cancer cells" Cancer & metabolism. Dec. 2014;2(1):27.
Huang et al. "ACSS2 promotes systemic fat storage and utilization through selective regulation of genes involved in lipid metabolism" Proceedings of the National Academy of Sciences. Oct. 2, 2018;115(40):E9499-506.
International Search Report for PCT Application No. PCT/IL2018/051232 dated Jan. 30, 2019.

(56) References Cited

OTHER PUBLICATIONS

Kamphorst et al. "Quantitative analysis of acetyl-CoA production in hypoxic cancer cells reveals substantial contribution from acetate" Cancer & metabolism. Dec. 2014;2(1):23.
Lakhter et al. "Glucose-independent acetate metabolism promotes melanoma cell survival and tumor growth" Journal of Biological Chemistry. Oct. 14, 2016;291(42):21869-79.
Li et al. "Nucleus-translocated ACSS2 promotes gene transcription for lysosomal biogenesis and autophagy" Molecular cell. Jun. 1, 2017;66(5):684-97.
Lyssiotis et al. "Acetate fuels the cancer engine. Cell" Dec. 18, 2014;159(7):1492-4.
Márquez et al. "Tricarboxylic Acid Cycle Activity and Remodeling of Glycerophosphocholine Lipids Support Cytokine Induction in Response to Fungal Patterns" Cell reports. Apr. 9, 2019;27(2):525-36.
Marzouk et al. "Synthesis and characterization of novel pyrazolone derivatives" European Journal of Chemistry. Mar. 31, 2014;5(1):24-32.
Mashimo et al. "Acetate is a bioenergetic substrate for human glioblastoma and brain metastases" Cell. Dec. 18, 2014;159(7):1603-14.
McKnight SL. "A hypothetical means of treating or preventing cancer" Cancer & metabolism. May 2014;2(1):O7.
Mews et al. "Acetyl-CoA synthetase regulates histone acetylation and hippocampal memory" Nature. Jun. 2017;546(7658):381.
Ribeiro et al. "Possible involvement of ACSS2 gene in alcoholism" Journal of Neural Transmission. Sep. 1, 2017;124(9):1151-8.
Schug et al. "Acetyl-CoA synthetase 2 promotes acetate utilization and maintains cancer cell growth under metabolic stress" Cancer cell. Jan. 12, 2015;27(1):57-71.
Schug et al. "The metabolic fate of acetate in cancer" Nature Reviews Cancer. Nov. 2016;16(11):708.
Vysochan et al. "ACSS2-mediated acetyl-CoA synthesis from acetate is necessary for human cytomegalovirus infection" Proceedings of the National Academy of Sciences. Feb. 21, 2017;114(8):E1528-35.
Wakil et al. "Fatty acid metabolism: target for metabolic syndrome" Journal of lipid research. Apr. 1, 2009;50(Supplement):S138-43.
Yoshii et al. "Cytosolic acetyl-CoA synthetase affected tumor cell survival under hypoxia: the possible function in tumor acetyl-CoA/acetate metabolism" Cancer science. May 2009;100(5):821-7.
Yoshii et al. "Tumor uptake of radiolabeled acetate reflects the expression of cytosolic acetyl-CoA synthetase: implications for the mechanism of acetate PET" Nuclear medicine and biology. Oct. 1, 2009;36(7):771-7.
Yoshii et al. "Acetate/acetyl-CoA metabolism associated with cancer fatty acid synthesis: overview and application" Cancer letters. Jan. 28, 2015;356(2):211-6.
Yun et al. "The importance of acetyl coenzyme A synthetase for 11C-acetate uptake and cell survival in hepatocellular carcinoma" Journal of nuclear medicine. Aug. 1, 2009;50(8):1222-8.
Zhao et al. "ATP-citrate lyase controls a glucose-to-acetate metabolic switch" Cell reports. Oct. 18, 2016;17(4):1037-52.
Zlotorynski E. "Gene expression: ACSS2 boosts local histone acetylation" Nature Reviews Molecular Cell Biology. Jun. 7, 2017;18(7):405.
CAS Registry Number: 97635-51-3; CA Index Name: Benzamide, 3-amino-N-[2,5- dihydro-5- oxo-1-(2,4,5-trichlorophenyl)-1H-pyrazol-4-yl]-; Entered STN: Aug. 13, 1985. See URL: or URL:. Aug. 18, 1985 (Aug. 18, 1985) & Commercially available online, such as in URL:
International Search Report for PCT Application No. PCT/IL2020/050524 dated May 14, 2020.
Kort, M. E., Atkinson, R. N., Thomas, J. B., Drizin, I., Johnson, M. S., Secrest, M. A., .., & Matulenko, M. A. (2010). Subtype-selective Nav1, 8 sodium channel blockers: Identification of potent, orally active nicotinamide derivatives. Bioorganic & medicinal chemistry letters, 20(22), 6812-6815.
Saeed, A., Ejaz, S. A., KhurshEd, A., Hassan, S., al-Rashida, M., Leta, M., . & Iqbal, J. (2015). Synthesis, characterization and biological evaluation of N-(2, 3-dimethyl-5-oxo-1-phenyl-2, 5-dihydro-1 H-pyrazol-4-y1) benzamides, RSC advances, 5(105), 86428-86439.

\* cited by examiner

ACSS2 INHIBITORS AND METHODS OF USE THEREOF

CROSS-REFERENCE TO RELATED APPLICATIONS

This Application is a Continuation-In-Part of PCT Application Number PCT/IL2018/051232, filed Nov. 15, 2018; which claims priority of U.S. Provisional Application Ser. No. 62/586,195, filed Nov. 15, 2017; both of which are herein incorporated by reference in their entirely.

FIELD OF THE INVENTION

The present invention relates to novel ACSS2 inhibitors, composition and methods of preparation thereof, and uses thereof for treating viral infection (e.g. CMV), alcoholism, alcoholic steatohepatitis (ASH), non-alcoholic steatohepatitis (NASH), metabolic disorders including: obesity, weight gain and hepatic steatosis, neuropsychiatric diseases including: anxiety, depression, schizophrenia, autism and post-traumatic stress disorder, inflammatory/autoimmune conditions and cancer, including metastatic cancer, advanced cancer, and drug resistant cancer of various types.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, Ga. (2008)). The rate of new cancer cases decreased by an average 0.6% per year among men between 2000 and 2009 and stayed the same for women. From 2000 through 2009, death rates from all cancers combined decreased on average 1.8% per year among men and 1.4% per year among women. This improvement in survival reflects progress in diagnosing at an earlier stage and improvements in treatment. Discovering highly effective anticancer agents with low toxicity is a primary goal of cancer research.

Cell growth and proliferation are intimately coordinated with metabolism. Potentially distinct differences in metabolism between normal and cancerous cells have sparked a renewed interest in targeting metabolic enzymes as an approach to the discovery of new anticancer therapeutics.

It is now appreciated that cancer cells within metabolically stressed microenvironments, herein defined as those with low oxygen and low nutrient availability (i.e., hypoxia conditions), adopt many tumour-promoting characteristics, such as genomic instability, altered cellular bioenergetics and invasive behaviour. In addition, these cancer cells are often intrinsically resistant to cell death and their physical isolation from the vasculature at the tumour site can compromise successful immune responses, drug delivery and therapeutic efficiency, thereby promoting relapse and metastasis, which ultimately translates into drastically reduced patient survival. Therefore, there is an absolute requirement to define therapeutic targets in metabolically stressed cancer cells and to develop new delivery techniques to increase therapeutic efficacy. For instance, the particular metabolic dependence of cancer cells on alternative nutrients (such as acetate) to support energy and biomass production may offer opportunities for the development of novel targeted therapies.

Acetyl-CoA Synthetase Enzyme, ACSS2 as a Target for Cancer Treatment

Acetyl-CoA represents a central node of carbon metabolism that plays a key role in bioenergetics, cell proliferation, and the regulation of gene expression. Highly glycolytic or hypoxic tumors must produce sufficient quantities of this metabolite to support cell growth and survival under nutrient-limiting conditions. Acetate is an important source of acetyl-CoA in hypoxia. Inhibition of acetate metabolism may impair tumor growth. The nucleocytosolic acetyl-CoA synthetase enzyme, ACSS2, supplies a key source of acetyl-CoA for tumors by capturing acetate as a carbon source. Despite exhibiting no gross deficits in growth or development, adult mice lacking ACSS2 exhibit a significant reduction in tumor burden in two different models of hepatocellular carcinoma. ACSS2 is expressed in a large proportion of human tumors, and its activity is responsible for the majority of cellular acetate uptake into both lipids and histones. Further, ACSS2 was identified in an unbiased functional genomic screen as a critical enzyme for the growth and survival of breast and prostate cancer cells cultured in hypoxia and low serum. High expression of ACSS2 is frequently found in invasive ductal carcinomas of the breast, triple-negative breast cancer, glioblastoma, ovarian cancer, pancreatic cancer and lung cancer, and often directly correlates with higher-grade tumours and poorer survival compared with tumours that have low ACSS2 expression. These observations may qualify ACSS2 as a targetable metabolic vulnerability of a wide spectrum of tumors.

Due to the nature of tumorigenesis, cancer cells constantly encounter environments in which nutrient and oxygen availability is severely compromised. In order to survive these harsh conditions, cancer cell transformation is often coupled with large changes in metabolism to satisfy the demands for energy and biomass imposed by continued cellular proliferation. Several recent reports discovered that acetate is used as an important nutritional source by some types of breast, prostate, liver and brain tumors in an acetyl-CoA synthetase 2 (ACSS2)-dependent manner. It was shown that acetate and ACSS2 supplied a significant fraction of the carbon within the fatty acid and phospholipid pools (Comerford et. al. Cell 2014; Mashimo et. al. Cell 2014; Schug et al Cancer Cell 2015*). High levels of ACSS2 due to copy-number gain or high expression were found to correlate with disease progression in human breast prostate and brain tumors. Furthermore, ACSS2, which is essential for tumor growth under hypoxic conditions, is dispensable for the normal growth of cells, and mice lacking ACSS2 demonstrated normal phenotype (Comerford et. al. 2014). The switch to increased reliance on ACSS2 is not due to genetic alterations, but rather due to metabolic stress conditions in the tumor microenvironment. Under normal oxidative conditions, acetyl-CoA is typically produced from citrate via citrate lyase activity. However, under hypoxia, when cells adapt to anaerobic metabolism, acetate becomes a key source for acetyl-CoA and hence, ACSS2 becomes essential and is, de facto, synthetically lethal with hypoxic conditions (see Schug et. al., Cancer Cell, 2015, 27:1, pp. 57-71). The accumulative evidences from several studies suggest that ACSS2 may be a targetable metabolic vulnerability of a wide spectrum of tumors.

In certain tumors expressing ACSS2, there is a strict dependency on acetate for their growth or survival, then selective inhibitors of this nonessential enzyme might represent an unusually ripe opportunity for the development of new anticancer therapeutics. If the normal human cells and tissues are not heavily reliant on the activity of the ACSS2 enzyme, it is possible that such agents might inhibit the growth of ACSS2-expressing tumors with a favorable therapeutic window.

Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). NAFLD is characterized by excessive fat accumulation in the liver (steatosis), without any other evident causes of chronic liver diseases (viral, autoimmune, genetic, etc.), and with an alcohol consumption ≤20-30 g/day. On the contrary, AFLD is defined as the presence of steatosis and alcohol consumption >20-30 g/day.

Hepatocyte ethanol metabolism produces free acetate as its endproduct which, largely in other tissues, can be incorporated into acetyl-coenzyme A (acetylcoA) for use in Krebs cycle oxidation, fatty acid synthesis, or as a substrate for protein acetylation. This conversion is catalyzed by the acyl-coenzyme A synthetase short-chain family members 1 and 2 (ACSS1 and ACSS2). The role of acetyl-coA synthesis in control of inflammation opens a novel field of study into the relationship between cellular energy supply and inflammatory disease. It has been shown that ethanol enhances macrophage cytokine production by uncoupling gene transcription from its normal regulatory mechanisms through increased histone acetylation, and that the conversion of the ethanol metabolite acetate to acetyl-coA is crucial to this process.

It was suggested that inflammation is enhanced in acute alcoholic hepatitis in which acetyl-coA synthetases are up-regulated and convert the ethanol metabolite acetate to an excess of acetyl-coA which increases proinflammatory cytokine gene histone acetylation by increased substrate concentration and histone deacetylases (HDAC) inhibition, leading to enhanced gene expression and perpetuation of the inflammatory response. The clinical implication of these findings is that modulation of HDAC or ACSS activity might affect the clinical course of alcoholic liver injury in humans. If inhibitors of ACSS1 and 2 can modulate ethanol-associated histone changes without affecting the flow of acetyl-coA through the normal metabolic pathways, then they have the potential to become much needed effective therapeutic options in acute alcoholic hepatitis. Therefore, synthesis of metabolically available acetyl-coA from acetate is critical to the increased acetylation of proinflammatory gene histones and consequent enhancement of the inflammatory response in ethanol-exposed macrophages. This mechanism is a potential therapeutic target in acute alcoholic hepatitis.

Cytosolic acetyl-CoA is the precursor of multiple anabolic reactions including de-novo fatty acids (FA) synthesis. Inhibition of FA synthesis may favorably affect the morbidity and mortality associated with Fatty-liver metabolic syndromes (Wakil S J, Abu-Elheiga L A. 2009. 'Fatty acid metabolism: Target for metabolic syndrome'. *J. Lipid Res.*) and because of the pivotal role of Acetyl-CoA Carboxylase (ACC) in regulating fatty acid metabolism, ACC inhibitors are under investigation as clinical drug targets in several metabolic diseases, including nonalcoholic fatty liver disease (NAFLD) and nonalcoholic steatohepatitis (NASH). Inhibition of ACSS2 is expected to directly reduce fatty-acid accumulation in the liver through its effect on Acetyl-CoA flux from acetate that is present in the liver at high levels due to the hepatocyte ethanol metabolism. Furthermore, ACSS2 inhibitors are expected to have a better safety profile than ACC inhibitors since they are expected only to affect the flux from Acetate that is not a major source for Ac-CoA in normal conditions (Harriman G et. al., 2016. "Acetyl-CoA carboxylase inhibition by ND-630 reduces hepatic steatosis, improves insulin sensitivity, and modulates dyslipidemia in rats" PNAS). In addition, mice lacking ACSS2 showed reduced body weight and hepatic steatosis in a diet-induced obesity model (Z. Huang et al., ACSS2 promotes systemic fat storage and utilization through selective regulation of genes involved in lipid metabolism PNAS 115, (40), E9499-E9506, 2018).

ACSS2 is also shown to enter the nucleus under certain condition (hypoxia, high fat etc.) and to affect histone acetylation and crotonylation by making available acetyl-CoA and crotonyl-CoA and thereby regulate gene expression. For example, ACSS2 decrease is shown to lower levels of nuclear acetyl-CoA and histone acetylation in neurons affecting the expression of many neuronal genes. In the hippocampus such reductions in ACSS2 lead to effects on memory and neuronal plasticity (Mews P, et al., Nature, Vol 546, 381, 2017). Such epigenetic modifications are implicated in neuropsychiatric diseases such as anxiety, PTSD, depression etc. (Graff, J et al. Histone acetylation: molecular mnemonics on chromatin. Nat Rev. Neurosci. 14, 97-111 (2013)). Thus, an inhibitor of ACSS2 may find useful application in these conditions.

Nuclear ACSS2 is also shown to promote lysosomal biogenesis, autophagy and to promote brain tumorigenesis by affecting Histone H3 acetylation (Li, X et al.: Nucleus-Translocated ACSS2 Promotes Gene Transcription for Lysosomal Biogenesis and Autophagy, Molecular Cell 66, 1-14, 2017). In addition, nuclear ACSS2 is shown to activate HIF-2alpha by acetylation and thus accelerate growth and metastasis of HIF2alpha-driven cancers such as certain Renal Cell Carcinoma and Glioblastomas (Chen, R. et al. Coordinate regulation of stress signaling and epigenetic events by ACSS2 and HIF-2 in cancer cells, Plos One, 12 (12) 1-31, 2017).

SUMMARY OF THE INVENTION

This invention provides a compound or its pharmaceutically acceptable salt, optical isomer, tautomer, hydrate, N-oxide, prodrug, isotopic variants (e.g., deuterated analog), PROTAC, pharmaceutical product or any combination thereof, represented by the structure of formula (I)-(V), and by the structures listed in Table 1, as defined herein below. In various embodiments, the compound is an Acyl-CoA Synthetase Short-Chain Family Member 2 (ACSS2) inhibitor.

This invention further provides a pharmaceutical composition comprising a compound or its pharmaceutically acceptable salt, optical isomer, tautomer, hydrate, N-oxide, prodrug, isotopic variants (e.g., deuterated analog), PROTAC, pharmaceutical product or any combination thereof, represented by the structure of formula (I)-(V), and by the structures listed in Table 1, as defined herein below, and a pharmaceutically acceptable carrier.

This invention further provides a method of treating, suppressing, reducing the severity, reducing the risk of developing or inhibiting cancer comprising administering a compound represented by the structure of formula (I)-(V), and by the structures listed in Table 1, as defined herein below, to a subject suffering from cancer under conditions effective to treat, suppress, reduce the severity, reduce the risk of developing, or inhibit said cancer. In various embodiments, the cancer is selected from the list of: hepatocellular carcinoma, melanoma (e.g., BRAF mutant melanoma), glioblastoma, breast cancer (e.g., invasive ductal carcinomas of the breast, triple-negative breast cancer), prostate cancer, liver cancer, brain cancer, ovarian cancer, lung cancer, Lewis lung carcinoma (LLC), colon carcinoma, pancreatic cancer, renal cell carcinoma and mammary carcinoma. In various embodiments, the cancer is early cancer, advanced cancer, invasive cancer, metastatic cancer, drug resistant cancer or any combination thereof. In various embodiments, the subject has been previously treated with chemotherapy, immunotherapy, radiotherapy, biological therapy, surgical intervention, or any combination thereof. In various embodiments, the compound is administered in combination with an anti-cancer therapy. In various embodiments, the anti-cancer therapy is chemotherapy, immunotherapy, radiotherapy, biological therapy, surgical intervention, or any combination thereof.

This invention further provides a method of suppressing, reducing or inhibiting tumour growth in a subject, comprising administering a compound represented by the structure of formula (I)-(V), and by the structures listed in Table 1, as defined herein below, to a subject suffering from cancer under conditions effective to suppress, reduce or inhibit said tumour growth in said subject. In various embodiments, the tumor growth is enhanced by increased acetate uptake by cancer cells of said cancer. In various embodiments, the increased acetate uptake is mediated by ACSS2. In various embodiments, the cancer cells are under hypoxic stress. In various embodiments, the tumor growth is suppressed due to suppression of lipid (e.g., fatty acid) synthesis and/or histones synthesis induced by ACSS2 mediated acetate metabolism to acetyl-CoA. In various embodiments, the tumor growth is suppressed due to suppressed regulation of histones acetylation and function induced by ACSS2 mediated acetate metabolism to acetyl-CoA.

This invention further provides a method of suppressing, reducing or inhibiting lipid synthesis and/or regulating histones acetylation and function in a cell, comprising contacting a compound represented by the structure of formula (I)-(V), and by the structures listed in Table 1, as defined herein below, with a cell under conditions effective to suppress, reduce or inhibit lipid synthesis and/or regulating histones acetylation and function in said cell. In various embodiments, the cell is a cancer cell.

This invention further provides a method of binding an ACSS2 inhibitor compound to an ACSS2 enzyme, comprising the step of contacting an ACSS2 enzyme with an ACSS2 inhibitor compound represented by the structure of formula (I)-(V), and by the structures listed in Table 1, as defined herein below, in an amount effective to bind the ACSS2 inhibitor compound to the ACSS2 enzyme.

This invention further provides a method of suppressing, reducing or inhibiting acetyl-CoA synthesis from acetate in a cell, comprising contacting a compound represented by the structure of formula (I)-(V), and by the structures listed in Table 1, as defined herein below, with a cell, under conditions effective to suppress, reduce or inhibit acetyl-CoA synthesis from acetate in said cell. In various embodiments, the cell is a cancer cell. In various embodiments, the synthesis is mediated by ACSS2.

This invention further provides a method of suppressing, reducing or inhibiting acetate metabolism in a cancer cell, comprising contacting a compound represented by the structure of formula (I)-(V), and by the structures listed in Table 1, as defined herein below, with a cancer cell, under conditions effective to suppress, reduce or inhibit acetate metabolism in said cells. In various embodiments, the acetate metabolism is mediated by ACSS2. In various embodiments, the cancer cell is under hypoxic stress.

This invention further provides a method of treating, suppressing, reducing the severity, reducing the risk of developing or inhibiting human alcoholism in a subject, comprising administering a compound represented by the structure of formula (I)-(V), and by the structures listed in Table 1, as defined herein below, to a subject suffering from alcoholism under conditions effective to treat, suppress, reduce the severity, reduce the risk of developing, or inhibit alcoholism in said subject.

This invention further provides a method of treating, suppressing, reducing the severity, reducing the risk of developing or inhibiting a viral infection in a subject, comprising administering a compound represented by the structure of formula (I)-(V), and by the structures listed in Table 1, as defined herein below, to a subject suffering from a viral infection under conditions effective to treat, suppress, reduce the severity, reduce the risk of developing, or inhibit the viral infection in said subject. In various embodiments, the viral infection is human cytomegalovirus (HCMV) infection.

This invention further provides a method of treating, suppressing, reducing the severity, reducing the risk of developing or inhibiting a non-alcoholic steatohepatitis (NASH) in a subject, comprising administering a compound represented by the structure of formula (I)-(V), and by the structures listed in Table 1, as defined herein below, to a subject suffering from non-alcoholic steatohepatitis (NASH) under conditions effective to treat, suppress, reduce the severity, reduce the risk of developing, or inhibit the non-alcoholic steatohepatitis (NASH) in said subject.

This invention further provides a method of treating, suppressing, reducing the severity, reducing the risk of developing or inhibiting an alcoholic steatohepatitis (ASH) in a subject, comprising administering a compound represented by the structure of formula (I)-(V), and by the structures listed in Table 1, as defined herein below, to a subject suffering from an alcoholic steatohepatitis (ASH) under conditions effective to treat, suppress, reduce the severity, reduce the risk of developing, or inhibit the alcoholic steatohepatitis (ASH) in said subject.

This invention further provides a method of treating, suppressing, reducing the severity, reducing the risk of developing or inhibiting a metabolic disorder in a subject, comprising administering a compound represented by the structure of formula (I)-(V), and by the structures listed in Table 1, as defined herein below, to a subject suffering from metabolic disorder under conditions effective to treat, suppress, reduce the severity, reduce the risk of developing, or inhibit metabolic disorder in said subject. In various embodiment, the metabolic disorder is selected from: obesity, weight gain, hepatic steatosis and fatty liver disease.

This invention further provides a method of treating, suppressing, reducing the severity, reducing the risk of developing or inhibiting a neuropsychiatric disease or disorder in a subject, comprising administering a compound represented by the structure of formula (I)-(V), and by the structures listed in Table 1, as defined herein below, to a subject suffering from neuropsychiatric disease or disorder under conditions effective to treat, suppress, reduce the severity, reduce the risk of developing, or inhibit neuropsychiatric disease or disorder in said subject. In some embodiments, the neuropsychiatric disease or disorder is selected from: anxiety, depression, schizophrenia, autism and post-traumatic stress disorder.

This invention further provides a method of treating, suppressing, reducing the severity, reducing the risk of developing or inhibiting inflammatory condition in a subject, comprising administering a compound represented by the structure of formula (I)-(V), and by the structures listed in Table 1, as defined herein below, to a subject suffering from inflammatory condition under conditions effective to treat, suppress, reduce the severity, reduce the risk of developing, or inhibit inflammatory condition in said subject.

This invention further provides a method of treating, suppressing, reducing the severity, reducing the risk of developing or inhibiting an autoimmune disease or disorder in a subject, comprising administering a compound represented by the structure of formula (I)-(V), and by the structures listed in Table 1, as defined herein below, to a subject suffering from an autoimmune disease or disorder under conditions effective to treat, suppress, reduce the severity, reduce the risk of developing, or inhibit the autoimmune disease or disorder in said subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
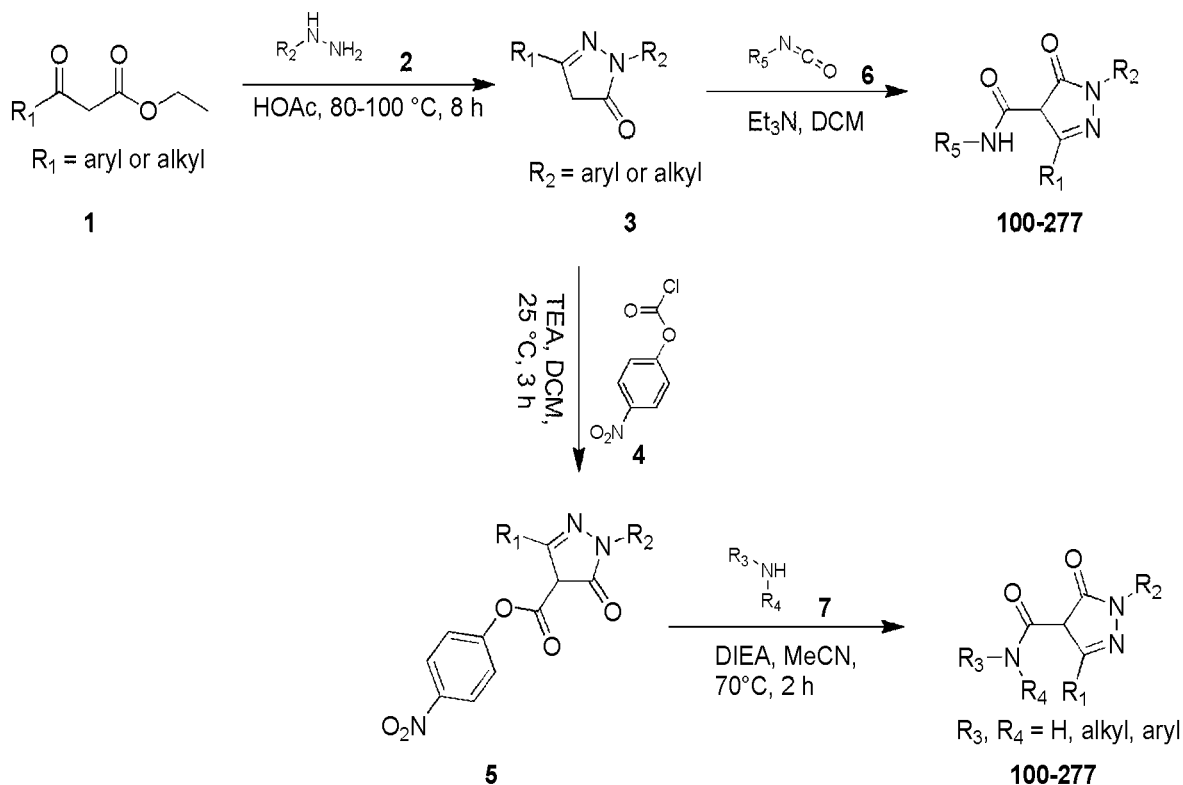
FIG. 1 depicts a general synthetic scheme for compounds of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In various embodiments, this invention is directed to a compound represented by the structure of formula (I):

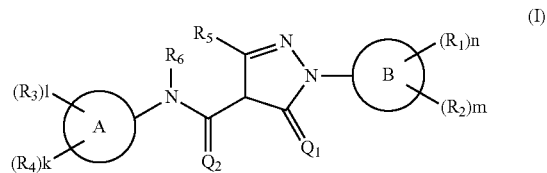

(I)

wherein

A and B rings are each independently a single or fused aromatic (e.g., phenyl) or heteroaromatic (e.g., indole, 2-, 3- or 4-pyridine, naphthalene, thiazole, benzimidazole, thiophene, imidazole, 1-methylimidazole, benzofuran) ring system, or a single or fused $C_3$-$C_{10}$ cycloalkyl (e.g. cyclohexyl) or a single or fused $C_3$-$C_{10}$ heterocyclic ring (e.g., benzofuran-2(3H)-one, benzo[d][1,3]dioxole, tetrahydrothiophene 1,1-dioxide, piperidine, 1-methylpiperidine, isoquinoline and 1,3-dihydroisobenzofuran);

$R_1$ and $R_2$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)N$(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl, $C(CH_3)(OH)Ph$), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1, 2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof), $CH(CF_3)(NH$—$R_{10})$; or $R_2$ and $R_1$ are joint together to form a 5 or 6 membered substituted or unsubstituted, aliphatic or aromatic, carbocyclic or heterocyclic ring (e.g., [1,3]dioxole, furan-2(3H)-one, benzene, pyridine, pyrrol); $R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$, $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., NHC(O)N$(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)$ $CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)$N(CH_3)_2$), $SO_2R$, $SO_2N(R_{10})$ $(R_{11})$ (e.g., $SO_2N(CH_3)_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl, C($CH_3$) (OH)Ph), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH$ $(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1, 2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), $C(O)R$, or $S(O)_2R$;

$R_8$ is $[CH_2]_p$
wherein p is between 1 and 10;
$R_9$ is $[CH]_q$, $[C]_q$
wherein q is between 2 and 10;

$R_{10}$ and $R_{11}$ are each independently H, $C_1$-$C_5$ linear or branched alkyl (e.g., methyl, ethyl), $C(O)R$, or $S(O)_2R$;

R is H, $C_1$-$C_5$ linear or branched alkyl (e.g., methyl, ethyl), $C_1$-$C_5$ linear or branched alkoxy, phenyl, aryl or heteroaryl, or two gem R substituents are joint together to form a 5 or 6 membered heterocyclic ring;

m, n, l and k are each independently an integer between 0 and 4;

$Q_1$ and $Q_2$ are each independently S, O, N—OH, $CH_2$, $C(R)_2$ or N—OMe;

or its pharmaceutically acceptable salt, optical isomer, tautomer, hydrate, N-oxide, prodrug, isotopic variant (e.g., deuterated analog), PROTAC, pharmaceutical product or any combination thereof.

In various embodiments, if rings A and B are each independently a phenyl or a fused aromatic ring system (e.g. naphtyl), then $R_1$, $R_2$, $R_3$ and $R_4$ cannot be H, alkyl, alkoxy, halide, or $CF_3$. In some embodiments, if rings A and B are both phenyls, then $R_1$ and $R_2$ cannot be both H. In some embodiments, if rings A and B are both phenyls, then $R_3$ and $R_4$ cannot be both H. In some embodiments, if rings A and B are each independently a phenyl or a fused aromatic ring system, then $R_5$ cannot be aryl. In some embodiments, ring B is not tetrahydrothiophene 1,1-dioxide. In some embodiments, ring A is not tetrahydrothiophene 1,1-dioxide.

In various embodiments, this invention is directed to a compound represented by the structure of formula (I):

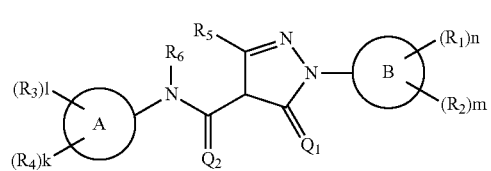

(I)

wherein

A and B rings are each independently a single or fused aromatic (e.g., phenyl) or heteroaromatic (e.g., indole, 2-, 3- or 4-pyridine, naphthalene, thiazole, benzimidazole, thiophene, imidazole, 1-methylimidazole, benzofuran) ring system, or a single or fused $C_3$-$C_{10}$ cycloalkyl (e.g. cyclohexyl) or a single or fused $C_3$-$C_{10}$ heterocyclic ring (e.g., benzofuran-2(3H)-one, benzo[d][1,3]dioxole, tetrahydrothiophene 1,1-dioxide, piperidine, 1-methylpiperidine, isoquinoline and 1,3-dihydroisobenzofuran);

$R_1$ and $R_2$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —$C(O)Ph$, $C(O)O$—$R_{10}$ (e.g. $C(O)O$—$CH_3$, $C(O)O$—$CH(CH_3)_2$, $C(O)O$—$CH_2CH_3$), $R_8$—$C(O)$—$R_{10}$ (e.g., $CH_2C(O)CH_3$), $C(O)H$, $C(O)$—$R_{10}$ (e.g., $C(O)$—$CH_3$, $C(O)$—$CH_2CH_3$, $C(O)$—$CH_2CH_2CH_3$), $C_1$-$C_5$ linear or branched $C(O)$-haloalkyl (e.g., $C(O)$—$CF_3$), —$C(O)NH_2$, $C(O)NHR$, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl, $C(CH_3)(OH)Ph$), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1, 2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_2$ and $R_1$ are joint together to form a 5 or 6 membered substituted or unsubstituted, aliphatic or aromatic, carbocyclic or heterocyclic ring (e.g., [1,3]dioxole, furan-2(3H)-one, benzene, pyridine, pyrrol);

$R_3$ is $C_2$-$C_5$ linear or branched haloalkyl, $CF_2CH_3$, $CH_2CF_3$, $CF_2CH_2CH_3$, $CH_2CH_2CF_3$, $CF_2CH(CH_3)_2$, or $CF(CH_3)$—$CH(CH_3)_2$);

$R_4$ is H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$, $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., $NHC(O)N(CH_3)_2$), COOH, —$C(O)Ph$, $C(O)O$—$R_{10}$ (e.g. $C(O)O$—$CH_3$, $C(O)O$—$CH_2CH_3$), $R_8$—$C(O)$—$R_{10}$ (e.g., $CH_2C(O)CH_3$), $C(O)H$, $C(O)$—$R_{10}$ (e.g., $C(O)$—$CH_3$, $C(O)$—$CH_2CH_3$, $C(O)$—$CH_2CH_2CH_3$), $C_1$-$C_5$ linear or branched $C(O)$-haloalkyl (e.g., $C(O)$—$CF_3$), —$C(O)NH_2$, C(O)NHR, C(O)N($R_{10}$)($R_{11}$) (e.g., C(O)N($CH_3$)$_2$), $SO_2$R, $SO_2$N($R_{10}$)($R_{11}$) (e.g., $SO_2$N($CH_3$)$_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl, C($CH_3$)(OH)Ph), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, N(R)$_2$, $CF_3$, aryl, phenyl, halophenyl, (benzyloxy) phenyl, CN, $NO_2$ or any combination thereof), CH($CF_3$)(NH—$R_{10}$);

$R_5$ is H, $C_1$-$C_5$ linear or branched, substituted or unsubstituted alkyl (e.g., methyl, $CH_2$SH, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, N(R)$_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), C(O)R, or S(O)$_2$R;

$R_8$ is [$CH_2$]$_p$
wherein p is between 1 and 10;
$R_9$ is [CH]$_q$, [C]$_q$
wherein q is between 2 and 10;
$R_{10}$ and $R_{11}$ are each independently H, $C_1$-$C_5$ linear or branched alkyl (e.g., methyl, ethyl), C(O)R, or S(O)$_2$R;

R is H, $C_1$-$C_5$ linear or branched alkyl (e.g., methyl, ethyl), $C_1$-$C_5$ linear or branched alkoxy, phenyl, aryl or heteroaryl, or two gem R substituents are joint together to form a 5 or 6 membered heterocyclic ring;

m, n, l and k are each independently an integer between 0 and 4;

$Q_1$ and $Q_2$ are each independently S, O, N—OH, $CH_2$, C(R)$_2$ or N—OMe;

or its pharmaceutically acceptable salt, optical isomer, tautomer, hydrate, N-oxide, prodrug, isotopic variant (e.g., deuterated analog), PROTAC, pharmaceutical product or any combination thereof.

In various embodiments, this invention is directed to a compound represented by the structure of formula (II)

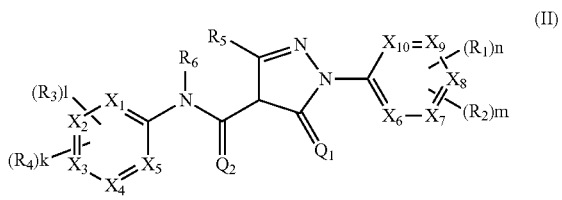

(II)

wherein
$R_1$ and $R_2$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $CF_3$, $CD_3$, $OCD_3$, CN, $NO_2$, —$CH_2$CN, —$R_8$CN, $NH_2$, NHR, N(R)$_2$, $R_8$—N($R_{10}$)($R_{11}$) (e.g., $CH_2$—$NH_2$, $CH_2$—N($CH_3$)$_2$), $R_9$—$R_8$—N($R_{10}$)($R_{11}$) (e.g., C≡C—$CH_2$—$NH_2$), B(OH)$_2$, —OC(O)$CF_3$, —OCH$_2$Ph, NHC(O)—$R_{10}$ (e.g., NHC(O)$CH_3$), NHCO—N($R_{10}$)($R_{11}$) (e.g., NHC(O)N($CH_3$)$_2$), COOH, —C(O)Ph, C(O)O—$R_{10}$ (e.g. C(O)O—$CH_3$, C(O)O—CH($CH_3$)$_2$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N($CH_3$)$_2$), $SO_2$R, $SO_2$N($R_{10}$)($R_{11}$) (e.g., $SO_2$N($CH_3$)$_2$), $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl, C($CH_3$)(OH)Ph), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl), OH, alkoxy, N(R)$_2$, $CF_3$, aryl, phenyl, halophenyl, (benzyloxy)phenyl, CN, $NO_2$ or any combination thereof), CH($CF_3$)(NH—$R_{10}$);

or $R_2$ and $R_1$ are joint together to form a 5 or 6 membered substituted or unsubstituted, aliphatic or aromatic, carbocyclic or heterocyclic ring (e.g., [1,3]dioxole, furan-2(3H)-one, benzene, pyridine, pyrrol);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, N(R)$_2$, $R_8$—N($R_{10}$)($R_{11}$) (e.g., $CH_2$—$NH_2$, $CH_2$—N($CH_3$)$_2$) $R_9$—$R_8$—N($R_{10}$)($R_{11}$), B(OH)$_2$, —OC(O)$CF_3$, —OCH$_2$Ph, —NHCO—$R_{10}$ (e.g., NHC(O)$CH_3$), NHCO—N($R_{10}$)($R_{11}$) (e.g., NHC(O)N($CH_3$)$_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N($CH_3$)$_2$), $SO_2$R, $SO_2$N($R_{10}$)($R_{11}$) (e.g., $SO_2$N($CH_3$)$_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl, C($CH_3$)(OH)Ph), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)-CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), C(O)R, or $S(O)_2R$;

$R_8$ is $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ linear or branched alkyl (e.g., methyl, ethyl), C(O)R, or $S(O)_2R$;

R is H, $C_1$-$C_5$ linear or branched alkyl (e.g., methyl, ethyl), $C_1$-$C_5$ linear or branched alkoxy, phenyl, aryl or heteroaryl, or two gem R substituents are joint together to form a 5 or 6 membered heterocyclic ring;

m, n, l and k are each independently an integer between 0 and 4;

$Q_1$ and $Q_2$ are each independently S, O, N—OH, $CH_2$, $C(R)_2$ or N—OMe;

$X_1$, $X_2$, $X_3$, $X_4$, $X_5$, $X_6$, $X_7$, $X_8$, $X_9$ or $X_{10}$ are each independently C or N;

or its pharmaceutically acceptable salt, optical isomer, tautomer, hydrate, N-oxide, prodrug, isotopic variant (e.g., deuterated analog), PROTAC, pharmaceutical product or any combination thereof.

In various embodiments, if $X_1$, $X_2$, $X_3$, $X_4$, $X_5$, $X_6$, $X_7$, $X_8$, $X_9$ or $X_{10}$ are all C, then $R_1$, $R_2$, $R_3$ and $R_4$ cannot be H, alkyl, alkoxy, halide, or $CF_3$. In some embodiments, $R_1$ and $R_2$ cannot be both H. In some embodiments, $R_3$ and $R_4$ cannot be both H. In some embodiments, if $X_1$, $X_2$, $X_3$, $X_4$, $X_5$, $X_6$, $X_7$, $X_8$, $X_9$ or $X_{10}$ are all C, then $R_5$ cannot be aryl.

In various embodiments, this invention is directed to a compound represented by the structure of formula (III)

(III)

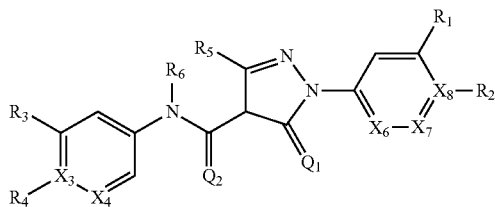

wherein $R_1$ and $R_2$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. $C(O)O—CH_3$, $C(O)O—CH(CH_3)_2$, $C(O)O—CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl, $C(CH_3)(OH)Ph$), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)—CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof), $CH(CF_3)(NH—R_{10})$;

or $R_2$ and $R_1$ are joint together to form a 5 or 6 membered substituted or unsubstituted, aliphatic or aromatic, carbocyclic or heterocyclic ring (e.g., [1,3]dioxole, furan-2(3H)-one, benzene, pyridine, pyrrol);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$), $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. $C(O)O—CH_3$, $C(O)O—CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, $C(OH)(CH_3)(Ph)$, ethyl, propyl, iso-propyl, t-Bu, iso-butyl, pentyl, $C(CH_3)(OH)Ph$), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)—CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1, 2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), $C(O)R$, or $S(O)_2R$;

$R_8$ is $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ linear or branched alkyl (e.g., methyl, ethyl), $C(O)R$, or $S(O)_2R$;

R is H, $C_1$-$C_5$ linear or branched alkyl (e.g., methyl, ethyl), $C_1$-$C_5$ linear or branched alkoxy, phenyl, aryl or heteroaryl, or two gem R substituents are joint together to form a 5 or 6 membered heterocyclic ring;

$Q_1$ and $Q_2$ are each independently S, O, N—OH, $CH_2$, $C(R)_2$ or N—OMe;

$X_3$ and $X_4$ are each independently C or N, wherein if $X_3$ is N, then $R_4$ is absent;

$X_6$, $X_7$ and $X_8$ are each independently C or N, wherein if $X_8$ is N, then $R_2$ is absent;

or its pharmaceutically acceptable salt, optical isomer, tautomer, hydrate, N-oxide, prodrug, isotopic variant (e.g., deuterated analog), PROTAC, pharmaceutical product or any combination thereof.

In various embodiments, if $X_3$, $X_4$, $X_6$, $X_7$, or $X_8$ are all C, then $R_1$, $R_2$, $R_3$ and $R_4$ cannot be H, alkyl, alkoxy, halide, or $CF_3$. In some embodiments, $R_1$ and $R_2$ cannot be both H. In some embodiments, $R_3$ and $R_4$ cannot be both H. In some embodiments, if $X_3$, $X_4$, $X_6$, $X_7$, or $X_8$ are all C, then $R_5$ cannot be aryl.

In various embodiments, this invention is directed to a compound represented by the structure of formula (IV)

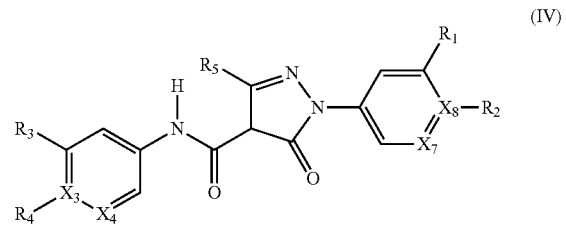

(IV)

wherein $R_1$ and $R_2$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)N$(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl, $C(CH_3)(OH)Ph$), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1, 2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_2$ and $R_1$ are joint together to form a 5 or 6 membered substituted or unsubstituted, aliphatic or aromatic, carbocyclic or heterocyclic ring (e.g., [1,3]dioxole, furan-2(3H)-one, benzene, pyridine, pyrrol);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$), $B(OH)_2$, —$OC(O)CF_3$, —$OCH_2Ph$, —NHCO—$R_{10}$ (e.g., NHC(O)$CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)$N(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, $C(OH)(CH_3)(Ph)$, ethyl, propyl, iso-propyl, t-Bu, iso-butyl, pentyl, $C(CH_3)(OH)Ph$), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, N(R)$_2$, CF$_3$, aryl, phenyl, halophenyl, (benzyloxy)phenyl, CN, NO$_2$ or any combination thereof), CH(CF$_3$)(NH—R$_{10}$);

or R$_3$ and R$_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

R$_5$ is H, $C_1$-$C_5$ linear or branched, substituted or unsubstituted alkyl (e.g., methyl, CH$_2$SH, ethyl, iso-propyl), $C_1$-$C_5$ linear or branched haloalkyl (e.g., CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, N(R)$_2$, CF$_3$, phenyl, halophenyl, (benzyloxy)phenyl, CN, NO$_2$ or any combination thereof);

R$_8$ is [CH$_2$]$_p$
wherein p is between 1 and 10;
R$_9$ is [CH]$_q$, [C]$_q$
wherein q is between 2 and 10;
R$_{10}$ and R$_{11}$ are each independently H, $C_1$-$C_5$ linear or branched alkyl (e.g., methyl, ethyl), C(O)R, or S(O)$_2$R;

R is H, $C_1$-$C_5$ linear or branched alkyl (e.g., methyl, ethyl), $C_1$-$C_5$ linear or branched alkoxy, phenyl, aryl or heteroaryl, or two gem R substituents are joint together to form a 5 or 6 membered heterocyclic ring;

X$_3$ and X$_4$ are each independently C or N, wherein if X$_3$ is N, then R$_4$ is absent;

X$_7$ and X$_8$ are each independently C or N, wherein if X$_8$ is N, then R$_2$ is absent;

or its pharmaceutically acceptable salt, optical isomer, tautomer, hydrate, N-oxide, prodrug, isotopic variant (e.g., deuterated analog), PROTAC, pharmaceutical product or any combination thereof.

In various embodiments, if X$_3$, X$_4$, X$_7$, or X$_8$ are all C, then R$_1$, R$_2$, R$_3$ and R$_4$ cannot be H, alkyl, alkoxy, halide, or CF$_3$. In some embodiments, R$_1$ and R$_2$ cannot be both H. In some embodiments, R$_3$ and R$_4$ cannot be both H. In some embodiments, if X$_3$, X$_4$, X$_7$, or X$_8$ are all C, then R$_5$ cannot be aryl.

In various embodiments, this invention is directed to a compound represented by the structure of formula (V)

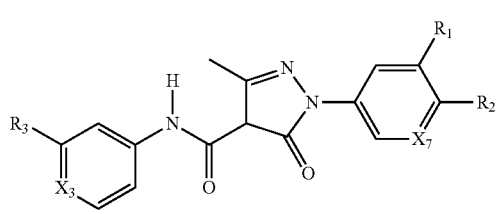

(V)

wherein

R$_1$ and R$_2$ are each independently H, F, Cl, Br, I, OH, SH, R$_8$—OH (e.g., CH$_2$—OH), R$_8$—SH, —R$_8$—O—R$_{10}$, (e.g., —CH$_2$—O—CH$_3$), CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$) (e.g., CH$_2$—NH$_2$, CH$_2$—N(CH$_3$)$_2$), R$_9$—R$_8$—N(R$_{10}$)(R$_{11}$) (e.g., C≡C—CH$_2$—NH$_2$), B(OH)$_2$, —OC(O)CF$_3$, —OCH$_2$Ph, NHC(O)—R$_{10}$ (e.g., NHC(O)CH$_3$), NHCO—N(R$_{10}$)(R$_{11}$) (e.g., NHC(O)N(CH$_3$)$_2$), COOH, —C(O)Ph, C(O)O—R$_{10}$ (e.g. C(O)O—CH$_3$, C(O)O—CH(CH$_3$)$_2$, C(O)O—CH$_2$CH$_3$), R$_8$—C(O)—R$_{10}$ (e.g., CH$_2$C(O)CH$_3$), C(O)H, C(O)—R$_{10}$ (e.g., C(O)—CH$_3$, C(O)—CH$_2$CH$_3$, C(O)—CH$_2$CH$_2$CH$_3$), $C_1$-$C_5$ linear or branched C(O)-haloalkyl (e.g., C(O)—CF$_3$), —C(O)NH$_2$, C(O)NHR, C(O)N(R$_{10}$)(R$_{11}$) (e.g., C(O)N(CH$_3$)$_2$), SO$_2$R, SO$_2$N(R$_{10}$)(R$_{11}$) (e.g., SO$_2$N(CH$_3$)$_2$, SO$_2$NHC(O)CH$_3$), $C_1$-$C_5$ linear or branched, substituted or unsubstituted alkyl (e.g., methyl, 2, 3, or 4-CH$_2$—C$_6$H$_4$—Cl, ethyl, propyl, iso-propyl, t-Bu, iso-butyl, pentyl, benzyl, C(CH$_3$)(OH)Ph), $C_1$-$C_5$ linear or branched haloalkyl (e.g., CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), $C_1$-$C_5$ linear, branched or cyclic alkoxy (e.g. methoxy, ethoxy, propoxy, isopropoxy, O—CH$_2$-cyclopropyl, O-cyclobutyl, O-cyclopentyl, O-cyclohexyl, 1-butoxy, 2-butoxy, O-tBu), optionally wherein at least one methylene group (CH$_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., OCF$_3$, OCHF$_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl), OH, alkoxy, N(R)$_2$, CF$_3$, aryl, phenyl, halophenyl, (benzyloxy)phenyl, CN, NO$_2$ or any combination thereof), CH(CF$_3$)(NH—R$_{10}$);

or R$_2$ and R$_1$ are joint together to form a 5 or 6 membered substituted or unsubstituted, aliphatic or aromatic, carbocyclic or heterocyclic ring (e.g., [1,3]dioxole, furan-2(3H)-one, benzene, pyridine, pyrrol);

R$_3$ is H, F, Cl, Br, I, OH, SH, R$_8$—OH (e.g., CH$_2$—OH), R$_8$—SH, —R$_8$—O—R$_{10}$, (e.g., CH$_2$—O—CH$_3$) CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$) (e.g., CH$_2$—NH$_2$, CH$_2$—N(CH$_3$)$_2$) R$_9$—R$_8$—N(R$_{10}$)(R$_{11}$), B(OH)$_2$, —OC(O)CF$_3$, —OCH$_2$Ph, —NHCO—R$_{10}$ (e.g., NHC(O)CH$_3$), NHCO—N(R$_{10}$)(R$_{11}$) (e.g., NHC(O)N(CH$_3$)$_2$), COOH, —C(O)Ph, C(O)O—R$_{10}$ (e.g. C(O)O—CH$_3$, C(O)O—CH$_2$CH$_3$), R$_8$—C(O)—R$_{10}$ (e.g., CH$_2$C(O)CH$_3$), C(O)H, C(O)—R$_{10}$ (e.g., C(O)—CH$_3$, C(O)—CH$_2$CH$_3$, C(O)—CH$_2$CH$_2$CH$_3$), $C_1$-$C_5$ linear or branched C(O)-haloalkyl (e.g., C(O)—CF$_3$), —C(O)NH$_2$, C(O)NHR, C(O)N(R$_{10}$)(R$_{11}$) (e.g., C(O)N(CH$_3$)$_2$), SO$_2$R, SO$_2$N(R$_{10}$)(R$_{11}$) (e.g., SO$_2$N(CH$_3$)$_2$), $C_1$-$C_5$ linear or branched, substituted or unsubstituted alkyl (e.g., methyl, C(OH)(CH$_3$)(Ph), ethyl, propyl, iso-propyl, t-Bu, iso-butyl, pentyl, C(CH$_3$)(OH)Ph), $C_1$-$C_5$ linear or branched haloalkyl (e.g., CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), $C_1$-$C_5$ linear, branched or cyclic alkoxy (e.g. methoxy, ethoxy, propoxy, isopropoxy, O—CH$_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy) phenyl, CN, $NO_2$ or any combination thereof), $CH(CF_3)$ $(NH-R_{10})$;

$R_8$ is $[CH_2]_p$
wherein p is between 1 and 10;

$R_9$ is $[CH]_q$, $[C]_q$
wherein q is between 2 and 10;

$R_{10}$ and $R_{11}$ are each independently H, $C_1$-$C_5$ linear or branched alkyl (e.g., methyl, ethyl), C(O)R, or $S(O)_2R$;

R is H, $C_1$-$C_5$ linear or branched alkyl (e.g., methyl, ethyl), $C_1$-$C_5$ linear or branched alkoxy, phenyl, aryl or heteroaryl, or two gem R substituents are joint together to form a 5 or 6 membered heterocyclic ring;

$X_3$ and $X_7$ are each independently C or N;

or its pharmaceutically acceptable salt, optical isomer, tautomer, hydrate, N-oxide, prodrug, isotopic variant (e.g., deuterated analog), PROTAC, pharmaceutical product or any combination thereof.

In various embodiments, if $X_3$ and $X_7$ are both C, then $R_1$, $R_2$, and $R_3$ cannot be H, alkyl, alkoxy, halide, or $CF_3$. In some embodiments, $R_1$ and $R_2$ cannot be both H. In some embodiments, $R_1$, $R_2$ and $R_3$ cannot be all H. In some embodiments, $R_3$ is $C_2$-$C_5$ haloalkyl.

In some embodiments, A of compound of formula I is a phenyl. In other embodiments, A is pyridinyl. In other embodiments, A is 2-pyridinyl. In other embodiments, A is 3-pyridinyl. In other embodiments, A is 4-pyridinyl. In other embodiments, A is naphthyl. In other embodiments, A is benzothiazolyl. In other embodiments, A is benzimidazolyl. In other embodiments, A is quinolinyl. In other embodiments, A is isoquinolinyl. In other embodiments, A is indolyl. In other embodiments, A is tetrahydronaphthyl. In other embodiments, A is indenyl. In other embodiments, A is benzofuran-2(3H)-one. In other embodiments, A is benzo[d][1,3]dioxole. In other embodiments, A is naphthalene. In other embodiments, A is tetrahydrothiophene1,1-dioxide. In other embodiments, A is thiazole. In other embodiments, A is benzimidazole. In others embodiment, A is piperidine. In other embodiments, A is 1-methylpiperidine. In other embodiments, A is imidazole. In other embodiments, A is 1-methylimidazole. In other embodiments, A is thiophene. In other embodiments, A is isoquinoline. In other embodiments, A is indole. In other embodiments, A is 1,3-dihydroisobenzofuran. In other embodiments, A is benzofuran. In other embodiments, A is single or fused $C_3$-$C_{10}$ cycloalkyl ring. In other embodiments, A is cyclohexyl.

In some embodiments, B of compound of formula I is a phenyl ring. In other embodiments, B is pyridinyl. In other embodiments, B is 2-pyridinyl. In other embodiments, B is 3-pyridinyl. In other embodiments, B is 4-pyridinyl. In other embodiments, B is naphthyl. In other embodiments, B is indolyl. In other embodiments, B is benzimidazolyl. In other embodiments, B is benzothiazolyl. In other embodiments, B is quinoxalinyl. In other embodiments, B is tetrahydronaphthyl. In other embodiments, B is quinolinyl. In other embodiments, B is isoquinolinyl. In other embodiments, B is indenyl. In other embodiments, B is naphthalene. In other embodiments, B is tetrahydrothiophene1,1-dioxide. In other embodiments, B is thiazole. In other embodiments, B is benzimidazole. In other embodiments, B is piperidine. In other embodiments, B is 1-methylpiperidine. In other embodiments, B is imidazole. In other embodiments, B is 1-methylimidazole. In other embodiments, B is thiophene. In other embodiments, B is isoquinoline. In other embodiments, B is indole. In other embodiments, B is 1,3-dihydroisobenzofuran. In other embodiments, B is benzofuran. In other embodiments, B is single or fused $C_3$-$C_{10}$ cycloalkyl ring. In other embodiments, B is cyclohexyl.

In some embodiments, $R_1$ of compound of formula I-V is H. In other embodiments, $R_1$ is F. In other embodiments, $R_1$ is Cl. In other embodiments, $R_1$ is Br. In other embodiments, $R_1$ is I. In other embodiments, $R_1$ is $C_1$-$C_5$ linear or branched haloalkyl. In other embodiments, $R_1$ is $CF_3$. In other embodiments, $R_1$ is $CF_2CH_3$. In other embodiments, $R_1$ is $CF_2CH_2CH_3$. In other embodiments, $R_1$ is $CH_2CH_2CF_3$. In other embodiments, $R_1$ is $CF_2CH(CH_3)_2$. In other embodiments, $R_1$ is $CF(CH_3)$—$CH(CH_3)_2$. In other embodiments, $R_1$ is $OCD_3$. In other embodiments, $R_1$ is $NO_2$. In other embodiments, $R_1$ is $NH_2$. In other embodiments, $R_1$ is $R_8$—$N(R_{10})(R_{11})$. In other embodiments, $R_1$ is $CH_2$—$NH_2$. In other embodiments, $R_1$ is $CH_2$—$N(CH_3)_2$. In other embodiments, $R_1$ is $R_9$—$R_8$—$N(R_{10})(R_{11})$. In other embodiments, $R_1$ is C≡C—$CH_2$—$NH_2$. In other embodiments, $R_1$ is $B(OH)_2$. In other embodiments, $R_1$ is NHC(O)—$R_{10}$. In other embodiments, $R_1$ is $NHC(O)CH_3$. In other embodiments, $R_1$ is NHCO—$N(R_{10})(R_{11})$. In other embodiments, $R_1$ is $NHC(O)N(CH_3)_2$. In other embodiments, $R_1$ is COOH. In other embodiments, $R_1$ is C(O)O—$R_{10}$. In other embodiments, $R_1$ is C(O)—$R_{10}$. In other embodiments, $R_1$ is C(O)—$CH_3$. In other embodiments, $R_1$ is C(O)O—$CH(CH_3)_2$. In other embodiments, $R_1$ is C(O)O—$CH_3$. In other embodiments, $R_1$ is $SO_2N(R_{10})(R_{11})$. In other embodiments, $R_1$ is $SO_2N(CH_3)_2$. In other embodiments, $R_1$ is $SO_2NHC(O)CH_3$. In other embodiments, $R_1$ is $C_1$-$C_5$ linear or branched, substituted or unsubstituted alkyl. In other embodiments, $R_1$ is methyl. In other embodiments, $R_1$ is 2-$CH_2$—$C_6H_4$—Cl. In other embodiments, $R_1$ is 3-$CH_2$—$C_6H_4$—Cl. In other embodiments, $R_1$ is 4-$CH_2$—$C_6H_4$—Cl. In other embodiments, $R_1$ is ethyl. In other embodiments, $R_1$ is propyl. In other embodiments, $R_1$ is iso-propyl. In other embodiments, $R_1$ is t-Bu. In other embodiments, $R_1$ is iso-butyl. In other embodiments, $R_1$ is pentyl. In other embodiments, $R_1$ is benzyl. In other embodiments, $R_1$ is $C(CH_3)(OH)Ph$. In other embodiments, $R_1$ is substituted or unsubstituted $C_3$-$C_8$ cycloalkyl (e.g., cyclopropyl, cyclopentyl). In other embodiments, $R_1$ is $C_1$-$C_5$ linear, branched or cyclic alkoxy. In other embodiments, $R_1$ is methoxy. In other embodiments, $R_1$ is ethoxy. In other embodiments, $R_1$ is propoxy. In other embodiments, $R_1$ is isopropoxy. In other embodiments, $R_1$ is O—$CH_2$-cyclopropyl. In other embodiments, $R_1$ is O-cyclobutyl. In other embodiments, $R_1$ is O-cyclopentyl. In other embodiments, $R_1$ is O-cyclohexyl. In other embodiments, $R_1$ is O-1-oxacyclobutyl. In other embodiments, $R_1$ is O-2-oxacyclobutyl. In other embodiments, $R_1$ is 1-butoxy. In other embodiments, $R_1$ is 2-butoxy. In other embodiments, $R_1$ is O-tBu. In other embodiments, $R_1$ is $C_1$-$C_5$ linear, branched or cyclic alkoxy wherein at least one methylene group ($CH_2$) in the alkoxy is replaced with an oxygen atom (O). In other embodiments, $R_1$ is O-1-oxacyclobutyl. In other embodiments, $R_1$ is O-2-oxacyclobutyl. In other embodiments, $R_1$ is $C_1$-$C_5$ linear or branched haloalkoxy. In other embodiments, $R_1$ is $OCF_3$. In other embodiments, $R_1$ is $OCHF_2$. In other embodiments, $R_1$ is substituted or unsubstituted $C_3$-$C_8$ cycloalkyl. In other embodiments, $R_1$ is cyclopropyl. In other embodiments, $R_1$ is substituted or unsubstituted $C_3$-$C_8$ heterocyclic ring. In other embodiments, $R_1$ is oxazole. In other embodiments, $R_1$ is methyl substituted oxazole. In other embodiments, $R_1$ is oxadiazole. In other embodiments, $R_1$ is methyl substituted oxadiazole. In other embodiments, $R_1$ is imidazole. In other embodiments, $R_1$ is methyl substituted imidazole. In other embodiments, $R_1$ is thiophene. In other embodiments, $R_1$ is triazole. In other embodiments, $R_1$ is pyridine. In other embodiments, $R_1$ is 2-pyridine. In other embodiments, $R_1$ is 3-pyridine. In other embodiments, $R_1$ is 4-pyridine. In other embodiments, $R_1$ is tetrazole. In other embodiments, $R_1$ is pyrimidine. In other embodiments, $R_1$ is pyrazine. In other embodiments, $R_1$ is oxacyclobutane. In other embodiments, $R_1$ is 1-oxacyclobutane. In other embodiments, $R_1$ is 2-oxacyclobutane. In other embodiments, $R_1$ is indole. In other embodiments, $R_1$ is pyridine oxide. In other embodiments, $R_1$ is protonated pyridine oxide. In other embodiments, $R_1$ is deprotonated pyridine oxide. In other embodiments, $R_1$ is 3-methyl-4H-1,2,4-triazole. In other embodiments, $R_1$ is 5-methyl-1,2,4-oxadiazole. In other embodiments, $R_1$ is substituted or unsubstituted aryl. In other embodiments, $R_1$ is phenyl. In other embodiments, $R_1$ is bromophenyl. In other embodiments, $R_1$ is 2-bromophenyl. In other embodiments, $R_1$ is 3-bromophenyl. In other embodiments, $R_1$ is 4-bromophenyl. In other embodiments, $R_1$ is $R_8$—$N(R_{10})(R_{11})$. In other embodiments, $R_1$ is $CH_2$—$NH_2$. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_2$ of compound of formula I-V is H. In other embodiments, $R_2$ is F. In other embodiments, $R_2$ is Cl. In other embodiments, $R_2$ is Br. In other embodiments, $R_2$ is I. In other embodiments, $R_2$ is $C_1$-$C_5$ linear or branched haloalkyl. In other embodiments, $R_2$ is $CF_3$. In other embodiments, $R_2$ is $CF_2CH_3$. In other embodiments, $R_2$ is $CF_2CH_2CF_3$. In other embodiments, $R_2$ is $CH_2CH_2CF_3$. In other embodiments, $R_2$ is $CF_2CH(CH_3)_2$. In other embodiments, $R_2$ is $CF(CH_3)$—$CH(CH_3)_2$. In other embodiments, $R_2$ is $OCD_3$. In other embodiments, $R_2$ is $NO_2$. In other embodiments, $R_2$ is $NH_2$. In other embodiments, $R_2$ is $R_8$—$N(R_{10})(R_{11})$. In other embodiments, $R_2$ is $CH_2$—$NH_2$. In other embodiments, $R_2$ is $CH_2$—$N(CH_3)_2$). In other embodiments, $R_2$ is $R_9$—$R_8$—$N(R_{10})(R_{11})$. In other embodiments, $R_2$ is C≡C—$CH_2$—$NH_2$. In other embodiments, $R_2$ is $B(OH)_2$. In other embodiments, $R_2$ is NHC(O)—$R_{10}$. In other embodiments, $R_2$ is $NHC(O)CH_3$. In other embodiments, $R_2$ is NHCO—$N(R_{10})(R_{11})$. In other embodiments, $R_2$ is $NHC(O)N(CH_3)_2$. In other embodiments, $R_2$ is COOH. In other embodiments, $R_2$ is C(O)O—$R_{10}$. In other embodiments, $R_2$ is C(O)—$R_{10}$. In other embodiments, $R_2$ is C(O)—$CH_3$. In other embodiments, $R_2$ is $C(O)O$—$CH(CH_3)_2$. In other embodiments, $R_2$ is C(O)O—$CH_3$. In other embodiments, $R_2$ is $SO_2N(R_{10})(R_{11})$. In other embodiments, $R_2$ is $SO_2N(CH_3)_2$. In other embodiments, $R_2$ is $SO_2NHC(O)CH_3$. In other embodiments, $R_2$ is $C_1$-$C_5$ linear or branched, substituted or unsubstituted alkyl. In other embodiments, $R_2$ is methyl. In other embodiments, $R_2$ is 2-$CH_2$—$C_6H_4$—Cl. In other embodiments, $R_2$ is 3-$CH_2$—$C_6H_4$—Cl. In other embodiments, $R_2$ is 4-$CH_2$—$C_6H_4$—Cl. In other embodiments, $R_2$ is ethyl. In other embodiments, $R_2$ is propyl. In other embodiments, $R_2$ is iso-propyl. In other embodiments, $R_2$ is t-Bu. In other embodiments, $R_2$ is iso-butyl. In other embodiments, $R_2$ is pentyl. In other embodiments, $R_2$ is benzyl. In other embodiments, $R_2$ is $C(CH_3)(OH)Ph$. In other embodiments, $R_2$ is substituted or unsubstituted $C_3$-$C_8$ cycloalkyl (e.g., cyclopropyl, cyclopentyl). In other embodiments, $R_2$ is $C_1$-$C_5$ linear, branched or cyclic alkoxy. In other embodiments, $R_2$ is methoxy. In other embodiments, $R_2$ is ethoxy. In other embodiments, $R_2$ is propoxy. In other embodiments, $R_2$ is isopropoxy. In other embodiments, $R_2$ is O—$CH_2$-cyclopropyl. In other embodiments, $R_2$ is O-cyclobutyl. In other embodiments, $R_2$ is O-cyclopentyl. In other embodiments, $R_2$ is O-cyclohexyl. In other embodiments, $R_2$ is O-1-oxacyclobutyl. In other embodiments, $R_2$ is O-2-oxacyclobutyl. In other embodiments, $R_2$ is 1-butoxy. In other embodiments, $R_2$ is 2-butoxy. In other embodiments, $R_2$ is O-tBu. In other embodiments, $R_2$ is $C_1$-$C_5$ linear, branched or cyclic alkoxy wherein at least one methylene group ($CH_2$) in the alkoxy is replaced with an oxygen atom (O). In other embodiments, $R_2$ is O-1-oxacyclobutyl. In other embodiments, $R_2$ is O-2-oxacyclobutyl. In other embodiments, $R_2$ is $C_1$-$C_5$ linear or branched haloalkoxy. In other embodiments, $R_2$ is $OCF_3$. In other embodiments, $R_2$ is $OCHF_2$. In other embodiments, $R_2$ is substituted or unsubstituted $C_3$-$C_8$ cycloalkyl. In other embodiments, $R_2$ is cyclopropyl. In other embodiments, $R_2$ is substituted or unsubstituted $C_3$-$C_8$ heterocyclic ring. In other embodiments, $R_2$ is oxazole or methyl substituted oxazole. In other embodiments, $R_2$ is oxadiazole or methyl substituted oxadiazole. In other embodiments, $R_2$ is imidazole or methyl substituted imidazole. In other embodiments, $R_2$ is thiophene. In other embodiments, $R_2$ is triazole. In other embodiments, $R_2$ is pyridine. In other embodiments, $R_2$ is 2-pyridine. In other embodiments, $R_2$ is 3-pyridine. In other embodiments, $R_2$ is 4-pyridine. In other embodiments, $R_2$ is tetrazole. In other embodiments, $R_2$ is pyrimidine. In other embodiments, $R_2$ is pyrazine. In other embodiments, $R_2$ is oxacyclobutane. In other embodiments, $R_2$ is 1-oxacyclobutane. In other embodiments, $R_2$ is 2-oxacyclobutane. In other embodiments, $R_2$ is indole. In other embodiments, $R_2$ is pyridine oxide. In other embodiments, $R_2$ is protonated pyridine oxide. In other embodiments, $R_2$ is deprotonated pyridine oxide. In other embodiments, $R_2$ is 3-methyl-4H-1,2,4-triazole. In other embodiments, $R_2$ is 5-methyl-1,2,4-oxadiazole. In other embodiments, $R_2$ is substituted or unsubstituted aryl. In other embodiments, $R_2$ is phenyl. In other embodiments, $R_2$ is bromophenyl. In other embodiments, $R_2$ is 2-bromophenyl. In other embodiments, $R_2$ is 3-bromophenyl. In other embodiments, $R_2$ is 4-bromophenyl. In other embodiments, $R_2$ is $R_8$—$N(R_{10})(R_{11})$. In other embodiments, $R_2$ is $CH_2$—$NH_2$. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_1$ and $R_2$ of compound of formula I-V are joint together to form a [1,3]dioxole ring. In some embodiments, $R_1$ and $R_2$ are joint together to form a furanone ring (e.g., furan-2(3H)-one). In some embodiments, $R_1$ and $R_2$ are joint together to form a benzene ring. In some embodiments, $R_1$ and $R_2$ are joint together to form a pyridine ring. In some embodiments, $R_1$ and $R_2$ are joint together to form a pyrrol ring.

In some embodiments, $R_1$ and $R_2$ of compound of formula I-V are both H. In some embodiments, at least one of $R_1$ and $R_2$ is not H.

In some embodiments, $R_3$ of compound of formula I-V is H. In other embodiments, $R_3$ is Cl. In other embodiments, $R_3$ is I. In other embodiments, $R_3$ is F. In other embodiments, $R_3$ is Br. In other embodiments, $R_3$ is OH. In other embodiments, $R_3$ is $CD_3$. In other embodiments, $R_3$ is $OCD_3$. In other embodiments, $R_3$ is $R_8$—OH. In other embodiments, $R_3$ is $CH_2$—OH. In other embodiments, $R_3$ is —$R_8$—O—$R_{10}$. In other embodiments, $R_3$ is $CH_2$—O—$CH_3$. In other embodiments, $R_3$ is $R_8$—$N(R_{10})(R_{11})$. In other embodiments, $R_3$ is $CH_2$—$NH_2$. In other embodiments, $R_3$ is $CH_2$—$N(CH_3)_2$. In other embodiments, $R_3$ is COOH. In other embodiments, $R_3$ is C(O)O—$R_{10}$. In other embodiments, $R_3$ is C(O)O—$CH_2CH_3$. In other embodiments, $R_3$ is $R_8$—C(O)—$R_{10}$. In other embodiments, $R_3$ is $CH_2$C(O)$CH_3$. In other embodiments, $R_3$ is C(O)—$R_{10}$. In other embodiments, $R_3$ is C(O)—$CH_3$. In other embodiments, $R_3$ is C(O)—$CH_2CH_3$. In other embodiments, $R_3$ is C(O)—$CH_2CH_2CH_3$. In other embodiments, $R_3$ is $C_1$-$C_5$ linear or branched C(O)-haloalkyl. In other embodiments, $R_3$ is C(O)—$CF_3$. In other embodiments, $R_3$ is C(O)N($R_{10}$)($R_{11}$). In other embodiments, $R_3$ is C(O)N($CH_3$)$_2$. In other embodiments, $R_3$ is $SO_2$N($R_{10}$)($R_{11}$). In other embodiments, $R_3$ is $SO_2$N($CH_3$)$_2$. In other embodiments, $R_3$ is $C_1$-$C_5$ linear or branched, substituted or unsubstituted alkyl. In other embodiments, $R_3$ is methyl. In other embodiments, $R_3$ is C(OH)($CH_3$)(Ph). In other embodiments, $R_3$ is ethyl. In other embodiments, $R_3$ is propyl. In other embodiments, $R_3$ is iso-propyl. In other embodiments, $R_3$ is t-Bu. In other embodiments, $R_3$ is iso-butyl. In other embodiments, $R_3$ is pentyl. In other embodiments, $R_3$ is C($CH_3$)(OH)Ph. In other embodiments, $R_3$ is $C_1$-$C_5$ linear or branched haloalkyl. In other embodiments, $R_3$ is $C_2$-$C_5$ linear or branched haloalkyl. In other embodiments, $R_3$ is $C_2$-$C_6$ linear or branched haloalkyl. In other embodiments, $R_3$ is $C_2$-$C_7$ linear or branched haloalkyl. In other embodiments, $R_3$ is $C_3$-$C_8$ linear or branched haloalkyl. In other embodiments, $R_3$ is $CF_2CH_3$. In other embodiments, $R_3$ is $CH_2CF_3$. In other embodiments, $R_3$ is $CF_2CH_2CH_3$. In other embodiments, $R_3$ is $CF_3$. In other embodiments, $R_3$ is $CF_2CH_2CH_3$. In other embodiments, $R_3$ is $CH_2CH_2CF_3$. In other embodiments, $R_3$ is $CF_2CH(CH_3)_2$. In other embodiments, $R_3$ is CF($CH_3$)—CH($CH_3$)$_2$. In other embodiments, $R_3$ is $C_1$-$C_5$ linear, branched or cyclic alkoxy. In other embodiments, $R_3$ is $C_1$-$C_5$ linear, branched or cyclic alkoxy. In other embodiments, $R_3$ is methoxy. In other embodiments, $R_3$ is iso-propoxy. In other embodiments, $R_3$ is substituted or unsubstituted $C_3$-$C_8$ cycloalkyl. In other embodiments, $R_3$ is cyclopropyl. In other embodiments, $R_3$ is cyclopentyl. In other embodiments, $R_3$ is substituted or unsubstituted $C_3$-$C_8$ heterocyclic ring. In other embodiments, $R_3$ is thiophene. In other embodiments, $R_3$ is oxazole. In other embodiments, $R_3$ is isoxazole. In other embodiments, $R_3$ is imidazole. In other embodiments, $R_3$ is furane. In other embodiments, $R_3$ is triazole. In other embodiments, $R_3$ is pyridine. In other embodiments, $R_3$ is 2-pyridine. In other embodiments, $R_3$ is 3-pyridine. In other embodiments, $R_3$ is 4-pyridine. In other embodiments, $R_3$ is pyrimidine. In other embodiments, $R_3$ is pyrazine. In other embodiments, $R_3$ is oxacyclobutane. In other embodiments, $R_3$ is 1-oxacyclobutane. In other embodiments, $R_3$ is 2-oxacyclobutane. In other embodiments, $R_3$ is indole. In other embodiments, $R_3$ is 3-methyl-4H-1,2,4-triazole. In other embodiments, $R_3$ is 5-methyl-1,2,4-oxadiazole. In other embodiments, $R_3$ is substituted or unsubstituted aryl. In other embodiments, $R_3$ is phenyl. In other embodiments, $R_3$ is CH($CF_3$)(NH—$R_{10}$). In other embodiments, substitutions include: F, Cl, Br, I, $C_1$-$C_5$ linear or branched alkyl, OH, alkoxy, N(R)$_2$, $CF_3$, aryl, phenyl, halophenyl, (benzyloxy)phenyl, CN, $NO_2$ or any combination thereof; each is a separate embodiment according to this invention.

In some embodiments, $R_4$ of compound of formula I-IV is H. In other embodiments, $R_4$ is Cl. In other embodiments, $R_4$ is I. In other embodiments, $R_4$ is F. In other embodiments, $R_4$ is Br. In other embodiments, $R_4$ is OH. In other embodiments, $R_4$ is $CD_3$. In other embodiments, $R_4$ is $OCD_3$. In other embodiments, $R_4$ is $R_8$—OH. In other embodiments, $R_4$ is $CH_2$—OH. In other embodiments, $R_4$ is —$R_8$—O—$R_{10}$. In other embodiments, $R_4$ is $CH_2$—O—$CH_3$. In other embodiments, $R_4$ is $R_8$—N($R_{10}$)($R_{11}$). In other embodiments, $R_4$ is $CH_2$—$NH_2$. In other embodiments, $R_4$ is $CH_2$—N($CH_3$)$_2$. In other embodiments, $R_4$ is COOH. In other embodiments, $R_4$ is C(O)O—$R_{10}$. In other embodiments, $R_4$ is C(O)O—$CH_2CH_3$. In other embodiments, $R_4$ is $R_8$—C(O)—$R_{10}$. In other embodiments, $R_4$ is $CH_2$C(O)$CH_3$. In other embodiments, $R_4$ is C(O)—$R_{10}$. In other embodiments, $R_4$ is C(O)—$CH_3$. In other embodiments, $R_4$ is C(O)—$CH_2CH_3$. In other embodiments, $R_4$ is C(O)—$CH_2CH_2CH_3$. In other embodiments, $R_4$ is $C_1$-$C_5$ linear or branched C(O)-haloalkyl. In other embodiments, $R_4$ is C(O)—$CF_3$. In other embodiments, $R_4$ is C(O)N($R_{10}$)($R_{11}$). In other embodiments, $R_4$ is C(O)N($CH_3$)$_2$. In other embodiments, $R_4$ is $SO_2$N($R_{10}$)($R_{11}$). In other embodiments, $R_4$ is $SO_2$N($CH_3$)$_2$. In other embodiments, $R_4$ is $C_1$-$C_5$ linear or branched, substituted or unsubstituted alkyl. In other embodiments, $R_4$ is methyl. In other embodiments, $R_4$ is C(OH)($CH_3$)(Ph). In other embodiments, $R_4$ is ethyl. In other embodiments, $R_4$ is propyl. In other embodiments, $R_4$ is iso-propyl. In other embodiments, $R_4$ is t-Bu. In other embodiments, $R_4$ is iso-butyl. In other embodiments, $R_4$ is pentyl. In other embodiments, $R_4$ is C($CH_3$)(OH)Ph. In other embodiments, $R_4$ is $C_1$-$C_5$ linear or branched haloalkyl. In other embodiments, $R_4$ is $C_2$-$C_5$ linear or branched haloalkyl. In other embodiments, $R_4$ is $C_2$-$C_6$ linear or branched haloalkyl. In other embodiments, $R_4$ is $C_2$-$C_7$ linear or branched haloalkyl. In other embodiments, $R_4$ is $C_3$-$C_8$ linear or branched haloalkyl. In other embodiments, $R_4$ is $CF_2CH_3$. In other embodiments, $R_4$ is $CH_2CF_3$. In other embodiments, $R_4$ is $CF_2CH_2CH_3$. In other embodiments, $R_4$ is $CF_3$. In other embodiments, $R_4$ is $CF_2CH_2CH_3$. In other embodiments, $R_4$ is $CH_2CH_2CF_3$. In other embodiments, $R_4$ is $CF_2CH(CH_3)_2$. In other embodiments, $R_4$ is CF($CH_3$)—CH($CH_3$)$_2$. In other embodiments, $R_4$ is $C_1$-$C_5$ linear, branched or cyclic alkoxy. In other embodiments, $R_4$ is $C_1$-$C_5$ linear, branched or cyclic alkoxy. In other embodiments, $R_4$ is methoxy. In other embodiments, $R_4$ is iso-propoxy. In other embodiments, $R_4$ is substituted or unsubstituted $C_3$-$C_8$ cycloalkyl. In other embodiments, $R_4$ is cyclopropyl. In other embodiments, $R_4$ is cyclopentyl. In other embodiments, $R_4$ is substituted or unsubstituted $C_3$-$C_8$ heterocyclic ring. In other embodiments, $R_4$ is thiophene. In other embodiments, $R_4$ is oxazole. In other embodiments, $R_4$ is isoxazole. In other embodiments, $R_4$ is imidazole. In other embodiments, $R_4$ is furane. In other embodiments, $R_4$ is triazole. In other embodiments, $R_4$ is pyridine. In other embodiments, $R_4$ is 2-pyridine. In other embodiments, $R_4$ is 3-pyridine. In other embodiments, $R_4$ is 4-pyridine. In other embodiments, $R_4$ is pyrimidine. In other embodiments, $R_4$ is pyrazine. In other embodiments, $R_4$ is oxacyclobutane. In other embodiments, $R_4$ is 1-oxacyclobutane. In other embodiments, $R_4$ is 2-oxacyclobutane. In other embodiments, $R_4$ is indole. In other embodiments, $R_4$ is 3-methyl-4H-1,2,4-triazole. In other embodiments, $R_4$ is 5-methyl-1,2,4-oxadiazole. In other embodiments, $R_4$ is substituted or unsubstituted aryl. In other embodiments, $R_4$ is phenyl. In other embodiments, $R_4$ is CH($CF_3$)(NH—$R_{10}$). In other embodiments, substitutions include: F, Cl, Br, I, $C_1$-$C_5$ linear or branched alkyl, OH, alkoxy, N(R)$_2$, $CF_3$, aryl, phenyl, halophenyl, (benzyloxy)phenyl, CN, $NO_2$ or any combination thereof; each is a separate embodiment according to this invention.

In some embodiments, $R_3$ and $R_4$ of compound of formula I-IV are joint together to form a [1,3]dioxole ring. In some embodiments, $R_3$ and $R_4$ are joint together to form a furanone ring (e.g., furan-2(3H)-one). In some embodiments, $R_3$ and $R_4$ are joint together to form a benzene ring. In some embodiments, $R_3$ and $R_4$ are joint together to form a cyclopentene ring. In some embodiments, $R_3$ and $R_4$ are joint together to form an imidazole ring. In some embodiments, $R_3$ and $R_4$ are joint together to form a pyrrol ring.

In some embodiments, $R_3$ and $R_4$ of compound of formula I-V are both H. In some embodiments, at least one of $R_3$ and $R_4$ is not H. In some embodiments, if $R_3$ is H, then $R_4$ is not H. In some embodiments, if $R_4$ is H, then $R_3$ is not H.

In some embodiments, $R_5$ of compound of formula I-IV is H. In other embodiments, $R_5$ is $C_1$-$C_5$ linear or branched, substituted or unsubstituted alkyl. In other embodiments, $R_5$ is methyl. In other embodiments, $R_5$ is $CH_2SH$. In other embodiments, $R_5$ is ethyl. In other embodiments, $R_5$ is iso-propyl. In other embodiments, $R_5$ is $C_1$-$C_5$ linear or branched haloalkyl. In other embodiments, $R_5$ is $CF_2CH_3$. In other embodiments, $R_5$ is $CH_2CF_3$. In other embodiments, $R_5$ is $CF_2CH_2CH_3$. In other embodiments, $R_5$ is $CF_3$. In other embodiments, $R_5$ is $CF_2CH_2CH_3$. In other embodiments, $R_5$ is $CH_2CH_2CF_3$. In other embodiments, $R_5$ is $CF_2CH(CH_3)_2$. In other embodiments, $R_5$ is $CF(CH_3)$—$CH(CH_3)_2$. In other embodiments, $R_5$ is $R_8$-aryl. In other embodiments, $R_5$ is $CH_2$-Ph (i.e., benzyl). In other embodiments, $R_5$ is substituted or unsubstituted aryl. In other embodiments, $R_5$ is phenyl. In other embodiments, $R_5$ is substituted or unsubstituted heteroaryl. In other embodiments, $R_5$ is pyridine. In other embodiments, $R_5$ is 2-pyridine. In other embodiments, $R_5$ is 3-pyridine. In other embodiments, $R_5$ is 4-pyridine.

In some embodiments, $R_6$ of compound of formula I-III is H. In other embodiments, $R_6$ is $C_1$-$C_5$ linear or branched alkyl. In other embodiments, $R_6$ is methyl.

In some embodiments, $R_8$ of compound of formula I-V is $CH_2$. In other embodiments, $R_8$ is $CH_2CH_2$. In other embodiments, $R_8$ is $CH_2CH_2CH_2$.

In some embodiments, p of compound of formula I-V is 1. In other embodiments, p is 2. In other embodiments, p is 3.

In some embodiments, $R_9$ of compound of formula I-V is C≡C.

In some embodiments, q of compound of formula I-V is 2.

In some embodiments, $R_{10}$ of compound of formula I-V is $C_1$-$C_5$ linear or branched alkyl. In other embodiments, $R_{10}$ is H. In other embodiments, $R_{10}$ is $CH_3$. In other embodiments, $R_{10}$ is $CH_2CH_3$. In other embodiments, $R_{10}$ is $CH_2CH_2CH_3$.

In some embodiments, $R_{11}$ of compound of formula I-V is $C_1$-$C_5$ linear or branched alkyl. In other embodiments, $R_{10}$ is H. In other embodiments, $R_{11}$ is $CH_3$.

In some embodiments, R of compound of formula I-V is H. In other embodiments, R is $C_1$-$C_5$ linear or branched alkyl. In other embodiments, R is methyl. In other embodiments, R is ethyl.

In some embodiments, m of compound of formula I-II is 1. In other embodiments, m is 0.

In some embodiments, n of compound of formula I-II is 1. In other embodiments, n is 0.

In some embodiments, k of compound of formula I-II is 1. In other embodiments, k is 0.

In some embodiments, l of compound of formula I-II is 1. In other embodiments, l is 0.

In some embodiments, $Q_1$ of compound of formula I-III is O.

In some embodiments, $Q_2$ of compound of formula I-III is O.

In some embodiments, $X_1$ of compound of formula II is C. In other embodiments, $X_1$ is N.

In some embodiments, $X_2$ of compound of formula II is C. In other embodiments, $X_2$ is N.

In some embodiments, $X_3$ of compound of formula II-V is C. In other embodiments, $X_3$ is N.

In some embodiments, $X_4$ of compound of formula II-IV is C. In other embodiments, $X_4$ is N.

In some embodiments, $X_5$ of compound of formula II is C. In other embodiments, $X_5$ is N.

In some embodiments, $X_6$ of compound of formula II-III is C. In other embodiments, $X_6$ is N.

In some embodiments, $X_7$ of compound of formula II-V is C. In other embodiments, $X_7$ is N.

In some embodiments, $X_8$ of compound of formula II-IV is C. In other embodiments, $X_8$ is N.

In some embodiments, $X_9$ of compound of formula II is C. In other embodiments, $X_9$ is N.

In some embodiments, $X_{10}$ of compound of formula II is C. In other embodiments, $X_{10}$ is N.

In various embodiments, this invention is directed to the compounds presented in Table 1, pharmaceutical compositions and/or method of use thereof:

TABLE 1

| Compound name | Structure |
|---|---|
| 100 | 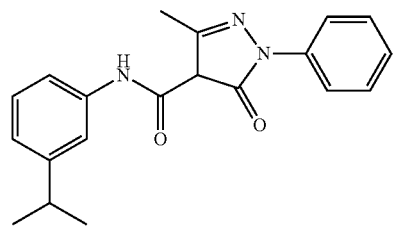 [SMILES: CC1=NN(c2ccccc2)C(=O)C1C(=O)Nc1cccc(C(C)C)c1] |

TABLE 1-continued

| Compound name | Structure |
|---|---|
| 101 | 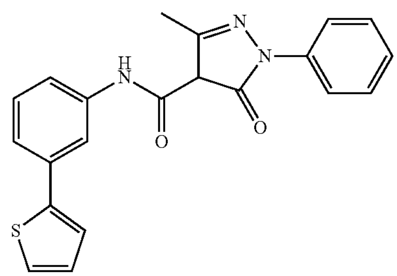 [SMILES: CC1=NN(c2ccccc2)C(=O)C1C(=O)Nc1cccc(-c2cccs2)c1] |
| 102 | 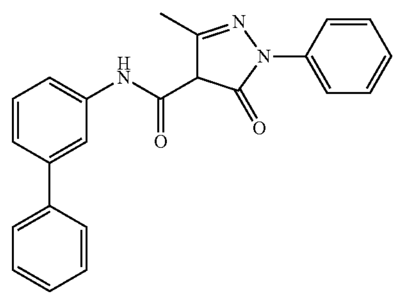 [SMILES: CC1=NN(c2ccccc2)C(=O)C1C(=O)Nc1cccc(-c2ccccc2)c1] |
| 103 | 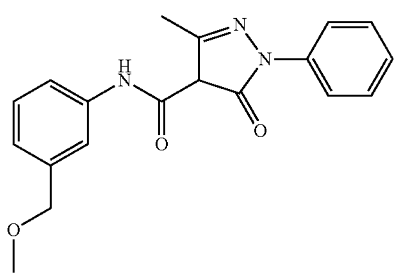 [SMILES: COCc1cccc(NC(=O)C2C(=O)N(c3ccccc3)N=C2C)c1] |
| 104 | 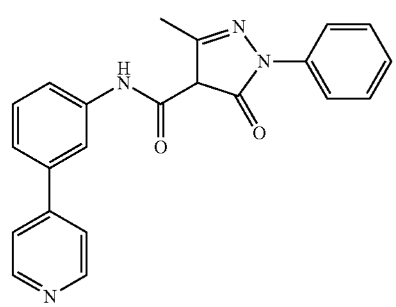 [SMILES: CC1=NN(c2ccccc2)C(=O)C1C(=O)Nc1cccc(-c2ccncc2)c1] |
| 105 | 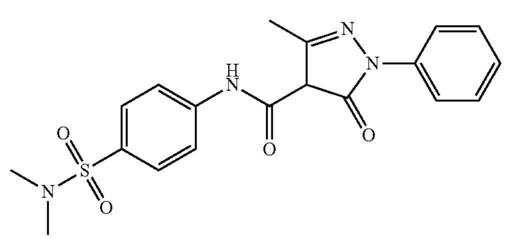 [SMILES: CC1=NN(c2ccccc2)C(=O)C1C(=O)Nc1ccc(S(=O)(=O)N(C)C)cc1] |

TABLE 1-continued

| Compound name | Structure |
|---|---|
| 106 | (structure) |
| 107 | (structure) |
| 108 | (structure) |
| 109 | (structure) |
| 110 | (structure) |
| 111 | (structure) |
| 112 | (structure) |

TABLE 1-continued

| Compound name | Structure |
|---|---|
| 113 | ethyl 3-[[(5-oxo-3-methyl-1-phenyl-4,5-dihydro-1H-pyrazol-4-yl)carbonyl]amino]benzoate |
| 114 | N-(3-butanoylphenyl)-5-oxo-3-methyl-1-phenyl-4,5-dihydro-1H-pyrazole-4-carboxamide |
| 115 | N-(3-tert-butylphenyl)-5-oxo-3-methyl-1-phenyl-4,5-dihydro-1H-pyrazole-4-carboxamide |
| 116 | 3-[[(5-oxo-3-methyl-1-phenyl-4,5-dihydro-1H-pyrazol-4-yl)carbonyl]amino]benzoic acid |
| 117 | N-(3-propanoylphenyl)-5-oxo-3-methyl-1-phenyl-4,5-dihydro-1H-pyrazole-4-carboxamide |
| 118 | N-(3-pentylphenyl)-5-oxo-3-methyl-1-phenyl-4,5-dihydro-1H-pyrazole-4-carboxamide |
| 119 | N-(3-cyclopropylphenyl)-5-oxo-3-methyl-1-phenyl-4,5-dihydro-1H-pyrazole-4-carboxamide |

TABLE 1-continued

| Compound name | Structure |
|---|---|
| 120 | 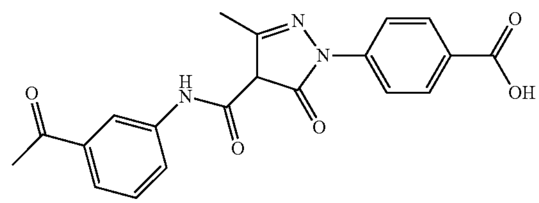 [SMILES: CC(=O)c1cccc(NC(=O)C2C(=O)N(c3ccc(C(=O)O)cc3)N=C2C)c1] |
| 121 | 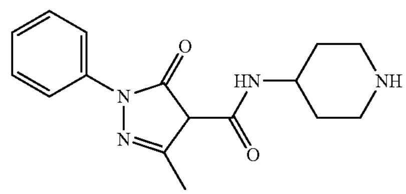 [SMILES: CC1=NN(c2ccccc2)C(=O)C1C(=O)NC1CCNCC1] |
| 122 | 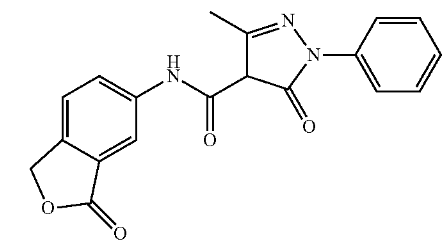 [SMILES: CC1=NN(c2ccccc2)C(=O)C1C(=O)Nc1ccc2c(c1)C(=O)OC2] |
| 123 | 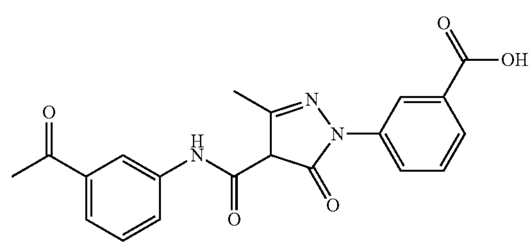 [SMILES: CC(=O)c1cccc(NC(=O)C2C(=O)N(c3cccc(C(=O)O)c3)N=C2C)c1] |
| 124 | 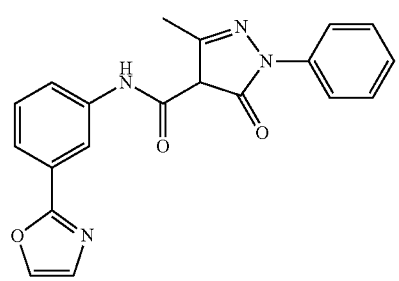 [SMILES: CC1=NN(c2ccccc2)C(=O)C1C(=O)Nc1cccc(-c2ncco2)c1] |
| 125 | 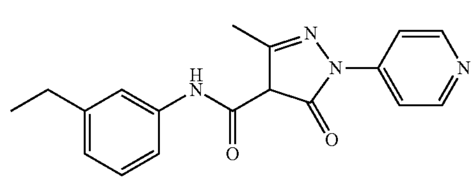 [SMILES: CCc1cccc(NC(=O)C2C(=O)N(c3ccncc3)N=C2C)c1] |

US 10,851,064 B2
TABLE 1-continued
| Compound name | Structure |
|---|---|
| 126 | 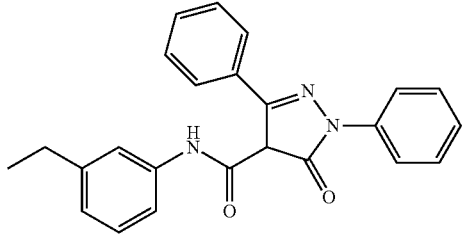 |
| 127 | 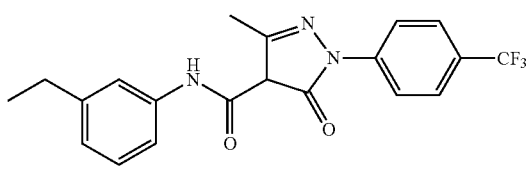 [SMILES: CCc1cccc(NC(=O)C2C(=O)N(c3ccc(C(F)(F)F)cc3)N=C2C)c1] |
| 128 | 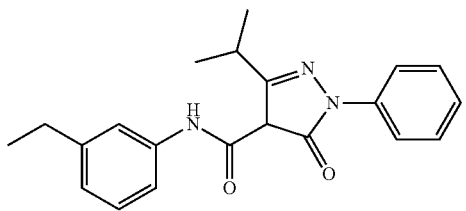 [SMILES: CCc1cccc(NC(=O)C2C(=O)N(c3ccccc3)N=C2C(C)C)c1] |
| 129 | 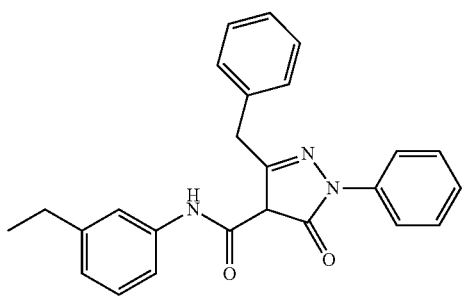 [SMILES: CCc1cccc(NC(=O)C2C(=O)N(c3ccccc3)N=C2Cc2ccccc2)c1] |
| 130 | 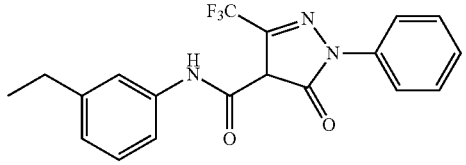 [SMILES: CCc1cccc(NC(=O)C2C(=O)N(c3ccccc3)N=C2C(F)(F)F)c1] |
| 131 | 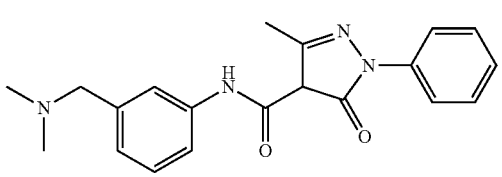 [SMILES: CC1=NN(c2ccccc2)C(=O)C1C(=O)Nc1cccc(CN(C)C)c1] |

TABLE 1-continued

| Compound name | Structure |
|---|---|
| 132 | 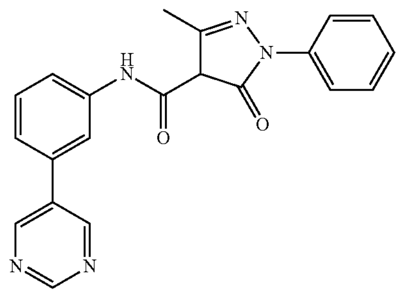 [SMILES: CC1=NN(c2ccccc2)C(=O)C1C(=O)Nc1cccc(-c2cncnc2)c1] |
| 133 | 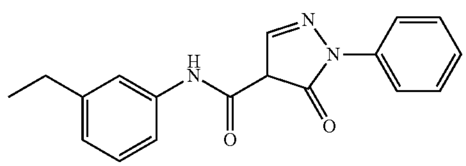 [SMILES: CCc1cccc(NC(=O)C2C=NN(c3ccccc3)C2=O)c1] |
| 134 | 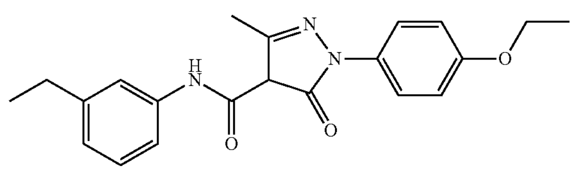 [SMILES: CCOc1ccc(N2N=C(C)C(C(=O)Nc3cccc(CC)c3)C2=O)cc1] |
| 135 | 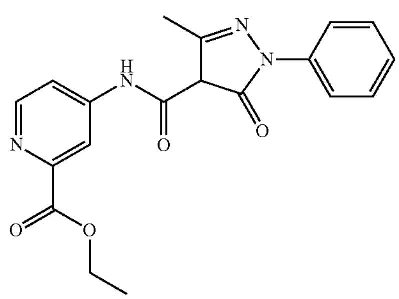 [SMILES: CCOC(=O)c1cc(NC(=O)C2C(=O)N(c3ccccc3)N=C2C)ccn1] |
| 136 | 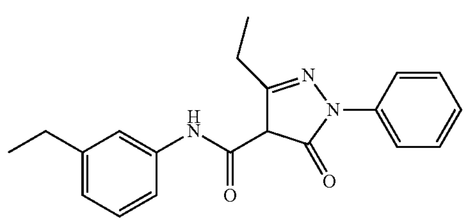 [SMILES: CCC1=NN(c2ccccc2)C(=O)C1C(=O)Nc1cccc(CC)c1] |
| 137 | 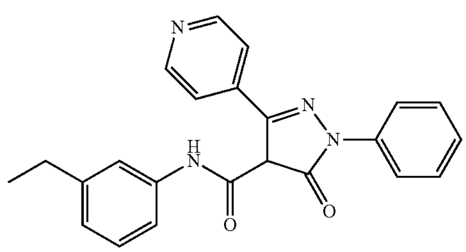 [SMILES: CCc1cccc(NC(=O)C2C(=O)N(c3ccccc3)N=C2c2ccncc2)c1] |

TABLE 1-continued

| Compound name | Structure |
|---|---|
| 138 | 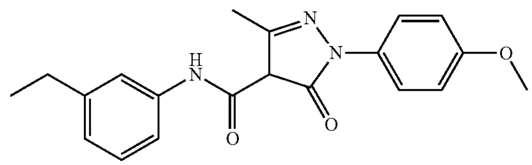 [SMILES: CCc1cccc(NC(=O)C2C(=O)N(c3ccc(OC)cc3)N=C2C)c1] |
| 139 | 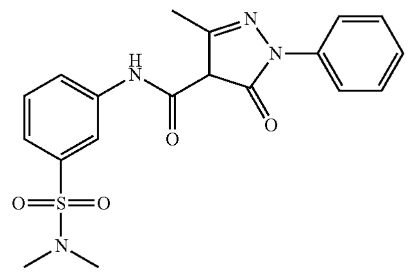 [SMILES: CC1=NN(c2ccccc2)C(=O)C1C(=O)Nc1cccc(S(=O)(=O)N(C)C)c1] |
| 140 | 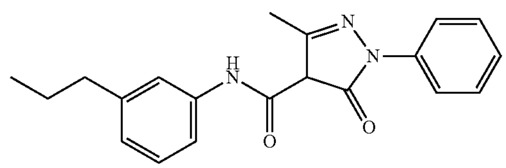 [SMILES: CCCc1cccc(NC(=O)C2C(=O)N(c3ccccc3)N=C2C)c1] |
| 141 | 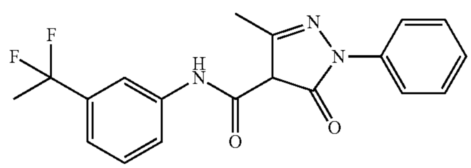 [SMILES: CC1=NN(c2ccccc2)C(=O)C1C(=O)Nc1cccc(C(C)(F)F)c1] |
| 142 | 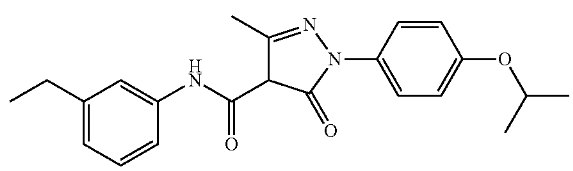 [SMILES: CCc1cccc(NC(=O)C2C(=O)N(c3ccc(OC(C)C)cc3)N=C2C)c1] |
| 143 | 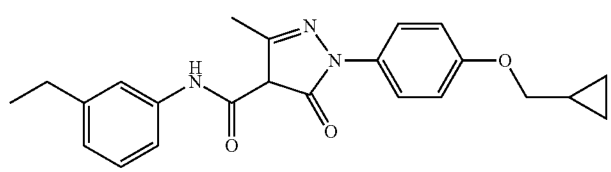 [SMILES: CCc1cccc(NC(=O)C2C(=O)N(c3ccc(OCC4CC4)cc3)N=C2C)c1] |
| 144 | 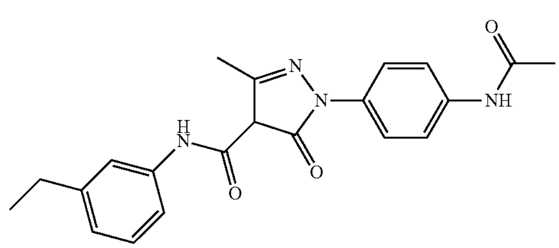 [SMILES: CCc1cccc(NC(=O)C2C(=O)N(c3ccc(NC(C)=O)cc3)N=C2C)c1] |

TABLE 1-continued
| Compound name | Structure |
|---|---|
| 145 | 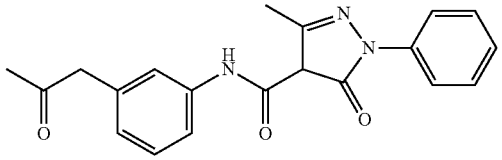 [SMILES: CC(=O)Cc1cccc(NC(=O)C2C(=O)N(c3ccccc3)N=C2C)c1] |
| 146 | 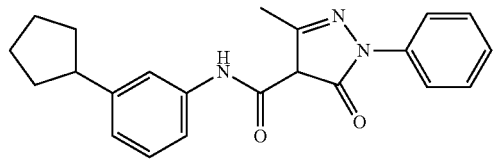 [SMILES: CC1=NN(c2ccccc2)C(=O)C1C(=O)Nc1cccc(C2CCCC2)c1] |
| 147 | 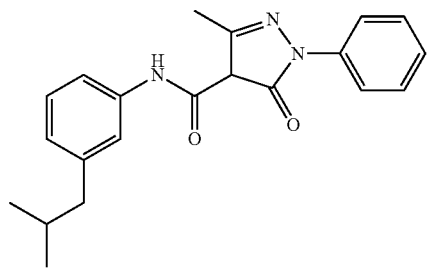 [SMILES: CC1=NN(c2ccccc2)C(=O)C1C(=O)Nc1cccc(CC(C)C)c1] |
| 148 | 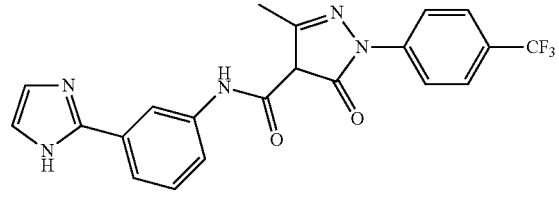 [SMILES: CC1=NN(c2ccc(C(F)(F)F)cc2)C(=O)C1C(=O)Nc1cccc(-c2ncc[nH]2)c1] |
| 149 | 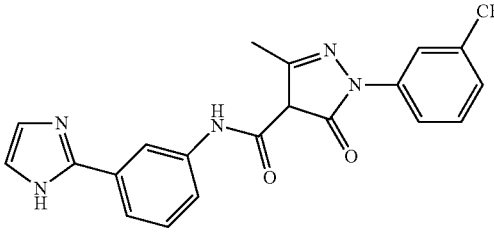 |
| 150 | 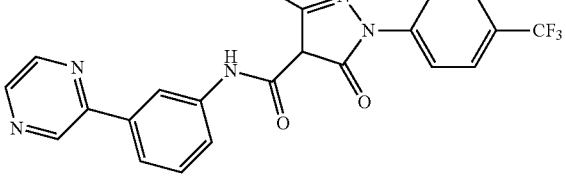 |
| 152 | 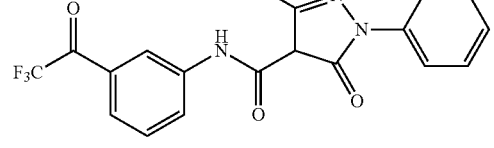 |

TABLE 1-continued

| Compound name | Structure |
|---|---|
| 153 | 3-methyl-1-(4-nitrophenyl)-5-oxo-N-(3-ethylphenyl)-4,5-dihydro-1H-pyrazole-4-carboxamide |
| 154 | 1-(4-aminophenyl)-3-methyl-5-oxo-N-(3-ethylphenyl)-4,5-dihydro-1H-pyrazole-4-carboxamide |
| 155 | 1-(4-(3,3-dimethylureido)phenyl)-3-methyl-5-oxo-N-(3-ethylphenyl)-4,5-dihydro-1H-pyrazole-4-carboxamide |
| 156 | 5-oxo-1-phenyl-3-(pyridin-2-yl)-N-(3-ethylphenyl)-4,5-dihydro-1H-pyrazole-4-carboxamide |
| 157 | 3-methyl-1-(4-nitrophenyl)-5-oxo-N-(3-ethylphenyl)-4,5-dihydro-1H-pyrazole-4-carboxamide |
| 158 | 3-methyl-5-oxo-1-(4-propoxyphenyl)-N-(3-ethylphenyl)-4,5-dihydro-1H-pyrazole-4-carboxamide |
| 159 | 3-(4-((3-(furan-2-yl)phenyl)carbamoyl)-3-methyl-5-oxo-4,5-dihydro-1H-pyrazol-1-yl)benzoic acid |

TABLE 1-continued

| Compound name | Structure |
|---|---|
| 160 | (structure) |
| 161 | (structure) |
| 162 | (structure) |
| 164 | (structure) |
| 165 | (structure) |
| 166 | (structure) |

TABLE 1-continued

| Compound name | Structure |
|---|---|
| 167 | 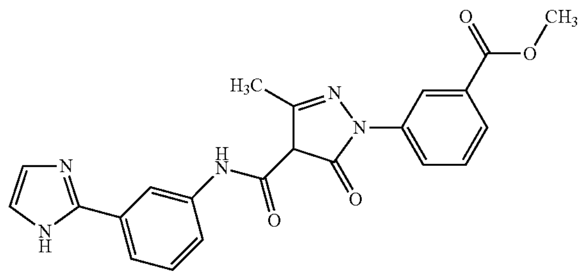 [SMILES: COC(=O)c1cccc(N2N=C(C)C(C(=O)Nc3cccc(-c4ncc[nH]4)c3)C2=O)c1] |
| 168 | 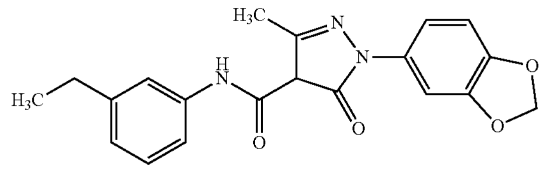 [SMILES: CCc1cccc(NC(=O)C2C(=O)N(c3ccc4c(c3)OCO4)N=C2C)c1] |
| 169 | 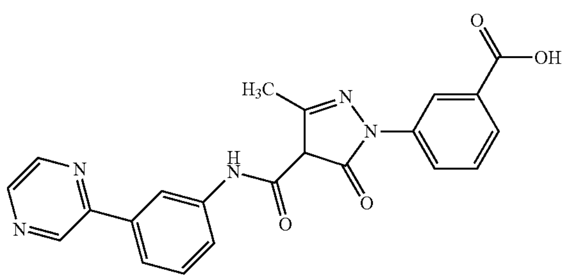 [SMILES: CC1=NN(c2cccc(C(=O)O)c2)C(=O)C1C(=O)Nc1cccc(-c2cnccn2)c1] |
| 170 | 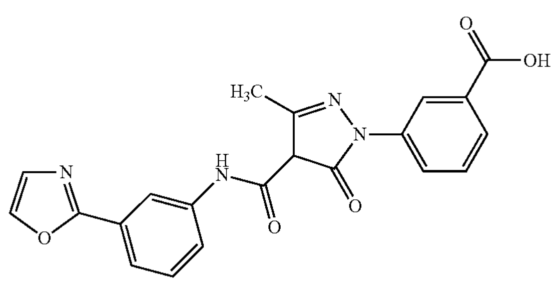 [SMILES: CC1=NN(c2cccc(C(=O)O)c2)C(=O)C1C(=O)Nc1cccc(-c2ncco2)c1] |
| 171 | 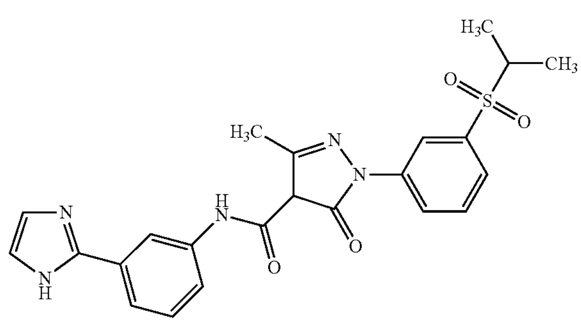 [SMILES: CC1=NN(c2cccc(S(=O)(=O)C(C)C)c2)C(=O)C1C(=O)Nc1cccc(-c2ncc[nH]2)c1] |

TABLE 1-continued

| Compound name | Structure |
|---|---|
| 172 | 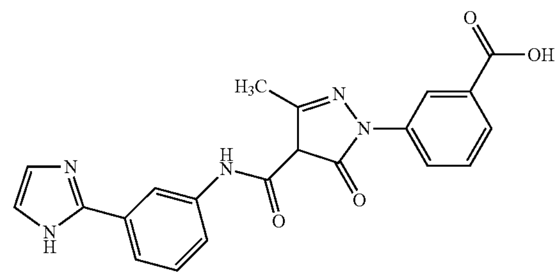 [SMILES: CC1=NN(c2cccc(C(=O)O)c2)C(=O)C1C(=O)Nc1cccc(-c2ncc[nH]2)c1] |
| 173 | 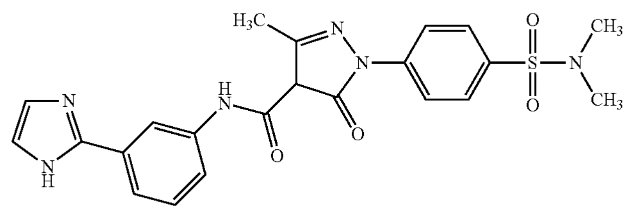 [SMILES: CC1=NN(c2ccc(S(=O)(=O)N(C)C)cc2)C(=O)C1C(=O)Nc1cccc(-c2ncc[nH]2)c1] |
| 174 | 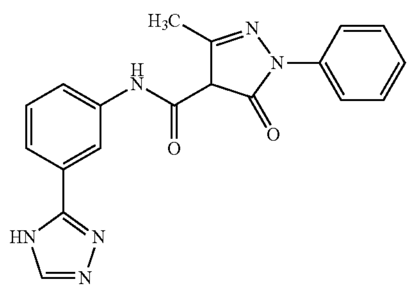 [SMILES: CC1=NN(c2ccccc2)C(=O)C1C(=O)Nc1cccc(-c2nnc[nH]2)c1] |
| 176 | 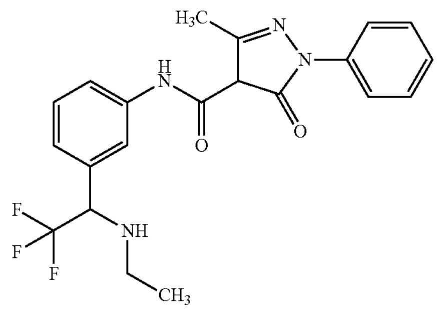 [SMILES: CCNC(c1cccc(NC(=O)C2C(=O)N(c3ccccc3)N=C2C)c1)C(F)(F)F] |
| 179 | 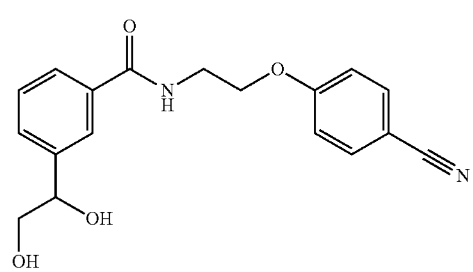 [SMILES: N#Cc1ccc(OCCNC(=O)c2cccc(C(O)CO)c2)cc1] |

TABLE 1-continued

| Compound name | Structure |
|---|---|
| 180 | 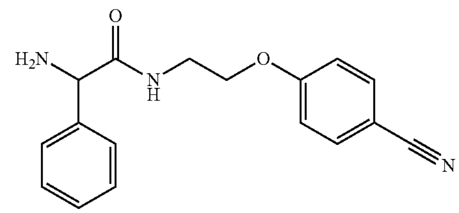 [SMILES: N#Cc1ccc(OCCNC(=O)C(N)c2ccccc2)cc1] |
| 182 | 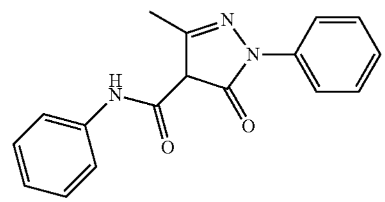 [SMILES: CC1=NN(c2ccccc2)C(=O)C1C(=O)Nc1ccccc1] |
| 183 | 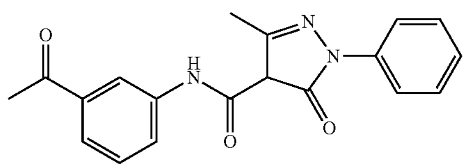 [SMILES: CC(=O)c1cccc(NC(=O)C2C(=O)N(c3ccccc3)N=C2C)c1] |
| 184 | 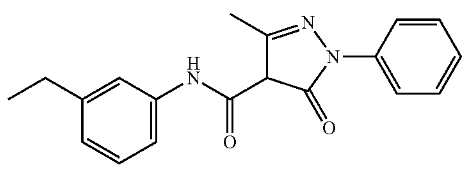 [SMILES: CCc1cccc(NC(=O)C2C(=O)N(c3ccccc3)N=C2C)c1] |
| 185 | 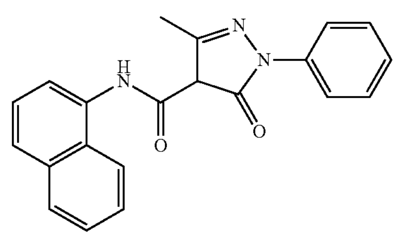 [SMILES: CC1=NN(c2ccccc2)C(=O)C1C(=O)Nc1cccc2ccccc12] |
| 186 | 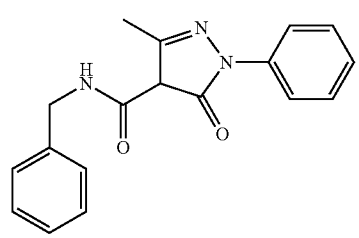 [SMILES: CC1=NN(c2ccccc2)C(=O)C1C(=O)NCc1ccccc1] |
| 187 | 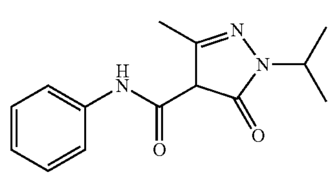 [SMILES: CC1=NN(C(C)C)C(=O)C1C(=O)Nc1ccccc1] |

TABLE 1-continued

| Compound name | Structure |
|---|---|
| 188 | 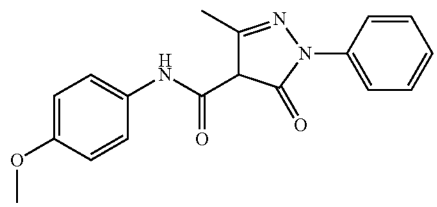 [SMILES: COc1ccc(NC(=O)C2C(=O)N(c3ccccc3)N=C2C)cc1] |
| 189 | 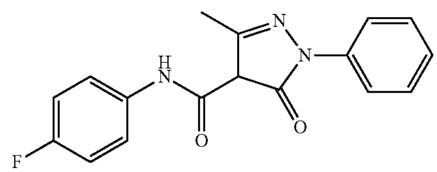 [SMILES: CC1=NN(c2ccccc2)C(=O)C1C(=O)Nc1ccc(F)cc1] |
| 190 | 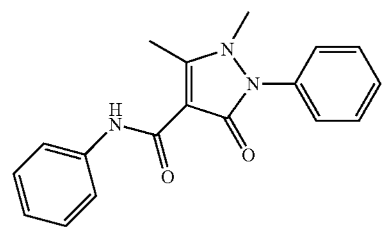 [SMILES: Cc1c(C(=O)Nc2ccccc2)c(=O)n(-c2ccccc2)n1C] |
| 191 | 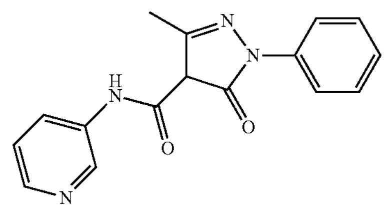 [SMILES: CC1=NN(c2ccccc2)C(=O)C1C(=O)Nc1cccnc1] |
| 192 | 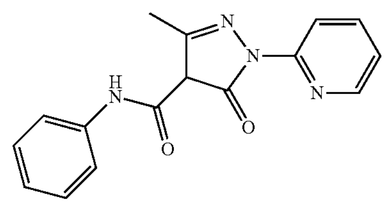 |
| 193 | 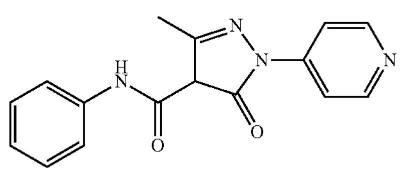 [SMILES: CC1=NN(c2ccncc2)C(=O)C1C(=O)Nc1ccccc1] |
| 194 | 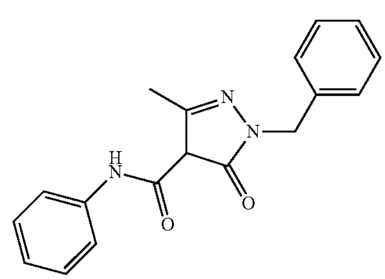 [SMILES: CC1=NN(Cc2ccccc2)C(=O)C1C(=O)Nc1ccccc1] |

TABLE 1-continued

| Compound name | Structure |
|---|---|
| 195 | *(structure)* |
| 196 | *(structure)* |
| 197 | *(structure)* |
| 198 | *(structure)* |
| 199 | *(structure)* |
| 200 | *(structure)* |
| 201 | *(structure)* |
| 202 | *(structure)* |

TABLE 1-continued

| Compound name | Structure |
|---|---|
| 203 | 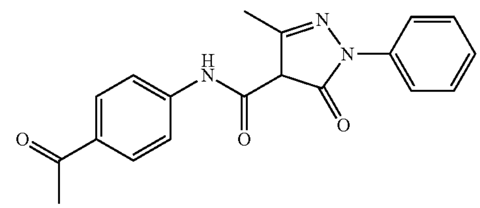 [SMILES: CC(=O)c1ccc(NC(=O)C2C(=O)N(c3ccccc3)N=C2C)cc1] |
| 204 | 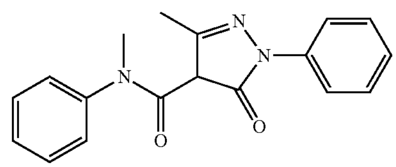 [SMILES: CC1=NN(c2ccccc2)C(=O)C1C(=O)N(C)c1ccccc1] |
| 205 | 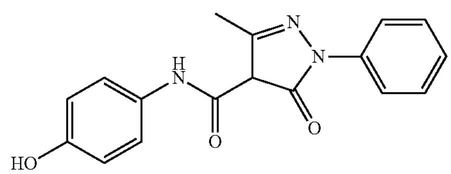 [SMILES: CC1=NN(c2ccccc2)C(=O)C1C(=O)Nc1ccc(O)cc1] |
| 206 | 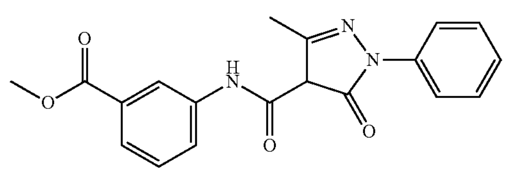 [SMILES: COC(=O)c1cccc(NC(=O)C2C(=O)N(c3ccccc3)N=C2C)c1] |
| 207 | 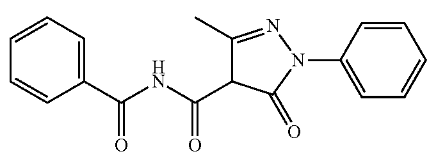 [SMILES: CC1=NN(c2ccccc2)C(=O)C1C(=O)NC(=O)c1ccccc1] |
| 208 | 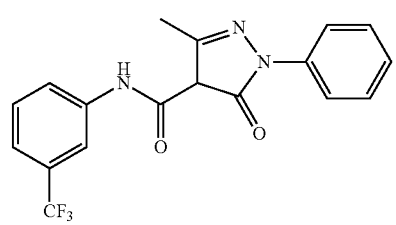 [SMILES: CC1=NN(c2ccccc2)C(=O)C1C(=O)Nc1cccc(C(F)(F)F)c1] |
| 209 | 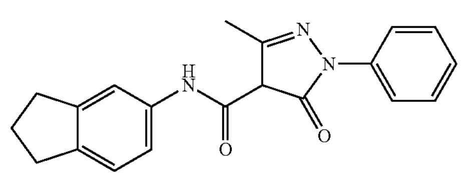 [SMILES: CC1=NN(c2ccccc2)C(=O)C1C(=O)Nc1ccc2c(c1)CCC2] |

US 10,851,064 B2
TABLE 1-continued
| Compound name | Structure |
|---|---|
| 210 | 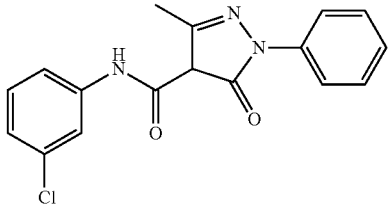 [SMILES: CC1=NN(c2ccccc2)C(=O)C1C(=O)Nc1cccc(Cl)c1] |
| 211 | 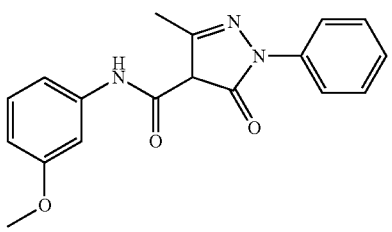 [SMILES: COc1cccc(NC(=O)C2C(=O)N(c3ccccc3)N=C2C)c1] |
| 212 | 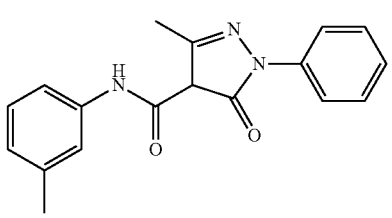 [SMILES: CC1=NN(c2ccccc2)C(=O)C1C(=O)Nc1cccc(C)c1] |
| 213 | 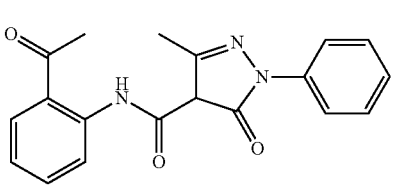 |
| 214 | 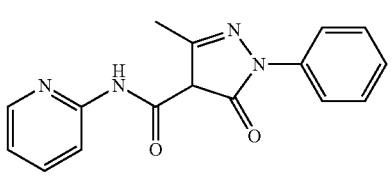 [SMILES: CC1=NN(c2ccccc2)C(=O)C1C(=O)Nc1ccccn1] |
| 215 | 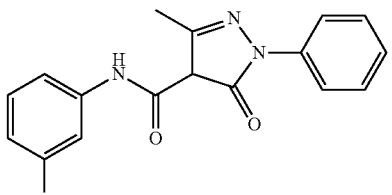 |
| 216 | 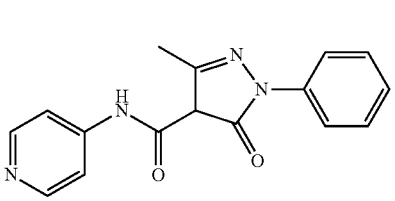 [SMILES: CC1=NN(c2ccccc2)C(=O)C1C(=O)Nc1ccncc1] |

TABLE 1-continued
| Compound name | Structure |
|---|---|
| 217 | 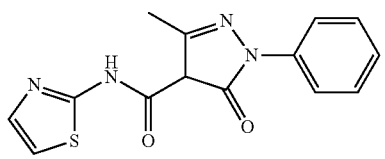 [SMILES: CC1=NN(c2ccccc2)C(=O)C1C(=O)Nc1nccs1] |
| 218 | 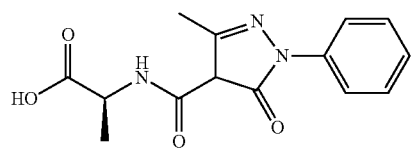 [SMILES: CC1=NN(c2ccccc2)C(=O)C1C(=O)N[C@@H](C)C(=O)O] |
| 219 | 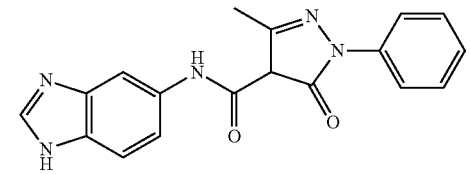 [SMILES: CC1=NN(c2ccccc2)C(=O)C1C(=O)Nc1ccc2[nH]cnc2c1] |
| 220 | 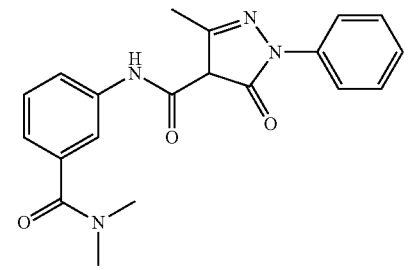 [SMILES: CC1=NN(c2ccccc2)C(=O)C1C(=O)Nc1cccc(C(=O)N(C)C)c1] |
| 221 | 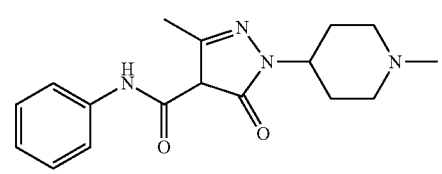 [SMILES: CC1=NN(C2CCN(C)CC2)C(=O)C1C(=O)Nc1ccccc1] |
| 222 | 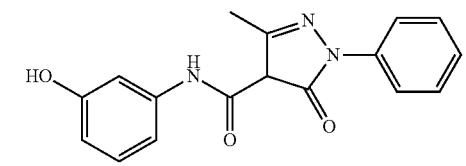 [SMILES: CC1=NN(c2ccccc2)C(=O)C1C(=O)Nc1cccc(O)c1] |
| 223 | 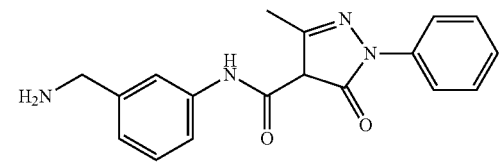 [SMILES: CC1=NN(c2ccccc2)C(=O)C1C(=O)Nc1cccc(CN)c1] |

TABLE 1-continued

| Compound name | Structure |
|---|---|
| 224 | (structure) |
| 226 | (structure) |
| 227 | (structure) |
| 228 | (structure) |
| 229 | (structure) |

TABLE 1-continued
| Compound name | Structure |
|---|---|
| 230 | 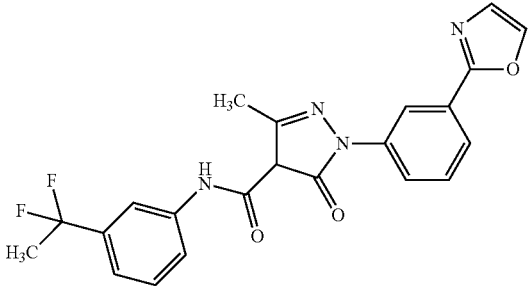 [SMILES: CC1=NN(c2cccc(-c3ncco3)c2)C(=O)C1C(=O)Nc1cccc(C(C)(F)F)c1] |
| 231 | 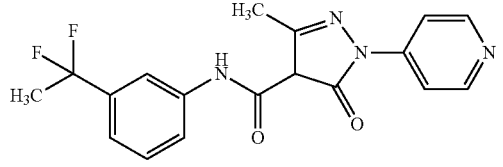 [SMILES: CC1=NN(c2ccncc2)C(=O)C1C(=O)Nc1cccc(C(C)(F)F)c1] |
| 232 | 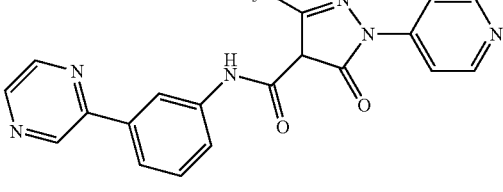 |
| 233 | 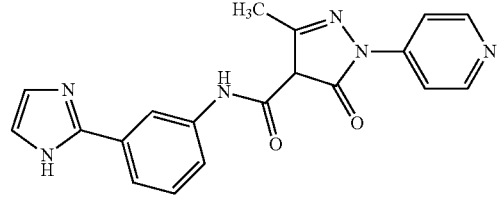 [SMILES: CC1=NN(c2ccncc2)C(=O)C1C(=O)Nc1cccc(-c2ncc[nH]2)c1] |
| 234 | 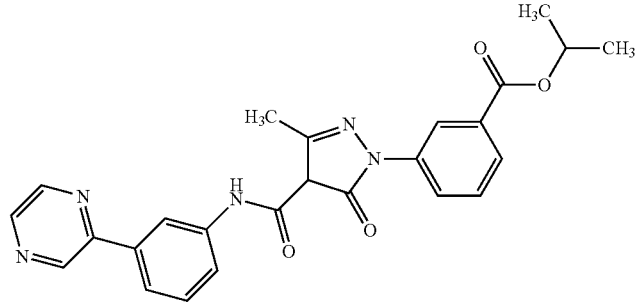 [SMILES: CC1=NN(c2cccc(C(=O)OC(C)C)c2)C(=O)C1C(=O)Nc1cccc(-c2cnccn2)c1] |

TABLE 1-continued

| Compound name | Structure |
|---|---|
| 235 | 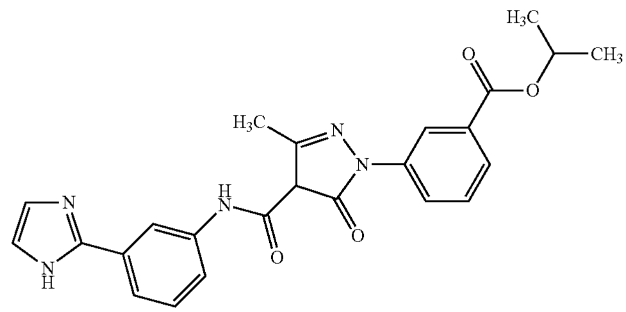 [SMILES: CC1=NN(c2cccc(C(=O)OC(C)C)c2)C(=O)C1C(=O)Nc1cccc(-c2ncc[nH]2)c1] |
| 236 | 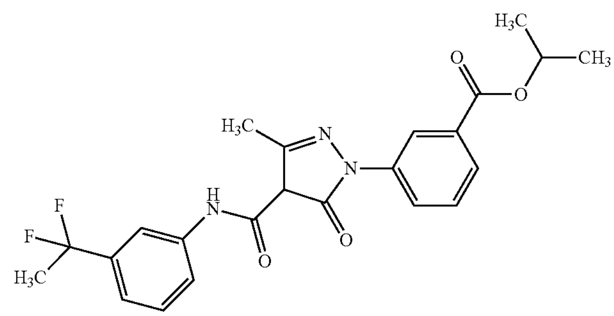 [SMILES: CC1=NN(c2cccc(C(=O)OC(C)C)c2)C(=O)C1C(=O)Nc1cccc(C(C)(F)F)c1] |
| 237 | 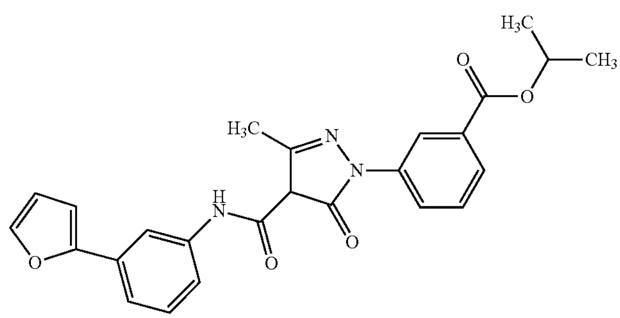 [SMILES: CC1=NN(c2cccc(C(=O)OC(C)C)c2)C(=O)C1C(=O)Nc1cccc(-c2ccco2)c1] |
| 238 | 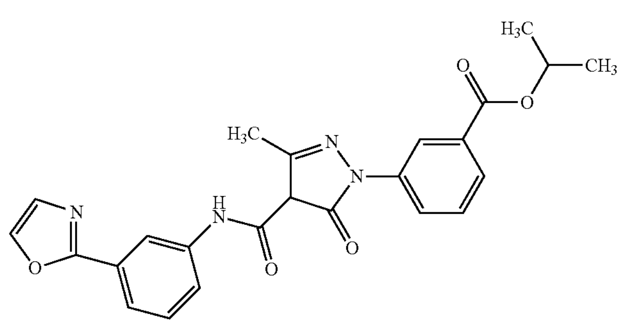 [SMILES: CC1=NN(c2cccc(C(=O)OC(C)C)c2)C(=O)C1C(=O)Nc1cccc(-c2ncco2)c1] |

TABLE 1-continued

| Compound name | Structure |
|---|---|
| 239 | 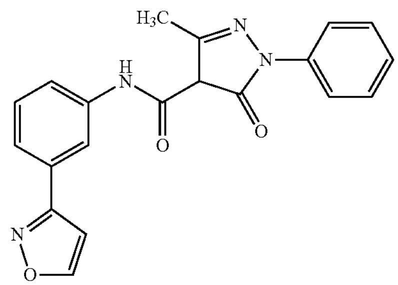 [SMILES: CC1=NN(c2ccccc2)C(=O)C1C(=O)Nc1cccc(-c2ccon2)c1] |
| 240 | 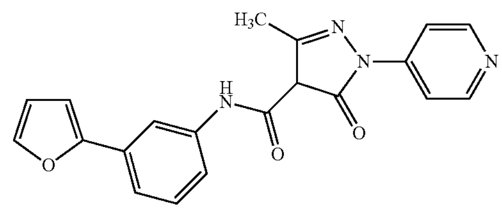 [SMILES: CC1=NN(c2ccncc2)C(=O)C1C(=O)Nc1cccc(-c2ccco2)c1] |
| 241 | 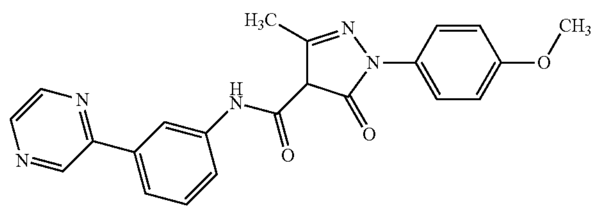 [SMILES: COc1ccc(N2N=C(C)C(C(=O)Nc3cccc(-c4cnccn4)c3)C2=O)cc1] |
| 242 | 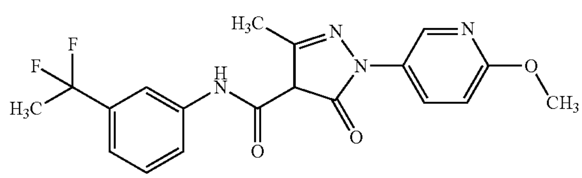 [SMILES: COc1ccc(N2N=C(C)C(C(=O)Nc3cccc(C(C)(F)F)c3)C2=O)cn1] |
| 243 | 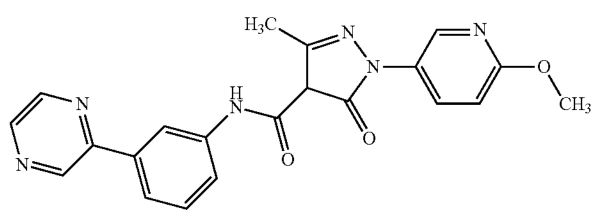 [SMILES: COc1ccc(N2N=C(C)C(C(=O)Nc3cccc(-c4cnccn4)c3)C2=O)cn1] |
| 244 | 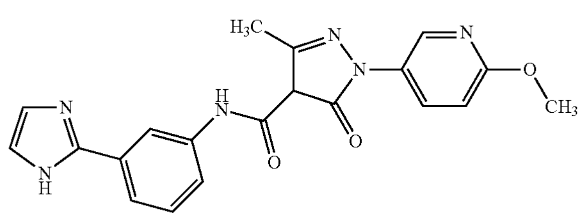 [SMILES: COc1ccc(N2N=C(C)C(C(=O)Nc3cccc(-c4ncc[nH]4)c3)C2=O)cn1] |

TABLE 1-continued

| Compound name | Structure |
|---|---|
| 245 | 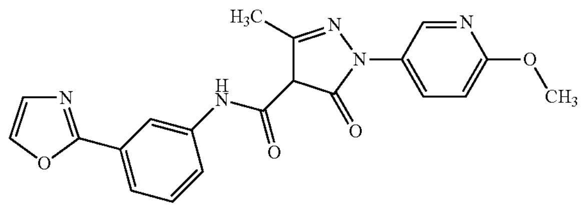 |
| 246 | 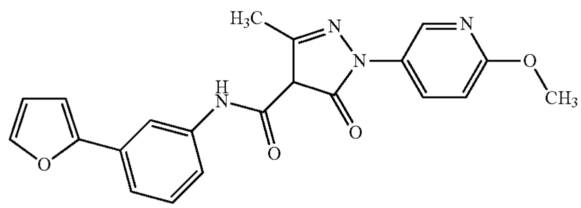 [SMILES: COc1ccc(N2N=C(C)C(C(=O)Nc3cccc(-c4ccco4)c3)C2=O)cn1] |
| 247 | 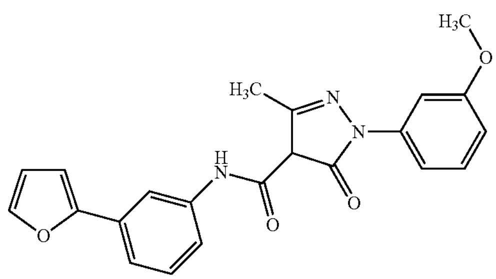 |
| 248 | 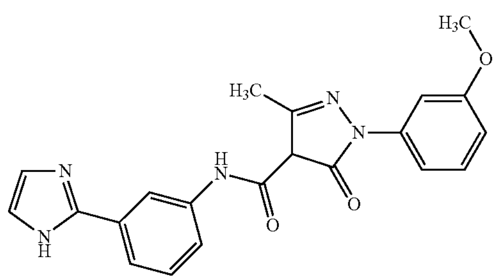 [SMILES: COc1cccc(N2N=C(C)C(C(=O)Nc3cccc(-c4ncc[nH]4)c3)C2=O)c1] |
| 249 | 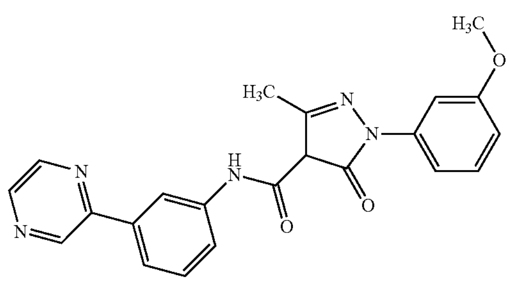 [SMILES: COc1cccc(N2N=C(C)C(C(=O)Nc3cccc(-c4cnccn4)c3)C2=O)c1] |
| 250 | 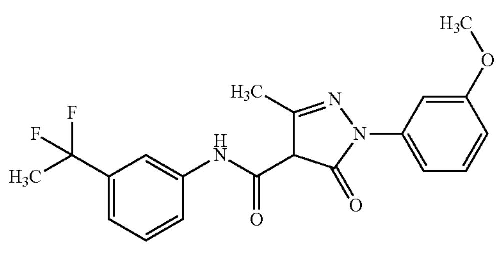 [SMILES: COc1cccc(N2N=C(C)C(C(=O)Nc3cccc(C(C)(F)F)c3)C2=O)c1] |

TABLE 1-continued

| Compound name | Structure |
|---|---|
| 251 | 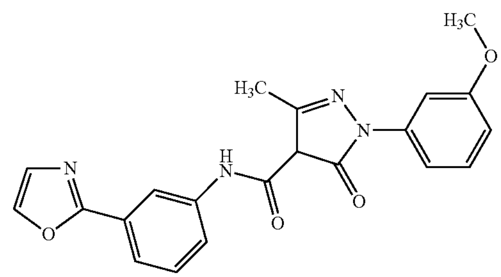 |
| 252 | 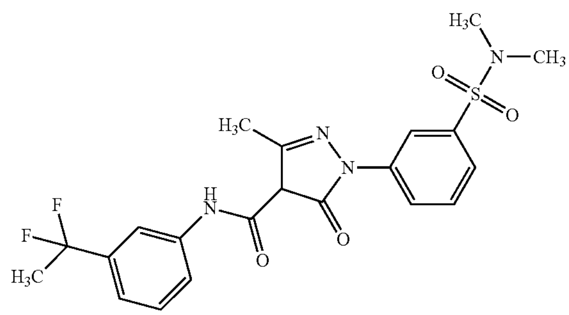 [SMILES: CC1=NN(c2cccc(S(=O)(=O)N(C)C)c2)C(=O)C1C(=O)Nc1cccc(C(C)(F)F)c1] |
| 253 | 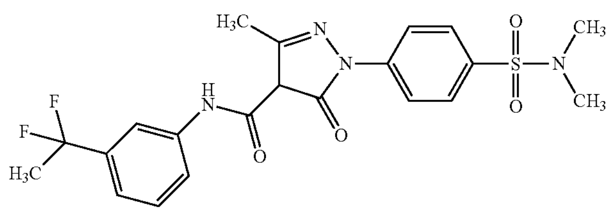 [SMILES: CC1=NN(c2ccc(S(=O)(=O)N(C)C)cc2)C(=O)C1C(=O)Nc1cccc(C(C)(F)F)c1] |
| 254 | 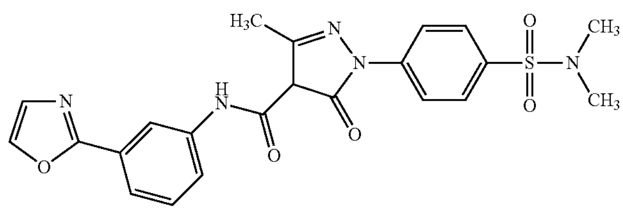 [SMILES: CC1=NN(c2ccc(S(=O)(=O)N(C)C)cc2)C(=O)C1C(=O)Nc1cccc(-c2ncco2)c1] |
| 255 | 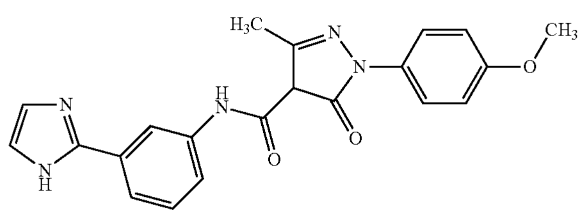 [SMILES: COc1ccc(N2N=C(C)C(C(=O)Nc3cccc(-c4ncc[nH]4)c3)C2=O)cc1] |
| 256 | 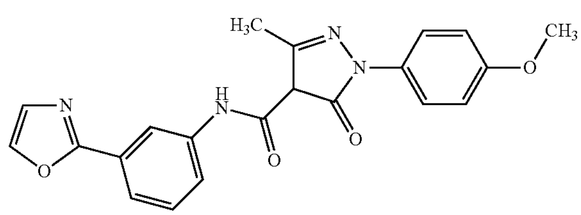 [SMILES: COc1ccc(N2N=C(C)C(C(=O)Nc3cccc(-c4ncco4)c3)C2=O)cc1] |

TABLE 1-continued

| Compound name | Structure |
|---|---|
| 257 | 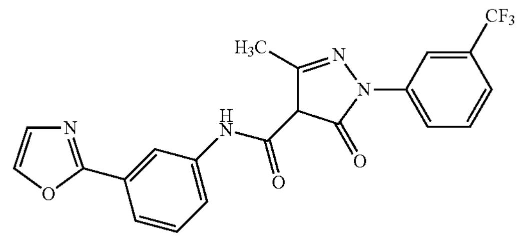 [SMILES: CC1=NN(c2cccc(C(F)(F)F)c2)C(=O)C1C(=O)Nc1cccc(-c2ncco2)c1] |
| 258 | 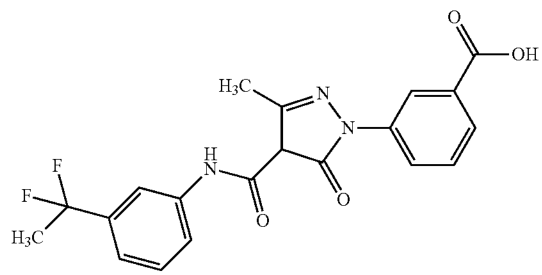 [SMILES: CC1=NN(c2cccc(C(=O)O)c2)C(=O)C1C(=O)Nc1cccc(C(C)(F)F)c1] |
| 259 | 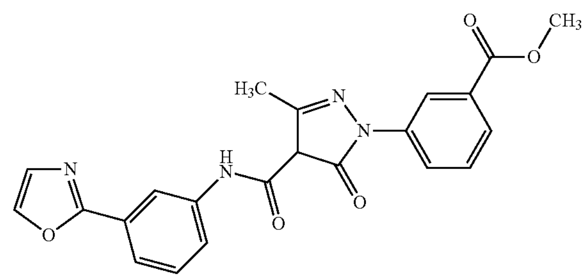 [SMILES: COC(=O)c1cccc(N2N=C(C)C(C(=O)Nc3cccc(-c4ncco4)c3)C2=O)c1] |
| 260 | 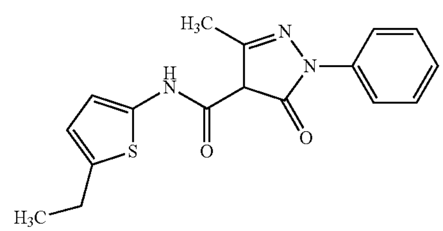 [SMILES: CCc1ccc(NC(=O)C2C(=O)N(c3ccccc3)N=C2C)s1] |
| 261 | 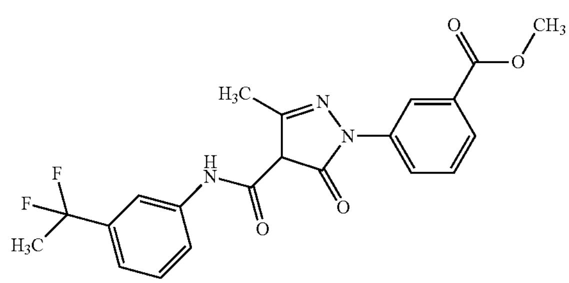 [SMILES: COC(=O)c1cccc(N2N=C(C)C(C(=O)Nc3cccc(C(C)(F)F)c3)C2=O)c1] |
| 262 | 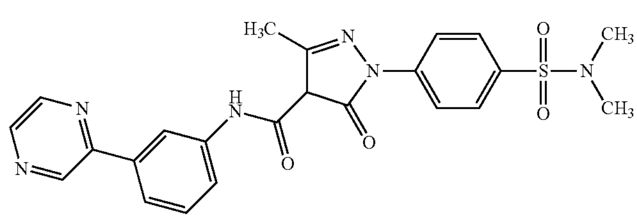 [SMILES: CC1=NN(c2ccc(S(=O)(=O)N(C)C)cc2)C(=O)C1C(=O)Nc1cccc(-c2cnccn2)c1] |

TABLE 1-continued

| Compound name | Structure |
|---|---|
| 263 | 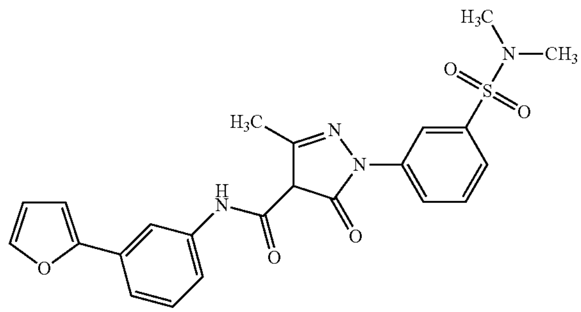 [SMILES: CC1=NN(c2cccc(S(=O)(=O)N(C)C)c2)C(=O)C1C(=O)Nc1cccc(-c2ccco2)c1] |
| 264 | 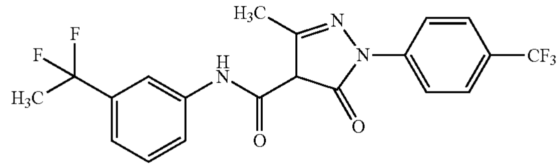 [SMILES: CC1=NN(c2ccc(C(F)(F)F)cc2)C(=O)C1C(=O)Nc1cccc(C(C)(F)F)c1] |
| 265 | 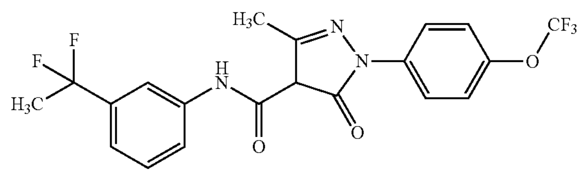 [SMILES: CC1=NN(c2ccc(OC(F)(F)F)cc2)C(=O)C1C(=O)Nc1cccc(C(C)(F)F)c1] |
| 266 | 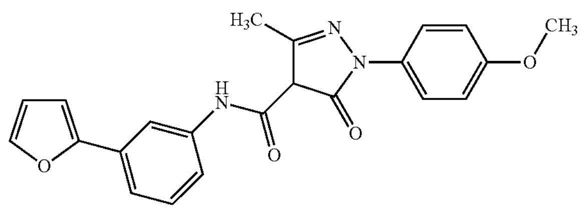 [SMILES: COc1ccc(N2N=C(C)C(C(=O)Nc3cccc(-c4ccco4)c3)C2=O)cc1] |
| 267 | 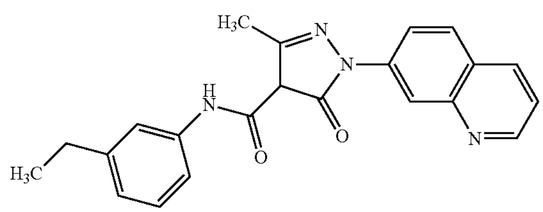 [SMILES: CCc1cccc(NC(=O)C2C(=O)N(c3ccc4cccnc4c3)N=C2C)c1] |
| 268 | 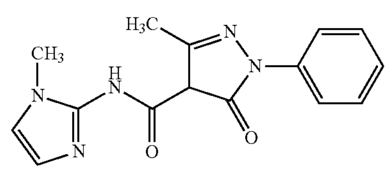 [SMILES: CC1=NN(c2ccccc2)C(=O)C1C(=O)Nc1nccn1C] |

TABLE 1-continued

| Compound name | Structure |
|---|---|
| 269 | methyl 3-[4-[[3-(furan-2-yl)phenyl]carbamoyl]-3-methyl-5-oxo-4H-pyrazol-1-yl]benzoate |
| 270 | 3-methyl-N-[3-(1,3-oxazol-2-yl)phenyl]-5-oxo-1-[4-(trifluoromethyl)phenyl]-4H-pyrazole-4-carboxamide |
| 271 | N-[3-(1,1-difluoroethyl)phenyl]-3-methyl-5-oxo-1-[3-(trifluoromethyl)phenyl]-4H-pyrazole-4-carboxamide |
| 272 | 1-[3-(dimethylsulfamoyl)phenyl]-3-methyl-5-oxo-N-(3-pyrazin-2-ylphenyl)-4H-pyrazole-4-carboxamide |
| 273 | 3-[4-[[3-(1H-imidazol-2-yl)phenyl]carbamoyl]-3-methyl-5-oxo-4H-pyrazol-1-yl]benzoic acid |

TABLE 1-continued
| Compound name | Structure |
|---|---|
| 274 | 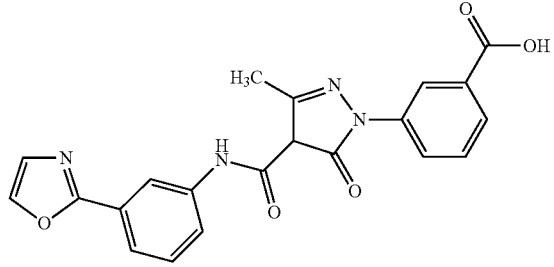 [SMILES: CC1=NN(c2cccc(C(=O)O)c2)C(=O)C1C(=O)Nc1cccc(-c2ncco2)c1] |
| 275 | 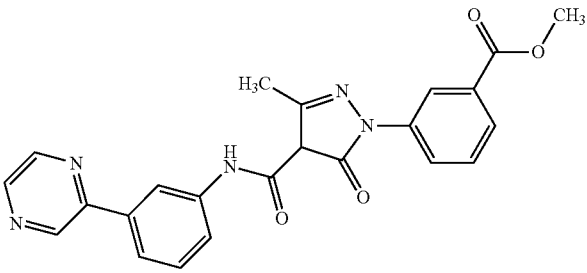 [SMILES: COC(=O)c1cccc(N2N=C(C)C(C(=O)Nc3cccc(-c4cnccn4)c3)C2=O)c1] |
| 276 | 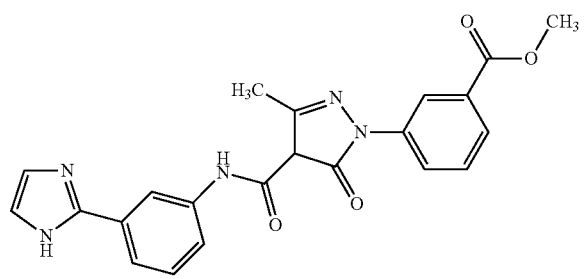 [SMILES: COC(=O)c1cccc(N2N=C(C)C(C(=O)Nc3cccc(-c4ncc[nH]4)c3)C2=O)c1] |
| 277 | 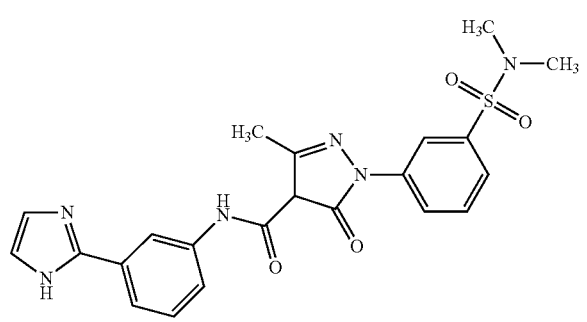 |
| 278 | 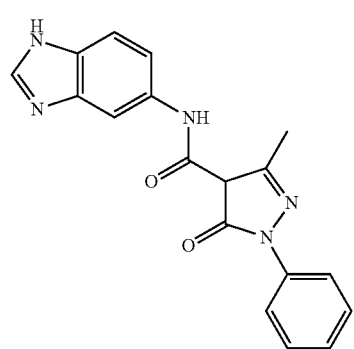 [SMILES: CC1=NN(c2ccccc2)C(=O)C1C(=O)Nc1ccc2[nH]cnc2c1] |

TABLE 1-continued

| Compound name | Structure |
|---|---|
| 279 | 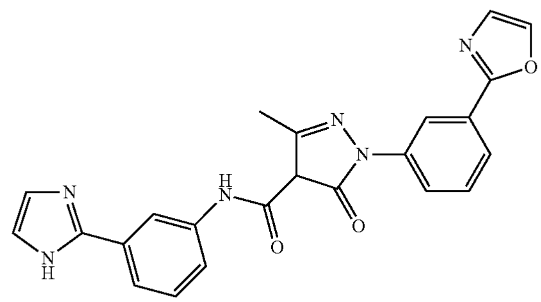 [SMILES: CC1=NN(c2cccc(-c3ncco3)c2)C(=O)C1C(=O)Nc1cccc(-c2ncc[nH]2)c1] |
| 280 | 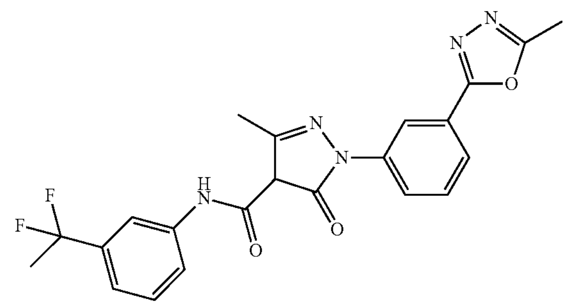 [SMILES: CC1=NN(c2cccc(-c3nnc(C)o3)c2)C(=O)C1C(=O)Nc1cccc(C(C)(F)F)c1] |
| 281 | 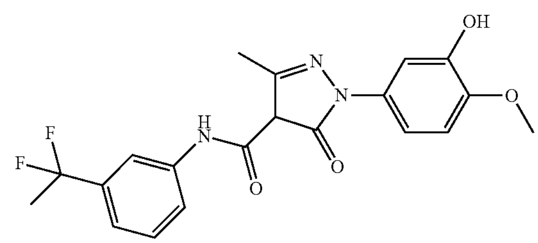 [SMILES: COc1ccc(N2N=C(C)C(C(=O)Nc3cccc(C(C)(F)F)c3)C2=O)cc1O] |
| 282 | 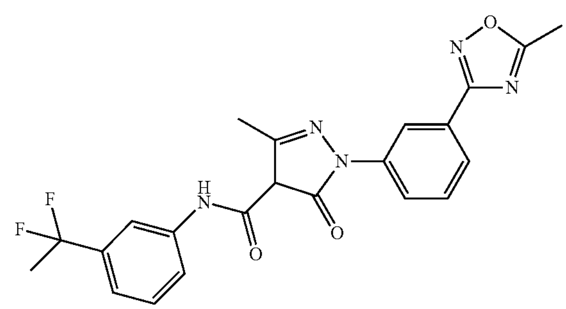 [SMILES: CC1=NN(c2cccc(-c3noc(C)n3)c2)C(=O)C1C(=O)Nc1cccc(C(C)(F)F)c1] |
| 283 | 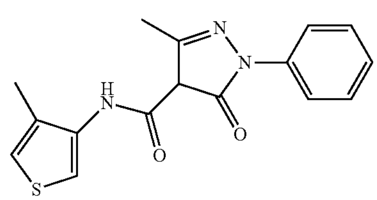 [SMILES: CC1=NN(c2ccccc2)C(=O)C1C(=O)Nc1cscc1C] |

TABLE 1-continued

| Compound name | Structure |
|---|---|
| 284 | 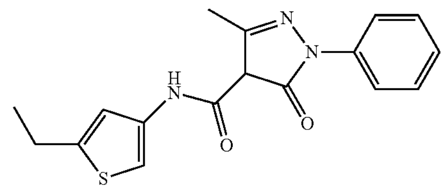 [SMILES: CCc1cc(NC(=O)C2C(=O)N(c3ccccc3)N=C2C)cs1] |
| 285 | 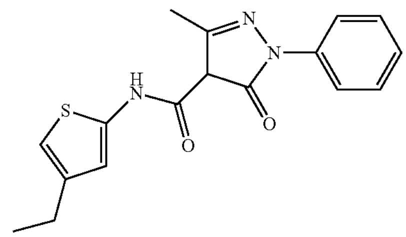 [SMILES: CCc1csc(NC(=O)C2C(=O)N(c3ccccc3)N=C2C)c1] |
| 286 | 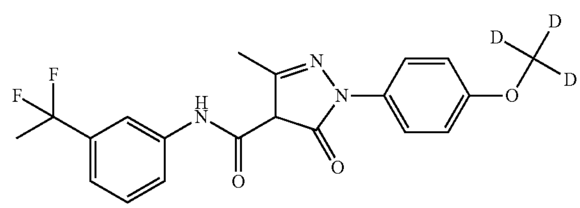 [SMILES: [2H]C([2H])([2H])Oc1ccc(N2N=C(C)C(C(=O)Nc3cccc(C(C)(F)F)c3)C2=O)cc1] |
| 287 | 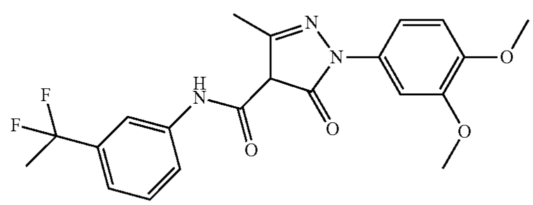 [SMILES: COc1ccc(N2N=C(C)C(C(=O)Nc3cccc(C(C)(F)F)c3)C2=O)cc1OC] |
| 288 | 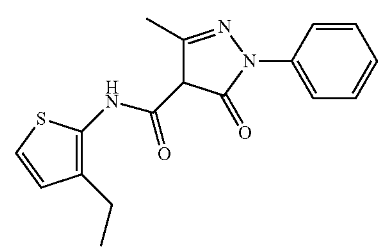 [SMILES: CCc1ccsc1NC(=O)C1C(=O)N(c2ccccc2)N=C1C] |
| 289 | 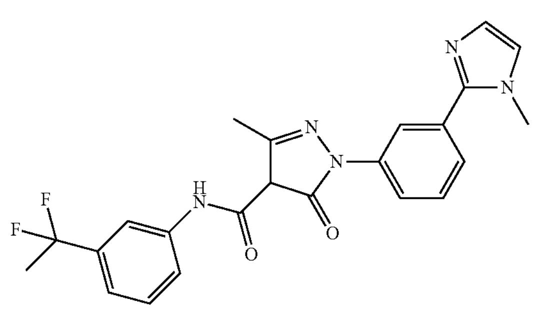 [SMILES: CC1=NN(c2cccc(-c3nccn3C)c2)C(=O)C1C(=O)Nc1cccc(C(C)(F)F)c1] |

US 10,851,064 B2
TABLE 1-continued
| Compound name | Structure |
|---|---|
| 290 | 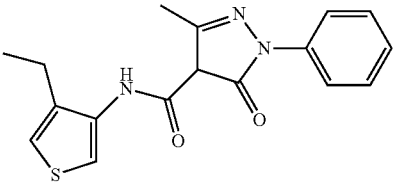 [SMILES: CCc1cscc1NC(=O)C1C(=O)N(c2ccccc2)N=C1C] |
| 291 | 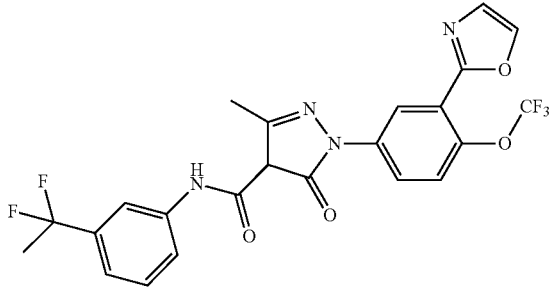 [SMILES: CC1=NN(c2ccc(OC(F)(F)F)c(-c3ncco3)c2)C(=O)C1C(=O)Nc1cccc(C(C)(F)F)c1] |
| 292 | 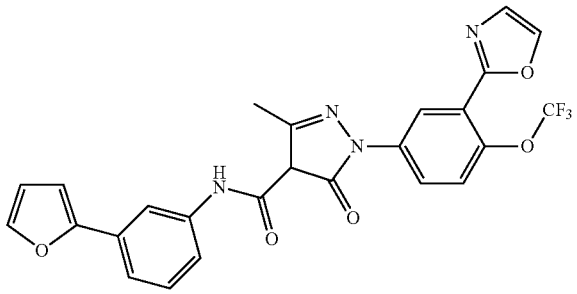 [SMILES: CC1=NN(c2ccc(OC(F)(F)F)c(-c3ncco3)c2)C(=O)C1C(=O)Nc1cccc(-c2ccco2)c1] |
| 293 | 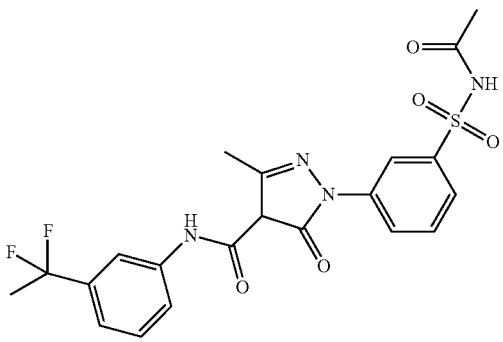 [SMILES: CC(=O)NS(=O)(=O)c1cccc(N2N=C(C)C(C(=O)Nc3cccc(C(C)(F)F)c3)C2=O)c1] |
| 294 | 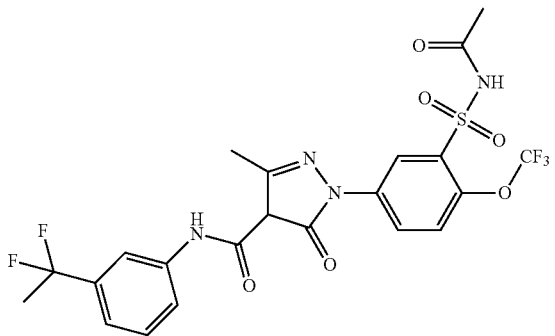 [SMILES: CC(=O)NS(=O)(=O)c1cc(N2N=C(C)C(C(=O)Nc3cccc(C(C)(F)F)c3)C2=O)ccc1OC(F)(F)F] |

TABLE 1-continued

| Compound name | Structure |
|---|---|
| 295 | 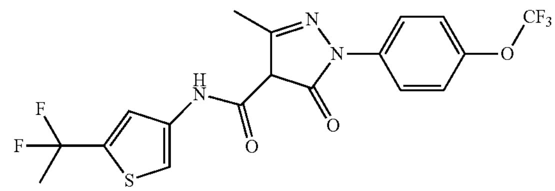 [SMILES: CC1=NN(c2ccc(OC(F)(F)F)cc2)C(=O)C1C(=O)Nc1csc(C(C)(F)F)c1] |
| 296 | 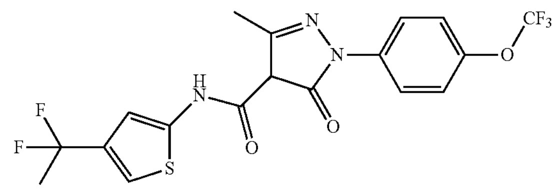 [SMILES: CC1=NN(c2ccc(OC(F)(F)F)cc2)C(=O)C1C(=O)Nc1cc(C(C)(F)F)cs1] |
| 297 | 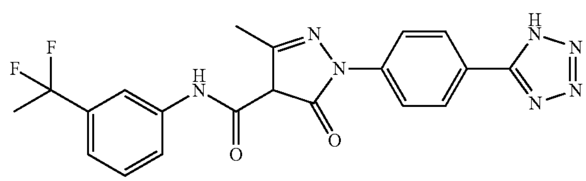 [SMILES: CC1=NN(c2ccc(-c3nnn[nH]3)cc2)C(=O)C1C(=O)Nc1cccc(C(C)(F)F)c1] |
| 298 | 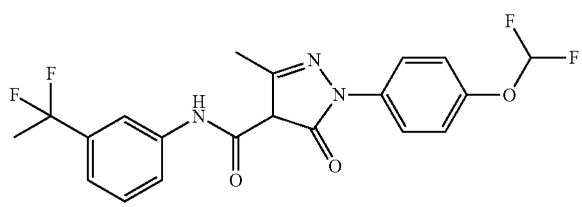 [SMILES: CC1=NN(c2ccc(OC(F)F)cc2)C(=O)C1C(=O)Nc1cccc(C(C)(F)F)c1] |
| 299 | 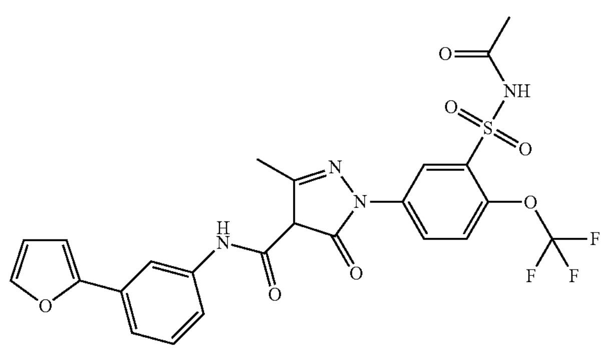 [SMILES: CC(=O)NS(=O)(=O)c1cc(N2N=C(C)C(C(=O)Nc3cccc(-c4ccco4)c3)C2=O)ccc1OC(F)(F)F] |
| 300 | 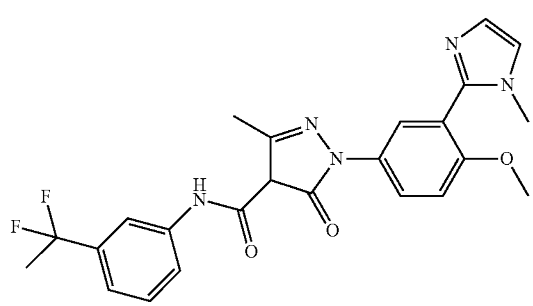 [SMILES: COc1ccc(N2N=C(C)C(C(=O)Nc3cccc(C(C)(F)F)c3)C2=O)cc1-c1nccn1C] |

TABLE 1-continued
| Compound name | Structure |
|---|---|
| 301 | 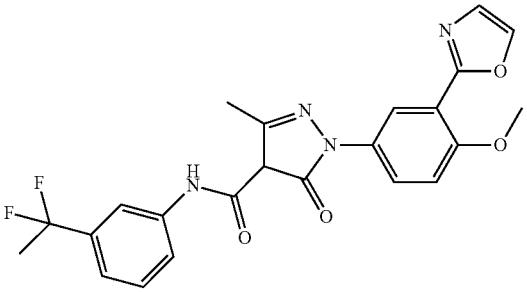 [SMILES: COc1ccc(N2N=C(C)C(C(=O)Nc3cccc(C(C)(F)F)c3)C2=O)cc1-c1ncco1] |
| 302 | 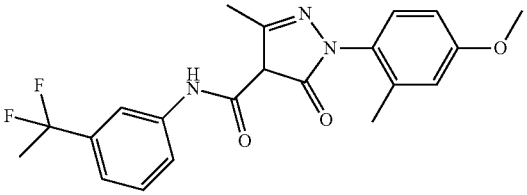 [SMILES: COc1ccc(N2N=C(C)C(C(=O)Nc3cccc(C(C)(F)F)c3)C2=O)c(C)c1] |
| 303 | 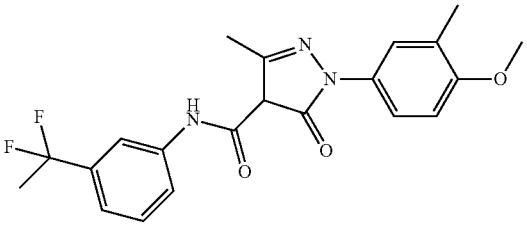 [SMILES: COc1ccc(N2N=C(C)C(C(=O)Nc3cccc(C(C)(F)F)c3)C2=O)cc1C] |
| 304 | 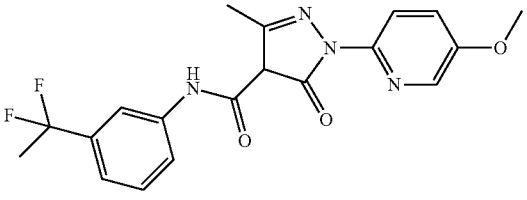 [SMILES: COc1ccc(N2N=C(C)C(C(=O)Nc3cccc(C(C)(F)F)c3)C2=O)nc1] |
| 305 | 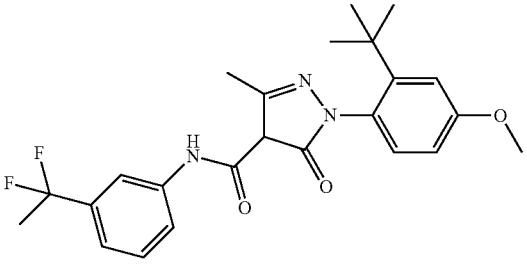 [SMILES: COc1ccc(N2N=C(C)C(C(=O)Nc3cccc(C(C)(F)F)c3)C2=O)c(C(C)(C)C)c1] |
| 306 | 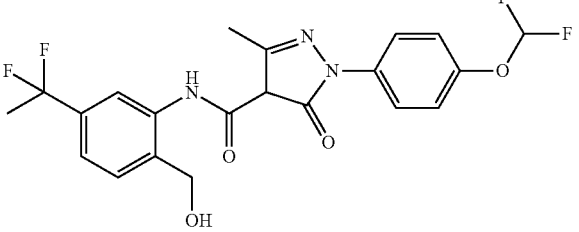 |

TABLE 1-continued
| Compound name | Structure |
|---|---|
| 307 | 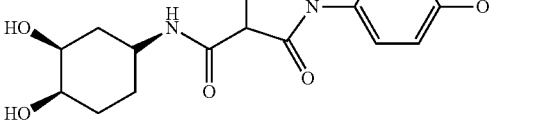 |
| 308 | 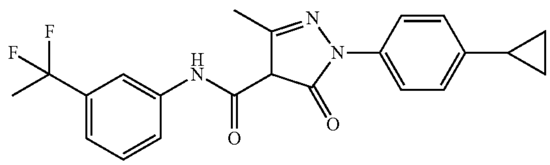 [SMILES: CC1=NN(c2ccc(C3CC3)cc2)C(=O)C1C(=O)Nc1cccc(C(C)(F)F)c1] |
| 309 | 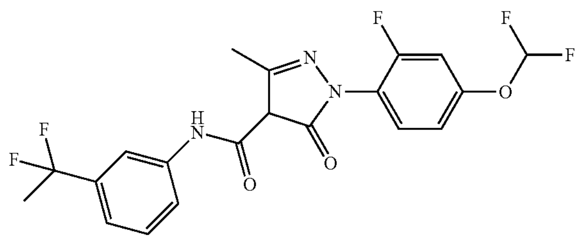 [SMILES: CC1=NN(c2ccc(OC(F)F)cc2F)C(=O)C1C(=O)Nc1cccc(C(C)(F)F)c1] |
| 310 | 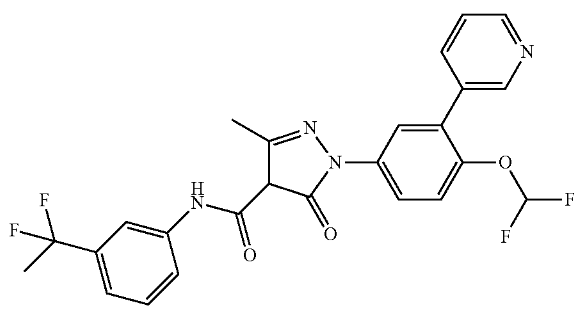 |
| 311 | 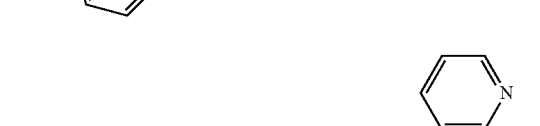 |
| 312 | 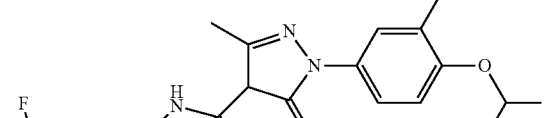 |

TABLE 1-continued

| Compound name | Structure |
|---|---|
| 313 | 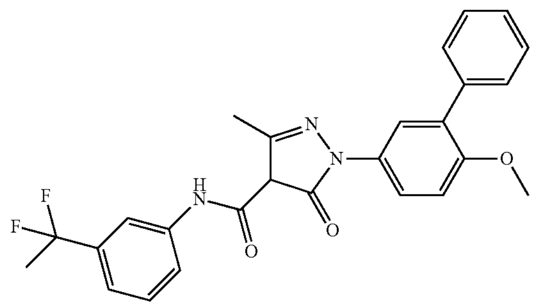 [SMILES: COc1ccc(N2N=C(C)C(C(=O)Nc3cccc(C(C)(F)F)c3)C2=O)cc1-c1ccccc1] |
| 314 | 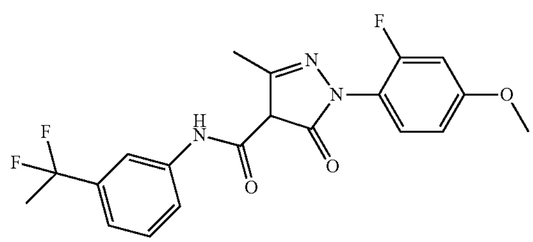 [SMILES: COc1ccc(N2N=C(C)C(C(=O)Nc3cccc(C(C)(F)F)c3)C2=O)c(F)c1] |
| 315 | 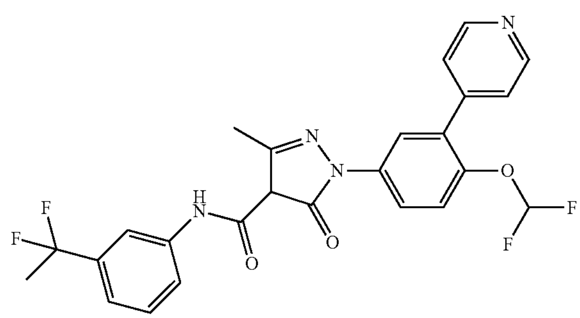 [SMILES: CC1=NN(c2ccc(OC(F)F)c(-c3ccncc3)c2)C(=O)C1C(=O)Nc1cccc(C(C)(F)F)c1] |
| 316 | 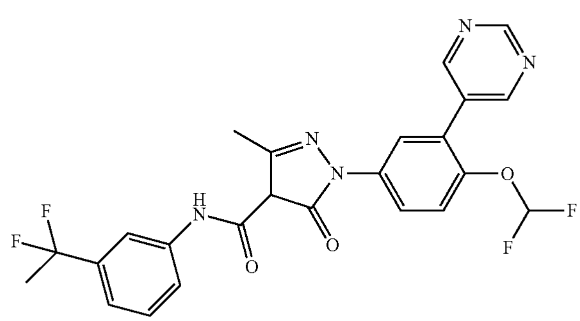 [SMILES: CC1=NN(c2ccc(OC(F)F)c(-c3cncnc3)c2)C(=O)C1C(=O)Nc1cccc(C(C)(F)F)c1] |
| 317 | 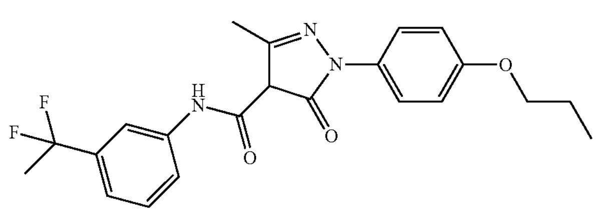 [SMILES: CCCOc1ccc(N2N=C(C)C(C(=O)Nc3cccc(C(C)(F)F)c3)C2=O)cc1] |

TABLE 1-continued

| Compound name | Structure |
|---|---|
| 318 | 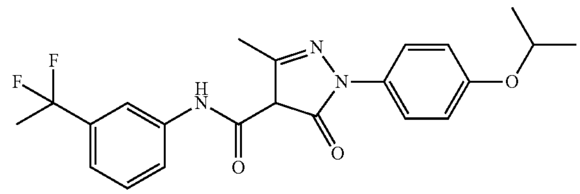 [SMILES: CC1=NN(c2ccc(OC(C)C)cc2)C(=O)C1C(=O)Nc1cccc(C(C)(F)F)c1] |
| 319 | 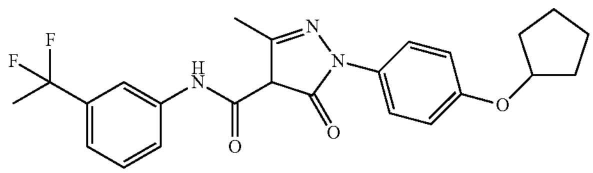 [SMILES: CC1=NN(c2ccc(OC3CCCC3)cc2)C(=O)C1C(=O)Nc1cccc(C(C)(F)F)c1] |
| 320 | 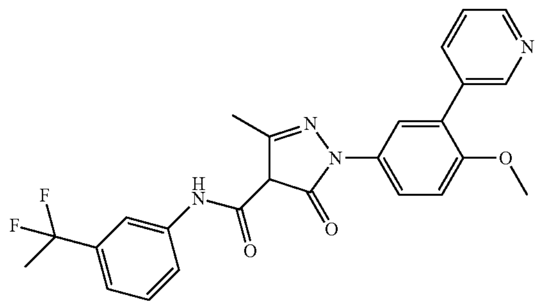 [SMILES: COc1ccc(N2N=C(C)C(C(=O)Nc3cccc(C(C)(F)F)c3)C2=O)cc1-c1cccnc1] |
| 321 | 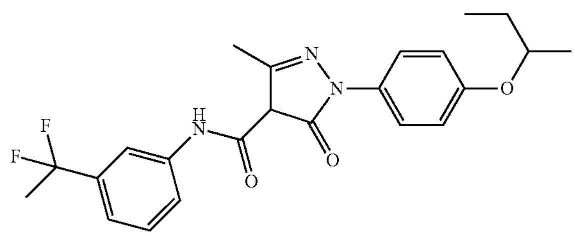 [SMILES: CCC(C)Oc1ccc(N2N=C(C)C(C(=O)Nc3cccc(C(C)(F)F)c3)C2=O)cc1] |
| 322 | 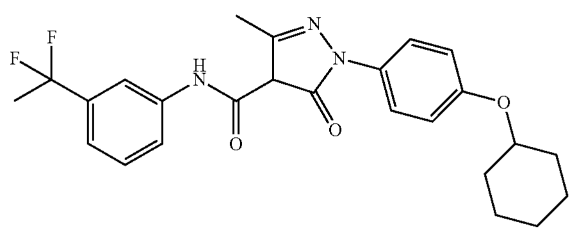 [SMILES: CC1=NN(c2ccc(OC3CCCCC3)cc2)C(=O)C1C(=O)Nc1cccc(C(C)(F)F)c1] |
| 323 | 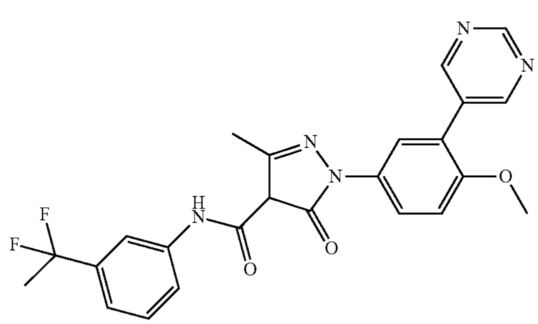 [SMILES: COc1ccc(N2N=C(C)C(C(=O)Nc3cccc(C(C)(F)F)c3)C2=O)cc1-c1cncnc1] |

TABLE 1-continued

| Compound name | Structure |
|---|---|
| 324 | 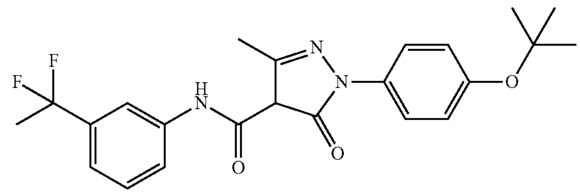 [SMILES: CC1=NN(c2ccc(OC(C)(C)C)cc2)C(=O)C1C(=O)Nc1cccc(C(C)(F)F)c1] |
| 325 | 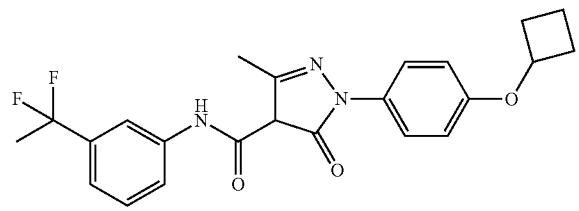 [SMILES: CC1=NN(c2ccc(OC3CCC3)cc2)C(=O)C1C(=O)Nc1cccc(C(C)(F)F)c1] |
| 326 | 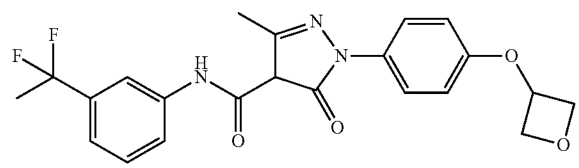 [SMILES: CC1=NN(c2ccc(OC3COC3)cc2)C(=O)C1C(=O)Nc1cccc(C(C)(F)F)c1] |
| 327 | 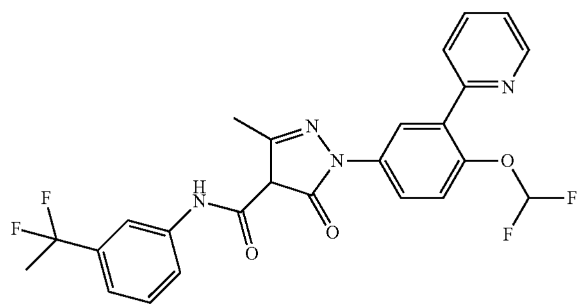 |
| 328 | 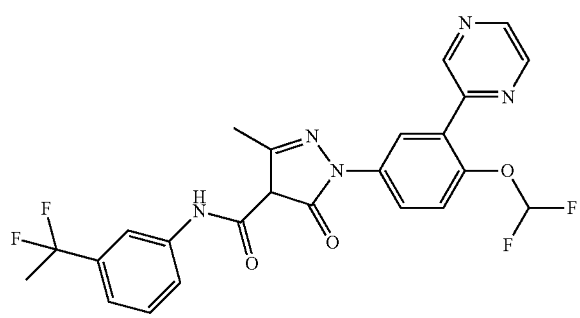 |
| 329 | 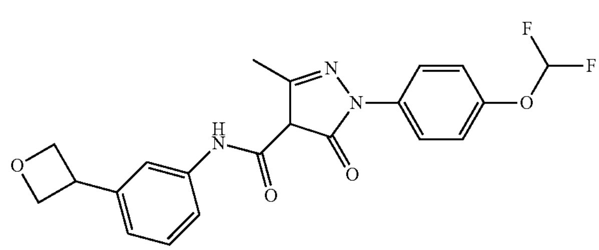 [SMILES: CC1=NN(c2ccc(OC(F)F)cc2)C(=O)C1C(=O)Nc1cccc(C2COC2)c1] |

TABLE 1-continued
| Compound name | Structure |
|---|---|
| 330 | 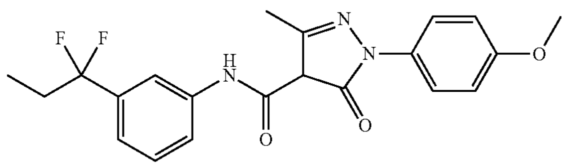 [SMILES: CCC(F)(F)c1cccc(NC(=O)C2C(=O)N(c3ccc(OC)cc3)N=C2C)c1] |
| 331 | 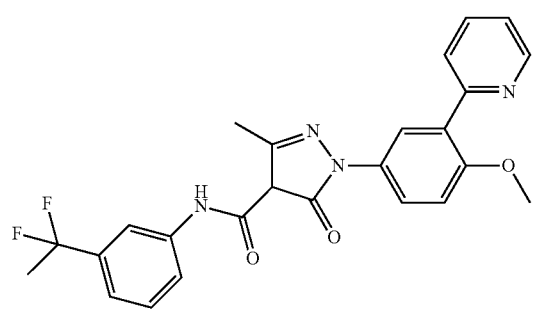 |
| 332 | 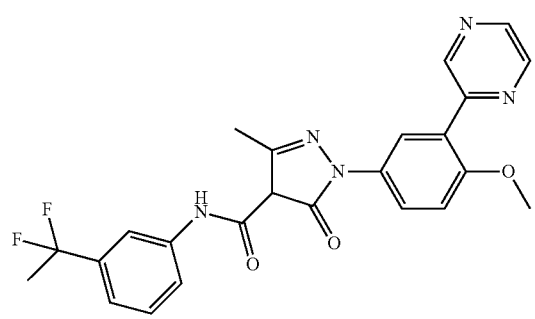 [SMILES: COc1ccc(N2N=C(C)C(C(=O)Nc3cccc(C(C)(F)F)c3)C2=O)cc1-c1cnccn1] |
| 333 | 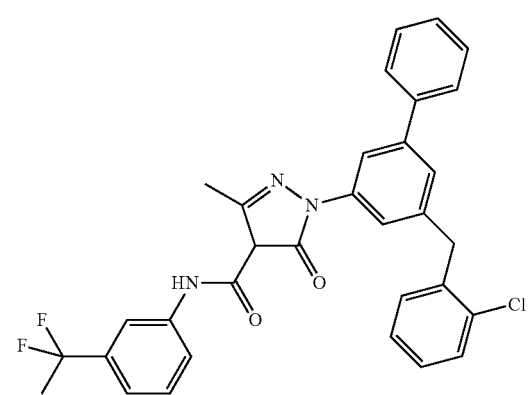 |
| 334 | 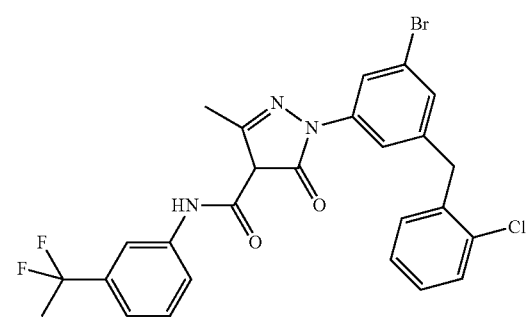 [SMILES: CC1=NN(c2cc(Br)cc(Cc3ccccc3Cl)c2)C(=O)C1C(=O)Nc1cccc(C(C)(F)F)c1] |

TABLE 1-continued

| Compound name | Structure |
|---|---|
| 335 | 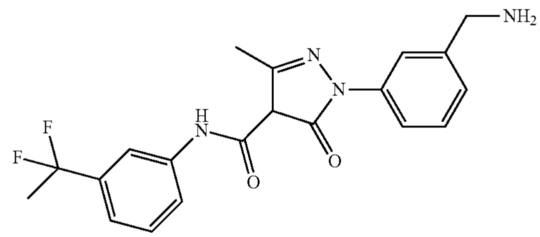 [SMILES: CC1=NN(c2cccc(CN)c2)C(=O)C1C(=O)Nc1cccc(C(C)(F)F)c1] |
| 336 | 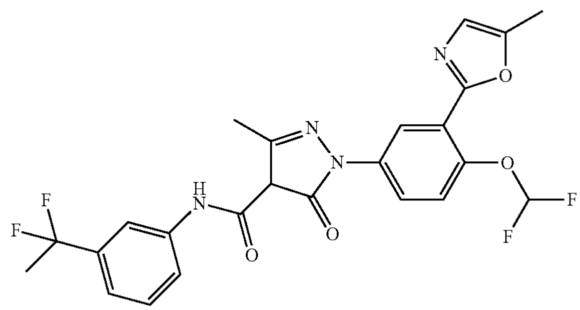 |
| 337 | 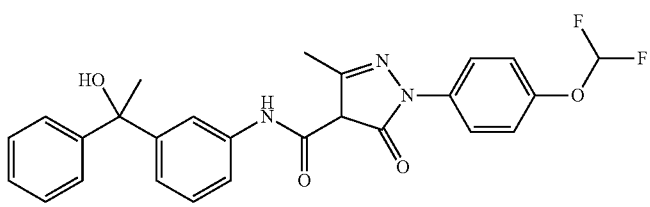 [SMILES: CC1=NN(c2ccc(OC(F)F)cc2)C(=O)C1C(=O)Nc1cccc(C(C)(O)c2ccccc2)c1] |
| 338 | 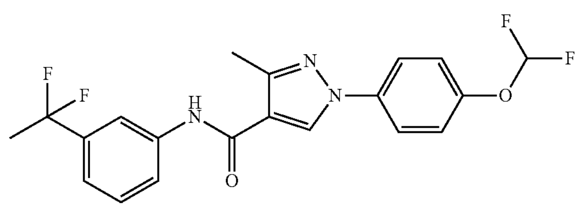 [SMILES: Cc1nn(-c2ccc(OC(F)F)cc2)cc1C(=O)Nc1cccc(C(C)(F)F)c1] |
| 339 | 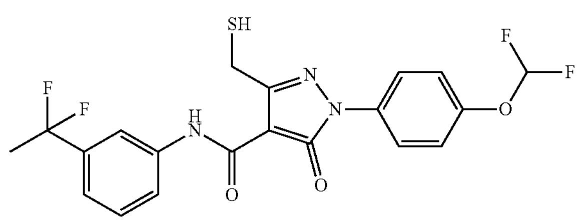 |
| 340 | 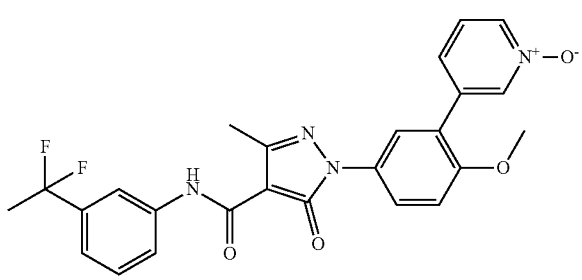 |

TABLE 1-continued

| Compound name | Structure |
|---|---|
| 341 | 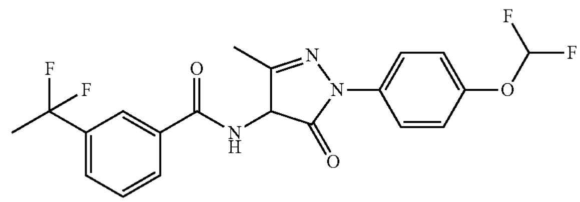 |
| 342 | 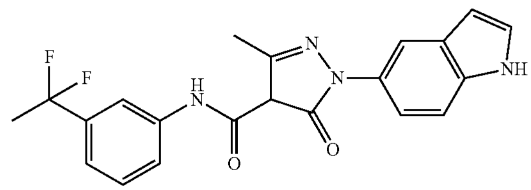 [SMILES: CC1=NN(c2ccc3[nH]ccc3c2)C(=O)C1C(=O)Nc1cccc(C(C)(F)F)c1] |
| 343 | 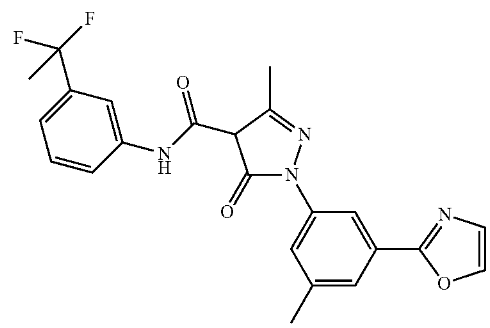 [SMILES: CC1=NN(c2cc(C)cc(-c3ncco3)c2)C(=O)C1C(=O)Nc1cccc(C(C)(F)F)c1] |
| 344 | 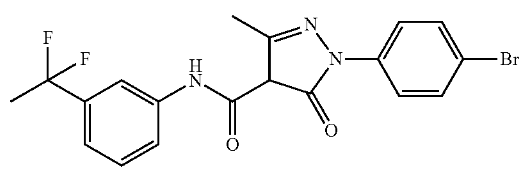 [SMILES: CC1=NN(c2ccc(Br)cc2)C(=O)C1C(=O)Nc1cccc(C(C)(F)F)c1] |
| 345 | 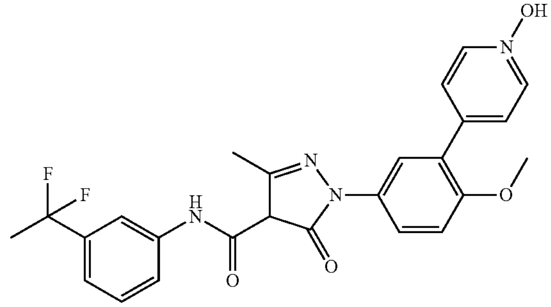 |
| 346 | 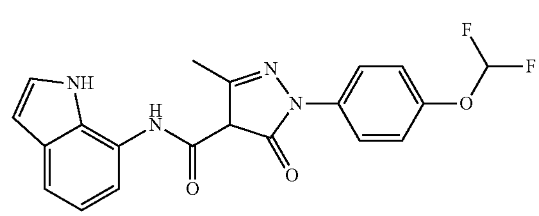 [SMILES: CC1=NN(c2ccc(OC(F)F)cc2)C(=O)C1C(=O)Nc1cccc2cc[nH]c12] |

TABLE 1-continued

| Compound name | Structure |
|---|---|
| 347 | 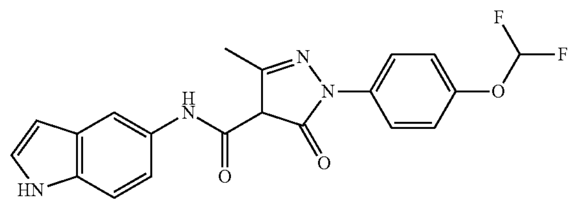 [SMILES: CC1=NN(c2ccc(OC(F)F)cc2)C(=O)C1C(=O)Nc1ccc2[nH]ccc2c1] |
| 348 | 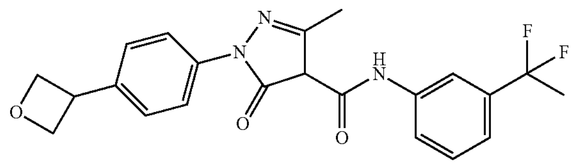 [SMILES: CC1=NN(c2ccc(C3COC3)cc2)C(=O)C1C(=O)Nc1cccc(C(C)(F)F)c1] |
| 349 | 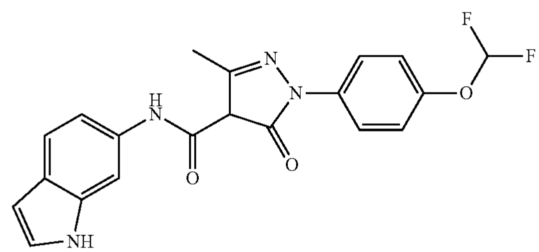 [SMILES: CC1=NN(c2ccc(OC(F)F)cc2)C(=O)C1C(=O)Nc1ccc2cc[nH]c2c1] |
| 350 | 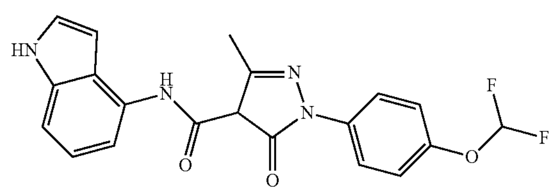 [SMILES: CC1=NN(c2ccc(OC(F)F)cc2)C(=O)C1C(=O)Nc1cccc2[nH]ccc12] |
| 351 | 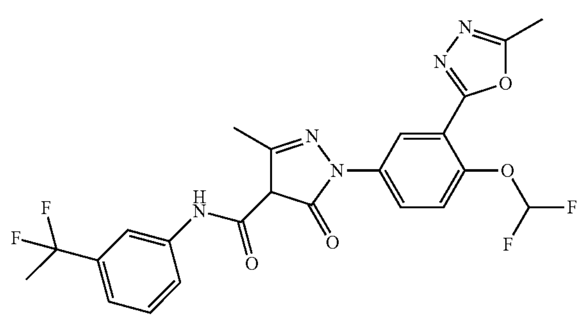 [SMILES: CC1=NN(c2ccc(OC(F)F)c(-c3nnc(C)o3)c2)C(=O)C1C(=O)Nc1cccc(C(C)(F)F)c1] |
| 352 | 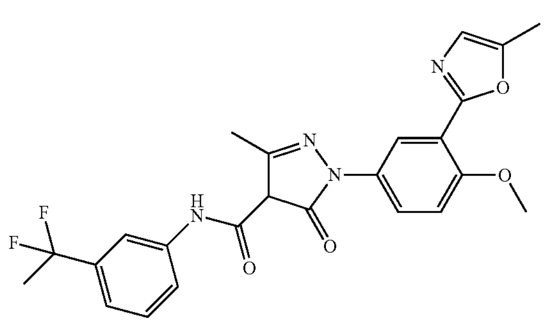 [SMILES: COc1ccc(N2N=C(C)C(C(=O)Nc3cccc(C(C)(F)F)c3)C2=O)cc1-c1ncc(C)o1] |

TABLE 1-continued

| Compound name | Structure |
|---|---|
| 353 | 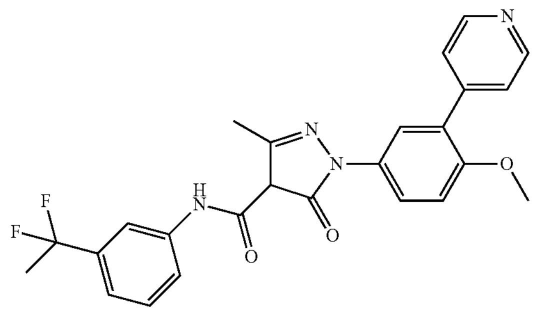 [SMILES: COc1ccc(N2N=C(C)C(C(=O)Nc3cccc(C(C)(F)F)c3)C2=O)cc1-c1ccncc1] |
| 354 | 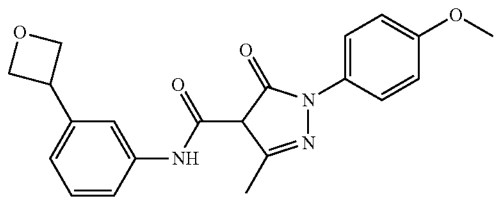 [SMILES: COc1ccc(N2N=C(C)C(C(=O)Nc3cccc(C4COC4)c3)C2=O)cc1] |
| 355 | 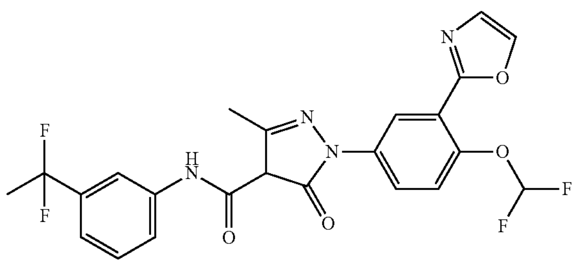 [SMILES: CC1=NN(c2ccc(OC(F)F)c(-c3ncco3)c2)C(=O)C1C(=O)Nc1cccc(C(C)(F)F)c1] |
| 356 | HCl |
| 357 | 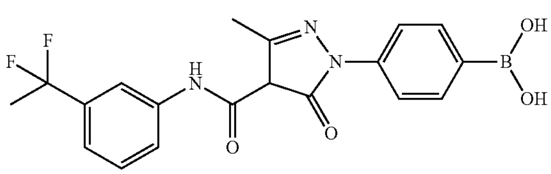 [SMILES: CC1=NN(c2ccc(B(O)O)cc2)C(=O)C1C(=O)Nc1cccc(C(C)(F)F)c1] |
| 358 | 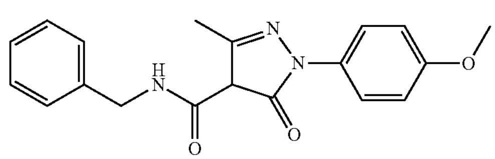 [SMILES: COc1ccc(N2N=C(C)C(C(=O)NCc3ccccc3)C2=O)cc1] |

TABLE 1-continued

| Compound name | Structure |
|---|---|
| 359 | 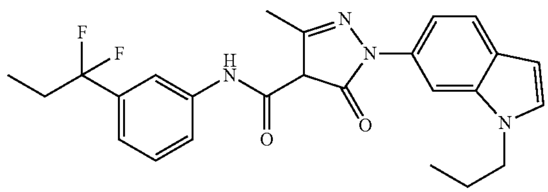 [SMILES: CCCn1ccc2ccc(N3N=C(C)C(C(=O)Nc4cccc(C(F)(F)CC)c4)C3=O)cc21] |
| 360 | 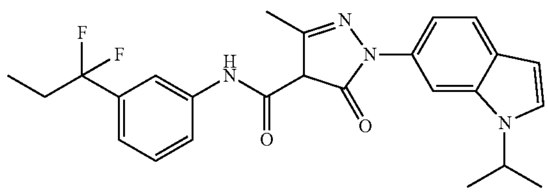 [SMILES: CCC(F)(F)c1cccc(NC(=O)C2C(=O)N(c3ccc4ccn(C(C)C)c4c3)N=C2C)c1] |
| 361 | 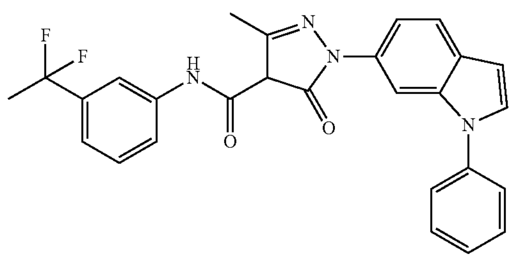 [SMILES: CC1=NN(c2ccc3ccn(-c4ccccc4)c3c2)C(=O)C1C(=O)Nc1cccc(C(C)(F)F)c1] |
| 362 | 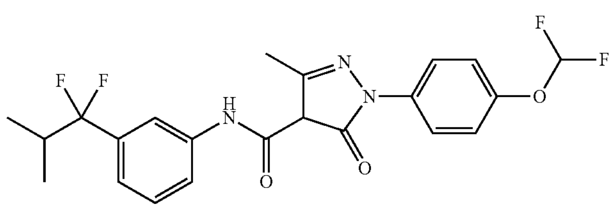 [SMILES: CC1=NN(c2ccc(OC(F)F)cc2)C(=O)C1C(=O)Nc1cccc(C(F)(F)C(C)C)c1] |
| 363 | 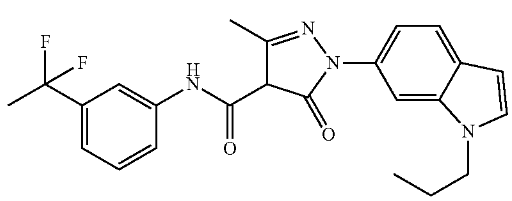 [SMILES: CCCn1ccc2ccc(N3N=C(C)C(C(=O)Nc4cccc(C(C)(F)F)c4)C3=O)cc21] |
| 364 | 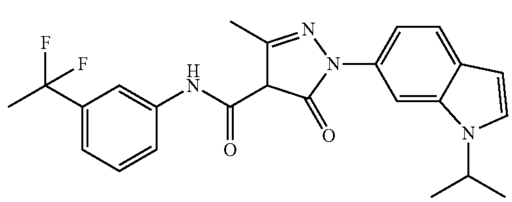 [SMILES: CC1=NN(c2ccc3ccn(C(C)C)c3c2)C(=O)C1C(=O)Nc1cccc(C(C)(F)F)c1] |

TABLE 1-continued

| Compound name | Structure |
|---|---|
| 365 | 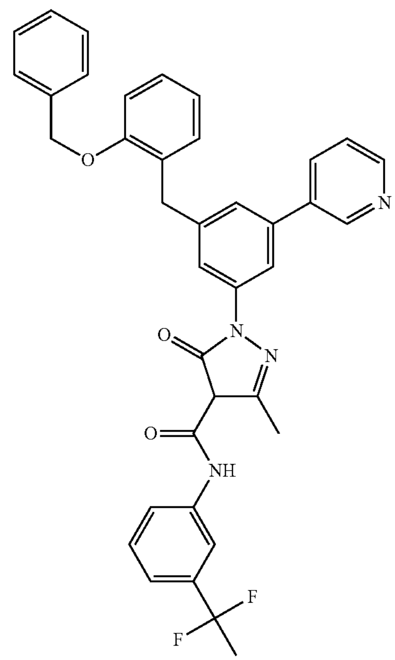 [SMILES: CC1=NN(c2cc(Cc3ccccc3OCc3ccccc3)cc(-c3cccnc3)c2)C(=O)C1C(=O)Nc1cccc(C(C)(F)F)c1] |
| 366 | 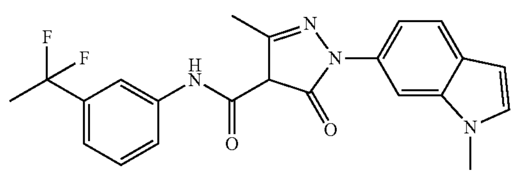 [SMILES: CC1=NN(c2ccc3ccn(C)c3c2)C(=O)C1C(=O)Nc1cccc(C(C)(F)F)c1] |
| 367 | 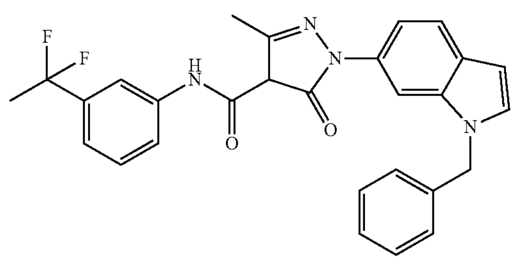 [SMILES: CC1=NN(c2ccc3ccn(Cc4ccccc4)c3c2)C(=O)C1C(=O)Nc1cccc(C(C)(F)F)c1] |
| 368 | 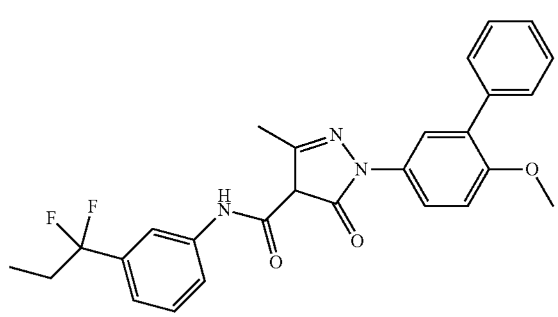 [SMILES: CCC(F)(F)c1cccc(NC(=O)C2C(=O)N(c3ccc(OC)c(-c4ccccc4)c3)N=C2C)c1] |

TABLE 1-continued
| Compound name | Structure |
| --- | --- |
| 369 | 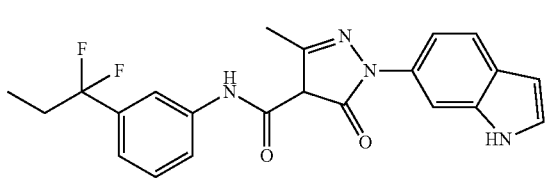 [SMILES: CCC(F)(F)c1cccc(NC(=O)C2C(=O)N(c3ccc4cc[nH]c4c3)N=C2C)c1] |
| 370 | 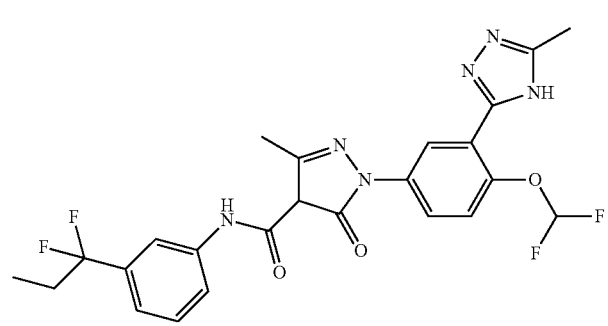 [SMILES: CCC(F)(F)c1cccc(NC(=O)C2C(=O)N(c3ccc(OC(F)F)c(-c4nnc(C)[nH]4)c3)N=C2C)c1] |
| 371 | 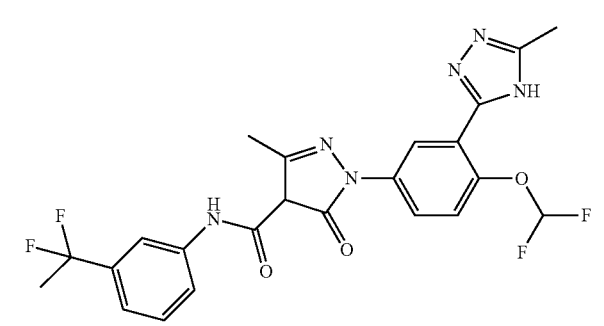 [SMILES: CC1=NN(c2ccc(OC(F)F)c(-c3nnc(C)[nH]3)c2)C(=O)C1C(=O)Nc1cccc(C(C)(F)F)c1] |
| 372 | 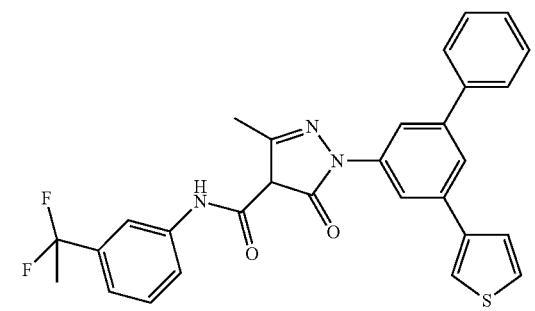 [SMILES: CC1=NN(c2cc(-c3ccccc3)cc(-c3ccsc3)c2)C(=O)C1C(=O)Nc1cccc(C(C)(F)F)c1] |

TABLE 1-continued
| Compound name | Structure |
|---|---|
| 373 | 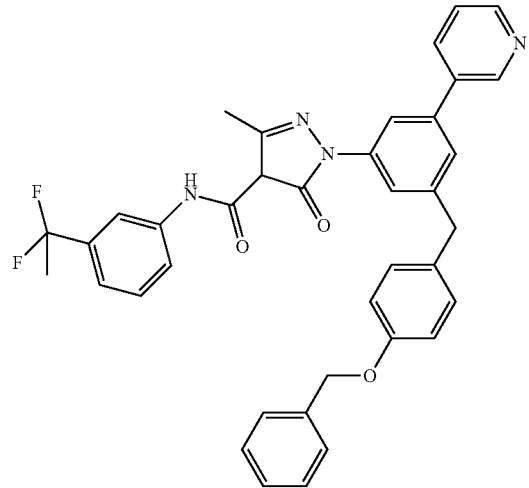 [SMILES: CC1=NN(c2cc(Cc3ccc(OCc4ccccc4)cc3)cc(-c3cccnc3)c2)C(=O)C1C(=O)Nc1cccc(C(C)(F)F)c1] |
| 374 | 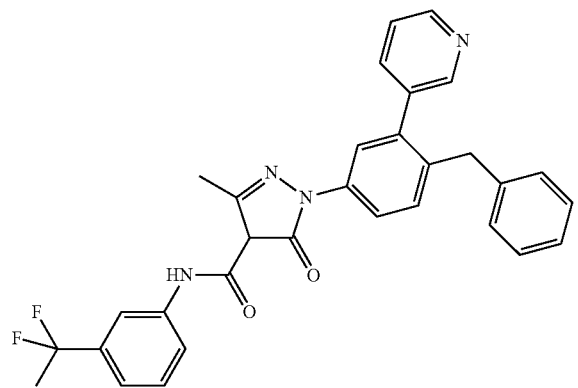 |
| 375 | 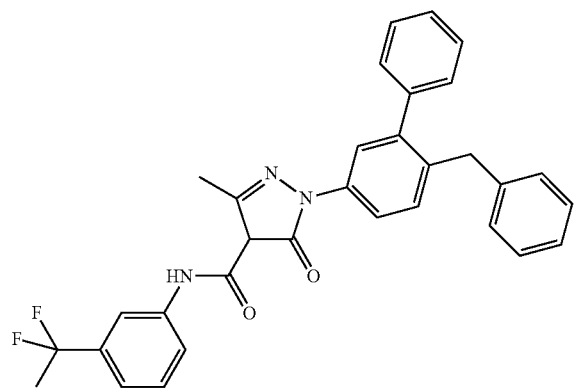 [SMILES: CC1=NN(c2ccc(Cc3ccccc3)c(-c3ccccc3)c2)C(=O)C1C(=O)Nc1cccc(C(C)(F)F)c1] |

TABLE 1-continued

| Compound name | Structure |
|---|---|
| 376 | 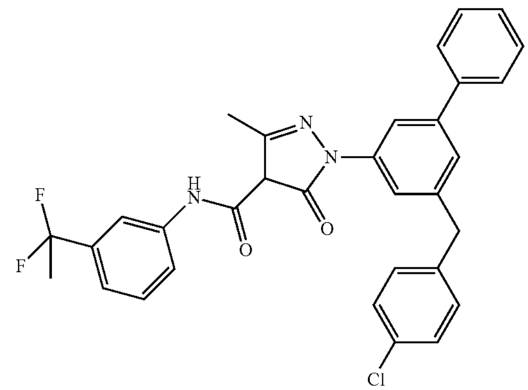 [SMILES: CC1=NN(c2cc(Cc3ccc(Cl)cc3)cc(-c3ccccc3)c2)C(=O)C1C(=O)Nc1cccc(C(C)(F)F)c1] |
| 377 | 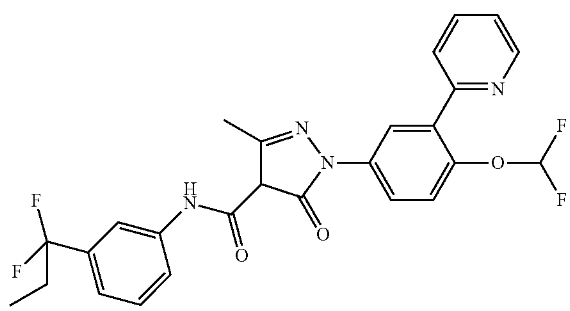 [SMILES: CCC(F)(F)c1cccc(NC(=O)C2C(=O)N(c3ccc(OC(F)F)c(-c4ccccn4)c3)N=C2C)c1] |
| 378 | 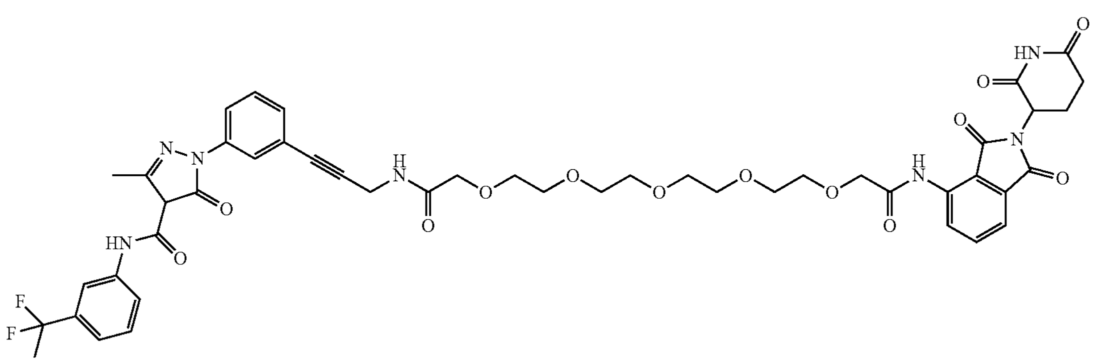 [SMILES: CC1=NN(c2cccc(C#CCNC(=O)COCCOCCOCCOCCOCC(=O)Nc3cccc4c3C(=O)N(C3CCC(=O)NC3=O)C4=O)c2)C(=O)C1C(=O)Nc1cccc(C(C)(F)F)c1] |
| 379 | 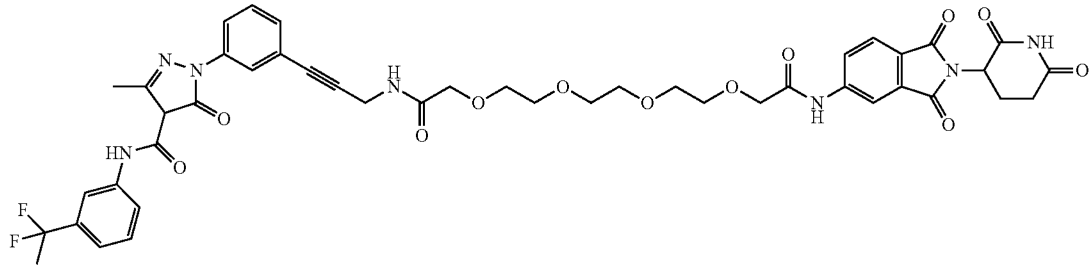 [SMILES: CC1=NN(c2cccc(C#CCNC(=O)COCCOCCOCCOCC(=O)Nc3ccc4c(c3)C(=O)N(C3CCC(=O)NC3=O)C4=O)c2)C(=O)C1C(=O)Nc1cccc(C(C)(F)F)c1] |

TABLE 1-continued

| Compound name | Structure |
|---|---|
| 380 | 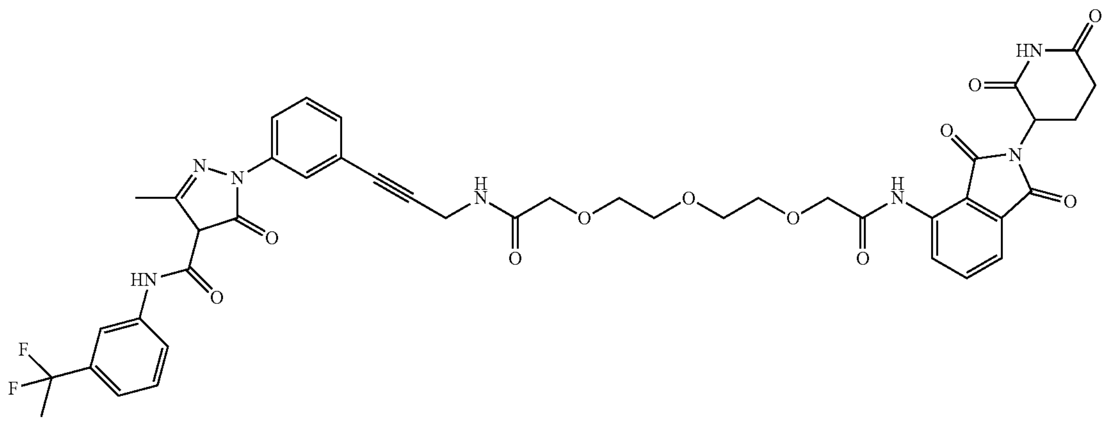 [SMILES: CC1=NN(c2cccc(C#CCNC(=O)COCCOCCOCC(=O)Nc3cccc4c3C(=O)N(C3CCC(=O)NC3=O)C4=O)c2)C(=O)C1C(=O)Nc1cccc(C(C)(F)F)c1] |
| 381 | 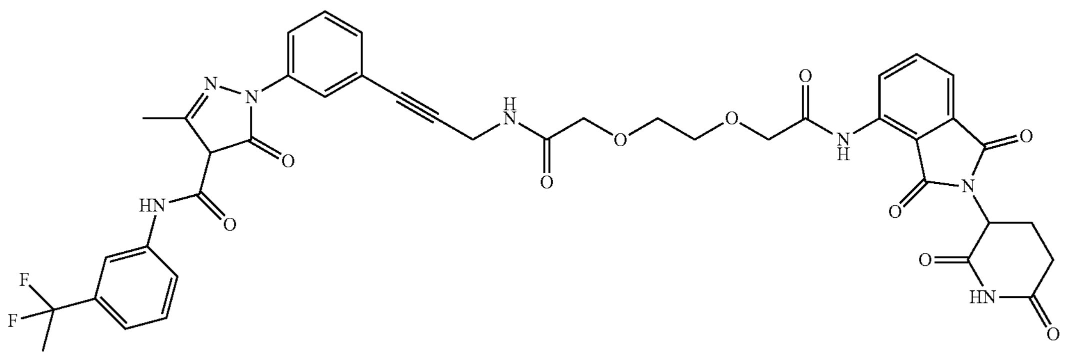 [SMILES: CC1=NN(c2cccc(C#CCNC(=O)COCCOCC(=O)Nc3cccc4c3C(=O)N(C3CCC(=O)NC3=O)C4=O)c2)C(=O)C1C(=O)Nc1cccc(C(C)(F)F)c1] |
| 382 | 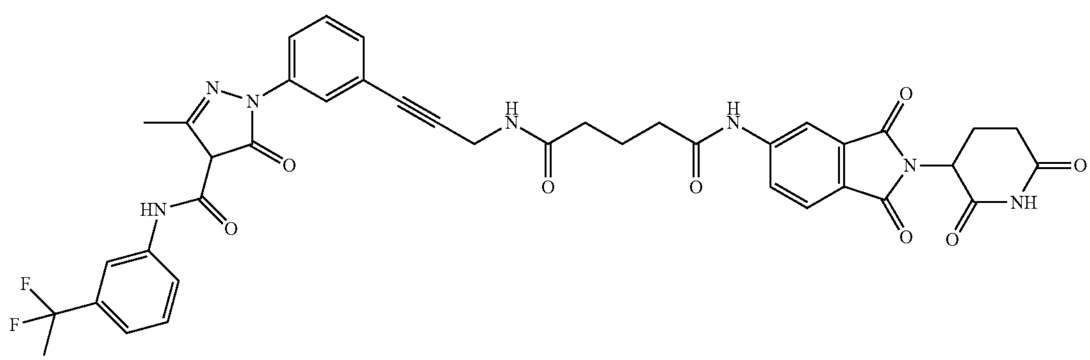 [SMILES: CC1=NN(c2cccc(C#CCNC(=O)CCCC(=O)Nc3ccc4c(c3)C(=O)N(C3CCC(=O)NC3=O)C4=O)c2)C(=O)C1C(=O)Nc1cccc(C(C)(F)F)c1] |
| 383 | 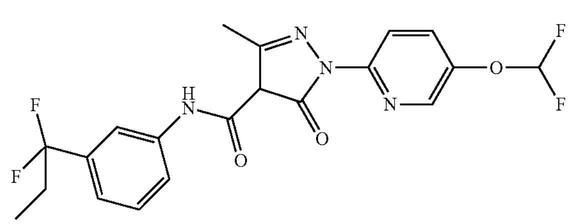 [SMILES: CCC(F)(F)c1cccc(NC(=O)C2C(=O)N(c3ccc(OC(F)F)cn3)N=C2C)c1] |

TABLE 1-continued
| Compound name | Structure |
|---|---|
| 384 | 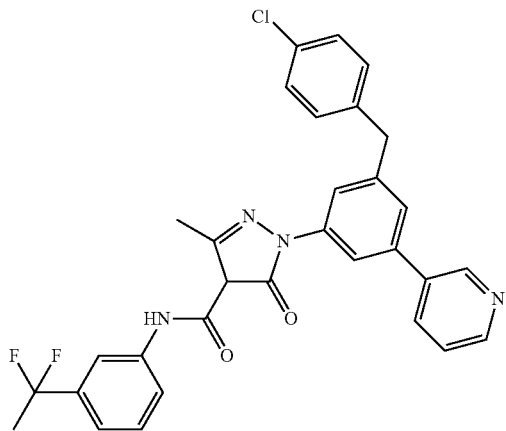 [SMILES: CC1=NN(c2cc(Cc3ccc(Cl)cc3)cc(-c3cccnc3)c2)C(=O)C1C(=O)Nc1cccc(C(C)(F)F)c1] |
| 385 | 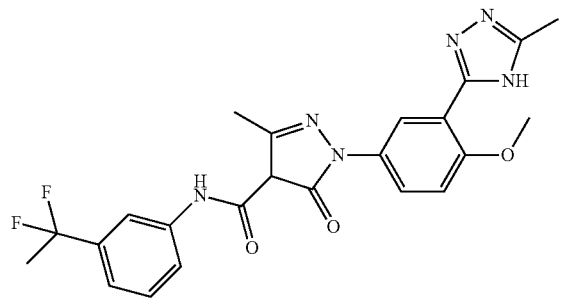 [SMILES: COc1ccc(N2N=C(C)C(C(=O)Nc3cccc(C(C)(F)F)c3)C2=O)cc1-c1nnc(C)[nH]1] |
| 386 | 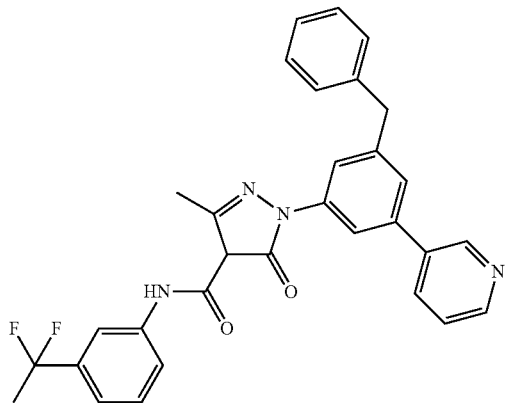 [SMILES: CC1=NN(c2cc(Cc3ccccc3)cc(-c3cccnc3)c2)C(=O)C1C(=O)Nc1cccc(C(C)(F)F)c1] |

TABLE 1-continued
| Compound name | Structure |
|---|---|
| 387 | 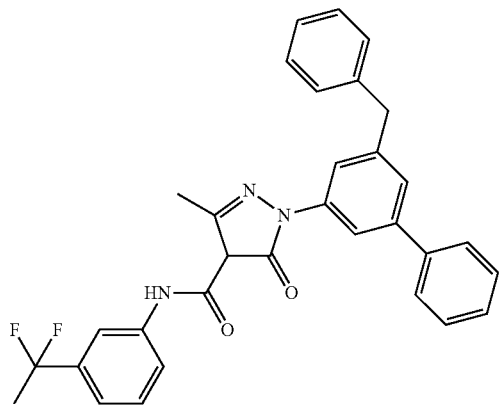 [SMILES: CC1=NN(c2cc(Cc3ccccc3)cc(-c3ccccc3)c2)C(=O)C1C(=O)Nc1cccc(C(C)(F)F)c1] |
| 388 | 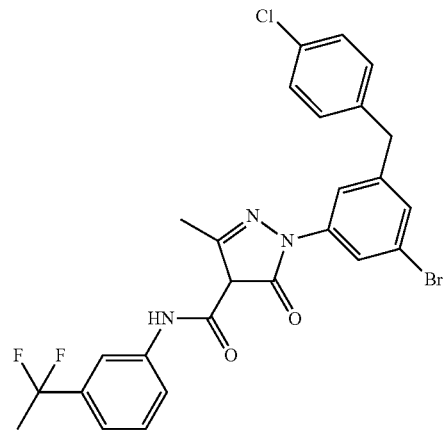 [SMILES: CC1=NN(c2cc(Br)cc(Cc3ccc(Cl)cc3)c2)C(=O)C1C(=O)Nc1cccc(C(C)(F)F)c1] |
| 389 | 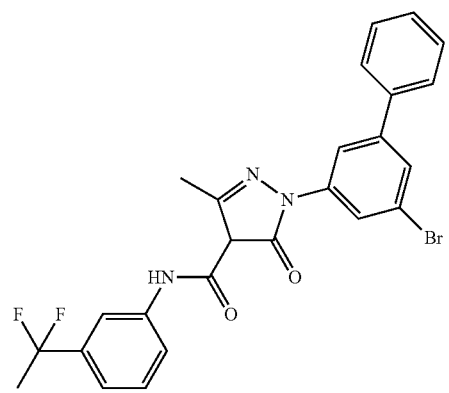 [SMILES: CC1=NN(c2cc(Br)cc(-c3ccccc3)c2)C(=O)C1C(=O)Nc1cccc(C(C)(F)F)c1] |

TABLE 1-continued
| Compound name | Structure |
|---|---|
| 390 | 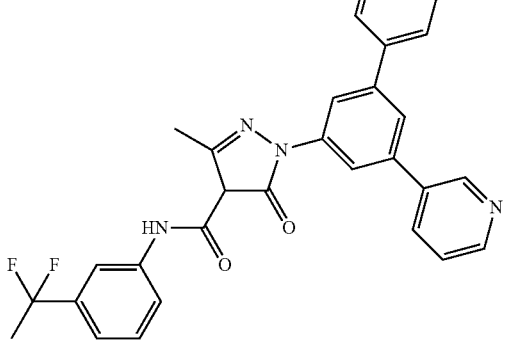 |
| 391 | 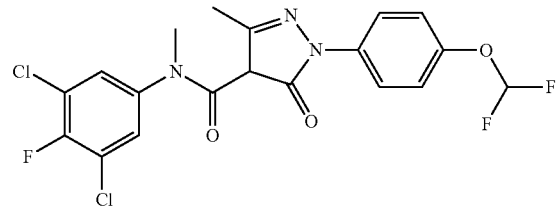 [SMILES: CC1=NN(c2ccc(OC(F)F)cc2)C(=O)C1C(=O)N(C)c1cc(Cl)c(F)c(Cl)c1] |
| 392 | 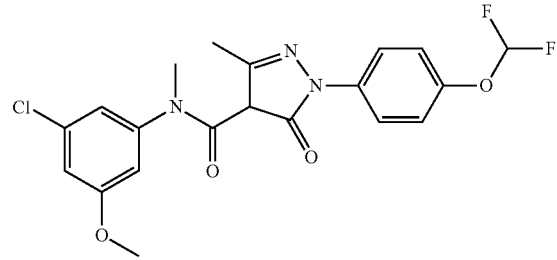 [SMILES: COc1cc(Cl)cc(N(C)C(=O)C2C(=O)N(c3ccc(OC(F)F)cc3)N=C2C)c1] |
| 393 | 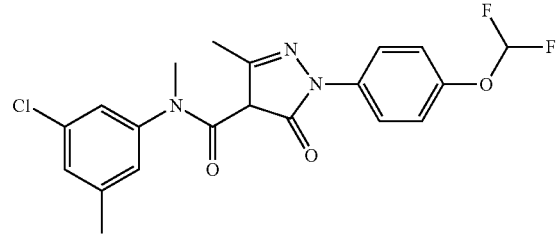 [SMILES: CC1=NN(c2ccc(OC(F)F)cc2)C(=O)C1C(=O)N(C)c1cc(C)cc(Cl)c1] |
| 394 | 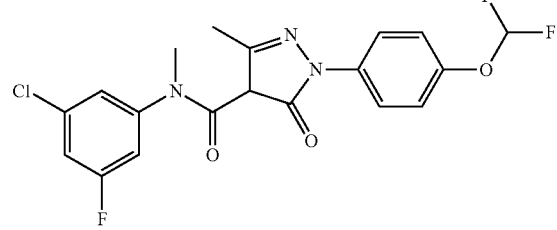 |

TABLE 1-continued

| Compound name | Structure |
|---|---|
| 395 | 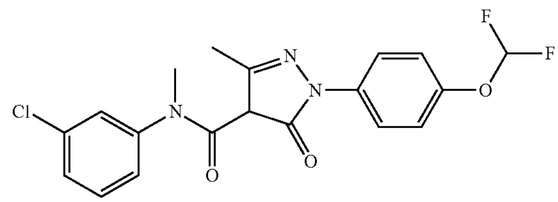 [SMILES: CC1=NN(c2ccc(OC(F)F)cc2)C(=O)C1C(=O)N(C)c1cccc(Cl)c1] |
| 396 | 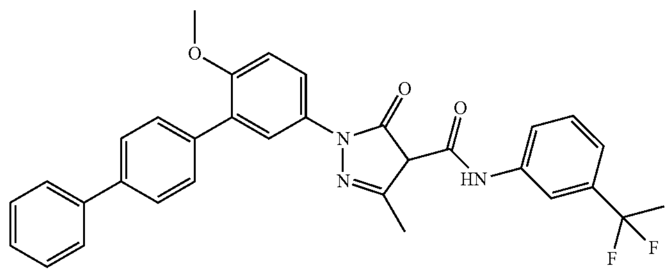 [SMILES: COc1ccc(N2N=C(C)C(C(=O)Nc3cccc(C(C)(F)F)c3)C2=O)cc1-c1ccc(-c2ccccc2)cc1] |
| 397 | 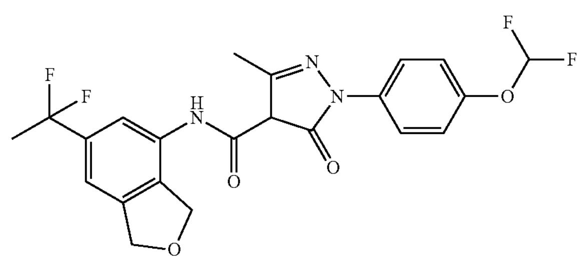 [SMILES: CC1=NN(c2ccc(OC(F)F)cc2)C(=O)C1C(=O)Nc1cc(C(C)(F)F)cc2c1COC2] |
| 398 | 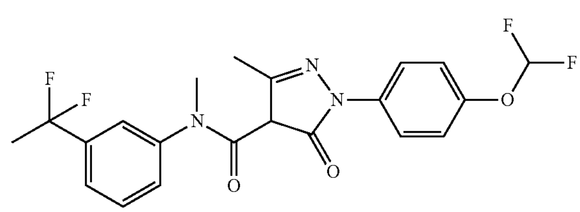 [SMILES: CC1=NN(c2ccc(OC(F)F)cc2)C(=O)C1C(=O)N(C)c1cccc(C(C)(F)F)c1] |
| 399 | 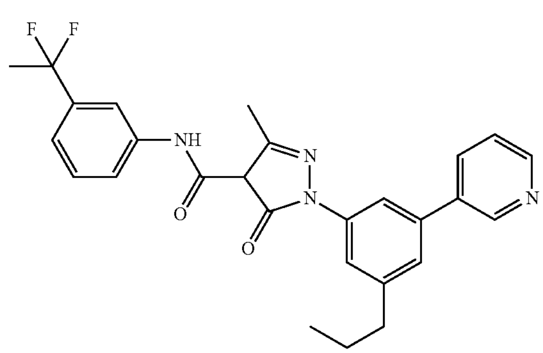 [SMILES: CCCc1cc(-c2cccnc2)cc(N2N=C(C)C(C(=O)Nc3cccc(C(C)(F)F)c3)C2=O)c1] |

TABLE 1-continued

| Compound name | Structure |
|---|---|
| 400 | 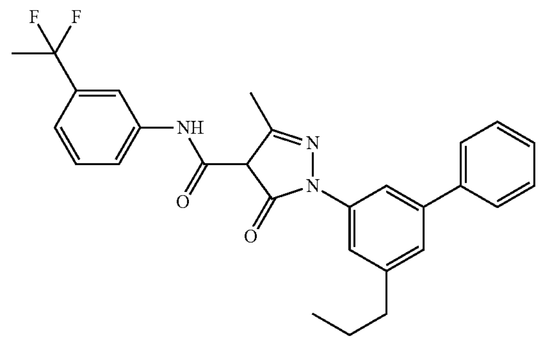 [SMILES: CCCc1cc(-c2ccccc2)cc(N2N=C(C)C(C(=O)Nc3cccc(C(C)(F)F)c3)C2=O)c1] |
| 401 | 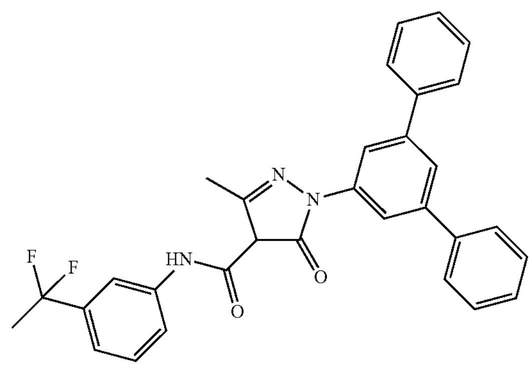 [SMILES: CC1=NN(c2cc(-c3ccccc3)cc(-c3ccccc3)c2)C(=O)C1C(=O)Nc1cccc(C(C)(F)F)c1] |
| 402 | 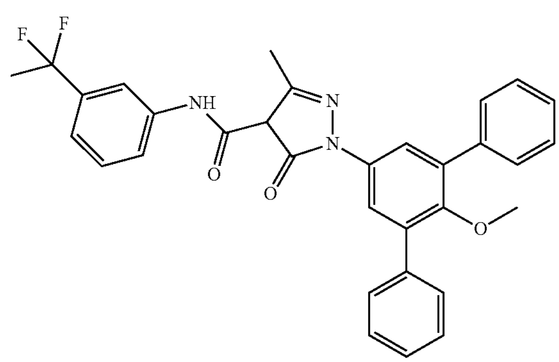 [SMILES: COc1c(-c2ccccc2)cc(N2N=C(C)C(C(=O)Nc3cccc(C(C)(F)F)c3)C2=O)cc1-c1ccccc1] |
| 403 | 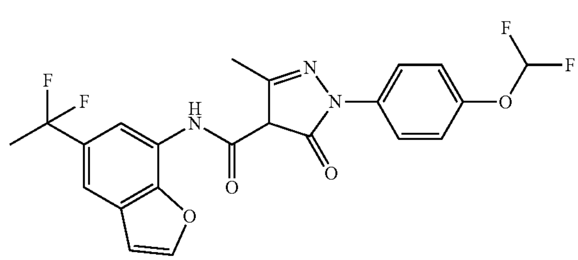 [SMILES: CC1=NN(c2ccc(OC(F)F)cc2)C(=O)C1C(=O)Nc1cc(C(C)(F)F)cc2ccoc12] |

TABLE 1-continued

| Compound name | Structure |
|---|---|
| 404 | 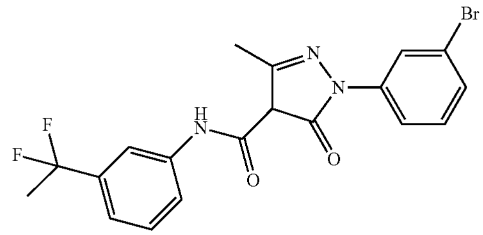 [SMILES: CC1=NN(c2cccc(Br)c2)C(=O)C1C(=O)Nc1cccc(C(C)(F)F)c1] |
| 405 | 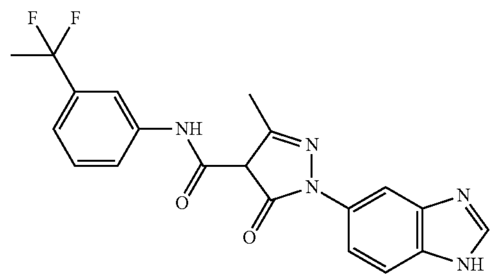 [SMILES: CC1=NN(c2ccc3[nH]cnc3c2)C(=O)C1C(=O)Nc1cccc(C(C)(F)F)c1] |
| 406 | 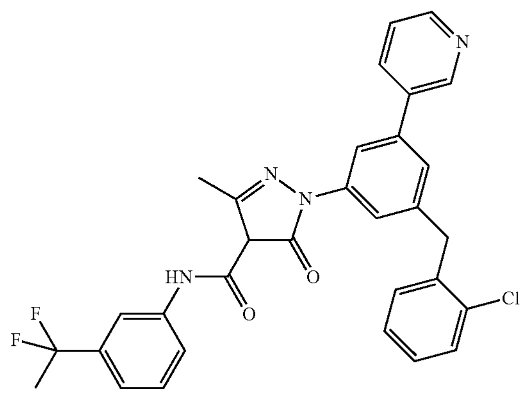 |
| 407 | 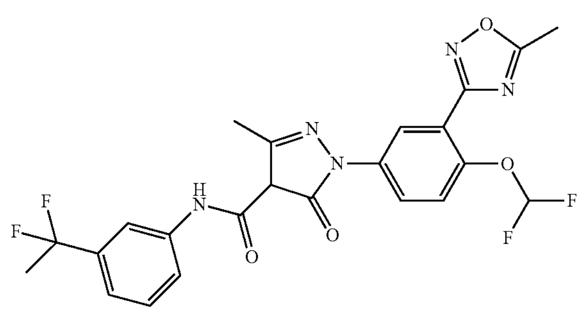 [SMILES: CC1=NN(c2ccc(OC(F)F)c(-c3noc(C)n3)c2)C(=O)C1C(=O)Nc1cccc(C(C)(F)F)c1] |
| 408 | 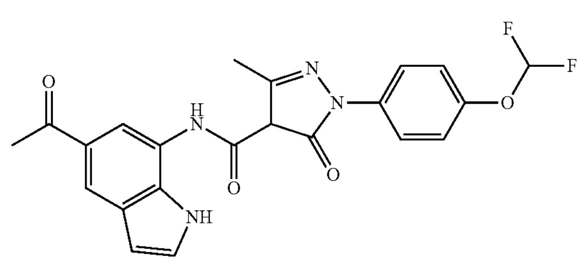 [SMILES: CC(=O)c1cc(NC(=O)C2C(=O)N(c3ccc(OC(F)F)cc3)N=C2C)c2[nH]ccc2c1] |

TABLE 1-continued

| Compound name | Structure |
|---|---|
| 409 | 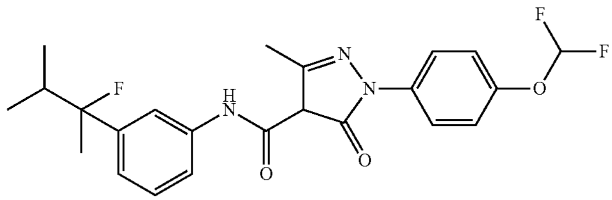 [SMILES: CC1=NN(c2ccc(OC(F)F)cc2)C(=O)C1C(=O)Nc1cccc(C(C)(F)C(C)C)c1] |
| 410 | 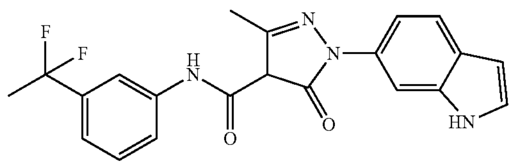 [SMILES: CC1=NN(c2ccc3cc[nH]c3c2)C(=O)C1C(=O)Nc1cccc(C(C)(F)F)c1] |
| 411 | 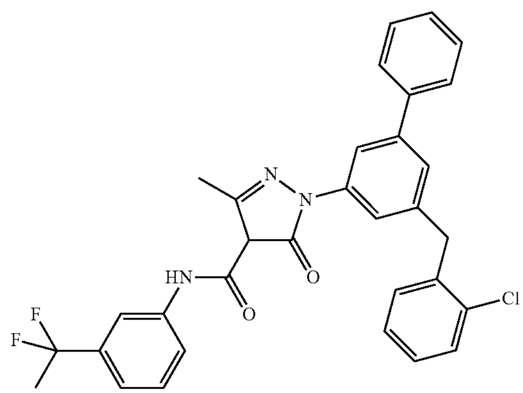 [SMILES: CC1=NN(c2cc(Cc3ccccc3Cl)cc(-c3ccccc3)c2)C(=O)C1C(=O)Nc1cccc(C(C)(F)F)c1] |
| 412 | 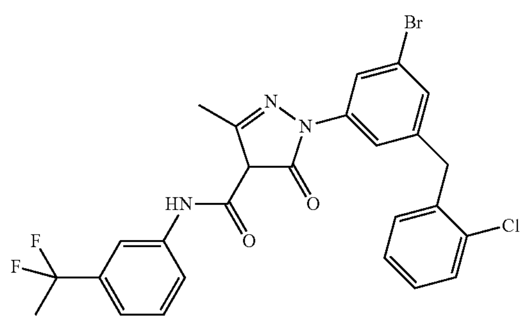 [SMILES: CC1=NN(c2cc(Br)cc(Cc3ccccc3Cl)c2)C(=O)C1C(=O)Nc1cccc(C(C)(F)F)c1] |
| 413 | (HCl) |

TABLE 1-continued

| Compound name | Structure |
|---|---|
| 414 | 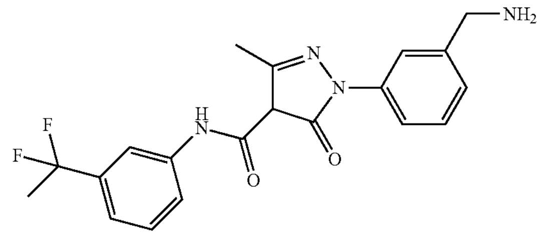 [SMILES: CC1=NN(c2cccc(CN)c2)C(=O)C1C(=O)Nc1cccc(C(C)(F)F)c1] |
| 415 | 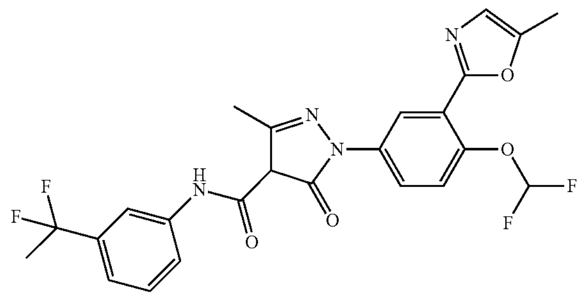 [SMILES: CC1=NN(c2ccc(OC(F)F)c(-c3ncc(C)o3)c2)C(=O)C1C(=O)Nc1cccc(C(C)(F)F)c1] |
| 416 | 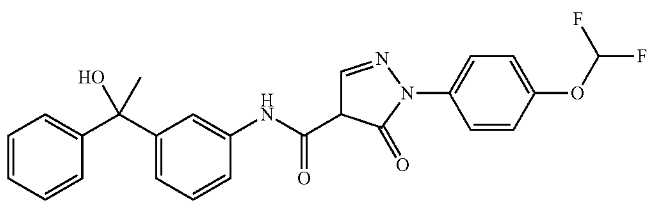 [SMILES: CC(O)(c1ccccc1)c1cccc(NC(=O)C2C=NN(c3ccc(OC(F)F)cc3)C2=O)c1] |
| 417 | 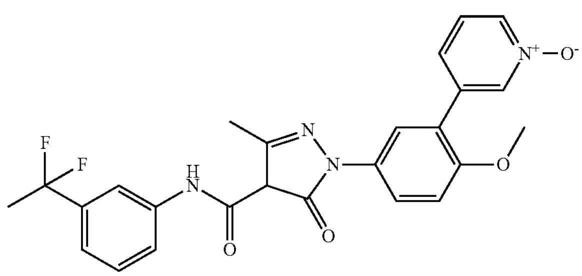 [SMILES: COc1ccc(N2N=C(C)C(C(=O)Nc3cccc(C(C)(F)F)c3)C2=O)cc1-c1ccc[n+]([O-])c1] |
| 418 | 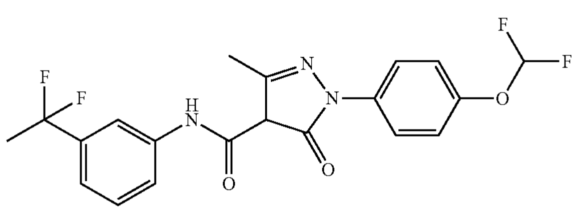 [SMILES: CC1=NN(c2ccc(OC(F)F)cc2)C(=O)C1C(=O)Nc1cccc(C(C)(F)F)c1] |
| 419 | 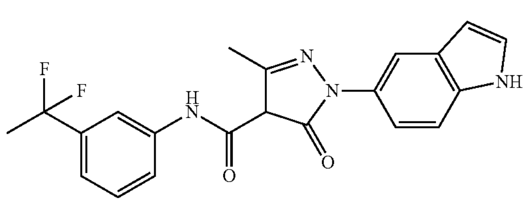 [SMILES: CC1=NN(c2ccc3[nH]ccc3c2)C(=O)C1C(=O)Nc1cccc(C(C)(F)F)c1] |

TABLE 1-continued

| Compound name | Structure |
|---|---|
| 420 | 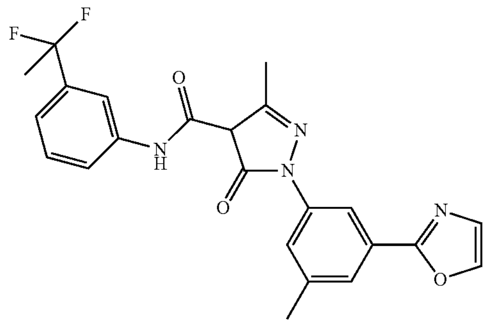 [SMILES: CC1=NN(c2cc(C)cc(-c3ncco3)c2)C(=O)C1C(=O)Nc1cccc(C(C)(F)F)c1] |
| 421 | 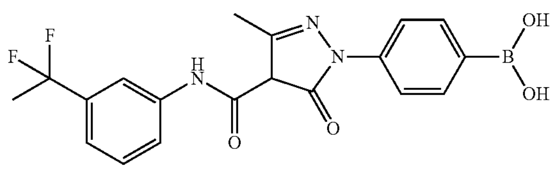 [SMILES: CC1=NN(c2ccc(B(O)O)cc2)C(=O)C1C(=O)Nc1cccc(C(C)(F)F)c1] |
| 422 | 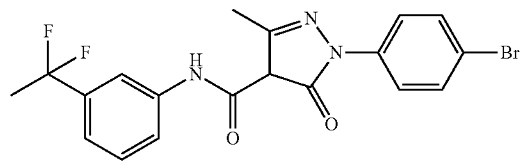 [SMILES: CC1=NN(c2ccc(Br)cc2)C(=O)C1C(=O)Nc1cccc(C(C)(F)F)c1] |
| 423 | 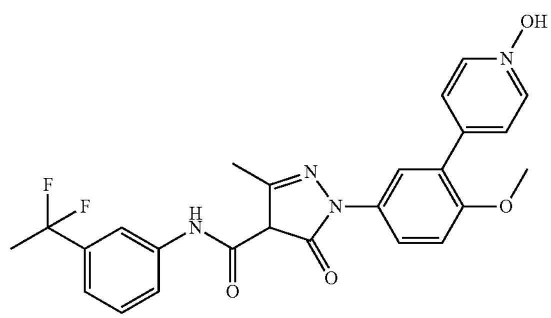 |
| 424 | 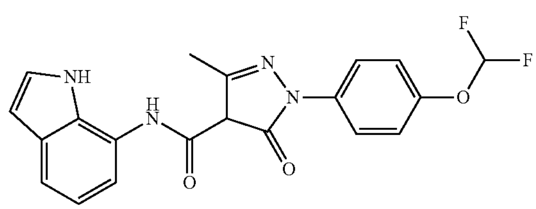 [SMILES: CC1=NN(c2ccc(OC(F)F)cc2)C(=O)C1C(=O)Nc1cccc2cc[nH]c12] |
| 425 | 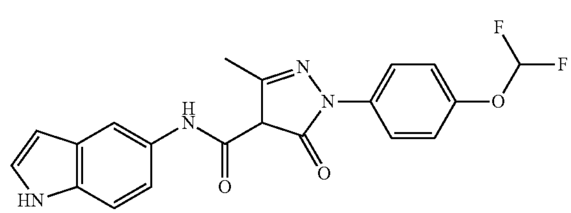 [SMILES: CC1=NN(c2ccc(OC(F)F)cc2)C(=O)C1C(=O)Nc1ccc2[nH]ccc2c1] |

TABLE 1-continued
| Compound name | Structure |
|---|---|
| 426 | 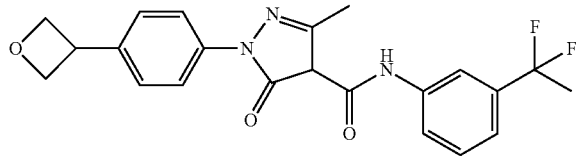 [SMILES: CC1=NN(c2ccc(C3COC3)cc2)C(=O)C1C(=O)Nc1cccc(C(C)(F)F)c1] |
| 427 | 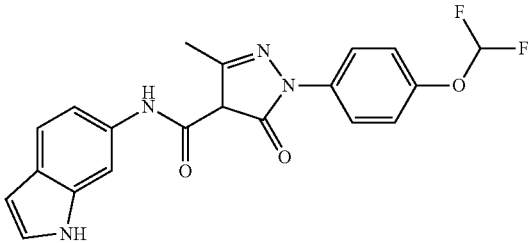 |
| 428 | 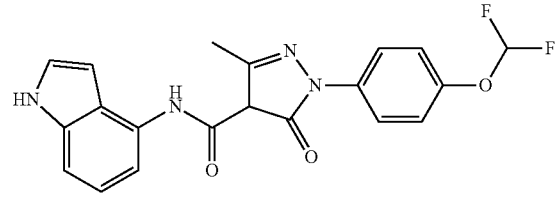 [SMILES: CC1=NN(c2ccc(OC(F)F)cc2)C(=O)C1C(=O)Nc1cccc2[nH]ccc12] |
| 429 | 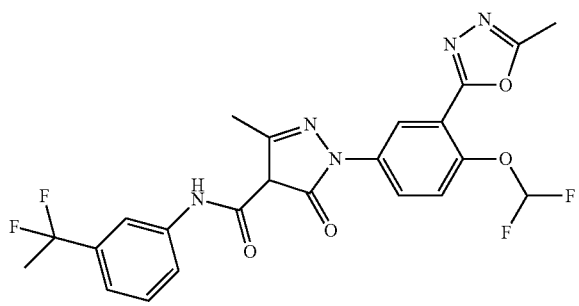 [SMILES: CC1=NN(c2ccc(OC(F)F)c(-c3nnc(C)o3)c2)C(=O)C1C(=O)Nc1cccc(C(C)(F)F)c1] |
| 430 | 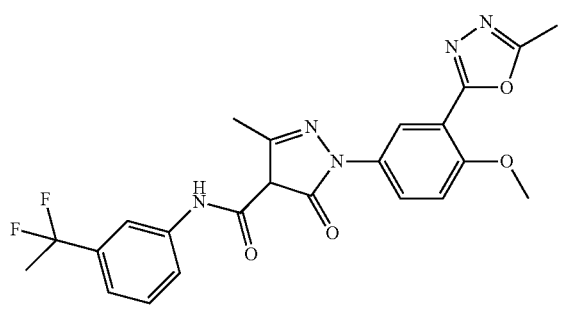 [SMILES: COc1ccc(N2N=C(C)C(C(=O)Nc3cccc(C(C)(F)F)c3)C2=O)cc1-c1nnc(C)o1] |

TABLE 1-continued

| Compound name | Structure |
|---|---|
| 431 | 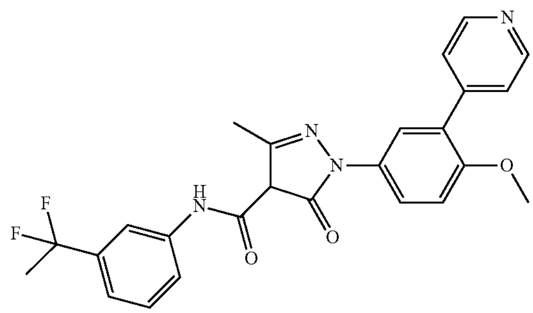 [SMILES: COc1ccc(N2N=C(C)C(C(=O)Nc3cccc(C(C)(F)F)c3)C2=O)cc1-c1ccncc1] |
| 432 | 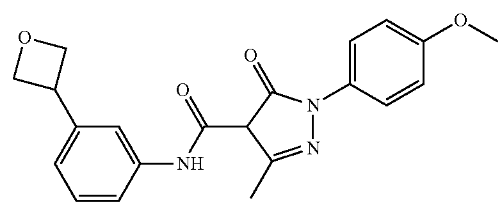 [SMILES: COc1ccc(N2N=C(C)C(C(=O)Nc3cccc(C4COC4)c3)C2=O)cc1] |
| 433 | 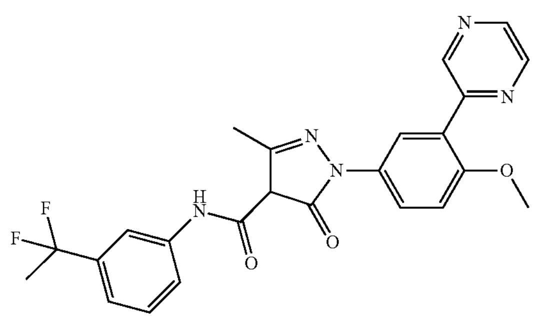 [SMILES: COc1ccc(N2N=C(C)C(C(=O)Nc3cccc(C(C)(F)F)c3)C2=O)cc1-c1cnccn1] |
| 434 | 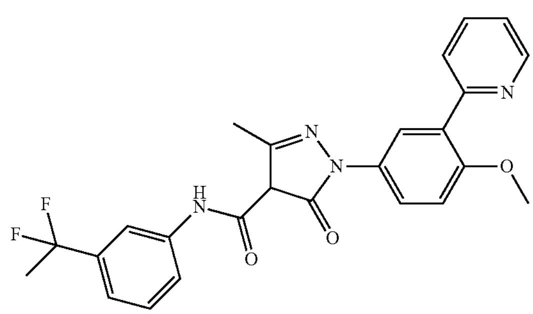 [SMILES: COc1ccc(N2N=C(C)C(C(=O)Nc3cccc(C(C)(F)F)c3)C2=O)cc1-c1ccccn1] |
| 435 | 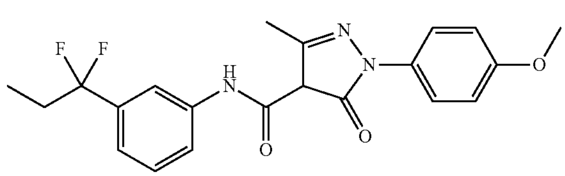 [SMILES: CCC(F)(F)c1cccc(NC(=O)C2C(=O)N(c3ccc(OC)cc3)N=C2C)c1] |

TABLE 1-continued
| Compound name | Structure |
|---|---|
| 436 | 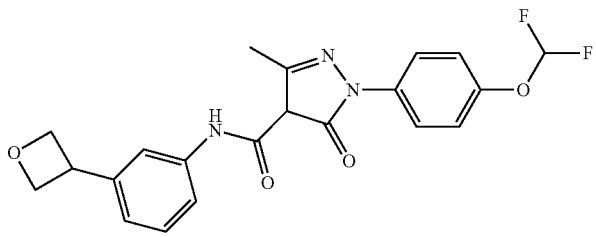 [SMILES: CC1=NN(c2ccc(OC(F)F)cc2)C(=O)C1C(=O)Nc1cccc(C2COC2)c1] |
| 437 | 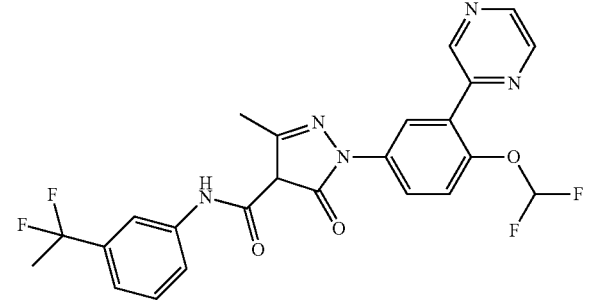 [SMILES: CC1=NN(c2ccc(OC(F)F)c(-c3cnccn3)c2)C(=O)C1C(=O)Nc1cccc(C(C)(F)F)c1] |
| 438 | 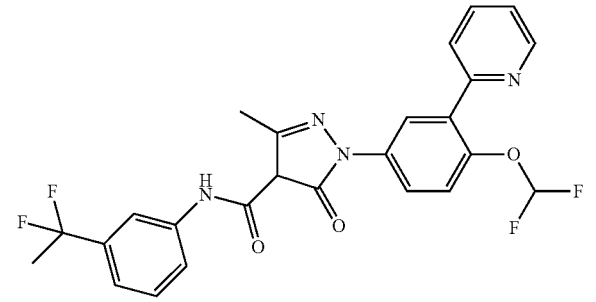 [SMILES: CC1=NN(c2ccc(OC(F)F)c(-c3ccccn3)c2)C(=O)C1C(=O)Nc1cccc(C(C)(F)F)c1] |
| 439 | 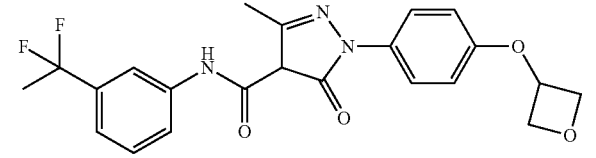 [SMILES: CC1=NN(c2ccc(OC3COC3)cc2)C(=O)C1C(=O)Nc1cccc(C(C)(F)F)c1] |
| 440 | 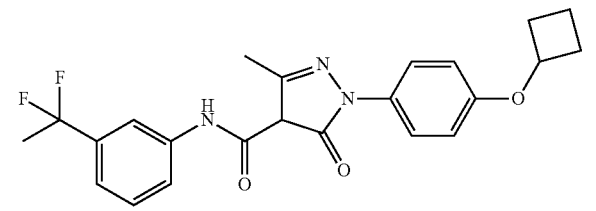 [SMILES: CC1=NN(c2ccc(OC3CCC3)cc2)C(=O)C1C(=O)Nc1cccc(C(C)(F)F)c1] |
| 441 | 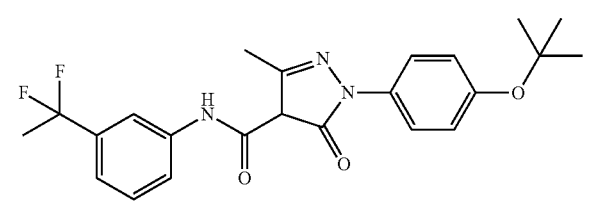 [SMILES: CC1=NN(c2ccc(OC(C)(C)C)cc2)C(=O)C1C(=O)Nc1cccc(C(C)(F)F)c1] |

TABLE 1-continued
| Compound name | Structure |
|---|---|
| 442 | 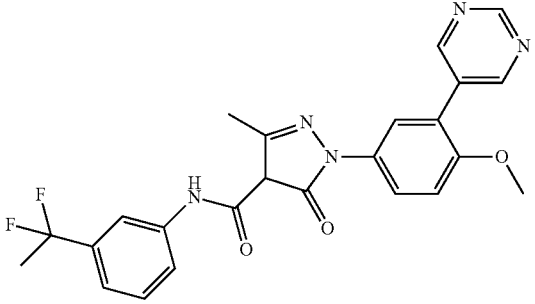 [SMILES: COc1ccc(N2N=C(C)C(C(=O)Nc3cccc(C(C)(F)F)c3)C2=O)cc1-c1cncnc1] |
| 443 | 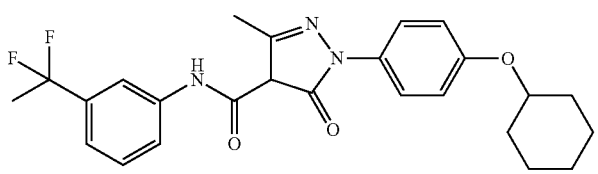 [SMILES: CC1=NN(c2ccc(OC3CCCCC3)cc2)C(=O)C1C(=O)Nc1cccc(C(C)(F)F)c1] |
| 444 | 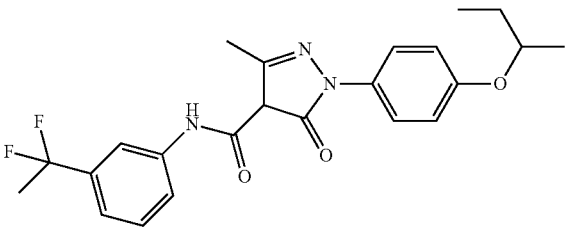 [SMILES: CCC(C)Oc1ccc(N2N=C(C)C(C(=O)Nc3cccc(C(C)(F)F)c3)C2=O)cc1] |
| 445 | 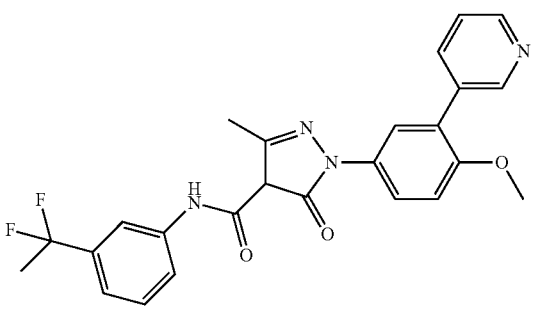 [SMILES: COc1ccc(N2N=C(C)C(C(=O)Nc3cccc(C(C)(F)F)c3)C2=O)cc1-c1cccnc1] |
| 446 | 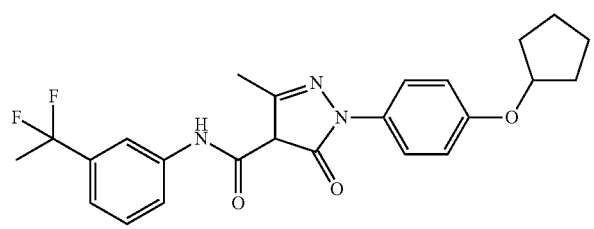 [SMILES: CC1=NN(c2ccc(OC3CCCC3)cc2)C(=O)C1C(=O)Nc1cccc(C(C)(F)F)c1] |
| 447 | 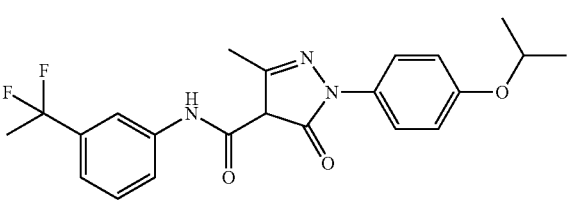 |

TABLE 1-continued
| Compound name | Structure |
|---|---|
| 448 | 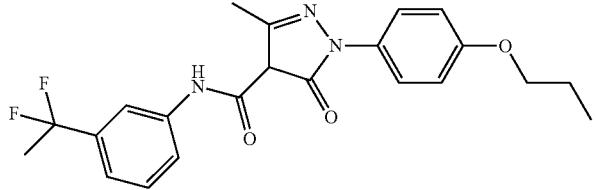 [SMILES: CCCOc1ccc(N2N=C(C)C(C(=O)Nc3cccc(C(C)(F)F)c3)C2=O)cc1] |
| 449 | 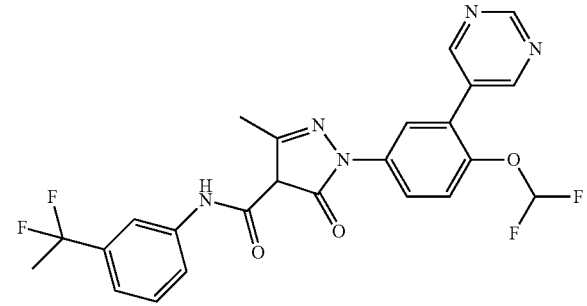 [SMILES: CC1=NN(c2ccc(OC(F)F)c(-c3cncnc3)c2)C(=O)C1C(=O)Nc1cccc(C(C)(F)F)c1] |
| 450 | 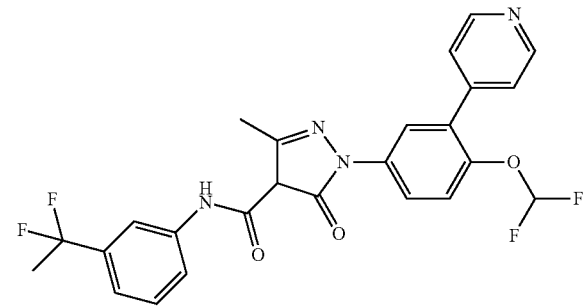 |
| 451 | 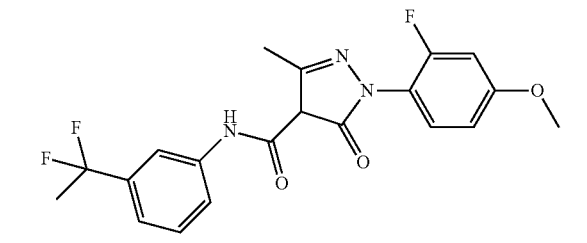 [SMILES: COc1ccc(N2N=C(C)C(C(=O)Nc3cccc(C(C)(F)F)c3)C2=O)c(F)c1] |
| 452 | 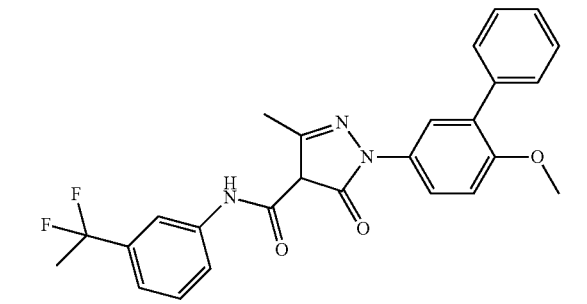 [SMILES: COc1ccc(N2N=C(C)C(C(=O)Nc3cccc(C(C)(F)F)c3)C2=O)cc1-c1ccccc1] |

TABLE 1-continued

| Compound name | Structure |
|---|---|
| 453 | 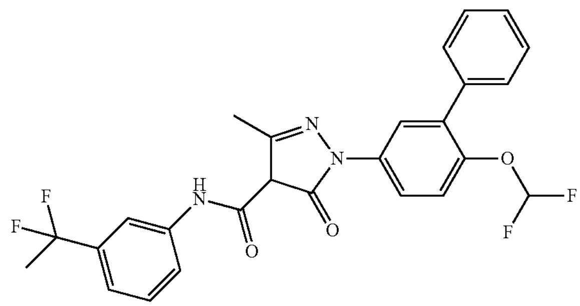 [SMILES: CC1=NN(c2ccc(OC(F)F)c(-c3ccccc3)c2)C(=O)C1C(=O)Nc1cccc(C(C)(F)F)c1] |
| 454 | 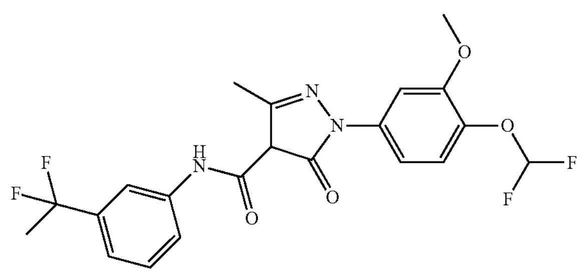 [SMILES: COc1cc(N2N=C(C)C(C(=O)Nc3cccc(C(C)(F)F)c3)C2=O)ccc1OC(F)F] |
| 455 | 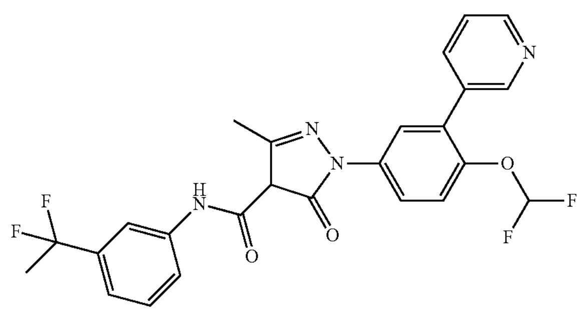 [SMILES: CC1=NN(c2ccc(OC(F)F)c(-c3cccnc3)c2)C(=O)C1C(=O)Nc1cccc(C(C)(F)F)c1] |
| 456 | 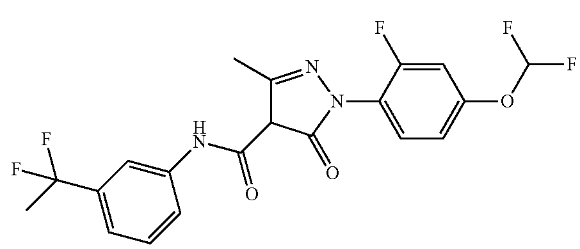 [SMILES: CC1=NN(c2ccc(OC(F)F)cc2F)C(=O)C1C(=O)Nc1cccc(C(C)(F)F)c1] |
| 457 | 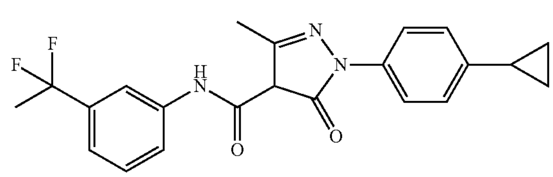 [SMILES: CC1=NN(c2ccc(C3CC3)cc2)C(=O)C1C(=O)Nc1cccc(C(C)(F)F)c1] |

TABLE 1-continued

| Compound name | Structure |
|---|---|
| 458 | (structure: (1S,2R)-cyclohexane-1,2-diol linked via NH-C(=O) to a 4-acyl-3-methyl-pyrazol-5(4H)-one, with N1 bearing a 4-(difluoromethoxy)phenyl group) |
| 459 | (structure: 2-(hydroxymethyl)-5-(1,1-difluoroethyl)aniline NH-C(=O)-linked to a 4-acyl-3-methyl-pyrazol-5(4H)-one, with N1 bearing a 4-(difluoromethoxy)phenyl group) |
| 460 | (structure: 3-(1,1-difluoroethyl)aniline NH-C(=O)-linked to a 4-acyl-3-methyl-pyrazol-5(4H)-one, with N1 bearing a 2-tert-butyl-4-methoxyphenyl group) |

It is well understood that in structures presented in this invention wherein the nitrogen atom has less than 3 bonds, H atoms are present to complete the valence of the nitrogen.

In some embodiments, this invention is directed to the compounds listed hereinabove, pharmaceutical compositions and/or method of use thereof, wherein the compound is pharmaceutically acceptable salt, optical isomer, tautomer, hydrate, N-oxide, prodrug, isotopic variant (deuterated analog), PROTAC, pharmaceutical product or any combination thereof. In some embodiments, the compounds are Acyl-CoA Synthetase Short-Chain Family Member 2 (ACSS2) inhibitors.

In various embodiments, the A ring of formula I is phenyl, naphthyl, pyridinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, isoquinoline, pyrazolyl, pyrrolyl, furanyl, thiophene-yl, isoquinolinyl, indolyl, 1H-indole, isoindolyl, naphthyl, anthracenyl, benzimidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, 2,3-dihydroindenyl, indenyl, tetrahydronaphthyl, 3,4-dihydro-2H-benzo[b][1,4]dioxepine, benzo[d][1,3]dioxole, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, benzo[d][1,3]dioxole, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, 1,3-dihydroisobenzofuran each definition is a separate embodiment according to this invention; or A is $C_3$-$C_8$ cycloalkyl (e.g. cyclohexyl) or $C_3$-$C_8$ heterocyclic ring including but not limited to: tetrahydropyran, piperidine, 1-methylpiperidine, tetrahydrothiophene 1,1-dioxide, 1-(piperidin-1-yl)ethanone or morpholine.

In various embodiments, the A ring of formula I is phenyl. In some embodiments, the A ring is naphtyl. In some embodiments, the A ring is pyridinyl. In some embodiments, the A ring is pyrimidinyl. In some embodiments, the A ring is pyridazinyl. In some embodiments, A is pyrazinyl. In some embodiments, the A ring is triazinyl. In some embodiments, the A ring is tetrazinyl. In some embodiments, the A ring is thiazolyl. In some embodiments, the A ring is isothiazolyl. In some embodiments, the A ring is oxazolyl. In some embodiments, the A ring is isoxazolyl. In some embodiments, the A ring is imidazolyl. In some embodiments, the A ring is 1-methylimidazole. In some embodiments, the A ring is pyrazolyl. In some embodiments, the A ring is pyrrolyl. In some embodiments, the A ring is furanyl. In some embodiments, the A ring is thiophene-yl. In some embodiments, the A ring is indolyl. In some embodiments, the A ring is indenyl. In some embodiments, the A ring is 2,3-dihydroindenyl. In some embodiments, the A ring is tetrahydronaphthyl. In some embodiments, the A ring is isoindolyl. In some embodiments, the A ring is naphthyl. In some embodiments, the A ring is anthracenyl. In some embodiments, the A ring is benzimidazolyl. In some embodiments, the A ring is indazolyl. In some embodiments, the A ring is purinyl. In some embodiments, the A ring is benzoxazolyl. In some embodiments, the A ring is benzisoxazolyl. In some embodiments, the A ring is benzothiazolyl. In some embodiments, the A ring is quinazolinyl. In some embodiments, the A ring is quinoxalinyl. In some embodiments, the A ring is cinnolinyl. In some embodiments, the A ring is phthalazinyl. In some embodiments, the A ring is quinolinyl. In some embodiments, the A ring is isoquinolinyl. In some embodiments, the A ring is 3,4-dihydro-2H-benzo[b][1,4]dioxepine. In some embodiments, the A ring is benzo[d][1,3]dioxole. In some embodiments, the A ring is benzofuran-2(3H)-one. In some embodiments, the A ring is benzodioxolyl. In some embodiments, the A ring is acridinyl. In some embodiments, the A ring is benzofuranyl. In some embodiments, the A ring is isobenzofuranyl. In some embodiments, the A ring is benzothiophenyl. In some embodiments, the A ring is benzo[c]thiophenyl. In some embodiments, the A ring is benzodioxolyl. In some embodiments, the A ring is thiadiazolyl. In some embodiments, the A ring is oxadiaziolyl. In some embodiments, the A ring is 7-oxo-6H,7H-[1,3]thiazolo[4,5-d]pyrimidine. In some embodiments, the A ring is [1,3]thiazolo[5,4-b]pyridine. In some embodiments, the A ring is thieno[3,2-d]pyrimidin-4(3H)-one. In some embodiments, the A ring is 4-oxo-4H-thieno[3,2-d][1,3]thiazin. In some embodiments, the A ring is pyrido[2,3-b]pyrazin or pyrido[2,3-b]pyrazin-3(4H)-one. In some embodiments, the A ring is quinoxalin-2(1H)-one. In some embodiments, the A ring is 1H-indole. In some embodiments, the A ring is 2H-indazole. In some embodiments, the A ring is 4,5,6,7-tetrahydro-2H-indazole. In some embodiments, the A ring is 3H-indol-3-one. In some embodiments, the A ring is 1,3-benzoxazolyl. In some embodiments, the A ring is 1,3-benzothiazole. In some embodiments, the A ring is 4,5,6,7-tetrahydro-1,3-benzothiazole. In some embodiments, the A ring is 1-benzofuran. In some embodiments, the A ring is [1,3]oxazolo[4,5-b]pyridine. In some embodiments, the A ring is imidazo[2,1-b][1,3]thiazole. In some embodiments, the A ring is 4H,5H,6H-cyclopenta[d][1,3]thiazole. In some embodiments, the A ring is 5H,6H,7H,8H-imidazo[1,2-a]pyridine. In some embodiments, the A ring is 2H,3H-imidazo[2,1-b][1,3]thiazole. In some embodiments, the A ring is imidazo[1,2-a]pyridine. In some embodiments, the A ring is pyrazolo[1,5-a]pyridine. In some embodiments, the A ring is imidazo[1,2-a]pyrazine. In some embodiments, the A ring is imidazo[1,2-a]pyrimidine. In some embodiments, the A ring is 4H-thieno[3,2-b]pyrrole. In some embodiments, the A ring is 1H-pyrrolo[2,3-b]pyridine. In some embodiments, the A ring is 1H-pyrrolo[3,2-b]pyridine. In some embodiments, the A ring is 7H-pyrrolo[2,3-d]pyrimidine. In some embodiments, the A ring is oxazolo[5,4-b]pyridine. In some embodiments, the A ring is thiazolo[5,4-b]pyridine. In some embodiments, the A ring is triazolyl. In some embodiments, the A ring is benzoxadiazole. In some embodiments, the A ring is benzo[c][1,2,5]oxadiazolyl. In some embodiments, the A ring is 1H-imidazo[4,5-b]pyridine. In some embodiments, the A ring is 3H-imidazo[4,5-c]pyridine. In some embodiments, the A ring is a $C_3$-$C_8$ cycloalkyl. In some embodiments, the A ring is $C_3$-$C_8$ heterocyclic ring. In some embodiments, the A ring is tetrahydropyran. In some embodiments, the A ring is piperidine. In some embodiments, the A ring is 1-(piperidin-1-yl)ethanone. In some embodiments, the A ring is morpholine. In some embodiments, the A ring is thieno[3,2-c]pyridine. In some embodiments, the A ring is 1-methylpiperidine. In some embodiments, the A ring is tetrahydrothiophene 1,1-dioxide. In some embodiments, the A ring is cyclohexyl. In some embodiments, the A ring is indole. In some embodiments, the A ring is 1,3-dihydroisobenzofuran. In some embodiments, the A ring is benzofuran. In some embodiments, the A ring is 1,3-dihydroisobenzofuran.

In various embodiments, the B ring of formula I is phenyl, naphthyl, pyridinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, isoquinoline, pyrazolyl, pyrrolyl, furanyl, thiophene-yl, isoquinolinyl, indolyl, 1H-indole, isoindolyl, naphthyl, anthracenyl, benzimidazolyl, 2,3-dihydro-1H-benzo[d]imidazolyl, tetrahydronaphthyl 3,4-dihydro-2H-benzo[b][1,4]dioxepine, benzofuran-2(3H)-one, benzo[d][1,3]dioxole, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, acridinyl, benzofuranyl, 1-benzofuran, isobenzofuranyl, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 3H-imidazo[4,5-b]pyridine, 3H-imidazo[4,5-c]pyridine, pyrazolo[1,5-a]pyridine, imidazo[1,2-a]pyrazine, imidazo[1,2-a]pyrimidine, pyrido[2,3-b]pyrazin or pyrido[2,3-b]pyrazin-3(4H)-one, 4H-thieno[3,2-b]pyrrole, quinoxalin-2(1H)-one, 1,2,3,4-tetrahydroquinoxaline, 1-(pyridin-1(2H)-yl)ethanone, 1H-pyrrolo[2,3-b]pyridine, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, $C_3$-$C_8$ cycloalkyl, or $C_3$-$C_8$ heterocyclic ring including but not limited to: tetrahydropyran, piperidine, 1-methylpiperidine, tetrahydrothiophene 1,1-dioxide, 1-(piperidin-1-yl)ethanone or morpholine, 1,3-dihydroisobenzofuran; each definition is a separate embodiment according to this invention.

In various embodiments, the B ring of formula I is phenyl. In some embodiments, the B ring is naphthyl. In some embodiments, the B ring is pyridinyl. In some embodiments, the B ring is pyrimidinyl. In some embodiments, the B ring is pyridazinyl. In some embodiments, the B ring is pyrazinyl. In some embodiments, the B ring is triazinyl. In some embodiments, the B ring is tetrazinyl. In some embodiments, the B ring is thiazolyl. In some embodiments, the B ring is isothiazolyl. In some embodiments, the B ring is oxazolyl. In some embodiments, the B ring is isoxazolyl. In some embodiments, the B ring is imidazolyl. In some embodiments, the B ring is 1-methylimidazole. In some embodiments, the B ring is pyrazolyl. In some embodiments, the B ring is pyrrolyl. In some embodiments, the B ring is furanyl. In some embodiments, the B ring is thiophene-yl. In some embodiments, the B ring is isoquinolinyl. In some embodiments, the B ring is indolyl. In some embodiments, the B ring is isoindolyl. In some embodiments, the B ring is naphthyl. In some embodiments, the B ring is anthracenyl. In some embodiments, the B ring is benzimidazolyl. In some embodiments, the B ring is 2,3-dihydro-1H-benzo[d]imidazole. In some embodiments, the B ring is indazolyl. In some embodiments, the B ring is purinyl. In some embodiments, the B ring is benzoxazolyl. In some embodiments, the B ring is benzisoxazolyl. In some embodiments, the B ring is benzothiazolyl. In some embodiments, the B ring is quinazolinyl. In some embodiments, the B ring is quinoxalinyl. In some embodiments, the B ring is 1,2,3,4-tetrahydroquinoxaline. In other embodiments, B is 1-(pyridin-1(2H)-yl)ethanone. In some embodiments, the B ring is benzo[d][1,3]dioxole. In some embodiments, the B ring is benzofuran-2(3H)-one. In some embodiments, the B ring is benzodioxolyl. In some embodiments, the B ring is tetrahydronaphthyl. In some embodiments, the B ring is cinnolinyl. In some embodiments, the B ring is phthalazinyl. In some embodiments, the B ring is quinolinyl. In some embodiments, the B ring is isoquinolinyl. In some embodiments, the B ring is acridinyl. In some embodiments, the B ring is benzofuranyl. In some embodiments, the B ring is isobenzofuranyl. In some embodiments, the B ring is benzothiophenyl. In some embodiments, the B ring is benzo[c]thiophenyl. In some embodiments, the B ring is benzodioxolyl. In some embodiments, the B ring is thiadiazolyl. In some embodiments, the B ring is oxadiaziolyl. In some embodiments, the B ring is 7-oxo-6H,7H-[1,3]thiazolo[4,5-d]pyrimidine. In some embodiments, the B ring is [1,3]thiazolo[5,4-b]pyridine. In some embodiments, the C ring is thieno[3,2-d]pyrimidin-4(3H)-one. In some embodiments, the B ring is 4-oxo-4H-thieno[3,2-d][1,3]thiazin. In some embodiments, the B ring is pyrido[2,3-b]pyrazin or pyrido[2,3-b]pyrazin-3(4H)-one. In some embodiments, the B ring is quinoxalin-2(1H)-one. In some embodiments, the B ring is 1H-indole. In some embodiments, the B ring is 2H-indazole. In some embodiments, the B ring is 4,5,6,7-tetrahydro-2H-indazole. In some embodiments, the B ring is 3H-indol-3-one. In some embodiments, the B ring is 1,3-benzoxazolyl. In some embodiments, the B ring is 1,3-benzothiazole. In some embodiments, the B ring is 4,5,6,7-tetrahydro-1,3-benzothiazole. In some embodiments, the B ring is 1-benzofuran. In some embodiments, the C ring is [1,3]oxazolo[4,5-b]pyridine. In some embodiments, the B ring is imidazo[2,1-b][1,3]thiazole. In some embodiments, the B ring is 4H,5H,6H-cyclopenta[d][1,3]thiazole. In some embodiments, the C ring is 5H,6H,7H,8H-imidazo[1,2-a]pyridine. In some embodiments, the B ring is 2H,3H-imidazo[2,1-b][1,3]thiazole. In some embodiments, the B ring is imidazo[1,2-a]pyridine. In some embodiments, the B ring is pyrazolo[1,5-a]pyridine. In some embodiments, the B ring is imidazo[1,2-a]pyrazine. In some embodiments, the B ring is imidazo[1,2-a]pyrimidine. In some embodiments, the B ring is 4H-thieno[3,2-b]pyrrole. In some embodiments, the B ring is 1H-pyrrolo[2,3-b]pyridine, In some embodiments, the B ring is 1H-pyrrolo[3,2-b]pyridine. In some embodiments, the B ring is 7H-pyrrolo[2,3-d]pyrimidine. In some embodiments, the B ring is oxazolo[5,4-b]pyridine. In some embodiments, the B ring is thiazolo[5,4-b]pyridine. In some embodiments, the B ring is triazolyl. In some embodiments, the B ring is benzoxadiazole. In some embodiments, the B ring is benzo[c][1,2,5]oxadiazolyl. In some embodiments, the B ring is 1H-imidazo[4,5-b]pyridine. In some embodiments, the B ring is 3H-imidazo[4,5-c]pyridine. In some embodiments, the B ring is a $C_3$—C cycloalkyl. In some embodiments, the B ring is $C_3$-$C_8$ heterocyclic ring. In some embodiments, the B ring is tetrahydropyran. In some embodiments, the B ring is piperidine. In some embodiments, the B ring is 1-(piperidin-1-yl)ethanone. In some embodiments, the B ring is morpholine. In some embodiments, the B ring is thieno[3,2-c]pyridine. In some embodiments, the B ring is 1-methylpiperidine. In some embodiments, the B ring is tetrahydrothiophene 1,1-dioxide. In some embodiments, the B ring is indole. In some embodiments, the B ring is 1,3-dihydroisobenzofuran. In some embodiments, the B ring is benzofuran. In some embodiments, the B ring is cyclohexyl. In some embodiments, the B ring is 1,3-dihydroisobenzofuran.

In various embodiments, compound of formula I is substituted by $R_1$ and $R_2$. Single substituents can be present at the ortho, meta, or para positions.

In various embodiments, $R_1$ of formula I-V is H. In some embodiments, $R_1$ is F. In some embodiments, $R_1$ is Cl. In some embodiments, $R_1$ is Br. In some embodiments, $R_1$ is I. In some embodiments, $R_1$ is OH. In some embodiments, $R_1$ is SH. In some embodiments, $R_1$ is $R_8$—OH. In some embodiments, $R_1$ is $CH_2$—OH. In some embodiments, $R_1$ is $R_8$—SH. In some embodiments, $R_1$ is —$R_8$—O—$R_{10}$. In some embodiments, $R_1$ is —$CH_2$—O—$CH_3$. In other embodiments, $R_1$ is $C_1$-$C_5$ linear or branched haloalkyl. In other embodiments, $R_1$ is $CF_3$. In other embodiments, $R_1$ is $CF_2CH_3$. In other embodiments, $R_1$ is $CF_2CH_2CH_3$. In other embodiments, $R_1$ is $CH_2CH_2CF_3$. In other embodiments, $R_1$ is $CF_2CH(CH_3)_2$. In other embodiments, $R_1$ is $CF(CH_3)$—$CH(CH_3)_2$. In other embodiments, $R_1$ is $CD_3$. In other embodiments, $R_1$ is $OCD_3$. In some embodiments, $R_1$ is CN. In some embodiments, $R_1$ is $NO_2$. In some embodiments, $R_1$ is —$CH_2CN$. In some embodiments, $R_1$ is —$R_8CN$. In some embodiments, $R_1$ is $NH_2$. In some embodiments, $R_1$ is NHR. In some embodiments, $R_1$ is $N(R)_2$. In some embodiments, $R_1$ is $R_8$—$N(R_{10})(R_{11})$. In other embodiments, $R_1$ is $CH_2$—$NH_2$. In some embodiments, $R_1$ is $CH_2$—$N(CH_3)_2$. In other embodiments, $R_1$ is $R_9$—$R_8$—$N(R_{10})(R_{11})$. In other embodiments, $R_1$ is C≡C—$CH_2$—$NH_2$. In other embodiments, $R_1$ is $B(OH)_2$. In some embodiments, $R_1$ is —OC(O)$CF_3$. In some embodiments, $R_1$ is —$OCH_2Ph$. In some embodiments, $R_1$ is NHC(O)—$R_{10}$. In some embodiments, $R_1$ is NHC(O)$CH_3$. In some embodiments, $R_1$ is NHCO—$N(R_{10})(R_{11})$. In some embodiments, $R_1$ is NHC(O)N($CH_3$)$_2$. In some embodiments, $R_1$ is COOH. In some embodiments, $R_1$ is —C(O)Ph. In some embodiments, $R_1$ is C(O)O—$R_{10}$. In some embodiments, $R_1$ is C(O)O—$CH_3$. In some embodiments, $R_1$ is C(O)—$R_{10}$. In some embodiments, $R_1$ is C(O)—$CH_3$. In some embodiments, $R_1$ is C(O)O—CH($CH_3$)$_2$. In some embodiments, $R_1$ is C(O)O—$CH_2CH_3$). In some embodiments, $R_1$ is $R_8$—C(O)—$R_{10}$. In some embodiments, $R_1$ is $CH_2C(O)CH_3$). In some embodiments, $R_1$ is C(O)H. In some embodiments, $R_1$ is C(O)—$R_{10}$. In some embodiments, $R_1$ is C(O)—$CH_3$. In some embodiments, $R_1$ is C(O)—$CH_2CH_3$. In some embodiments, $R_1$ is C(O)—$CH_2CH_2CH_3$). In some embodiments, $R_1$ is $C_1$-$C_5$ linear or branched C(O)-haloalkyl. In some embodiments, $R_1$ is C(O)—$CF_3$. In some embodiments, $R_1$ is —C(O)$NH_2$. In some embodiments, $R_1$ is C(O)NHR. In some embodiments, $R_1$ is C(O)N($R_{10}$)($R_{11}$). In some embodiments, $R_1$ is C(O)N($CH_3$)$_2$. In some embodiments, $R_1$ is $SO_2R$. In some embodiments, $R_1$ is $SO_2N(R_{10})(R_{11})$. In some embodiments, $R_1$ is $SO_2N(CH_3)_2$. In some embodiments, $R_1$ is $C_1$-$C_5$ linear or branched, substituted or unsubstituted alkyl. In some embodiments, $R_1$ is methyl, 2,3, or 4-$CH_2$—$C_6H_4$—Cl, ethyl, propyl, iso-propyl, t-Bu, iso-butyl, pentyl, benzyl, or C(CH$_3$)(OH)Ph, each represents a separate embodiment according to this invention. In some embodiments, R$_1$ is C$_1$-C$_5$ linear or branched haloalkyl. In other embodiments, R$_1$ is CF$_2$CH$_3$. In other embodiments, R$_1$ is CH$_2$CF$_3$. In other embodiments, R$_1$ is CF$_2$CH$_2$CH$_3$. In other embodiments, R$_1$ is CF$_3$. In other embodiments, R$_1$ is CF$_2$CH$_2$CH$_3$. In other embodiments, R$_1$ is CH$_2$CH$_2$CF$_3$. In other embodiments, R$_1$ is CF$_2$CH(CH$_3$)$_2$. In other embodiments, R$_1$ is CF(CH$_3$)—CH(CH$_3$)$_2$. In some embodiments, R$_1$ is C$_1$-C$_5$ linear, branched or cyclic alkoxy. In some embodiments, R$_1$ is methoxy, ethoxy, propoxy, isopropoxy or O—CH$_2$-cyclopropyl, O-cyclobutyl, O-cyclopentyl, O-cyclohexyl, 1-butoxy, 2-butoxy, O-tBu, each represents a separate embodiment according to this invention. In other embodiments, R$_1$ is C$_1$-C$_5$ linear, branched or cyclic alkoxy wherein at least one methylene group (CH$_2$) in the alkoxy is replaced with an oxygen atom (O). In some embodiments, R$_1$ is O-1-oxacyclobutyl, O-2-oxacyclobutyl, each represents a separate embodiment according to this invention. In some embodiments, R$_1$ is C$_1$-C$_5$ linear or branched thioalkoxy. In some embodiments, R$_1$ is C$_1$-C$_5$ linear or branched haloalkoxy. In some embodiments, R$_1$ is OCF$_3$. In some embodiments, R$_1$ is OCHF$_2$. In some embodiments, R$_1$ is C$_1$-C$_5$ linear or branched alkoxyalkyl. In some embodiments, R$_1$ is substituted or unsubstituted C$_3$-C$_8$ cycloalkyl. In some embodiments, R$_1$ is cyclopropyl. In some embodiments, R$_1$ is cyclopentyl. In some embodiments, R$_1$ is substituted or unsubstituted C$_3$-C$_8$ heterocyclic ring. In some embodiments, R$_1$ is thiophene, oxazole, oxadiazole, imidazole, furane, triazole, tetrazole, pyridine (2, 3, or 4-pyridine), pyrimidine, pyrazine, 1 or 2-oxacyclobutane, indole, protonated or deprotonated pyridine oxide, 3-methyl-4H-1,2,4-triazole, 5-methyl-1,2,4-oxadiazole, each represents a separate embodiment according to this invention. In some embodiments, R is methyl substituted oxazole. In some embodiments, R is methyl substituted oxadiazole. In some embodiments, R$_1$ is methyl substituted imidazole. In other embodiments, R$_1$ is thiophene. In other embodiments, R$_1$ is triazole. In other embodiments, R$_1$ is tetrazole. In some embodiments, R is substituted aryl. In some embodiments, R$_1$ is phenyl. In some embodiments, substitutions include: F, Cl, Br, I, C$_1$-C$_5$ linear or branched alkyl (e.g. methyl, ethyl), OH, alkoxy, N(R)$_2$, CF$_3$, phenyl, halophenyl, (benzyloxy)phenyl, CN, NO$_2$ or any combination thereof. In some embodiments, R$_1$ is CH(CF$_3$)(NH—R$_{10}$). In some embodiments, R$_1$ is 2,3, or 4 bromophenyl, each is a separate embodiment according to this invention. In other embodiments, substitutions include: F, Cl, Br, I, C$_1$-C$_5$ linear or branched alkyl (e.g. methyl, ethyl), OH, alkoxy, N(R)$_2$, CF$_3$, aryl, phenyl, halophenyl, (benzyloxy)phenyl, CN, NO$_2$ or any combination thereof; each is a separate embodiment according to this invention.

In some embodiments, R$_1$ and R$_2$ are joint together to form a 5 or 6 membered substituted or unsubstituted, aliphatic or aromatic, carbocyclic or heterocyclic ring. In some embodiments, R$_1$ and R$_2$ are joined together to form a 5 or 6 membered heterocyclic ring. In some embodiments, R$_1$ and R$_2$ are joined together to form a [1,3]dioxole ring. In some embodiments, R$_1$ and R$_2$ are joined together to form a furan-2(3H)-one ring. In some embodiments, R$_1$ and R$_2$ are joint together to form a benzene ring. In some embodiments, R$_1$ and R$_2$ are joined together to form a pyridine ring. In some embodiments, R$_1$ and R$_2$ are joined together to form a morpholine ring. In some embodiments, R$_1$ and R$_2$ are joined together to form a piperazine ring. In some embodiments, R$_1$ and R$_2$ are joined together to form an imidazole ring. In some embodiments, R$_1$ and R$_2$ are joined together to form a pyrrole ring. In some embodiments, R$_1$ and R$_2$ are joined together to form a cyclohexene ring. In some embodiments, R$_1$ and R$_2$ are joined together to form a pyrazine ring. In some embodiments, R$_1$ and R$_2$ are joint together to form a pyrrol ring.

In various embodiments, R$_2$ of formula I-V is H. In some embodiments, R$_2$ is F. In some embodiments, R$_2$ is Cl. In some embodiments, R$_2$ is Br. In some embodiments, R$_2$ is I. In some embodiments, R$_2$ is OH. In some embodiments, R$_2$ is SH. In some embodiments, R$_2$ is R$_8$—OH. In some embodiments, R$_2$ is CH$_2$—OH. In some embodiments, R$_2$ is R$_8$—SH. In some embodiments, R$_1$ is —R$_8$—O—R$_{10}$. In some embodiments, R$_2$ is —CH$_2$—O—CH$_3$. In other embodiments, R$_2$ is C$_1$-C$_5$ linear or branched haloalkyl. In other embodiments, R$_2$ is CF$_2$CH$_3$. In other embodiments, R$_2$ is CF$_2$CH$_3$. In other embodiments, R$_2$ is CH$_2$CF$_3$. In other embodiments, R$_2$ is CF$_2$CH$_2$CH$_3$. In other embodiments, R$_2$ is CF$_3$. In other embodiments, R$_2$ is CF$_2$CH$_2$CH$_3$. In other embodiments, R$_2$ is CH$_2$CH$_2$CF$_3$. In other embodiments, R$_2$ is CF$_2$CH(CH$_3$)$_2$. In other embodiments, R$_2$ is CF(CH$_3$)—CH(CH$_3$)$_2$. In other embodiments, R$_2$ is CD$_3$. In other embodiments, R$_2$ is OCD$_3$. In some embodiments, R$_2$ is CN. In some embodiments, R$_2$ is NO$_2$. In some embodiments, R$_2$ is —CH$_2$CN. In some embodiments, R$_2$ is —R$_8$CN. In some embodiments, R$_2$ is NH$_2$. In some embodiments, R$_2$ is NHR. In some embodiments, R$_2$ is N(R)$_2$. In some embodiments, R$_2$ is R$_8$—N(R$_{10}$)(R$_{11}$). In other embodiments, R$_2$ is CH$_2$—NH$_2$. In some embodiments, R$_2$ is CH$_2$—N(CH$_3$)$_2$. In other embodiments, R$_2$ is R$_9$—R$_8$—N(R$_{10}$)(R$_{11}$). In other embodiments, R$_2$ is C≡C—CH$_2$—NH$_2$. In other embodiments, R$_2$ is B(OH)$_2$. In some embodiments, R$_2$ is —OC(O)CF$_3$. In some embodiments, R$_2$ is —OCH$_2$Ph. In some embodiments, R$_2$ is NHC(O)—R$_{10}$. In some embodiments, R$_2$ is NHC(O)CH$_3$. In some embodiments, R$_2$ is NHCO—N(R$_{10}$)(R$_{11}$). In some embodiments, R$_2$ is NHC(O)N(CH$_3$)$_2$. In some embodiments, R$_2$ is COOH. In some embodiments, R$_2$ is —C(O)Ph. In some embodiments, R$_2$ is C(O)O—R$_{10}$. In some embodiments, R$_2$ is C(O)O—CH(CH$_3$)$_2$. In some embodiments, R$_2$ is C(O)O—CH$_3$. In some embodiments, R$_2$ is C(O)O—CH$_2$CH$_3$). In some embodiments, R$_2$ is R$_8$—C(O)—R$_{10}$. In some embodiments, R$_2$ is CH$_2$C(O)CH$_3$). In some embodiments, R$_2$ is C(O)H. In some embodiments, R$_2$ is C(O)—R$_{10}$. In some embodiments, R$_2$ is C(O)—CH$_3$. In some embodiments, R$_2$ is C(O)—CH$_2$CH$_3$. In some embodiments, R$_2$ is C(O)—CH$_2$CH$_2$CH$_3$). In some embodiments, R$_2$ is C$_1$-C$_5$ linear or branched C(O)-haloalkyl. In some embodiments, R$_2$ is C(O)—CF$_3$. In some embodiments, R$_2$ is —C(O)NH$_2$. In some embodiments, R$_2$ is C(O)NHR. In some embodiments, R$_2$ is C(O)N(R$_{10}$)(R$_{11}$). In some embodiments, R$_2$ is C(O)N(CH$_3$)$_2$. In some embodiments, R$_2$ is SO$_2$R. In some embodiments, R$_2$ is SO$_2$N(R$_{10}$)(R$_{11}$). In some embodiments, R$_2$ is SO$_2$N(CH$_3$)$_2$. In some embodiments, R$_2$ is C$_1$-C$_5$ linear or branched, substituted or unsubstituted alkyl. In some embodiments, R$_2$ is methyl, 2, 3, or 4-CH$_2$—C$_6$H$_4$—Cl, ethyl, propyl, iso-propyl, t-Bu, iso-butyl, pentyl, benzyl or C(CH$_3$)(OH)Ph; each represents a separate embodiment according to this invention. In some embodiments, R$_2$ is C$_1$-C$_5$ linear or branched haloalkyl. In other embodiments, R$_2$ is CF$_2$CH$_3$. In other embodiments, R$_2$ is CH$_2$CF$_3$. In other embodiments, R$_2$ is CF$_2$CH$_2$CH$_3$. In other embodiments, R$_2$ is CF$_3$. In other embodiments, R$_2$ is CF$_2$CH$_2$CH$_3$. In other embodiments, R$_2$ is CH$_2$CH$_2$CF$_3$. In other embodiments, R$_2$ is CF$_2$CH(CH$_3$)$_2$. In other embodiments, R$_2$ is CF(CH$_3$)—CH(CH$_3$)$_2$. In some embodiments, R$_2$ is C$_1$-C$_5$ linear, branched or cyclic alkoxy. In some embodiments, R$_2$ is methoxy, ethoxy, propoxy, isopropoxy or O—CH$_2$-cyclopropyl, O-cyclobutyl, O-cyclopentyl, O-cyclohexyl, O-1-oxacyclobutyl, O-2-oxacyclobutyl, 1-butoxy, 2-butoxy, O-tBu, each represents a separate embodiment according to this invention. In other embodiments, $R_2$ is $C_1$-$C_5$ linear, branched or cyclic alkoxy wherein at least one methylene group ($CH_2$) in the alkoxy is replaced with an oxygen atom (O). In some embodiments, $R_2$ is O-1-oxacyclobutyl or O-2-oxacyclobutyl, each represents a separate embodiment according to this invention. In some embodiments, $R_2$ is $C_1$-$C_5$ linear or branched thioalkoxy. In some embodiments, $R_2$ is $C_1$-$C_5$ linear or branched haloalkoxy. In some embodiments, $R_2$ is $OCF_3$. In some embodiments, $R_2$ is $OCHF_2$. In some embodiments, $R_2$ is $C_1$-$C_5$ linear or branched alkoxyalkyl. In some embodiments, $R_2$ is substituted or unsubstituted $C_3$-$C_8$ cycloalkyl. In some embodiments, $R_2$ is cyclopropyl. In some embodiments, $R_2$ is cyclopentyl. In some embodiments, $R_2$ is substituted or unsubstituted $C_3$-$C_8$ heterocyclic ring. In some embodiments, $R_2$ is thiophene, oxazole, oxadiazole, imidazole, furane, triazole, tetrazole, pyridine (2, 3, or 4-pyridine), pyrimidine, pyrazine, 1 or 2-oxacyclobutane, indole, protonated or deprotonated pyridine oxide, 3-methyl-4H-1,2,4-triazole, 5-methyl-1,2,4-oxadiazole, each represents a separate embodiment according to this invention. In some embodiments, $R_2$ is methyl substituted oxazole. In some embodiments, $R_2$ is methyl substituted oxadiazole. In some embodiments, $R_2$ is methyl substituted imidazole. In some embodiments, $R_2$ is thiophene. In some embodiments, $R_2$ is triazole. In other embodiments, $R_2$ is tetrazole. In some embodiments, $R_2$ is substituted aryl. In some embodiments, $R_2$ is phenyl. In some embodiments, substitutions include: F, Cl, Br, I, $C_1$-$C_5$ linear or branched alkyl (e.g. methyl, ethyl), OH, alkoxy, $N(R)_2$, $CF_3$, phenyl, halophenyl, (benzyloxy)phenyl, CN, $NO_2$ or any combination thereof. In some embodiments, $R_2$ is $CH(CF_3)(NH-R_{10})$. In some embodiments, $R_2$ is 2, 3, or 4 bromophenyl, each represents a separate embodiment according to this invention. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_1$ and $R_2$ of compound of formula I-V are both H. In some embodiments, at least one of $R_1$ and $R_2$ is not H.

In various embodiments, compound of formula I-V is substituted by $R_3$ and $R_4$. Single substituents can be present at the ortho, meta, or para positions.

In various embodiments, $R_3$ of formula I-V is H. In some embodiments, $R_3$ is F. In some embodiments, $R_3$ is Cl. In some embodiments, $R_3$ is Br. In some embodiments, $R_3$ is I. In some embodiments, $R_3$ is OH. In some embodiments, $R_3$ is SH. In some embodiments, $R_3$ is $R_8$—OH. In some embodiments, $R_3$ is $CH_2$—OH. In some embodiments, $R_3$ is $R_8$—SH. In some embodiments, $R_3$ is —$R_8$—O—$R_{10}$. In some embodiments, $R_3$ is $CH_2$—O—$CH_3$. In other embodiments, $R_3$ is $C_1$-$C_5$ linear or branched haloalkyl. In other embodiments, $R_3$ is $C_2$-$C_5$ linear or branched haloalkyl. In other embodiments, $R_3$ is $C_3$-$C_8$ linear or branched haloalkyl. In other embodiments, $R_3$ is $C_2$-$C_6$ linear or branched haloalkyl. In other embodiments, $R_3$ is $C_2$-$C_7$ linear or branched haloalkyl. In other embodiments, $R_3$ is $CF_2CH_3$. In other embodiments, $R_3$ is $CH_2CF_3$. In other embodiments, $R_3$ is $CF_2CH_2CH_3$. In other embodiments, $R_3$ is $CF_3$. In other embodiments, $R_3$ is $CF_2CH_2CH_3$. In other embodiments, $R_3$ is $CH_2CH_2CF_3$. In other embodiments, $R_3$ is $CF_2CH(CH_3)_2$. In other embodiments, $R_3$ is $CF(CH_3)$—$CH(CH_3)_2$. In other embodiments, $R_3$ is $CD_3$. In other embodiments, $R_3$ is $OCD_3$. In some embodiments, $R_3$ is CN. In some embodiments, $R_3$ is $NO_2$. In some embodiments, $R_3$ is —$CH_2CN$. In some embodiments, $R_3$ is —$R_8CN$. In some embodiments, $R_3$ is $NH_2$. In some embodiments, $R_3$ is NHR. In some embodiments, $R_3$ is $N(R)_2$. In some embodiments, $R_3$ is $R_8$—$N(R_{10})(R_{11})$. In some embodiments, $R_3$ is $CH_2$—$NH_2$. In some embodiments, $R_3$ is $CH_2$—$N(CH_3)_2$. In other embodiments, $R_3$ is $R_9$—$R_8$—$N(R_{10})(R_{11})$. In other embodiments, $R_3$ is C≡C—$CH_2$—$NH_2$. In other embodiments, $R_3$ is $B(OH)_2$. In some embodiments, $R_3$ is —OC(O)$CF_3$. In some embodiments, $R_3$ is —$OCH_2Ph$. In some embodiments, $R_3$ is —NHCO—$R_{10}$. In some embodiments, $R_3$ is $NHC(O)CH_3$. In some embodiments, $R_3$ is NHCO—$N(R_{10})(R_{11})$. In some embodiments, $R_3$ is $NHC(O)N(CH_3)_2$. In some embodiments, $R_3$ is COOH. In some embodiments, $R_3$ is —C(O)Ph. In some embodiments, $R_3$ is C(O)O—$R_{10}$. In some embodiments, $R_3$ is C(O)O—$CH_3$. In some embodiments, $R_3$ is C(O)O—$CH_2CH_3$. In some embodiments, $R_3$ is $R_8$—C(O)—$R_{10}$. In some embodiments, $R_3$ is $CH_2C(O)CH_3$. In some embodiments, $R_3$ is C(O)H. In some embodiments, $R_3$ is $C_1$-$C_5$ linear or branched C(O)—$R_{10}$. In some embodiments, $R_3$ is C(O)—$CH_3$. In some embodiments, $R_3$ is C(O)—$CH_2CH_3$. In some embodiments, $R_3$ is C(O)—$CH_2CH_2CH_3$. In some embodiments, $R_3$ is $C_1$-$C_5$ linear or branched C(O)-haloalkyl. In some embodiments, $R_3$ is C(O)—$CF_3$. In some embodiments, $R_3$ is —C(O)$NH_2$. In some embodiments, $R_3$ is C(O)NHR. In some embodiments, $R_3$ is $C(O)N(R_{10})(R_1)$. In some embodiments, $R_3$ is $C(O)N(CH_3)_2$. In some embodiments, $R_3$ is $SO_2R$. In some embodiments, $R_3$ is $SO_2N(R_{10})(R_{11})$. In some embodiments, $R_3$ is $SO_2N(CH_3)_2$. In some embodiments, $R_3$ is $C_1$-$C_5$ linear or branched, substituted or unsubstituted alkyl. In some embodiments, $R_3$ is methyl, C(OH)($CH_3$)(Ph), ethyl, propyl, iso-propyl, t-Bu, iso-butyl, pentyl, benzyl or C($CH_3$)(OH)Ph; each represents a separate embodiment of this invention. In some embodiments, $R_3$ is $C_1$-$C_5$ linear or branched haloalkyl. In other embodiments, $R_3$ is $CF_3$. In other embodiments, $R_3$ is $CF_2CH_2CH_3$. In other embodiments, $R_3$ is $CH_2CH_2CF_3$. In other embodiments, $R_3$ is $CF_2CH(CH_3)_2$. In other embodiments, $R_3$ is $CF(CH_3)$—$CH(CH_3)_2$. In some embodiments, $R_3$ is $C_1$-$C_5$ linear, branched or cyclic alkoxy. In some embodiments, $R_3$ is methoxy, ethoxy, propoxy, isopropoxy, O—$CH_2$-cyclopropyl; each represents a separate embodiment of this invention. In some embodiments, $R_3$ is $C_1$-$C_5$ linear or branched thioalkoxy. In some embodiments, $R_3$ is $C_1$-$C_5$ linear or branched haloalkoxy. In some embodiments, $R_3$ is $C_1$-$C_5$ linear or branched alkoxyalkyl. In some embodiments, $R_3$ is substituted or unsubstituted $C_3$-$C_8$ cycloalkyl. In some embodiments, $R_3$ is cyclopropyl. In some embodiments, $R_3$ is cyclopentyl. In some embodiments, $R_3$ is substituted or unsubstituted $C_3$-$C_8$ heterocyclic ring. In some embodiments, $R_3$ is thiophene, oxazole, isoxazole, imidazole, furane, triazole, pyridine (2, 3, or 4-pyridine), pyrimidine, pyrazine, oxacyclobutane (1 or 2-oxacyclobutane), indole, 3-methyl-4H-1,2,4-triazole, 5-methyl-1,2,4-oxadiazole; each represents a separate embodiment of this invention. In some embodiments, $R_3$ is substituted or unsubstituted aryl. In some embodiments, $R_3$ is phenyl. In some embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof. In some embodiments, $R_3$ is $CH(CF_3)(NH-R_{10})$.

In some embodiments, $R_3$ and $R_4$ are joint together to form a 5 or 6 membered substituted or unsubstituted, aliphatic or aromatic, carbocyclic or heterocyclic ring. In some embodiments, $R_3$ and $R_4$ are joint together to form a 5 or 6 membered carbocyclic ring. In some embodiments, $R_3$ and $R_4$ are joined together to form a 5 or 6 membered heterocyclic ring. In some embodiments, $R_3$ and $R_4$ are joined together to form a dioxole ring. [1,3]dioxole ring. In some embodiments, $R_3$ and $R_4$ are joined together to form a dihydrofuran-2(3H)-one ring. In some embodiments, $R_3$ and $R_4$ are joined together to form a furan-2(3H)-one ring. In some embodiments, $R_3$ and $R_4$ are joined together to form a benzene ring. In some embodiments, $R_3$ and $R_4$ are joint together to form an imidazole ring. In some embodiments, $R_3$ and $R_4$ are joined together to form a pyridine ring. In some embodiments, $R_3$ and $R_4$ are joined together to form a pyrrole ring. In some embodiments, $R_3$ and $R_4$ are joined together to form a cyclohexene ring. In some embodiments, $R_3$ and $R_4$ are joined together to form a cyclopentene ring. In some embodiments, $R_4$ and $R_3$ are joint together to form a dioxepine ring.

In various embodiments, $R_4$ of formula I-IV is H. In some embodiments, $R_4$ is F. In some embodiments, $R_4$ is Cl. In some embodiments, $R_4$ is Br. In some embodiments, $R_4$ is I. In some embodiments, $R_4$ is OH. In some embodiments, $R_4$ is SH. In some embodiments, $R_4$ is $R_8$—OH. In some embodiments, $R_4$ is $CH_2$—OH. In some embodiments, $R_4$ is $R_8$—SH. In some embodiments, $R_4$ is —$R_8$—O—$R_{10}$. In some embodiments, $R_4$ is $CH_2$—O—$CH_3$. In other embodiments, $R_4$ is $CD_3$. In other embodiments, $R_4$ is $OCD_3$. In some embodiments, $R_4$ is CN. In some embodiments, $R_4$ is $NO_2$. In some embodiments, $R_4$ is —$CH_2CN$. In some embodiments, $R_4$ is —$R_8CN$. In some embodiments, $R_4$ is $NH_2$. In some embodiments, $R_4$ is NHR. In some embodiments, $R_4$ is $N(R)_2$. In some embodiments, $R_4$ is $R_8$—N$(R_{10})(R_{11})$. In other embodiments, $R_4$ is $CH_2$—$NH_2$. In some embodiments, $R_4$ is $CH_2$—$N(CH_3)_2$. In other embodiments, $R_4$ is $R_9$—$R_8$—$N(R_{10})(R_{11})$. In other embodiments, $R_4$ is C≡C—$CH_2$—$NH_2$. In other embodiments, $R_4$ is $B(OH)_2$. In some embodiments, $R_4$ is —$OC(O)CF_3$. In some embodiments, $R_4$ is —$OCH_2Ph$. In some embodiments, $R_4$ is —NHCO—$R_{10}$. In some embodiments, $R_4$ is NHC(O)$CH_3$). In some embodiments, $R_4$ is NHCO—$N(R_{10})(R_{11})$. In some embodiments, $R_4$ is NHC(O)$N(CH_3)_2$. In some embodiments, $R_4$ is COOH. In some embodiments, $R_4$ is —C(O)Ph. In some embodiments, $R_4$ is C(O)O—$R_{10}$. In some embodiments, $R_4$ is C(O)O—$CH_3$. In some embodiments, $R_4$ is C(O)O—$CH_2CH_3$. In some embodiments, $R_4$ is $R_8$—C(O)—$R_{10}$. In some embodiments, $R_4$ is $CH_2C(O)CH_3$. In some embodiments, $R_4$ is C(O)H. In some embodiments, $R_4$ is $C_1$-$C_5$ linear or branched C(O)—$R_{10}$. In some embodiments, $R_4$ is C(O)—$CH_3$. In some embodiments, $R_4$ is C(O)—$CH_2CH_3$. In some embodiments, $R_4$ is C(O)—$CH_2CH_2CH_3$. In some embodiments, $R_4$ is $C_1$-$C_5$ linear or branched C(O)-haloalkyl. In some embodiments, $R_4$ is C(O)—$CF_3$. In some embodiments, $R_4$ is —C(O)$NH_2$. In some embodiments, $R_4$ is C(O)NHR. In some embodiments, $R_4$ is C(O)$N(R_{10})(R_{11})$. In some embodiments, $R_4$ is C(O)$N(CH_3)_2$. In some embodiments, $R_4$ is $SO_2R$. In some embodiments, $R_4$ is $SO_2N(R_{10})(R_{11})$. In some embodiments, $R_4$ is $SO_2N(CH_3)_2$. In some embodiments, $R_4$ is $C_1$-$C_5$ linear or branched, substituted or unsubstituted alkyl. In some embodiments, $R_4$ is methyl, $C(OH)(CH_3)(Ph)$, ethyl, propyl, iso-propyl, t-Bu, iso-butyl, pentyl, benzyl or $C(CH_3)(OH)Ph$; each represents a separate embodiment of this invention. In some embodiments, $R_4$ is $C_1$-$C_5$ linear or branched haloalkyl. In other embodiments, $R_4$ is $C_2$-$C_5$ linear or branched haloalkyl. In other embodiments, $R_4$ is $C_3$-$C_8$ linear or branched haloalkyl. In other embodiments, $R_4$ is $C_2$-$C_6$ linear or branched haloalkyl. In other embodiments, $R_4$ is $C_2$-$C_7$ linear or branched haloalkyl. In other embodiments, $R_4$ is $CF_2CH_3$. In other embodiments, $R_4$ is $CH_2CF_3$. In other embodiments, $R_4$ is $CF_2CH_2CH_3$. In other embodiments, $R_4$ is $CF_3$. In other embodiments, $R_4$ is $CF_2CH_2CH_3$. In other embodiments, $R_4$ is $CH_2CH_2CF_3$. In other embodiments, $R_4$ is $CF_2CH(CH_3)_2$. In other embodiments, $R_4$ is $CF(CH_3)$—$CH(CH_3)_2$. In some embodiments, $R_4$ is $C_1$-$C_5$ linear, branched or cyclic alkoxy. In some embodiments, $R_4$ is methoxy, ethoxy, propoxy, isopropoxy, O—$CH_2$-cyclopropyl; each represents a separate embodiment of this invention. In some embodiments, $R_4$ is $C_1$-$C_5$ linear or branched thioalkoxy. In some embodiments, $R_4$ is $C_1$-$C_5$ linear or branched haloalkoxy. In some embodiments, $R_4$ is $C_1$-$C_5$ linear or branched alkoxyalkyl. In some embodiments, $R_4$ is substituted or unsubstituted $C_3$-$C_8$ cycloalkyl. In some embodiments, $R_4$ is cyclopropyl. In some embodiments, $R_4$ is cyclopentyl. In some embodiments, $R_4$ is substituted or unsubstituted $C_3$-$C_8$ heterocyclic ring. In some embodiments, $R_4$ is thiophene, oxazole, isoxazole, imidazole, furane, triazole, pyridine (2, 3, or 4-pyridine), pyrimidine, pyrazine, oxacyclobutane (1 or 2-oxacyclobutane), indole, 3-methyl-4H-1,2,4-triazole, 5-methyl-1,2,4-oxadiazole; each represents a separate embodiment of this invention. In some embodiments, $R_4$ is substituted or unsubstituted aryl. In some embodiments, $R_4$ is phenyl. In some embodiments, substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof. In some embodiments, $R_4$ is $CH(CF_3)(NH$—$R_{10})$.

In some embodiments, $R_3$ and $R_4$ of compound of formula I-V are both H. In some embodiments, at least one of $R_3$ and $R_4$ is not H. In some embodiments, if $R_3$ is H, then $R_4$ is not H. In some embodiments, if $R_4$ is H, then $R_3$ is not H.

In various embodiments, $R_5$ of compound of formula I-IV is H. In some embodiments, $R_5$ is $C_1$-$C_5$ linear or branched, substituted or unsubstituted alkyl. In some embodiments, $R_5$ is methyl, $CH_2SH$, ethyl, iso-propyl; each represent a separate embodiment of this invention. In some embodiments, $R_5$ is $C_1$-$C_5$ linear or branched haloalkyl. In other embodiments, $R_5$ is $CF_2CH_3$. In other embodiments, $R_5$ is $CH_2CF_3$. In other embodiments, $R_5$ is $CF_2CH_2CH_3$. In other embodiments, $R_5$ is $CF_3$. In other embodiments, $R_5$ is $CF_2CH_2CH_3$. In other embodiments, $R_5$ is $CH_2CH_2CF_3$. In other embodiments, $R_5$ is $CF_2CH(CH_3)_2$. In other embodiments, $R_5$ is $CF(CH_3)$—$CH(CH_3)_2$. In some embodiments, $R_5$ is $R_8$-aryl. In some embodiments, $R_5$ is $CH_2$-Ph. In some embodiments, $R_5$ is substituted or unsubstituted aryl. In some embodiments, $R_5$ is phenyl. In some embodiments, $R_5$ is substituted or unsubstituted heteroaryl. In some embodiments, $R_5$ is pyridine. In some embodiments, $R_5$ is 2-pyridine. In some embodiments, $R_5$ is 3-pyridine. In some embodiments, $R_5$ is 4-pyridine. In some embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof.

In various embodiments, n of compound of formula I-II is 0. In some embodiments, n is 0 or 1. In some embodiments, n is between 1 and 3. In some embodiments, n is between 1 and 4. In some embodiments, n is between 0 and 2. In some embodiments, n is between 0 and 3. In some embodiments, n is between 0 and 4. In some embodiments, n is 1. In some embodiments, n is 2. In some embodiments, n is 3. In some embodiments, n is 4.

In various embodiments, m of compound of formula I-II is 0. In some embodiments, m is 0 or 1. In some embodiments, m is between 1 and 3. In some embodiments, m is between 1 and 4. In some embodiments, m is between 0 and 2. In some embodiments, m is between 0 and 3. In some embodiments, m is between 0 and 4. In some embodiments, m is 1. In some embodiments, m is 2. In some embodiments, m is 3. In some embodiments, m is 4.

In various embodiments, l of compound of formula I-II is 0. In some embodiments, l is 0 or 1. In some embodiments, l is between 1 and 3. In some embodiments, l is between 1 and 4. In some embodiments, l is between 0 and 2. In some embodiments, l is between 0 and 3. In some embodiments, l is between 0 and 4. In some embodiments, l is 1. In some embodiments, l is 2. In some embodiments, l is 3. In some embodiments, l is 4.

In various embodiments, k of compound of formula I-II is 0. In some embodiments, k is 0 or 1. In some embodiments, k is between 1 and 3. In some embodiments, k is between 1 and 4. In some embodiments, k is between 0 and 2. In some embodiments, k is between 0 and 3. In some embodiments, k is between 0 and 4. In some embodiments, k is 1. In some embodiments, k is 2. In some embodiments, k is 3. In some embodiments, k is 4.

It is understood that for heterocyclic rings, n, m, l and/or k are limited to the number of available positions for substitution, i.e. to the number of CH or NH groups minus one. Accordingly, if A and/or B rings are, for example, furanyl, thiophenyl or pyrrolyl, n, m, l and k are between 0 and 2; and if A and/or B rings are, for example, oxazolyl, imidazolyl or thiazolyl, n, m, l and k are either 0 or 1; and if A and/or B rings are, for example, oxadiazolyl or thiadiazolyl, n, m, l and k are 0.

In various embodiments, $R_6$ of compound of formula I-III is H. In some embodiments, $R_6$ is $C_1$-$C_5$ linear or branched alkyl. In some embodiments, $R_6$ is methyl. In some embodiments, $R_6$ is ethyl. In some embodiments, $R_6$ is C(O)R wherein R is $C_1$-$C_5$ linear or branched alkyl, $C_1$-$C_5$ linear or branched alkoxy, phenyl, aryl or heteroaryl. In some embodiments, $R_6$ is $S(O)_2R$ wherein R is $C_1$-$C_5$ linear or branched alkyl, $C_1$-$C_5$ linear or branched alkoxy, phenyl, aryl or heteroaryl.

In various embodiments, $R_8$ of compound of formula I-V is $CH_2$. In some embodiments, $R_8$ is $CH_2CH_2$. In some embodiments, $R_8$ is $CH_2CH_2CH_2$. In some embodiments, $R_8$ is $CH_2CH_2CH_2CH_2$.

In various embodiments, p is 1. In some embodiments, p is 2. In some embodiments, p is 3. In some embodiments, p is 4. In some embodiments, p is 5. In some embodiments, p is between 1 and 3. In some embodiments, p is between 1 and 5. In some embodiments, p is between 1 and 10.

In some embodiments, $R_9$ of compound of formula I-V is C≡C. In some embodiments, $R_9$ is C≡C—C≡C. In some embodiments, $R_9$ is CH=CH. In some embodiments, $R_9$ is CH=CH—CH=CH.

In some embodiments, q of compound of formula I-V is 2. In some embodiments, q is 4. In some embodiments, q is 6. In some embodiments, q is 8. In some embodiments, q is between 2 and 6.

In various embodiments, $R_{10}$ of compound of formula I-V is H. In some embodiments, $R_{10}$ is $C_1$-$C_5$ linear or branched alkyl. In some embodiments, $R_{10}$ is methyl. In some embodiments, $R_{10}$ is ethyl. In some embodiments, $R_{10}$ is propyl. In some embodiments, $R_{10}$ is isopropyl. In some embodiments, $R_{10}$ is butyl. In some embodiments, $R_{10}$ is isobutyl. In some embodiments, $R_{10}$ is t-butyl. In some embodiments, $R_{10}$ is cyclopropyl. In some embodiments, $R_{10}$ is pentyl. In some embodiments, $R_{10}$ is isopentyl. In some embodiments, $R_{10}$ is neopentyl. In some embodiments, $R_{10}$ is benzyl. In some embodiments, $R_{10}$ is C(O)R. In some embodiments, $R_{10}$ is $S(O)_2R$.

In various embodiments, $R_{11}$ of compound of formula I-V is H. In some embodiments, $R_{11}$ is $C_1$-$C_5$ linear or branched alkyl. In some embodiments, $R_{11}$ is methyl. In some embodiments, $R_{11}$ is ethyl. In some embodiments, $R_{10}$ is propyl. In some embodiments, $R_{11}$ is isopropyl. In some embodiments, $R_{11}$ is butyl. In some embodiments, $R_{11}$ is isobutyl. In some embodiments, $R_{11}$ is t-butyl. In some embodiments, $R_{11}$ is cyclopropyl. In some embodiments, $R_{11}$ is pentyl. In some embodiments, $R_{11}$ is isopentyl. In some embodiments, $R_{11}$ is neopentyl. In some embodiments, $R_{11}$ is benzyl. In some embodiments, $R_{11}$ is C(O)R. In some embodiments, $R_{11}$ is $S(O)_2R$.

In various embodiments, R of compound of formula I-V is H. In other embodiments, R is $C_1$-$C_5$ linear or branched alkyl. In other embodiments, R is methyl. In other embodiments, R is ethyl. In other embodiments, R is $C_1$-$C_5$ linear or branched alkoxy. In other embodiments, R is phenyl. In other embodiments, R is aryl. In other embodiments, R is heteroaryl. In other embodiments, two gem R substituents are joint together to form a 5 or 6 membered heterocyclic ring.

In various embodiments, $Q_1$ of compound of formula I-III is O. In other embodiments, $Q_1$ is S. In other embodiments, $Q_1$ is N—OH. In other embodiments, $Q_1$ is $CH_2$. In other embodiments, $Q_1$ is $C(R)_2$. In other embodiments, $Q_1$ is N—OMe.

In various embodiments, $Q_2$ of compound of formula I-III is O. In other embodiments, $Q_2$ is S. In other embodiments, $Q_2$ is N—OH. In other embodiments, $Q_2$ is $CH_2$. In other embodiments, $Q_2$ is $C(R)_2$. In other embodiments, $Q_2$ is N—OMe.

In various embodiments, $X_1$ of compound of formula II is C. In other embodiments, $X_1$ is N.

In various embodiments, $X_2$ of compound of formula II is C. In other embodiments, $X_2$ is N.

In various embodiments, $X_3$ of compound of formula II-V is C. In other embodiments, $X_3$ is N.

In various embodiments, $X_4$ of compound of formula II-IV is C. In other embodiments, $X_4$ is N.

In various embodiments, $X_5$ of compound of formula II is C. In other embodiments, $X_5$ is N.

In various embodiments, $X_6$ of compound of formula II-III is C. In other embodiments, $X_6$ is N.

In various embodiments, $X_7$ of compound of formula II-V is C. In other embodiments, $X_7$ is N.

In various embodiments, $X_8$ of compound of formula II-IV is C. In other embodiments, $X_8$ is N.

In various embodiments, $X_9$ of compound of formula II is C. In other embodiments, $X_9$ is N.

In various embodiments, $X_{10}$ of compound of formula II is C. In other embodiments, $X_{10}$ is N.

As used herein, "single or fused aromatic or heteroaromatic ring systems" can be any such ring, including but not limited to phenyl, naphthyl, pyridinyl, (2-, 3-, and 4-pyridinyl), quinolinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, quinolinyl, isoquinolinyl, 2,3-dihydroindenyl, indenyl, tetrahydronaphthyl, 3,4-dihydro-2H-benzo[b][1,4]dioxepine benzodioxolyl, benzo[d][1,3]dioxole, tetrahydronaphthyl, indolyl, 1H-indole, isoindolyl, anthracenyl, benzimidazolyl, 2,3-dihydro-1H-benzo[d]imidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, 1,2,3,4-tetrahydroquinoxaline, 1-(pyridin-1(2H)-yl)

ethanone, cinnolinyl, phthalazinyl, quinolinyl, isoquinolinyl, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, oxadiazolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, 3-methyl-4H-1,2,4-triazole, 5-methyl-1,2,4-oxadiazole, etc.

As used herein, the term "alkyl" can be any straight- or branched-chain alkyl group containing up to about 30 carbons unless otherwise specified. In various embodiments, an alkyl includes $C_1$-$C_5$ carbons. In some embodiments, an alkyl includes $C_1$-$C_6$ carbons. In some embodiments, an alkyl includes $C_1$-$C_8$ carbons. In some embodiments, an alkyl includes $C_1$-$C_{10}$ carbons. In some embodiments, an alkyl is a $C_1$-$C_{12}$ carbons. In some embodiments, an alkyl is a $C_1$-$C_{20}$ carbons. In some embodiments, branched alkyl is an alkyl substituted by alkyl side chains of 1 to 5 carbons. In various embodiments, the alkyl group may be unsubstituted. In some embodiments, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, N(alkyl)$_2$, —OC(O)$CF_3$, —OCH$_2$Ph, —NHCO-alkyl, —C(O)Ph, C(O)O-alkyl, C(O)H, —C(O)NH$_2$ or any combination thereof.

The alkyl group can be a sole substituent or it can be a component of a larger substituent, such as in an alkoxy, alkoxyalkyl, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, 2, 3, or 4-CH$_2$—C$_6$H$_4$—Cl, C(OH)(CH$_3$)(Ph), etc.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, indolyl, phenylmethyl, phenylethyl, phenylamino, phenylamido, 3-methyl-4H-1,2,4-triazolyl, 5-methyl-1,2,4-oxadiazolyl, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, phenyl, halophenyl, (benzyloxy)phenyl, CN, $NO_2$, —$CH_2CN$, $NH_2$, NH-alkyl, N(alkyl)$_2$, hydroxyl, —OC(O)$CF_3$, —OCH$_2$Ph, —NHCO-alkyl, COOH, —C(O)Ph, C(O)O— alkyl, C(O)H, —C(O)NH$_2$ or any combination thereof.

As used herein, the term "alkoxy" refers to an ether group substituted by an alkyl group as defined above. Alkoxy refers both to linear and to branched alkoxy groups. Nonlimiting examples of alkoxy groups are methoxy, ethoxy, propoxy, iso-propoxy, tert-butoxy.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are —N(Me)$_2$, —NHMe, —NH$_3$.

A "haloalkyl" group refers, in some embodiments, to an alkyl group as defined above, which is substituted by one or more halogen atoms, e.g. by F, Cl, Br or I. The term "haloalkyl" include but is not limited to fluoroalkyl, i.e., to an alkyl group bearing at least one fluorine atom. Nonlimiting examples of haloalkyl groups are $CF_3$, $CF_2CF_3$, $CF_2CH_3$, $CH_2CF_3$, $CF_2CH_2CH_3$, $CH_2CH_2CF_3$, $CF_2CH(CH_3)_2$ and $CF(CH_3)$—$CH(CH_3)_2$.

A "halophenyl" group refers, in some embodiments, to a phenyl substitutent which is substituted by one or more halogen atoms, e.g. by F, Cl, Br or I. In one embodiment, the halophenyl is 4-chlorophenyl.

An "alkoxyalkyl" group refers, in some embodiments, to an alkyl group as defined above, which is substituted by alkoxy group as defined above, e.g. by methoxy, ethoxy, propoxy, i-propoxy, t-butoxy etc. Nonlimiting examples of alkoxyalkyl groups are —CH$_2$—O—CH$_3$, —CH$_2$—O—CH(CH$_3$)$_2$, —CH$_2$—O—C(CH$_3$)$_3$, —CH$_2$—CH$_2$—O—CH$_3$, —CH$_2$—CH$_2$—O—CH(CH$_3$)$_2$, —CH$_2$—CH$_2$—O—C(CH$_3$)$_3$.

A "cycloalkyl" or "carbocyclic" group refers, In various embodiments, to a ring structure comprising carbon atoms as ring atoms, which may be either saturated or unsaturated, substituted or unsubstituted, single or fused. In some embodiments the cycloalkyl is a 3-10 membered ring. In some embodiments the cycloalkyl is a 3-12 membered ring. In some embodiments the cycloalkyl is a 6 membered ring. In some embodiments the cycloalkyl is a 5-7 membered ring. In some embodiments the cycloalkyl is a 3-8 membered ring. In some embodiments, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy) phenyl, —$CH_2CN$, $NH_2$, NH-alkyl, N(alkyl)$_2$, —OC(O)$CF_3$, —OCH$_2$Ph, —NHCO-alkyl, —C(O)Ph, C(O)O-alkyl, C(O)H, —C(O)NH$_2$ or any combination thereof. In some embodiments, the cycloalkyl ring may be fused to another saturated or unsaturated cycloalkyl or heterocyclic 3-8 membered ring. In some embodiments, the cycloalkyl ring is a saturated ring. In some embodiments, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cyclooctyl, cyclooctadienyl (COD), cyclooctaene (COE) etc.

A "heterocycle" or "heterocyclic" group refers, in various embodiments, to a ring structure comprising in addition to carbon atoms, sulfur, oxygen, nitrogen or any combination thereof, as part of the ring. A "heteroaromatic ring" refers in various embodiments, to an aromatic ring structure comprising in addition to carbon atoms, sulfur, oxygen, nitrogen or any combination thereof, as part of the ring. In some embodiments the heterocycle or heteroaromatic ring is a 3-10 membered ring. In some embodiments the heterocycle or heteroaromatic ring is a 3-12 membered ring. In some embodiments the heterocycle or heteroaromatic ring is a 6 membered ring. In some embodiments the heterocycle or heteroaromatic ring is a 5-7 membered ring. In some embodiments the heterocycle or heteroaromatic ring is a 3-8 membered ring. In some embodiments, the heterocycle group or heteroaromatic ring may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, N(alkyl)$_2$, —OC(O)$CF_3$, —OCH$_2$Ph, —NHCO-alkyl, —C(O)Ph, C(O)O-alkyl, C(O)H, —C(O)NH$_2$ or any combination thereof. In some embodiments, the heterocycle ring or heteroaromatic ring may be fused to another saturated or unsaturated cycloalkyl or heterocyclic 3-8 membered ring. In some embodiments, the heterocyclic ring is a saturated ring. In some embodiments, the heterocyclic ring is an unsaturated ring. Non limiting examples of a heterocyclic ring or heteroaromatic ring systems comprise pyridine, piperidine, morpholine, piperazine, thiophene, pyrrole, benzodioxole, benzofuran-2(3H)-one, benzo[d][1,3]dioxole, indole, oxazole, isoxazole, imidazole and 1-methylimidazole, furane, triazole, pyrimidine, pyrazine, oxacyclobutane (1 or 2-oxacyclobutane), naphthalene, tetrahydrothiophene 1,1-dioxide, thiazole, benzimidazole, piperidine, 1-methylpiperidine, isoquinoline, 1,3-dihydroisobenzofuran, benzofuran, 3-methyl-4H-1,2,4-triazole, 5-methyl-1,2,4-oxadiazole, or indole.

In various embodiments, this invention provides a compound of this invention or its isomer, metabolite, pharmaceutically acceptable salt, pharmaceutical product, tautomer, hydrate, N-oxide, prodrug, isotopic variant (deuterated analog), PROTAC, polymorph, or crystal or combinations thereof. In various embodiments, this invention provides an isomer of the compound of this invention. In some embodiments, this invention provides a metabolite of the compound of this invention. In some embodiments, this invention provides a pharmaceutically acceptable salt of the compound of this invention. In some embodiments, this invention provides a pharmaceutical product of the compound of this invention. In some embodiments, this invention provides a tautomer of the compound of this invention. In some embodiments, this invention provides a hydrate of the compound of this invention. In some embodiments, this invention provides an N-oxide of the compound of this invention. In some embodiments, this invention provides a prodrug of the compound of this invention. In some embodiments, this invention provides an isotopic variant (including but not limited to deuterated analog) of the compound of this invention. In some embodiments, this invention provides a PROTAC (Proteolysis targeting chimera) of the compound of this invention. In some embodiments, this invention provides a polymorph of the compound of this invention. In some embodiments, this invention provides a crystal of the compound of this invention. In some embodiments, this invention provides composition comprising a compound of this invention, as described herein, or, In some embodiments, a combination of an isomer, metabolite, pharmaceutically acceptable salt, pharmaceutical product, tautomer, hydrate, N-oxide, prodrug, isotopic variant (deuterated analog), PROTAC, polymorph, or crystal of the compound of this invention. In another embodiment, compounds 378-382 of this invention are non limiting examples of PROTAC compounds. In another embodiment, compounds 378-382 of this invention are designed to be heterodimeric degrading compounds.

In various embodiments, the term "isomer" includes, but is not limited to, optical isomers and analogs, structural isomers and analogs, conformational isomers and analogs, and the like. In some embodiments, the isomer is an optical isomer.

In various embodiments, this invention encompasses the use of various optical isomers of the compounds of the invention. It will be appreciated by those skilled in the art that the compounds of the present invention may contain at least one chiral center. Accordingly, the compounds used in the methods of the present invention may exist in, and be isolated in, optically-active or racemic forms. Accordingly, the compounds according to this invention may exist as optically-active isomers (enantiomers or diastereomers, including but not limited to: the (R), (S), (R)(R), (R)(S), (S)(S), (S)(R), (R)(R)(R), (R)(R)(S), (R)(S)(R), (S)(R)(R), (R)(S)(S), (S)(R)(S), (S)(S)(R) or (S)(S)(S) isomers); as racemic mixtures, or as enantiomerically enriched mixtures. Some compounds may also exhibit polymorphism. It is to be understood that the present invention encompasses any racemic, optically-active, polymorphic, or stereoisomeric form, or mixtures thereof, which form possesses properties useful in the treatment of the various conditions described herein.

It is well known in the art how to prepare optically-active forms (for example, by resolution of the racemic form by recrystallization techniques, by synthesis from optically-active starting materials, by chiral synthesis, or by chromatographic separation using a chiral stationary phase).

The compounds of the present invention can also be present in the form of a racemic mixture, containing substantially equivalent amounts of stereoisomers. In some embodiments, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Compounds of the present invention can also be in the form of a hydrate, which means that the compound further includes a stoichiometric or non-stoichiometric amount of water bound by non-covalent intermolecular forces.

As used herein, when some chemical functional group (e.g. alkyl or aryl) is said to be "substituted", it is herein defined that one or more substitutions are possible.

Compounds of the present invention may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example the following tautomers, but not limited to these, are included:

Tautomerization of the Imidazole Ring

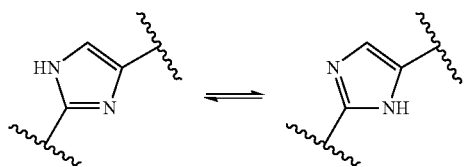 [SMILES: *c1c[nH]c(*)n1 ; *c1cnc(*)[nH]1]

Tautomerization of the Pyrazolone Ring:

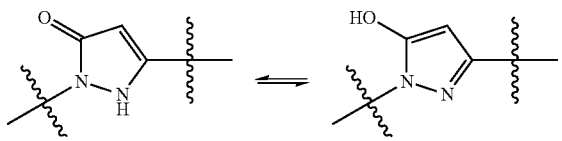 [SMILES: *c1cc(=O)n(*)[nH]1 ; *c1cc(O)n(*)n1]

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds the compounds of this invention may be prepared from an inorganic acid or from an organic acid. In various embodiments, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In various embodiments, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(betaoxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In various embodiments, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In some embodiments, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In various embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In some embodiments, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In various embodiments, the compounds of this invention are administered in combination with an anti-cancer agent. In various embodiments, the anti-cancer agent is a monoclonal antibody. In some embodiments, the monoclonal antibodies are used for diagnosis, monitoring, or treatment of cancer. In various embodiments, monoclonal antibodies react against specific antigens on cancer cells. In various embodiments, the monoclonal antibody acts as a cancer cell receptor antagonist. In various embodiments, monoclonal antibodies enhance the patient's immune response. In various embodiments, monoclonal antibodies act against cell growth factors, thus blocking cancer cell growth. In various embodiments, anti-cancer monoclonal antibodies are conjugated or linked to anti-cancer drugs, radioisotopes, other biologic response modifiers, other toxins, or a combination thereof. In various embodiments, anti-cancer monoclonal antibodies are conjugated or linked to a compound of this invention as described hereinabove.

In various embodiments, the compounds of this invention are administered in combination with an agent treating Alzheimer's disease.

In various embodiments, the compounds of this invention are administered in combination with an anti-viral agent.

In various embodiments, the compounds of this invention are administered in combination with at least one of the following: chemotherapy, molecularly-targeted therapies, DNA damaging agents, hypoxia-inducing agents, or immunotherapy, each possibility represents a separate embodiment of this invention.

Yet another aspect of the present invention relates to a method of treating cancer that includes selecting a subject in need of treatment for cancer and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

In various embodiments, the invention provides compounds and compositions, including any embodiment described herein, for use in any of the methods of this invention. In various embodiments, use of a compound of this invention or a composition comprising the same, will have utility in inhibiting, suppressing, enhancing or stimulating a desired response in a subject, as will be understood by one skilled in the art. In some embodiments, the compositions may further comprise additional active ingredients, whose activity is useful for the particular application for which the compound of this invention is being administered.

Acetate is an important source of acetyl-CoA in hypoxia. Inhibition of acetate metabolism may impair tumor growth. The nucleocytosolic acetyl-CoA synthetase enzyme, ACSS2, supplies a key source of acetyl-CoA for tumors by capturing acetate as a carbon source. Despite exhibiting no gross deficits in growth or development, adult mice lacking ACSS2 exhibit a significant reduction in tumor burden in two different models of hepatocellular carcinoma. ACSS2 is expressed in a large proportion of human tumors, and its activity is responsible for the majority of cellular acetate uptake into both lipids and histones. Further, ACSS2 was identified in an unbiased functional genomic screen as a critical enzyme for the growth and survival of breast and prostate cancer cells cultured in hypoxia and low serum. Indeed, high expression of ACSS2 is frequently found in invasive ductal carcinomas of the breast, triple-negative breast cancer, glioblastoma, ovarian cancer, pancreatic cancer and lung cancer, and often directly correlates with higher-grade tumours and poorer survival compared with tumours that have low ACSS2 expression. These observations may qualify ACSS2 as a targetable metabolic vulnerability of a wide spectrum of tumors.

Therefore, in various embodiments, this invention is directed to a method of treating, suppressing, reducing the severity, reducing the risk of developing or inhibiting cancer comprising administering a compound of this invention to a subject suffering from cancer under conditions effective to treat, suppress, reduce the severity, reduce the risk of developing, or inhibit the cancer. In some embodiments, the compound is an ACSS2 inhibitor. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer. In some embodiments, the cancer is selected from the list presented below: Cancer, bladder (urothelial carcinoma) ignore the box Cancer, bladder (urothelial carcinoma)
Myelodysplasia
Cancer, breast (inflammatory)
Cancer, cervix
Cancer, endometrium
Cancer, esophagus
Cancer, head and neck (squamous cell carcinoma)
Cancer, kidney (renal cell carcinoma) Cancer, kidney (renal cell carcinoma, clear cell)
Cancer, liver (hepatocellular carcinoma)
Cancer, lung (non-small cell) (NSCLC)
Cancer, metastatic (to brain)
Cancer, nasopharynx
Cancer, solid tumor
Cancer, stomach
Carcinoma, adrenocortical
Glioblastoma multiforme
Leukemia, acute myeloid
Leukemia, chronic lymphocytic
Lymphoma, Hodgkin's (classical)
Lymphoma, diffuse large B-cell
Lymphoma, primary central nervous system
Melanoma, malignant
Melanoma, uveal
Meningioma
Multiple myeloma
Cancer, breast
Cancer
Cancer, anus
Cancer, anus (squamous cell)
Cancer, biliary
Cancer, bladder, muscle invasive urothelial carcinoma
Cancer, breast metastatic
Cancer, colorectal
Cancer, colorectal metastatic
Cancer, fallopian tube
Cancer, gastroesophageal junction
Cancer, gastroesophageal junction (adenocarcinoma)
Cancer, larynx (squamous cell)
Cancer, lung (non-small cell) (NSCLC) (squamous cell carcinoma)
Cancer, lung (non-small cell) (NSCLC) metastatic
Cancer, lung (small cell) (SCLC)
Cancer, lung (small cell) (SCLC) (extensive)
Cancer, merkel cell
Cancer, mouth
Cancer, ovary
Cancer, ovary (epithelial)
Cancer, pancreas
Cancer, pancreas (adenocarcinoma)
Cancer, pancreas metastatic
Cancer, penis
Cancer, penis (squamous cell carcinoma)
Cancer, peritoneum
Cancer, prostate (castration-resistant)
Cancer, prostate (castration-resistant), metastatic
Cancer, rectum
Cancer, skin (basal cell carcinoma)
Cancer, skin (squamous cell carcinoma)
Cancer, small intestine (adenocarcinoma)
Cancer, testis
Cancer, thymus
Cancer, thyroid, anaplastic
Cholangiocarcinoma
Chordoma
Cutaneous T-cell lymphoma
Digestive-gastrointestinal cancer
Familial pheochromocytoma-paraganglioma
Glioma
HTLV-1-associated adult T-cell leukemia-lymphoma
Hematologic-blood cancer
Hepatitis C (HCV)
Infection, papillomaviral respiratory
Leiomyosarcoma, uterine
Leukemia, acute lymphocytic
Leukemia, chronic myeloid
Lymphoma, T-cell
Lymphoma, follicular
Lymphoma, primary mediastinal large B-cell
Lymphoma, testicular, diffuse large B-cell Melanoma
Mesothelioma, malignant
Mesothelioma, pleural
Mycosis fungoides
Neuroendocrine cancer
Oral epithelial dysplasia
Sarcoma
Sepsis, severe
Sezary syndrome
Smoldering myeloma
Soft tissue sarcoma
T-cell lymphoma, nasal natural killer (NK) cell
T-cell lymphoma, peripheral In some embodiments, the cancer is selected from the list of: hepatocellular carcinoma, melanoma (e.g., BRAF mutant melanoma), glioblastoma, breast cancer, prostate cancer, liver cancer, brain cancer, Lewis lung carcinoma (LLC), colon carcinoma, pancreatic cancer, renal cell carcinoma, and mammary carcinoma. In some embodiments, the cancer is selected from the list of: melanoma, non-small cell lung cancer, kidney cancer, bladder cancer, head and neck cancers, Hodgkin lymphoma, Merkel cell skin cancer (Merkel cell carcinoma), esophagus cancer; gastroesophageal junction cancer; liver cancer, (hepatocellular carcinoma); lung cancer, (small cell) (SCLC); stomach cancer; upper urinary tract cancer, (urothelial carcinoma); multiforme Glioblastoma; Multiple myeloma; anus cancer, (squamous cell); cervix cancer; endometrium cancer; nasopharynx cancer; ovary cancer; metastatic pancreas cancer; solid tumor cancer; adrenocortical Carcinoma; HTLV-1-associated adult T-cell leukemia-lymphoma; uterine Leiomyosarcoma; acute myeloid Leukemia; chronic lymphocytic Leukemia; diffuse large B-cell Lymphoma; follicular Lymphoma; uveal Melanoma; Meningioma; pleural Mesothelioma; Myelodysplasia; Soft tissue sarcoma; breast cancer; colon cancer; Cutaneous T-cell lymphoma; and peripheral T-cell lymphoma. In some embodiments, the cancer is selected from the list of: glioblastoma, melanoma, lymphoma, breast cancer, ovarian cancer, glioma, digestive system cancer, central nervous system cancer, hepatocellular cancer, hematological cancer, colon cancer or any combination thereof. In some embodiments, the compound is any one of the compounds listed in Table 1; each compound represents a separate embodiment according to this invention.

It has been shown that glucose-independent acetate metabolism promotes melanoma cell survival and tumor growth. Glucose-starved melanoma cells are highly dependent on acetate to sustain ATP levels, cell viability and proliferation. Conversely, depletion of ACSS1 or ACSS2 reduced melanoma tumor growth in mice. Collectively, this data demonstrates acetate metabolism as a liability in melanoma.

Accordingly, in various embodiments, this invention is directed to a method of treating, suppressing, reducing the severity, reducing the risk of developing or inhibiting melanoma comprising administering a compound of this invention to a subject suffering from melanoma under conditions effective to treat, suppress, reduce the severity, reduce the risk of developing, or inhibit the melanoma. In some embodiments, the melanoma is early melanoma. In some embodiments, the melanoma is advanced melanoma. In some embodiments, the melanoma is invasive melanoma. In some embodiments, the melanoma is metastatic melanoma. In some embodiments, the melanoma is drug resistant melanoma. In some embodiments, the melanoma is BRAF mutant melanoma. In some embodiments, the compound is an ACSS2 inhibitor. In some embodiments, the compound is any one of the compounds listed in Table 1; each compound represents a separate embodiment according to this invention.

Acetyl-CoA synthetases that catalyse the conversion of acetate to acetyl-CoA have now been implicated in the growth of hepatocellular carcinoma, glioblastoma, breast cancer and prostate cancer.

Hepatocellular carcinoma (HCC) is a deadly form of liver cancer, and it is currently the second leading cause of cancer-related deaths worldwide (European Association For The Study Of The Liver; European Organisation For Research And Treatment Of Cancer, 2012). Despite a number of available treatment strategies, the survival rate for HCC patients is low. Considering its rising prevalence, more targeted and effective treatment strategies are highly desirable for HCC.

In various embodiments, this invention is directed to a method of treating, suppressing, reducing the severity, reducing the risk of developing or inhibiting hepatocellular carcinoma (HCC) comprising administering a compound of this invention to a subject suffering from hepatocellular carcinoma (HCC) under conditions effective to treat, suppress, reduce the severity, reduce the risk of developing, or inhibit the hepatocellular carcinoma (HCC). In some embodiments, the hepatocellular carcinoma (HCC) is early hepatocellular carcinoma (HCC). In some embodiments, the hepatocellular carcinoma (HCC) is advanced hepatocellular carcinoma (HCC). In some embodiments, the hepatocellular carcinoma (HCC) is invasive hepatocellular carcinoma (HCC). In some embodiments, the hepatocellular carcinoma (HCC) is metastatic hepatocellular carcinoma (HCC). In some embodiments, the hepatocellular carcinoma (HCC) is drug resistant hepatocellular carcinoma (HCC). In some embodiments, the compound is an ACSS2 inhibitor. In some embodiments, the compound is any one of the compounds listed in Table 1; each compound represents a separate embodiment according to this invention.

ACSS2-mediated acetate metabolism contributes to lipid synthesis and aggressive growth in glioblastoma and breast cancer.

Nuclear ACSS2 is shown to activate HIF-2alpha by acetylation and thus accelerate growth and metastasis of HIF2alpha-driven cancers such as certain Renal Cell Carcinoma and Glioblastomas (Chen, R. et al. Coordinate regulation of stress signaling and epigenetic events by Acss2 and HIF-2 in cancer cells, Plos One, 12 (12) 1-31, 2017).

Therefore, and in various embodiments, this invention is directed to a method of treating, suppressing, reducing the severity, reducing the risk of developing or inhibiting glioblastoma comprising administering a compound of this invention to a subject suffering from glioblastoma under conditions effective to treat, suppress, reduce the severity, reduce the risk of developing, or inhibit the glioblastoma. In some embodiments, the glioblastoma is early glioblastoma. In some embodiments, the glioblastoma is advanced glioblastoma. In some embodiments, the glioblastoma is invasive glioblastoma. In some embodiments, the glioblastoma is metastatic glioblastoma. In some embodiments, the glioblastoma is drug resistant glioblastoma. In some embodiments, the compound is an ACSS2 inhibitor. In some embodiments, the compound is any one of the compounds listed in Table 1; each compound represents a separate embodiment according to this invention.

Therefore, and in various embodiments, this invention is directed to a method of treating, suppressing, reducing the severity, reducing the risk of developing or inhibiting Renal Cell Carcinoma comprising administering a compound of this invention to a subject suffering from Renal Cell Carcinoma under conditions effective to treat, suppress, reduce the severity, reduce the risk of developing, or inhibit the Renal Cell Carcinoma. In some embodiments, the Renal Cell Carcinoma is early Renal Cell Carcinoma. In some embodiments, the Renal Cell Carcinoma is advanced Renal Cell Carcinoma. In some embodiments, the Renal Cell Carcinoma is invasive Renal Cell Carcinoma. In some embodiments, the Renal Cell Carcinoma is metastatic Renal Cell Carcinoma. In some embodiments, the Renal Cell Carcinoma is drug resistant Renal Cell Carcinoma. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting breast cancer comprising administering a compound of this invention to a subject suffering from breast cancer under conditions effective to treat, suppress, reduce the severity, reduce the risk of developing, or inhibit the breast cancer. In some embodiments, the breast cancer is early breast cancer. In some embodiments, the breast cancer is advanced breast cancer. In some embodiments, the breast cancer is invasive breast cancer. In some embodiments, the breast cancer is metastatic breast cancer. In some embodiments, the breast cancer is drug resistant breast cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting prostate cancer comprising administering a compound of this invention to a subject suffering from prostate cancer under conditions effective to treat, suppress, reduce the severity, reduce the risk of developing, or inhibit the prostate cancer. In some embodiments, the prostate cancer is early prostate cancer. In some embodiments, the prostate cancer is advanced prostate cancer. In some embodiments, the prostate cancer is invasive prostate cancer. In some embodiments, the prostate cancer is metastatic prostate cancer. In some embodiments, the prostate cancer is drug resistant prostate cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting liver cancer comprising administering a compound of this invention to a subject suffering from liver cancer under conditions effective to treat, suppress, reduce the severity, reduce the risk of developing, or inhibit the liver cancer. In some embodiments, the liver cancer is early liver cancer. In some embodiments, the liver cancer is advanced liver cancer. In some embodiments, the liver cancer is invasive liver cancer. In some embodiments, the liver cancer is metastatic liver cancer. In some embodiments, the liver cancer is drug resistant liver cancer. In some embodiments, the compound is an ACSS2 inhibitor. In some embodiments, the compound is any one of the compounds listed in Table 1; each compound represents a separate embodiment according to this invention.

Nuclear ACSS2 is also shown to promote lysosomal biogenesis, autophagy and to promote brain tumorigenesis by affecting Histone H3 acetylation (Li, X et al.: Nucleus-Translocated ACSS2 Promotes Gene Transcription for Lysosomal Biogenesis and Autophagy, *Molecular Cell* 66, 1-14, 2017).

In various embodiments, this invention is directed to a method of treating, suppressing, reducing the severity, reducing the risk of developing or inhibiting brain cancer comprising administering a compound of this invention to a subject suffering from brain cancer under conditions effective to treat, suppress, reduce the severity, reduce the risk of developing, or inhibit the brain cancer. In some embodiments, the brain cancer is early brain cancer. In some embodiments, the brain cancer is advanced brain cancer. In some embodiments, the brain cancer is invasive brain cancer. In some embodiments, the brain cancer is metastatic brain cancer. In some embodiments, the brain cancer is drug resistant brain cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting pancreatic cancer comprising administering a compound of this invention to a subject suffering from pancreatic cancer under conditions effective to treat, suppress, reduce the severity, reduce the risk of developing, or inhibit the pancreatic cancer. In some embodiments, the pancreatic cancer is early pancreatic cancer. In some embodiments, the pancreatic cancer is advanced pancreatic cancer. In some embodiments, the pancreatic cancer is invasive pancreatic cancer. In some embodiments, the pancreatic cancer is metastatic pancreatic cancer. In some embodiments, the pancreatic cancer is drug resistant pancreatic cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting Lewis lung carcinoma (LLC) comprising administering a compound of this invention to a subject suffering from Lewis lung carcinoma (LLC) under conditions effective to treat, suppress, reduce the severity, reduce the risk of developing, or inhibit the Lewis lung carcinoma (LLC). In some embodiments, the Lewis lung carcinoma (LLC) is early Lewis lung carcinoma (LLC). In some embodiments, the Lewis lung carcinoma (LLC) is advanced Lewis lung carcinoma (LLC). In some embodiments, the Lewis lung carcinoma (LLC) is invasive Lewis lung carcinoma (LLC). In some embodiments, the Lewis lung carcinoma (LLC) is metastatic Lewis lung carcinoma (LLC). In some embodiments, the Lewis lung carcinoma (LLC) is drug resistant Lewis lung carcinoma (LLC). In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colon carcinoma comprising administering a compound of this invention to a subject suffering from colon carcinoma under conditions effective to treat, suppress, reduce the severity, reduce the risk of developing, or inhibit the colon carcinoma. In some embodiments, the colon carcinoma is early colon carcinoma. In some embodiments, the colon carcinoma is advanced colon carcinoma. In some embodiments, the colon carcinoma is invasive colon carcinoma. In some embodiments, the colon carcinoma is metastatic colon carcinoma. In some embodiments, the colon carcinoma is drug resistant colon carcinoma. In some embodiments, the compound is a 'program cell death receptor 1' (PD-1) modulator. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting mammary carcinoma comprising administering a compound of this invention to a subject suffering from mammary carcinoma under conditions effective to treat, suppress, reduce the severity, reduce the risk of developing, or inhibit the mammary carcinoma. In some embodiments, the mammary carcinoma is early mammary carcinoma. In some embodiments, the mammary carcinoma is advanced mammary carcinoma. In some embodiments, the mammary carcinoma is invasive mammary carcinoma. In some embodiments, the mammary carcinoma is metastatic mammary carcinoma. In some embodiments, the mammary carcinoma is drug resistant mammary carcinoma. In some embodiments, the compound is an ACSS2 inhibitor. In some embodiments, the compound is any one of the compounds listed in Table 1; each compound represents a separate embodiment according to this invention.

In various embodiments, this invention is directed to a method of suppressing, reducing or inhibiting tumour growth in a subject, comprising administering a compound according to this invention, to a subject suffering from a proliferative disorder (e.g., cancer) under conditions effective to suppress, reduce or inhibit said tumour growth in said subject. In some embodiments, the tumor growth is enhanced by increased acetate uptake by cancer cells. In some embodiments, the increase in acetate uptake is mediated by ACSS2. In some embodiments, the cancer cells are under hypoxic stress. In some embodiments, the compound is an ACSS2 inhibitor. In some embodiments, the tumor growth is suppressed due to suppression of lipid synthesis (e.g., fatty acid) induced by ACSS2 mediated acetate metabolism to acetyl-CoA. In some embodiments, the tumor growth is suppressed due to suppression of the regulation of histones acetylation and function induced by ACSS2 mediated acetate metabolism to acetyl-CoA. In some embodiments, the synthesis is suppressed under hypoxia (hypoxic stress). In some embodiments, the compound is any one of the compounds listed in Table 1; each compound represents a separate embodiment according to this invention.

In various embodiments, this invention is directed to a method of suppressing, reducing or inhibiting lipid synthesis and/or regulating histones acetylation and function in a cell, comprising contacting a compound of this invention, with a cell under conditions effective to suppress, reduce or inhibit lipid synthesis and/or regulating histones acetylation and function in said cell. In various embodiments, the method is carried out in vitro. In various embodiments, the method is carried out in vivo. In various embodiments, the lipid synthesis is induced by ACSS2 mediated acetate metabolism to acetyl-CoA. In various embodiments, regulating histones acetylation and function is induced by ACSS2 mediated acetate metabolism to acetyl-CoA. In various embodiments, the cell is cancer cell. In various embodiments, the lipid is fatty acid. In various embodiments, the acetate metabolism to acetyl-CoA is carried out under hypoxia (i.e., hypoxic stress). In some embodiments, the compound is an ACSS2 inhibitor. In some embodiments, the compound is any one of the compounds listed in Table 1; each compound represents a separate embodiment according to this invention.

In various embodiments, this invention is directed to a method of suppressing, reducing or inhibiting fatty-acid accumulation in the liver, comprising administering a compound of this invention to a subject in need thereof, under conditions effective to suppress, reduce or inhibit fatty-acid accumulation in the liver of said subject. In various embodiments, the fatty-acid accumulation is induced by ACSS2 mediated acetate metabolism to acetyl-CoA. In various embodiments, the subject suffers from a fatty liver condition. In various embodiments, the acetate metabolism to acetyl-CoA in the liver is carried out under hypoxia (i.e., hypoxic stress). In some embodiments, the compound is an ACSS2 inhibitor. In some embodiments, the compound is any one of the compounds listed in Table 1; each compound represents a separate embodiment according to this invention.

In various embodiments, this invention is directed to a method of binding an ACSS2 inhibitor compound to an ACSS2 enzyme, comprising the step of contacting an ACSS2 enzyme with an ACSS2 inhibitor compound of this invention, in an amount effective to bind the ACSS2 inhibitor compound to the ACSS2 enzyme. In some embodiments, the method is carried out in vitro. In another embodiment, the method is carried out in vivo. In some embodiments, the compound is any one of the compounds listed in Table 1; each compound represents a separate embodiment according to this invention.

In various embodiments, this invention is directed to a method of suppressing, reducing or inhibiting acetyl-CoA synthesis from acetate in a cell, comprising contacting a compound according to this invention with a cell, under conditions effective to suppress, reduce or inhibit acetyl-CoA synthesis from acetate in said cell. In some embodiments, the cell is a cancer cell. In some embodiments, the method is carried out in vitro. In another embodiment, the method is carried out in vivo. In some embodiments, the synthesis is mediated by ACSS2. In some embodiments, the compound is an ACSS2 inhibitor. In some embodiments, the cell is under hypoxic stress. In some embodiments, the compound is any one of the compounds listed in Table 1; each compound represents a separate embodiment according to this invention.

In various embodiments, this invention is directed to a method of suppressing, reducing or inhibiting acetate metabolism in a cancer cell, comprising contacting a compound according to this invention with a cancer cell, under conditions effective to suppress, reduce or inhibit acetate metabolism in said cell. In some embodiments, the acetate metabolism is mediated by ACSS2. In some embodiments, the compound is an ACSS2 inhibitor. In some embodiments, the cancer cell is under hypoxic stress. In some embodiments, the compound is any one of the compounds listed in Table 1; each compound represents a separate embodiment according to this invention.

In various embodiments, this invention provides methods for treating, suppressing, reducing the severity, reducing the risk, or inhibiting metastatic cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for increasing the survival of a subject suffering from metastatic cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for treating, suppressing, reducing the severity, reducing the risk, or inhibiting advanced cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for increasing the survival of a subject suffering from advanced cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

The compounds of the present invention are useful in the treatment, reducing the severity, reducing the risk, or inhibition of cancer, metastatic cancer, advanced cancer, drug resistant cancer, and various forms of cancer. In a preferred embodiment the cancer is hepatocellular carcinoma, melanoma (e.g., BRAF mutant melanoma), glioblastoma, breast cancer, prostate cancer, liver cancer, brain cancer, pancreatic cancer, Lewis lung carcinoma (LLC), colon carcinoma, renal cell carcinoma, and/or mammary carcinoma; each represents a separate embodiment according to this invention. Based upon their believed mode of action, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In various embodiments, other types of cancers that may be treatable with the ACSS2 inhibitors according to this invention include: adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metastic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, hepatocellular cancer, hematological cancer or any combination thereof. In some embodiments the cancer is invasive. In some embodiments the cancer is metastatic cancer. In some embodiments the cancer is advanced cancer. In some embodiments the cancer is drug resistant cancer.

In various embodiments "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In various embodiments "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism; g) Cells and tumors with activating RAS mutations are relatively resistant to most anti-cancer agents. Thus, the resistance to anticancer agents used in chemotherapy is the main cause of treatment failure in malignant disorders, provoking tumors to become resistant. Drug resistance is the major cause of cancer chemotherapy failure.

In various embodiments "resistant cancer" refers to drug-resistant cancer as described herein above. In some embodiments "resistant cancer" refers to cancer cells that acquire resistance to any treatment such as chemotherapy, radiotherapy or biological therapy.

In various embodiments, this invention is directed to treating, suppressing, reducing the severity, reducing the risk, or inhibiting cancer in a subject, wherein the subject has been previously treated with chemotherapy, radiotherapy or biological therapy.

In various embodiments "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In various embodiments, "Radiotherapy" (also referred herein as "Radiation therapy") refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In various embodiments "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

It is this kind of metabolic plasticity—the ability to exploit and survive on a variety of nutritional sources—that confers resistance to many of the current cancer metabolism drugs as monotherapies. Interestingly, ACSS2 is highly expressed in many cancer tissues, and its upregulation by hypoxia and low nutrient availability indicates that it is an important enzyme for coping with the typical stresses within the tumour microenvironment and, as such, a potential Achilles heel. Moreover, highly stressed regions of tumours have been shown to select for apoptotic resistance and promote aggressive behaviour, treatment resistance and relapse. In this way, the combination of ACSS2 inhibitors with a therapy that specifically targets well-oxygenated regions of tumours (for example, radiotherapy) could prove to be an effective regimen.

Accordingly, and in various embodiments, the compound according to this invention, is administered in combination with an anti-cancer therapy. Examples of such therapies include but are not limited to: chemotherapy, immunotherapy, radiotherapy, biological therapy, surgical intervention, and combinations thereof. In some embodiments, the compound according to this invention is administered in combination with a therapy that specifically targets well-oxygenated regions of tumours. In some embodiments, the compound according to this invention is administered in combination with radiotherapy.

In various embodiments, the compound is administered in combination with an anti-cancer agent by administering the compounds as herein described, alone or in combination with other agents.

In various embodiments, the composition for cancer treatment of the present invention can be used together with existing chemotherapy drugs or be made as a mixture with them. Such a chemotherapy drug includes, for example, alkylating agents, nitrosourea agents, antimetabolites, antitumor antibiotics, alkaloids derived from plant, topoisomerase inhibitors, hormone therapy medicines, hormone antagonists, aromatase inhibitors, P-glycoprotein inhibitors, platinum complex derivatives, other immunotherapeutic drugs, and other anticancer agents. Further, they can be used together with hypoleukocytosis (neutrophil) medicines that are cancer treatment adjuvant, thrombopenia medicines, antiemetic drugs, and cancer pain medicines for patient's QOL recovery or be made as a mixture with them.

In various embodiments, this invention is directed to a method of destroying a cancerous cell comprising: providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture).

In some embodiments, the cancer is selected from the group consisting of melanoma, non-small cell lung cancer, kidney cancer, bladder cancer, head and neck cancers, Hodgkin lymphoma, glioblastoma, renal cell carcinoma, Merkel cell skin cancer (Merkel cell carcinoma), and combinations thereof. In some embodiments, the cancer is selected from the group consisting of: melanoma, non-small cell lung cancer, kidney cancer, bladder cancer, head and neck cancers, Hodgkin lymphoma, glioblastoma, Merkel cell skin cancer (Merkel cell carcinoma), esophagus cancer; gastroesophageal junction cancer; liver cancer, (hepatocellular carcinoma); lung cancer, (small cell) (SCLC); stomach cancer; upper urinary tract cancer, (urothelial carcinoma); multiforme Glioblastoma; Multiple myeloma; anus cancer, (squamous cell); cervix cancer; endometrium cancer; nasopharynx cancer; ovary cancer; metastatic pancreas cancer; solid tumor cancer; adrenocortical Carcinoma; HTLV-1-associated adult T-cell leukemia-lymphoma; uterine Leiomyosarcoma; acute myeloid Leukemia; chronic lymphocytic Leukemia; diffuse large B-cell Lymphoma; follicular Lymphoma; uveal Melanoma; Meningioma; pleural Mesothelioma; Myelodysplasia; Soft tissue sarcoma; breast cancer; colon cancer; pancreatic cancer, Cutaneous T-cell lymphoma; peripheral T-cell lymphoma or any combination thereof.

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to other embodiments, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

ACSS2 gene has recently been suggested to be associated with human alcoholism and ethanol intake. Accordingly, in various embodiments, this invention is directed to a method of treating, suppressing, reducing the severity, reducing the risk of developing or inhibiting human alcoholism in a subject, comprising administering a compound of this invention, to a subject suffering from alcoholism under conditions effective to treat, suppress, reduce the severity, reduce the risk of developing, or inhibit alcoholism in said subject. In some embodiments, the compound is an ACSS2 inhibitor. In some embodiments, the compound is any one of the compounds listed in Table 1; each compound represents a separate embodiment according to this invention.

Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). NAFLD is characterized by excessive fat accumulation in the liver (steatosis), without any other evident causes of chronic liver diseases (viral, autoimmune, genetic, etc.), and with an alcohol consumption $ 20-30 g/day. On the contrary, AFLD is defined as the presence of steatosis and alcohol consumption >20-30 g/day.

It has been shown that synthesis of metabolically available acetyl-coA from acetate is critical to the increased acetylation of proinflammatory gene histones and consequent enhancement of the inflammatory response in ethanol-exposed macrophages. This mechanism is a potential therapeutic target in acute alcoholic hepatitis.

Accordingly, in various embodiments, this invention is directed to a method of treating, suppressing, reducing the severity, reducing the risk of developing or inhibiting alcoholic steatohepatitis (ASH) in a subject, comprising administering a compound of this invention, to a subject suffering from alcoholic steatohepatitis (ASH) under conditions effective to treat, suppress, reduce the severity, reduce the risk of developing, or inhibit alcoholic steatohepatitis (ASH) in said subject. In some embodiments, the compound is an ACSS2 inhibitor. In some embodiments, the compound is any one of the compounds listed in Table 1; each compound represents a separate embodiment according to this invention.

Accordingly, in various embodiments, this invention is directed to a method of treating, suppressing, reducing the severity, reducing the risk of developing or inhibiting non alcoholic fatty liver disease (NAFLD) in a subject, comprising administering a compound of this invention, to a subject suffering from non alcoholic fatty liver disease (NAFLD) under conditions effective to treat, suppress, reduce the severity, reduce the risk of developing, or inhibit non alcoholic fatty liver disease (NAFLD) in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting non-alcoholic steatohepatitis (NASH) in a subject, comprising administering a compound of this invention, to a subject suffering from non-alcoholic steatohepatitis (NASH) under conditions effective to treat, suppress, reduce the severity, reduce the risk of developing, or inhibit non-alcoholic steatohepatitis (NASH) in said subject. In some embodiments, the compound is an ACSS2 inhibitor. In some embodiments, the compound is any one of the compounds listed in Table 1; each compound represents a separate embodiment according to this invention.

ACSS2-mediated acetyl-CoA synthesis from acetate has also been shown to be necessary for human cytomegalovirus infection. It has been shown that glucose carbon can be converted to acetate and used to make cytosolic acetyl-CoA by acetyl-CoA synthetase short-chain family member 2 (ACSS2) for lipid synthesis, which is important for HCMV-induced lipogenesis and the viral growth. Accordingly, ACSS2 inhibitors are expected to be useful as an antiviral therapy, and in the treatment of HCMV infection.

Therefore, in various embodiments, this invention is directed to a method of treating, suppressing, reducing the severity, reducing the risk of developing or inhibiting a viral infection in a subject, comprising administering a compound of this invention, to a subject suffering from a viral infection under conditions effective to treat, suppress, reduce the severity, reduce the risk of developing, or inhibit the viral infection in said subject. In some embodiments, the viral infection is HCMV. In some embodiments, the compound is an ACSS2 inhibitor. In some embodiments, the compound is any one of the compounds listed in Table 1; each compound represents a separate embodiment according to this invention.

It was found that mice lacking ACSS2 showed reduced body weight and hepatic steatosis in a diet-induced obesity model (Z. Huang et al., "ACSS2promotes systemic fat storage and utilization through selective regulation of genes involved in lipid metabolism" *PNAS* 115, (40), E9499-E9506, 2018).

Accordingly, in various embodiments, this invention is directed to a method of treating, suppressing, reducing the severity, reducing the risk of developing or inhibiting a metabolic disorder in a subject, comprising administering a compound of this invention, to a subject suffering from a metabolic disorder under conditions effective to treat, suppress, reduce the severity, reduce the risk of developing, or inhibit the metabolic disorder in said subject. In some embodiments, the metabolic disorder is obesity. In other embodiments, the metabolic disorder is weight gain. In other embodiments, the metabolic disorder is hepatic steatosis. In other embodiments, the metabolic disorder is fatty liver disease. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting obesity in a subject, comprising administering a compound of this invention, to a subject suffering from obesity under conditions effective to treat, suppress, reduce the severity, reduce the risk of developing, or inhibit the obesity in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting weight gain in a subject, comprising administering a compound of this invention, to a subject suffering from weight gain under conditions effective to treat, suppress, reduce the severity, reduce the risk of developing, or inhibit the weight gain in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting hepatic steatosis in a subject, comprising administering a compound of this invention, to a subject suffering from hepatic steatosis under conditions effective to treat, suppress, reduce the severity, reduce the risk of developing, or inhibit the hepatic steatosis in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting fatty liver disease in a subject, comprising administering a compound of this invention, to a subject suffering from fatty liver disease under conditions effective to treat, suppress, reduce the severity, reduce the risk of developing, or inhibit the fatty liver disease in said subject. In some embodiments, the compound is an ACSS2 inhibitor. In some embodiments, the compound is any one of the compounds listed in Table 1; each compound represents a separate embodiment according to this invention.

ACSS2 is also shown to enter the nucleus under certain condition (hypoxia, high fat etc.) and to affect histone acetylation and crotonylation by making available acetyl-CoA and crotonyl-CoA and thereby regulate gene expression. For example, ACSS2 decrease is shown to lower levels of nuclear acetyl-CoA and histone acetylation in neurons affecting the expression of many neuronal genes. In the hippocampus such redIt was found that functions in ACSS2 lead to effects on memory and neuronal plasticity (Mews P, et al., Nature, Vol 546, 381, 2017). Such epigenetic modifications are implicated in neuropsychiatric diseases such as anxiety, PTSD, depression etc. (Graff, J et al. Histone acetylation: molecular mnemonics on chromatin. Nat Rev. Neurosci. 14, 97-111 (2013)). Thus, an inhibitor of ACSS2 may find useful application in these conditions.

Accordingly, in various embodiments, this invention is directed to a method of treating, suppressing, reducing the severity, reducing the risk of developing or inhibiting neuropsychiatric disease or disorder in a subject, comprising administering a compound of this invention, to a subject suffering from neuropsychiatric disease or disorder under conditions effective to treat, suppress, reduce the severity, reduce the risk of developing, or inhibit the neuropsychiatric disease or disorder in said subject. In some embodiments, the neuropsychiatric disease or disorder is selected from: anxiety, depression, schizophrenia, autism and/or or post-traumatic stress disorder; each represents a separate embodiment according to this invention. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting anxiety in a subject, comprising administering a compound of this invention, to a subject suffering from anxiety under conditions effective to treat, suppress, reduce the severity, reduce the risk of developing, or inhibit the anxiety in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting depression disorder in a subject, comprising administering a compound of this invention, to a subject suffering from depression under conditions effective to treat, suppress, reduce the severity, reduce the risk of developing, or inhibit the depression in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting post-traumatic stress disorder in a subject, comprising administering a compound of this invention, to a subject suffering from post-traumatic stress disorder under conditions effective to treat, suppress, reduce the severity, reduce the risk of developing, or inhibit the post-traumatic stress disorder in said subject. In some embodiments, the compound is an ACSS2 inhibitor. In some embodiments, the compound is any one of the compounds listed in Table 1; each compound represents a separate embodiment according to this invention.

In some embodiments, this invention is directed to a method of treating, suppressing, reducing the severity, reducing the risk of developing or inhibiting inflammatory condition in a subject, comprising administering a compound of this invention, to a subject suffering from inflammatory condition under conditions effective to treat, suppress, reduce the severity, reduce the risk of developing, or inhibit the inflammatory condition in said subject. In some embodiments, the compound is an ACSS2 inhibitor. In some embodiments, the compound is any one of the compounds listed in Table 1; each compound represents a separate embodiment according to this invention.

In some embodiments, this invention is directed to a method of treating, suppressing, reducing the severity, reducing the risk of developing or inhibiting an autoimmune disease or disorder in a subject, comprising administering a compound of this invention, to a subject suffering from an autoimmune disease or disorder under conditions effective to treat, suppress, reduce the severity, reduce the risk of developing, or inhibit the autoimmune disease or disorder in said subject. In some embodiments, the compound is an ACSS2 inhibitor. In some embodiments, the compound is any one of the compounds listed in Table 1; each compound represents a separate embodiment according to this invention.

As used herein, subject or patient refers to any mammalian patient, including without limitation, humans and other primates, dogs, cats, horses, cows, sheep, pigs, rats, mice, and other rodents. In various embodiments, the subject is male. In some embodiments, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The following examples are presented in order to more fully illustrate the preferred embodiments of the invention. They should in no way, however, be construed as limiting the broad scope of the invention.

EXAMPLES

Example 1

Figure 2:
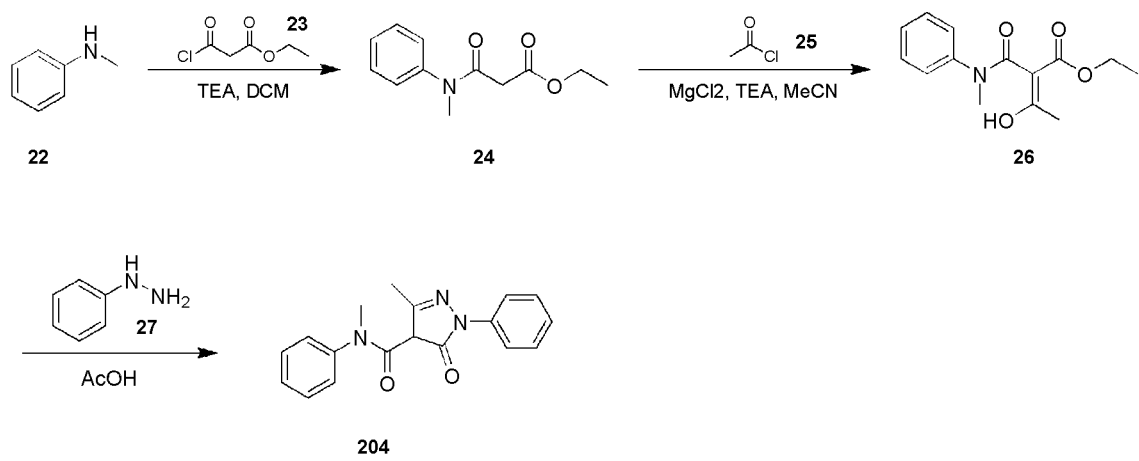
FIG. 2 depicts a synthetic scheme for compound 204.
Figure 3:
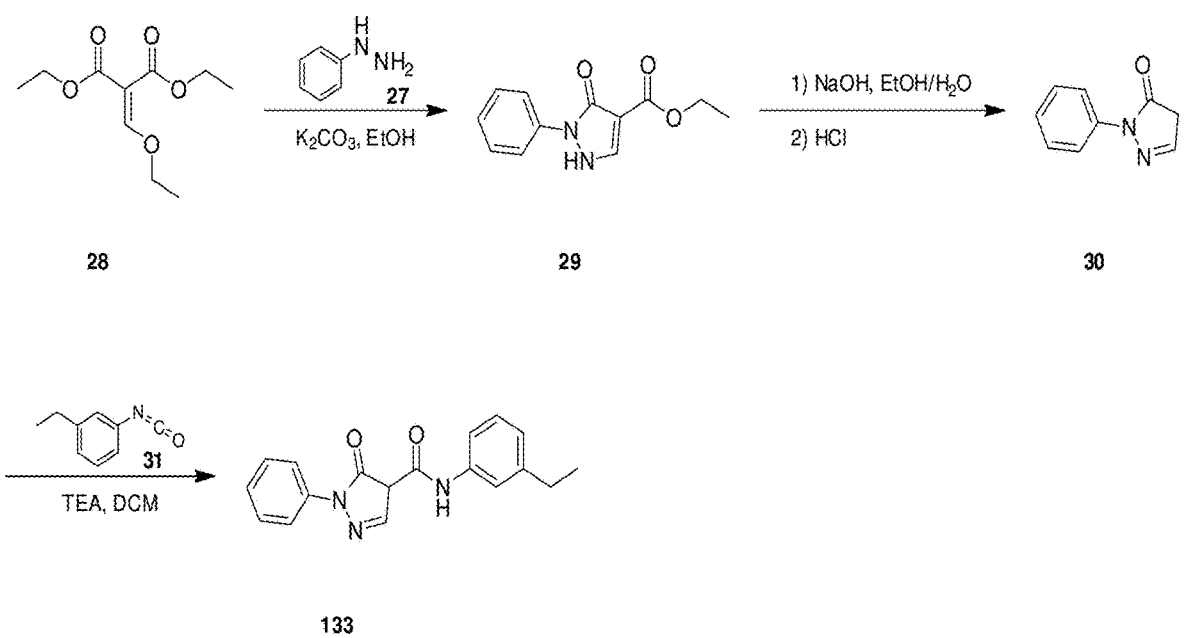
FIG. 3 depicts a synthetic scheme for compound 133.

Synthetic Details for Compounds of the Invention
(FIGS. 1-3)

Experimental Procedure:
General Synthesis of Compound 3

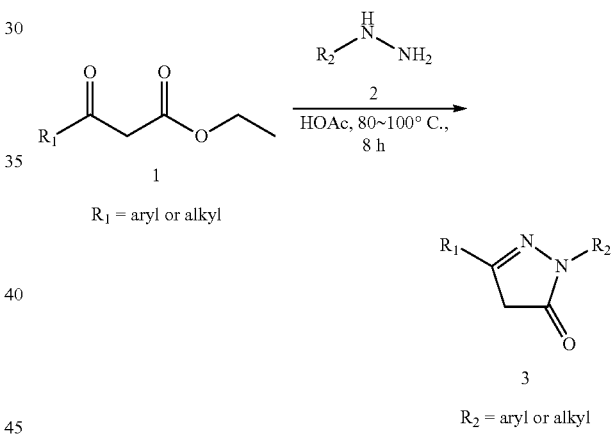

A solution of compound 1 (1.00 eq), compound 2 (1.0 eq) in AcOH (0.5-10 mL) was stirred at 90° C. for 3-10 hours under $N_2$. The mixture was concentrated in vacuo. The residue was purified by trituration (in Ethyl acetate or EtOH) to give compound 3.

General Preparation of Compound 5

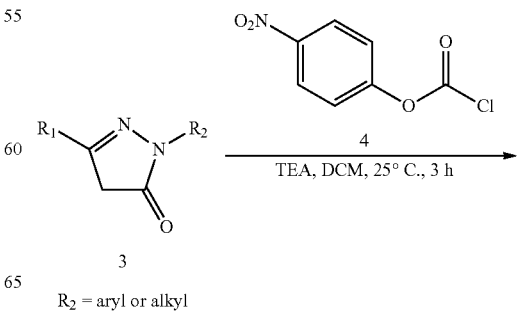

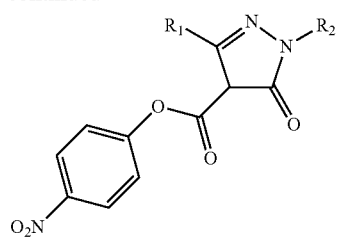

5

To a solution of compound 3 (1.00 eq) in DCM (5-10 mL) Et₃N (2.00 eq) was added. After stirring at 25° C. for 30 minutes, compound 4 (1.00 eq) was added, and then the mixture was stirred at 25° C. for 2.5 hours under N₂. It was concentrated in vacuum to give the crude compound 5, which was used in the next step as is.

General Preparation of Final Compounds 100-277
Method 1

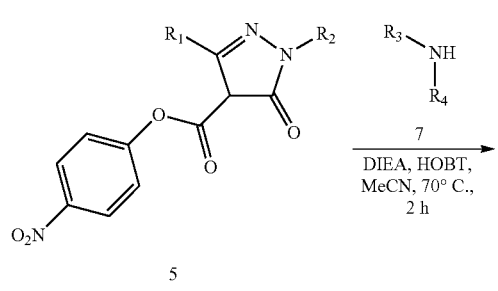

To a solution of compound 5 (1.50 eq) in MeCN (10 mL), HOBT (2.00 eq), compound 7 (1.00 eq) and DIEA (3.00 eq) were added. The mixture was stirred at 70° C. for 2 hours. It was concentrated in vacuum. The residue was purified by prep-HPLC to afford the final compounds 100-277.

Method 2

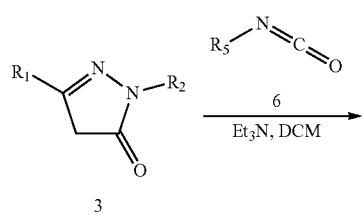

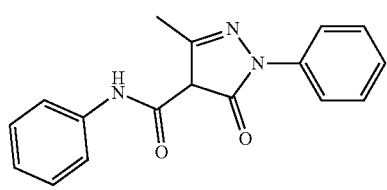 [SMILES: CC1=NN(c2ccccc2)C(=O)C1C(=O)Nc1ccccc1]

To a solution of compound 3 (1.00 eq) in DCM (1-10 mL) Et₃N (2.00 eq) was added. After stirring for 0.5 hours at 20° C., Compound 6 (1.00 eq) was added into it, following by stirring of the mixture at 20° C. for 10 hours. The mixture was concentrated in vacuum, and the residue was purified by prep-HPLC to give compounds 100-277.

Analytical Data 3-methyl-5-oxo-N,1-diphenyl-4,5-dihydro-1H-pyrazole-4-carboxamide Compound ID: 182

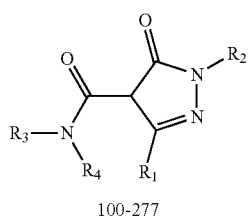

LCMS: m/z 294.2 [M+H]+;

$^1$HNMR (400 MHz, DMSO-d₆) δ 13.39 (s, 1H), 10.68 (s, 1H), 7.75 (d, J=8.4 Hz, 2H), 7.62 (dd, J=7.6, 1.2 Hz, 2H), 7.52 (t, J=8.0 Hz, 2H), 7.34-7.29 (m, 3H), 7.03 (t, J=8.0 Hz, 1H), 2.57 (s, 3H).

N-(3-acetylphenyl)-3-methyl-5-oxo-1-phenyl-4,5-dihydro-1H yrazole-4-carboxamide

Compound ID: 183 Batch2

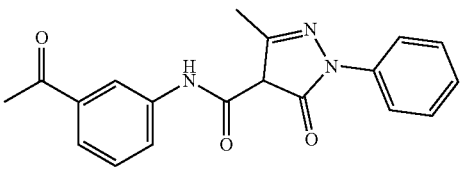 [SMILES: CC(=O)c1cccc(NC(=O)C2C(=O)N(c3ccccc3)N=C2C)c1]

LCMS: m/z 336.2 [M+H]+;

$^1$H NMR (400 MHz, DMSO-d₆) δ 10.84 (s, 1H), 8.24 (s, 1H), 7.84 (d, J=8.0 Hz, 1H), 7.74 (d, J=7.6 Hz, 2H), 7.64 (d, J=8.0 Hz, 1H), 7.55 (t, J=8.0 Hz, 2H), 7.48 (t, J=8.0 Hz, 1H), 7.38-7.31 (m, 1H), 2.60 (s, 3H), 2.58 (s, 3H)

N-(3-ethylphenyl)-3-methyl-5-oxo-1-phenyl-4,5-dihydro-1H-pyrazole-4-carboxamide

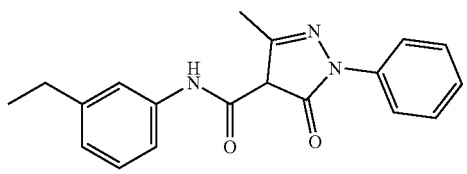 [SMILES: CCc1cccc(NC(=O)C2C(=O)N(c3ccccc3)N=C2C)c1]

LCMS: m/z 322.2 [M+H]+;

$^1$H NMR (400 MHz, DMSO-d$_6$) δ 10.65 (s, 1H), 7.71 (dd, J=1.0, 8.4 Hz, 2H), 7.57-7.50 (m, 2H), 7.47 (s, 1H), 7.44 (d, J=8.0 Hz, 1H), 7.37-7.29 (m, 1H), 7.22 (t, J=7.6 Hz, 1H), 6.89 (d, J=7.6 Hz, 1H), 2.62-2.57 (m, 2H), 2.56 (s, 3H), 1.18 (t, J=7.6 Hz, 3H).

$^1$H NMR (400 MHz, CHLOROFORM-d) δ 8.02 (s, 1H), 7.95 (d, J=8.0 Hz, 1H), 7.86 (br s, 1H), 7.69 (d, J=7.6 Hz, 1H), 7.43 (t, J=8.0 Hz, 1H), 2.61 (s, 3H), 2.22 (s, 3H).

3-methyl-N-(naphthalen-1-yl)-5-oxo-1-phenyl-4,5-dihydro-1H-pyrazole-4-carboxamide Compound ID: 185

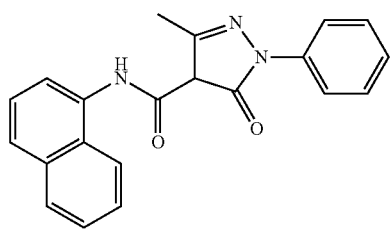 [SMILES: CC1=NN(c2ccccc2)C(=O)C1C(=O)Nc1cccc2ccccc12]

LCMS: m/z 344.2 [M+H]+;

$^1$H NMR (400 MHz, MeOH) δ 8.28-8.30 (d, J=8.0 Hz, 2H), 7.86-7.88 (d, J=8.0 Hz, 1H), 7.72-7.74 (d, J=8.0 Hz, 2H), 7.63-7.65 (d, J=8.0 Hz, 1H), 7.45-7.57 (m, 5H), 7.36 (t, J=8.0 Hz, 1H), 3.31 (s, 1H).

N-benzyl-3-methyl-5-oxo-1-phenyl-4,5-dihydro-1H-pyrazole-4-carboxamide

Compound ID: 186

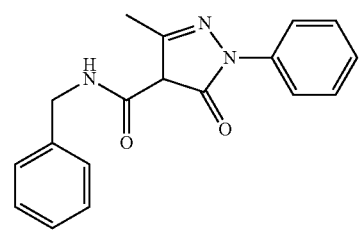 [SMILES: CC1=NN(c2ccccc2)C(=O)C1C(=O)NCc1ccccc1]

LCMS: m/z 308.0 [M+H]+;

$^1$H NMR (400 MHz, DMSO-d$_6$) δ 8.8 (s, 1H), 7.68-7.71 (m, 2H), 7.49 (t, J=8.8, 2H), 7.23-7.32 (m, 6H), 4.54 (s, 2H), 2.54-2.56 (m, 3H).

1-isopropyl-3-methyl-5-oxo-N-phenyl-4,5-dihydro-1H-pyrazole-4-carboxamide

Compound ID: 187

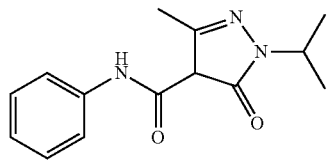 [SMILES: CC1=NN(C(C)C)C(=O)C1C(=O)Nc1ccccc1]

LCMS: m/z 260.1 [M+H]+;

$^1$H NMR (400 MHz, DMSO-d$_6$) δ 10.84 (s, 1H), 7.56 (d, J=7.6, 2H), 7.29 (t, J=8.0, 2H), 7.00 (t, J=7.2, 1H), 4.50-4.57 (m, 1H), 2.45 (s, 3H), 1.28 (d, J=6.8 Hz, 6H).

N-(4-methoxyphenyl)-3-methyl-5-oxo-1-phenyl-4,5-dihydro-1H-pyrazole-4-carboxamide Compound ID: 188

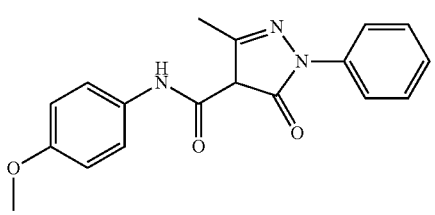 [SMILES: COc1ccc(NC(=O)C2C(=O)N(c3ccccc3)N=C2C)cc1]

LCMS: m/z 324.1 [M+H]+;

$^1$H NMR (400 MHz, DMSO-d$_6$) δ 13.24 (s, 1H), 10.52 (s, 1H), 7.72 (d, J=7.6 Hz, 2H), 7.55-7.50 (m, 4H), 7.35-7.32 (m, 1H), 6.90 (d, J=7.2 Hz, 2H), 3.73 (s, 3H), 2.55 (s, 3H)

N-(4-fluorophenyl)-3-methyl-5-oxo-1-phenyl-4,5-dihydro-1H-pyrazole-4-carboxamide Compound ID: 189

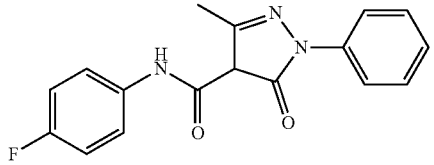

LCMS: m/z 312.0 [M+H]+;

$^1$H NMR (400 MHz, DMSO-d$_6$) δ=13.18 (s, 1H), 10.68 (s, 1H), 7.73-7.72 (m, 2H), 7.71-7.64 (m, 2H), 7.64-7.52 (m, 2H), 7.40-7.30 (m, 1H), 7.18-7.15 (m, 2H), 2.55 (s, 3H)

1,5-dimethyl-3-oxo-N,2-diphenyl-2,3-dihydro-1H-pyrazole-4-carboxamide

Compound ID: 190

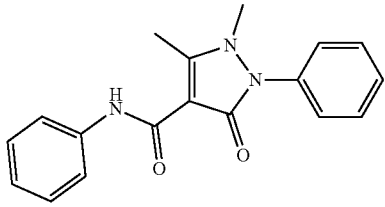 [SMILES: Cc1c(C(=O)Nc2ccccc2)c(=O)n(-c2ccccc2)n1C]

LCMS: m/z 308.3 [M+H]+;

¹HNMR (400 MHz, DMSO-d$_6$) δ=10.60 (s, 1H), 7.59 (d, J=8.0 Hz, 2H), 7.48 (t, J=7.6 Hz, 2H), 7.38 (t, J=7.6 Hz, 1H), 7.29 (d, J=7.6 Hz, 2H), 7.23 (t, J=7.6 Hz, 2H), 6.98 (t, J=7.2 Hz, 1H), 3.27 (s, 3H), 2.72 (s, 3H).

3-methyl-5-oxo-1-phenyl-N-(pyridin-3-yl)-4,5-dihydro-1H-pyrazole-4-carboxamide Compound ID: 191

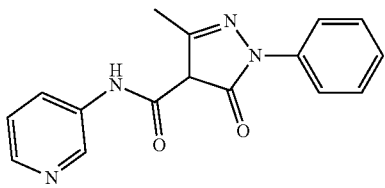 [SMILES: CC1=NN(c2ccccc2)C(=O)C1C(=O)Nc1cccnc1]

LCMS: m/z 295.2 [M+H]+;

¹H NMR (400 MHz, DMSO-d$_6$) δ=11.32 (s, 1H), 8.83 (s, 1H), 8.13-8.09 (m, 2H), 8.01 (d, J=8.0 Hz, 2H), 7.35 (t, J=8.0 Hz, 3H), 7.07 (t, J=7.6 Hz, 1H), 2.34 (s, 3H).

5-hydroxy-3-methyl-N-phenyl-1-(pyridin-2-yl)-1H-pyrazole-4-carboxamide

Compound ID: 192

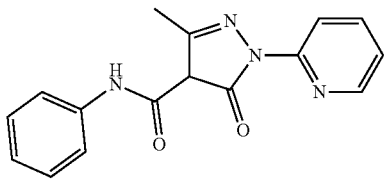 [SMILES: CC1=NN(c2ccccn2)C(=O)C1C(=O)Nc1ccccc1]

LCMS: m/z 295.0 [M+H]+;

¹H NMR (400 MHz, DMSO-d$_6$) δ=10.53 (s, 1H), 8.49 (d, J=8.0 Hz, 1H), 8.40 (d, J=8.0 Hz, 1H), 8.02 (d, J=8.0 Hz, 1H), 7.61 (d, J=8.0 Hz, 2H), 7.29-7.35 (m, 3H), 7.03 (d, J=8.0 Hz, 1H), 2.52 (s, 3H).

3-methyl-5-oxo-N-phenyl-1-(pyridin-4-yl)-4,5-dihydro-1H-pyrazole-4-carboxamide Compound ID: 193

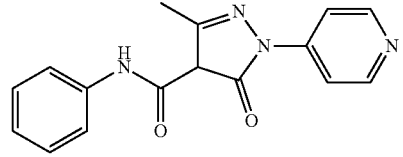

LCMS: m/z 295.2 [M+H]+;

¹H NMR (400 MHz, DMSO-d$_6$) δ=10.51 (s, 1H), 8.65-8.41 (m, 4H), 7.57 (d, J=7.6 Hz, 2H), 7.25 (t, J=7.2 Hz, 2H), 6.93 (t, J=7.2 Hz, 1H), 2.32 (s, 3H).

1-benzyl-5-hydroxy-3-methyl-N-phenyl-1H-pyrazole-4-carboxamide

Compound ID: 194

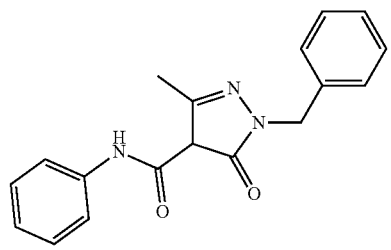 [SMILES: CC1=NN(Cc2ccccc2)C(=O)C1C(=O)Nc1ccccc1]

LCMS: m/z 308.1 [M+H]+;

¹H NMR (400 MHz, DMSO-d$_6$) δ 10.80 (s, 1H), 7.59 (d, J=7.6 Hz, 2H), 7.37 (t, J=7.6 Hz, 2H), 7.30 (t, J=8.0 Hz, 3H), 7.23 (d, J=7.2 Hz, 2H), 7.01 (t, J=8.0 Hz, 1H), 4.98 (s, 2H), 2.41 (s, 3H).

3-methyl-5-oxo-N-phenyl-1-(pyridin-3-yl)-4,5-dihydro-1H-pyrazole-4-carboxamide Compound ID: 195

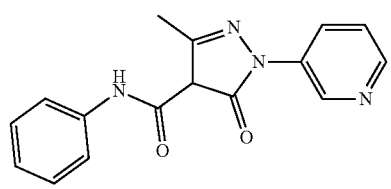 [SMILES: CC1=NN(c2cccnc2)C(=O)C1C(=O)Nc1ccccc1]

LCMS: m/z 295.1 [M+H]+;

¹H NMR (400 MHz, DMSO-d$_6$) δ 10.60 (s, 1H), 9.38 (s, 1H), 8.71 (d, J=8.0 Hz, 1H), 8.52 (dd, J=1.2, 5.2 Hz, 1H), 7.86 (dd, J=5.2, 8.4 Hz, 1H), 7.60 (d, J=7.6 Hz, 2H), 7.28 (t, J=8.0 Hz, 2H), 7.06-6.88 (m, 1H), 2.42 (s, 3H).

1,3-dimethyl-5-oxo-N-phenyl-4,5-dihydro-1H-pyrazole-4-carboxamide

Compound ID: 196

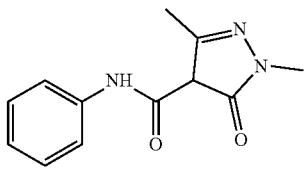 [SMILES: CC1=NN(C)C(=O)C1C(=O)Nc1ccccc1]

LCMS: m/z 232.2 [M+H]+;

<sup>1</sup>H NMR (400 MHz, DMSO-d<sub>6</sub>) δ 10.80 (s, 1H), 7.59 (d, J=7.6 Hz, 2H), 7.28-7.32 (m, 2H), 6.99-7.03 (m, 1H), 3.35 (s, 3H), 2.43 (s, 3H).

1-(4-methoxyphenyl)-3-methyl-5-oxo-N-phenyl-4,5-dihydro-1H-pyrazole-4-carboxamide Compound ID: 197

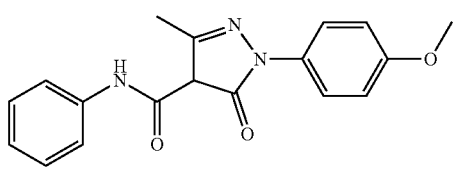 [SMILES: COc1ccc(N2N=C(C)C(C(=O)Nc3ccccc3)C2=O)cc1]

LCMS: m/z 324.1 [M+H]+;

<sup>1</sup>H NMR (400 MHz, DMSO-d<sub>6</sub>) δ 10.76 (s, 1H), 7.59-7.61 (m, 4H), 7.29 (t, J=8.0 Hz, 2H), 7.06-7.07 (m, 2H), 7.00-7.05 (m, 1H), 3.79 (s, 3H), 2.48 (s, 3H).

<sup>1</sup>H NMR (400 MHz, DMSO-d<sub>6</sub>) δ 12.58 (s, 1H), 8.72 (d, J=7.2 Hz, 1H), 7.90 (dd, J=1.6, 8.0 Hz, 1H), 7.46-7.34 (m, 1H), 7.18 (t, J=7.2 Hz, 2H), 6.93-6.85 (m, 2H), 6.79 (s, 3H), 4.29 (m, 1H), 3.88-3.69 (m, 1H), 2.45-2.36 (m, 1H), 2.04-1.90 (m, 2H), 1.84-1.69 (m, 1H), 1.68-1.60 (m, 1H), 1.59-1.47 (m, 1H).

5-hydroxy-3-methyl-1-(naphthalen-2-yl)-N-phenyl-1H-pyrazole-4-carboxamide

Compound ID: 198

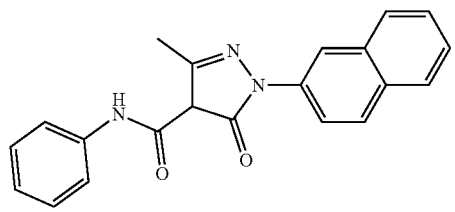 [SMILES: CC1=NN(c2ccc3ccccc3c2)C(=O)C1C(=O)Nc1ccccc1]

LCMS: m/z 366.0 [M+H]+;

<sup>1</sup>H NMR (400 MHz, DMSO-d<sub>6</sub>) δ 10.73 (s, 1H), 8.24 (s, 1H), 8.07 (d, J=8.8 Hz, 1H), 8.05-7.94 (m, 3H), 7.64 (d, J=7.6 Hz, 2H), 7.63-7.49 (m, 2H), 7.32 (t, J=8.0 Hz, 2H), 7.03 (t, J=7.2 Hz, 1H), 2.58 (s, 3H)

N,3-dimethyl-5-oxo-1-phenyl-4,5-dihydro-1H-pyrazole-4-carboxamide

Compound ID: 199

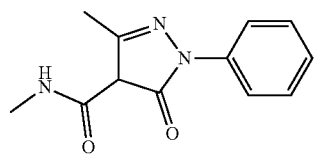 [SMILES: CNC(=O)C1C(=O)N(c2ccccc2)N=C1C]

LCMS: m/z 232.1 [M+H]+;

<sup>1</sup>H NMR (400 MHz, CHLOROFORM-d) δ 11.10 (s, 1H), 7.96 (s, 1H), 7.45 (m, 2H), 7.37 (m, 2H), 7.29 (m, 1H), 2.78 (s, 3H), 2.40 (s, 3H).

N-isopropyl-3-methyl-5-oxo-1-phenyl-4,5-dihydro-1H-pyrazole-4-carboxamide

Compound ID: 200

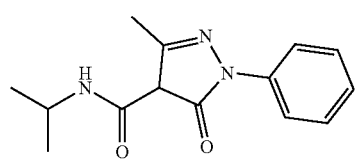 [SMILES: CC1=NN(c2ccccc2)C(=O)C1C(=O)NC(C)C]

LCMS: m/z 260.2 [M+H]+;

<sup>1</sup>H NMR (400 MHz, DMSO-d<sub>6</sub>) δ 12.83 (s, 1H), 8.30 (s, 1H), 7.70 (d, J=7.6 Hz, 2H), 7.47 (t, J=8.0 Hz, 2H), 7.27 (t, J=7.2 Hz, 1H), 4.00 (dt, J=12.8, 6.4 Hz, 1H), 2.46 (s, 3H), 1.12 (d, J=6.8 Hz, 6H)

3-methyl-5-oxo-N-phenyl-1-(4-(trifluoromethyl)phenyl)-4,5-dihydro-1H-pyrazole-4-carboxamide Compound ID: 201

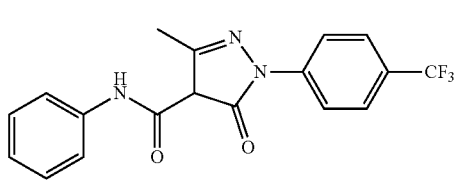

LCMS: m/z 362.1 [M+H]+;

<sup>1</sup>H NMR (400 MHz, DMSO-d<sub>6</sub>) δ 10.56 (s, 1H), 8.03 (d, J=8.4 Hz, 2H), 7.89 (d, J=8.8 Hz, 2H), 7.62 (dd, J=8.8, 1.2 Hz, 2H), 7.32 (t, J=8.0 Hz, 2H), 7.04 (t, J=7.2 Hz, 1H), 2.57 (s, 3H)

201

1-(1,1-dioxidotetrahydrothiophen-3-yl)-3-methyl-5-oxo-N-phenyl-4,5-dihydro-1H-pyrazole-4-carboxamide Compound ID: 202

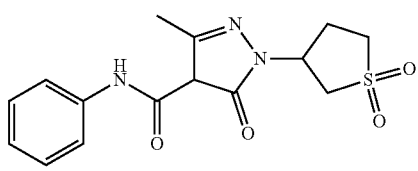 [SMILES: CC1=NN(C2CCS(=O)(=O)C2)C(=O)C1C(=O)Nc1ccccc1]

LCMS: m/z 336.0 [M+H]+;

$^1$H NMR (400 MHz, DMSO-d$_6$) δ 10.54 (s, 1H), 7.56 (d, J=8.0 Hz, 2H), 7.30 (t, J=7.6 Hz, 2H), 7.02 (t, J=7.6 Hz, 1H), 5.15-5.04 (m, 1H), 3.58-3.52 (m, 1H), 3.50-3.42 (m, 1H), 3.36-3.20 (m, 2H), 2.49-2.46 (m, 2H), 2.44 (s, 3H)

N-(4-acetylphenyl)-3-methyl-5-oxo-1-phenyl-4,5-dihydro-1H-pyrazole-4-carboxamide Compound ID: 203

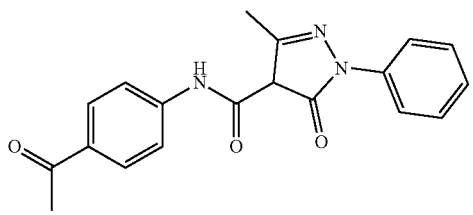 [SMILES: CC(=O)c1ccc(NC(=O)C2C(=O)N(c3ccccc3)N=C2C)cc1]

LCMS: m/z 336.2 [M+H]+;

$^1$H NMR (400 MHz, DMSO-d$_6$) δ 11.33 (s, 1H), 7.95-7.85 (m, 4H), 7.73 (d, J=8.4 Hz, 2H), 7.41 (t, J=8.0 Hz, 2H), 7.15 (t, J=7.6 Hz, 1H), 2.40 (s, 3H)

N,3-dimethyl-5-oxo-N,1-diphenyl-4,5-dihydro-1H-pyrazole-4-carboxamide

Compound ID: 204

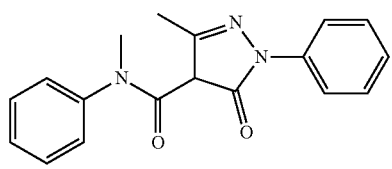 [SMILES: CC1=NN(c2ccccc2)C(=O)C1C(=O)N(C)c1ccccc1]

LCMS: m/z 308.1 [M+H]+;

$^1$H NMR (400 MHz, DMSO-d$_6$+D$_2$O) δ 7.48 (d, J=7.6 Hz, 2H), 7.38 (t, J=7.2 Hz, 2H), 7.28 (t, J=8.0 Hz, 2H), 7.23-7.10 (m, 4H), 3.31 (s, 3H), 1.98 (s, 3H)

202

N-(4-hydroxyphenyl)-3-methyl-5-oxo-1-phenyl-4,5-dihydro-1H-pyrazole-4-carboxamide Compound ID: 205

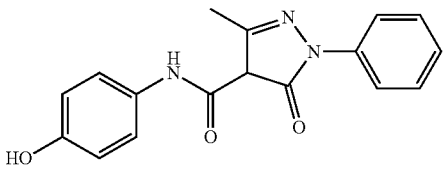 [SMILES: CC1=NN(c2ccccc2)C(=O)C1C(=O)Nc1ccc(O)cc1]

LCMS: m/z 310.2 [M+H]+;

$^1$H NMR (400 MHz, DMSO-d$_6$) δ 13.07 (s, 1H), 10.42 (s, 1H), 9.17 (s, 1H), 7.72 (d, J=7.6 Hz, 2H), 7.52 (d, J=7.6 Hz, 2H), 7.41-7.38 (m, 2H), 7.38-7.31 (m, 1H), 6.72-6.69 (m, 2H), 2.53 (s, 3H)

3-(3-methyl-5-oxo-1-phenyl-4,5-dihydro-1H-pyrazole-4-carboxamido)benzoate

Compound ID: 206

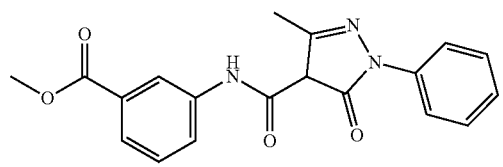 [SMILES: COC(=O)c1cccc(NC(=O)C2C(=O)N(c3ccccc3)N=C2C)c1]

LCMS: m/z 352.2 [M+H]+;

$^1$H NMR (400 MHz, DMSO-d$_6$) δ 11.03 (s, 1H), 8.36 (s, 1H), 7.83 (d, J=6.8 Hz, 2H), 7.76 (d, J=8.8 Hz, 1H), 7.59 (d, J=7.2 Hz, 1H), 7.48-7.42 (m, 3H), 7.25-7.23 (m, 1H), 3.86 (s, 3H), 2.47 (s, 3H).

N-benzoyl-3-methyl-5-oxo-1-phenyl-4,5-dihydro-1H-pyrazole-4-carboxamide

Compound ID: 207

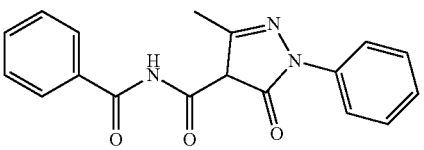 [SMILES: CC1=NN(c2ccccc2)C(=O)C1C(=O)NC(=O)c1ccccc1]

LCMS: m/z 322.1 [M+H]+;

$^1$H NMR (400 MHz, DMSO-d$_6$) δ 12.42 (s, 1H), 7.97 (d, J=7.6 Hz, 2H), 7.74 (d, J=7.6 Hz, 2H), 7.68-7.62 (m, 1H), 7.61-7.55 (m, 2H), 7.52 (t, J=8.0 Hz, 2H), 7.37-7.28 (m, 1H), 2.52 (s, 3H)

203

3-methyl-5-oxo-1-phenyl-N-(3-(trifluoromethyl)phenyl)-4,5-dihydro-1H-pyrazole-4-carboxamide Compound ID: 208

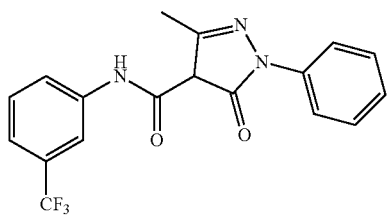 [SMILES: CC1=NN(c2ccccc2)C(=O)C1C(=O)Nc1cccc(C(F)(F)F)c1]

LCMS: m/z 362.0 [M+H]+;

$^1$H NMR (400 MHz, DMSO-d$_6$) δ 10.95 (s, 1H), 8.28 (s, 1H), 7.72 (d, J=8.0 Hz, 2H), 7.67 (d, J=8.4 Hz, 1H), 7.57-7.50 (m, 3H), 7.38 (d, J=7.6 Hz, 1H), 7.36-7.29 (m, 1H), 2.55 (s, 3H)

N-(2,3-dihydro-1H-inden-5-yl)-3-methyl-5-oxo-1-phenyl-4,5-dihydro-1H-pyrazole-4-carboxamide Compound ID: 209

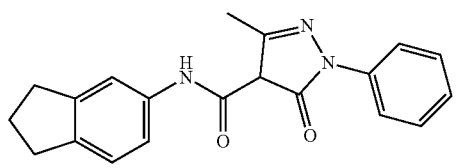 [SMILES: CC1=NN(c2ccccc2)C(=O)C1C(=O)Nc1ccc2c(c1)CCC2]

LCMS: m/z 334.1 [M+H]+;

$^1$H NMR (400 MHz, DMSO-d$_6$) δ 10.63 (s, 1H), 7.75 (d, J=7.6 Hz, 2H), 7.58 (s, 1H), 7.52 (t, J=7.6 Hz, 2H), 7.34-7.26 (m, 2H), 7.14 (d, J=8.0 Hz, 1H), 2.87-2.79 (m, 4H), 2.54 (s, 3H), 2.06-1.97 (m, 2H)

N-(3-chlorophenyl)-3-methyl-5-oxo-1-phenyl-4,5-dihydro-1H-pyrazole-4-carboxamide Compound ID: 210

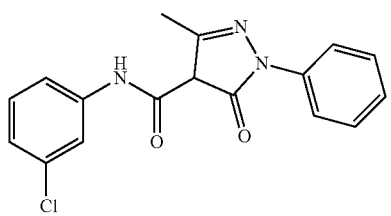 [SMILES: CC1=NN(c2ccccc2)C(=O)C1C(=O)Nc1cccc(Cl)c1]

LCMS: m/z 350.2 [M+Na]+;

$^1$H NMR (400 MHz, DMSO-d$_6$) δ 10.84 (s, 1H), 8.05-7.91 (m, 1H), 7.79-7.65 (m, 2H), 7.56-7.47 (m, 2H), 7.36-7.26 (m, 3H), 7.14-7.00 (m, 1H), 2.54 (s, 3H).

204

N-(3-methoxyphenyl)-3-methyl-5-oxo-1-phenyl-4,5-dihydro-1H-pyrazole-4-carboxamide Compound ID: 211

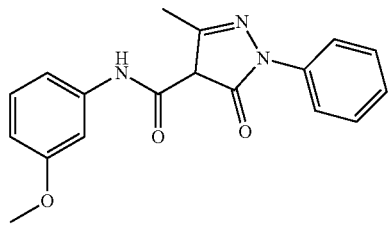 [SMILES: COc1cccc(NC(=O)C2C(=O)N(c3ccccc3)N=C2C)c1]

LCMS: m/z 324.2 [M+H]$^+$;

$^1$H NMR (400 MHz, DMSO-d$_6$) δ 10.71 (s, 1H), 7.75-7.66 (m, 2H), 7.52 (t, J=7.6 Hz, 2H), 7.39 (t, J=2.4 Hz, 1H), 7.36-7.29 (m, 1H), 7.24-7.16 (m, 1H), 7.08-7.04 (m, 1H), 6.61 (dd, J=1.6, 8.0 Hz, 1H), 3.75 (s, 3H), 2.54 (s, 3H)

3-methyl-5-oxo-1-phenyl-N-(m-tolyl)-4,5-dihydro-1H-pyrazole-4-carboxamide

Compound ID: 212

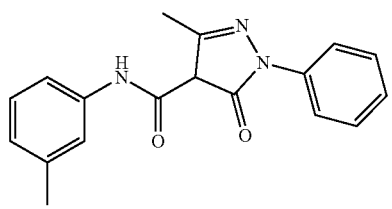 [SMILES: CC1=NN(c2ccccc2)C(=O)C1C(=O)Nc1cccc(C)c1]

LCMS: m/z 308.1 [M+H]$^+$;

$^1$H NMR (400 MHz, DMSO-d$_6$) δ 10.72 (s, 1H), 7.78 (d, J=8.0 Hz, 2H), 7.53-7.44 (m, 3H), 7.40 (d, J=8.0 Hz, 1H), 7.27 (t, J=8.0 Hz, 1H), 7.17 (t, J=7.6 Hz, 1H), 6.83 (d, J=7.6 Hz, 1H), 2.53 (s, 3H), 2.28 (s, 3H)

3-methyl-5-oxo-1-phenyl-N-(3-(pyrazin-2-yl)phenyl)-4,5-dihydro-1H-pyrazole-4-carboxamide Compound ID: 213

LCMS: m/z 336.1 [M+H]$^+$;

$^1$H NMR (400 MHz, DMSO-d$_6$) δ 11.81 (s, 1H), 8.42 (d, J=8.0 Hz, 1H), 7.89 (dd, J=1.2, 7.6 Hz, 1H), 7.77 (d, J=7.6 Hz, 2H), 7.56-7.45 (m, 3H), 7.27 (t, J=7.2 Hz, 1H), 7.19-7.10 (m, 1H), 2.57 (s, 3H), 2.51-2.55 (m, 3H)

3-methyl-5-oxo-1-phenyl-N-(pyridin-2-yl)-4,5-dihydro-1H-pyrazole-4-carboxamide Compound ID: 214

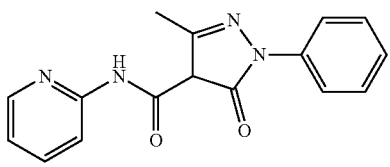 [SMILES: CC1=NN(c2ccccc2)C(=O)C1C(=O)Nc1ccccn1]

LCMS: m/z 295.0 [M+H]⁺;
¹H NMR (400 MHz, DMSO-d₆) δ 11.64 (s, 1H), 8.27 (d, J=4.4 Hz, 1H), 8.11-8.00 (m, 1H), 7.95-7.76 (m, 3H), 7.45 (t, J=7.6 Hz, 2H), 7.22 (t, J=7.6 Hz, 1H), 7.12 (t, J=6.8 Hz, 1H), 2.46 (s, 3H).

N-(3-bromophenyl)-3-methyl-5-oxo-1-phenyl-4,5-dihydro-1H-pyrazole-4-carboxamide Compound ID: 215

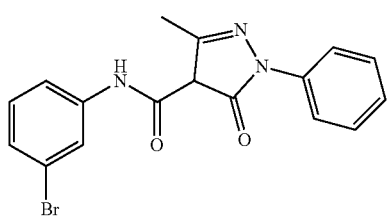 [SMILES: CC1=NN(c2ccccc2)C(=O)C1C(=O)Nc1cccc(Br)c1]

LCMS: m/z 371.9 [M+H]⁺;
¹H NMR (400 MHz, DMSO-d₆) δ=10.84 (s, 1H), 8.14 (s, 1H), 7.74 (d, J=8.0 Hz, 2H), 7.53 (t, J=7.6 Hz, 2H), 7.40 (d, J=7.6 Hz, 1H), 7.35-7.19 (m, 3H), 2.54 (s, 3H).

3-methyl-5-oxo-1-phenyl-N-(pyridin-4-yl)-4,5-dihydro-1H-pyrazole-4-carboxamide Compound ID: 216

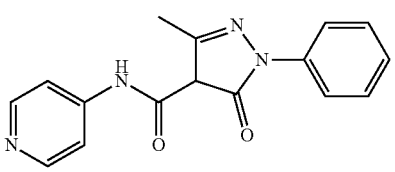 [SMILES: CC1=NN(c2ccccc2)C(=O)C1C(=O)Nc1ccncc1]

LCMS: m/z 295.0 [M+H]⁺;
¹H NMR (400 MHz, DMSO-d₆) δ 12.58 (s, 1H), 8.49 (d, J=6.8 Hz, 2H), 8.14-7.97 (m, 4H), 7.32 (t, J=7.6 Hz, 2H), 7.03 (t, J=7.6 Hz, 1H), 2.27 (s, 3H)
¹³C NMR (101 MHz, DMSO-d₆) δ 165.63, 163.57, 154.18, 149.06, 142.29, 141.04, 128.79, 122.97, 118.23, 113.47, 93.82, 15.84

3-methyl-5-oxo-1-phenyl-N-(thiazol-2-yl)-4,5-dihydro-1H-pyrazole-4-carboxamide Compound ID: 217

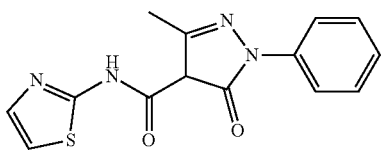 [SMILES: CC1=NN(c2ccccc2)C(=O)C1C(=O)Nc1nccs1]

LCMS: m/z 301.2 [M+H]⁺;
¹H NMR (400 MHz, METHANOL-d₄) δ 7.65 (d, J=7.6 Hz, 2H), 7.54 (t, J=8.0 Hz, 2H), 7.47 (d, J=3.6 Hz, 1H), 7.43-7.34 (m, 1H), 7.16 (d, J=3.6 Hz, 1H), 2.63 (s, 3H).

(2S)-2-(3-methyl-5-oxo-1-phenyl-4,5-dihydro-1H-pyrazole-4-carboxamido)propanoic acid Compound ID: 218

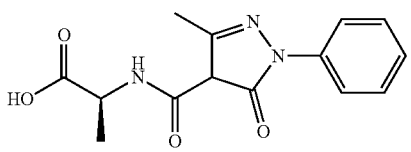

LCMS: m/z 290.4 [M+H]⁺;
¹H NMR (400 MHz, DMSO-d₆) δ 12.72 (s, 1H), 8.77 (d, J=6.4 Hz, 1H), 7.72 (d, J=8.0 Hz, 2H), 7.49 (t, J=8.0 Hz, 2H), 7.28 (t, J=8.0 Hz, 1H), 4.41 (m, 1H), 2.47 (s, 3H), 1.34 (d, J=7.2 Hz, 3H).

N-(1H-benzo[d]imidazol-5-yl)-3-methyl-5-oxo-1-phenyl-4,5-dihydro-1H-pyrazole-4-carboxamide Compound ID: 219

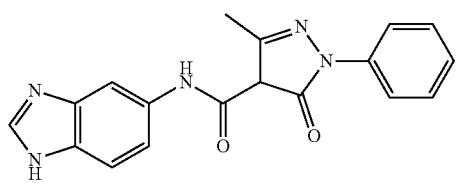 [SMILES: CC1=NN(c2ccccc2)C(=O)C1C(=O)Nc1ccc2[nH]cnc2c1]

LCMS: m/z 334.2 [M+H]⁺;
¹H NMR (400 MHz, DMSO-d₆) δ=11.05 (d, J=9.2 Hz, 1H), 9.49 (d, J=14.8 Hz, 1H), 8.51 (d, J=1.6 Hz, 1H), 7.86-7.70 (m, 3H), 7.59-7.44 (m, 3H), 7.33 (t, J=7.2 Hz, 1H), 2.59 (d, J=4.0 Hz, 3H).

207

N-(3-(dimethylcarbamoyl)phenyl)-3-methyl-5-oxo-1-phenyl-4,5-dihydro-1H-pyrazole-4-carboxamide Compound ID: 220

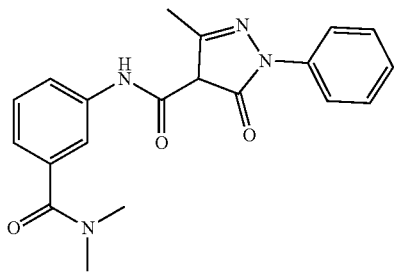 [SMILES: CC1=NN(c2ccccc2)C(=O)C1C(=O)Nc1cccc(C(=O)N(C)C)c1]

LCMS: m/z 365.3 [M+H]+;

$^1$H NMR (400 MHz, DMSO-d$_6$) δ 10.81 (s, 1H), 7.79 (t, J=1.6 Hz, 1H), 7.76-7.69 (m, 2H), 7.56-7.47 (m, 3H), 7.37 (t, J=8.0 Hz, 1H), 7.35-7.29 (m, 1H), 7.04 (d, J=7.6 Hz, 1H), 3.08-2.84 (m, 6H), 2.54 (s, 3H).

3-methyl-1-(1-methylpiperidin-4-yl)-5-oxo-N-phenyl-4,5-dihydro-1H-pyrazole-4-carboxamide Compound ID: 221

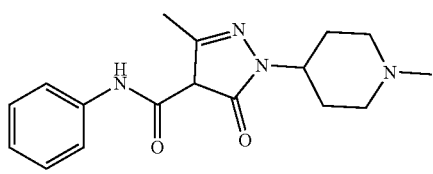 [SMILES: CC1=NN(C2CCN(C)CC2)C(=O)C1C(=O)Nc1ccccc1]

LCMS: m/z 315.2 [M+H]+;

$^1$H NMR (400 MHz, DMSO-d$_6$) δ 11.19 (s, 1H), 8.16 (s, 1H), 7.52 (d, J=7.6 Hz, 2H), 7.19 (t, J=7.6 Hz, 2H), 6.84 (t, J=7.6 Hz, 1H), 4.25-4.15 (m, 1H), 3.34-3.33 (m, 2H), 2.93 (t, J=12.0 Hz, 2H), 2.68 (s, 3H), 2.15 (s, 3H), 2.14-2.03 (m, 2H), 1.78 (d, J=11.7 Hz, 2H)

N-(3-hydroxyphenyl)-3-methyl-5-oxo-1-phenyl-4,5-dihydro-1H-pyrazole-4-carboxamide Compound ID: 222

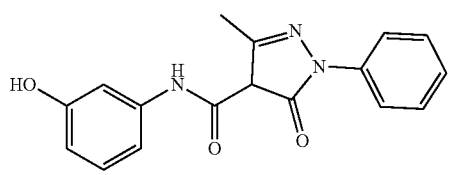 [SMILES: CC1=NN(c2ccccc2)C(=O)C1C(=O)Nc1cccc(O)c1]

LCMS: m/z 310.2 [M+H]+;

$^1$H NMR (400 MHz, DMSO-d$_6$) δ 10.76 (s, 1H), 9.28 (s, 1H), 7.86 (d, J=7.6 Hz, 2H), 7.44 (t, J=7.6 Hz, 2H), 7.25 (t, J=2.0 Hz, 1H), 7.23-7.17 (m, 1H), 7.08-7.02 (m, 1H), 6.92-6.87 (m, 1H), 6.39 (dd, J=1.6, 7.2 Hz, 1H), 2.45 (s, 3H).

208

N-(3-isopropylphenyl)-3-methyl-5-oxo-1-phenyl-4,5-dihydro-1H-pyrazole-4-carboxamide Compound ID: 100

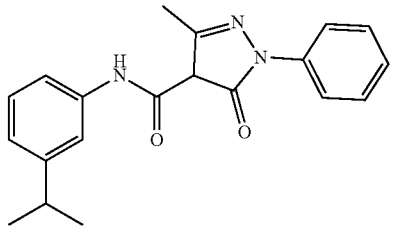 [SMILES: CC1=NN(c2ccccc2)C(=O)C1C(=O)Nc1cccc(C(C)C)c1]

LCMS: m/z 336.1 [M+H]+;

$^1$H NMR (400 MHz, DMSO-d$_6$) δ 10.68 (s, 1H), 7.74 (d, J=7.6 Hz, 2H), 7.56-7.41 (m, 4H), 7.37-7.29 (m, 1H), 7.23 (t, J=7.6 Hz, 1H), 6.92 (d, J=8.0 Hz, 1H), 2.95-2.80 (m, 1H), 2.55 (s, 3H), 1.21 (d, J=6.8 Hz, 6H).

3-methyl-5-oxo-1-phenyl-N-(3-(thiophen-2-yl)phenyl)-4,5-dihydro-1H-pyrazole-4-carboxamide Compound ID: 101

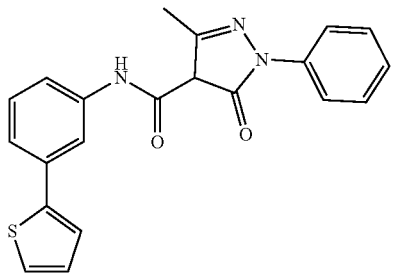 [SMILES: CC1=NN(c2ccccc2)C(=O)C1C(=O)Nc1cccc(-c2cccs2)c1]

LCMS: m/z 376.2 [M+H]+;

$^1$H NMR (400 MHz, DMSO-d$_6$) δ 10.81 (s, 1H), 8.03 (s, 1H), 7.74 (d, J=7.6 Hz, 2H), 7.58-7.45 (m, 5H), 7.37-7.29 (m, 3H), 7.14 (dd, J=4.0, 5.2 Hz, 1H), 2.56 (s, 3H).

N-([1,1'-biphenyl]-3-yl)-3-methyl-5-oxo-1-phenyl-4,5-dihydro-1H-pyrazole-4-carboxamide Compound ID: 102

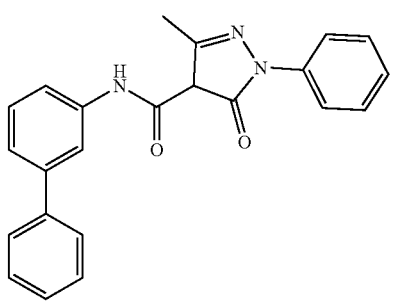 [SMILES: CC1=NN(c2ccccc2)C(=O)C1C(=O)Nc1cccc(-c2ccccc2)c1]

LCMS: m/z 370.1 [M+H]+;

$^1$H NMR (400 MHz, DMSO-d$_6$) δ 10.84 (s, 1H), 7.99 (s, 1H), 7.75 (d, J=7.7 Hz, 2H), 7.65 (d, J=7.4 Hz, 2H), 7.56 (d,

J=8.8 Hz, 1H), 7.54-7.45 (m, 4H), 7.43-7.35 (m, 2H), 7.34-7.28 (m, 2H), 2.55 (s, 3H)

N-(3-(methoxymethyl)phenyl)-3-methyl-5-oxo-1-phenyl-4,5-dihydro-1H-pyrazole-4-carboxamide Compound ID: 103

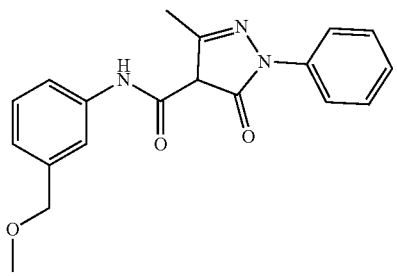 [SMILES: COCc1cccc(NC(=O)C2C(=O)N(c3ccccc3)N=C2C)c1]

LCMS: m/z 338.2[M+H]$^+$;
$^1$H NMR (400 MHz, DMSO-d$_6$) δ 11.18 (s, 1H), 8.13 (s, 1H), 8.06 (s, 2H), 7.60 (s, 1H), 7.49 (d, J=8.0 Hz, 1H), 7.30 (s, 2H), 7.20 (t, J=7.6 Hz, 1H), 7.00 (s, 1H), 6.84 (d, J=7.6 Hz, 1H), 4.37 (s, 2H), 3.29 (s, 3H), 2.28 (s, 3H).

3-methyl-5-oxo-1-phenyl-N-(3-(pyridin-4-yl)phenyl)-4,5-dihydro-1H-pyrazole-4-carboxamide Compound ID: 104

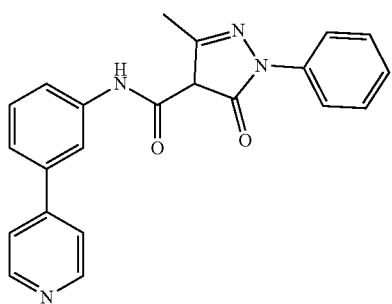 [SMILES: CC1=NN(c2ccccc2)C(=O)C1C(=O)Nc1cccc(-c2ccncc2)c1]

LCMS: m/z 371.3 [M+H]$^+$;
$^1$H NMR (400 MHz, DMSO-d$_6$) δ 10.99 (s, 1H), 8.71 (d, J=5.2 Hz, 2H), 8.16 (d, J=13.8 Hz, 1H), 7.88-7.78 (m, 4H), 7.77-7.65 (m, 1H), 7.53-7.45 (m, 4H), 7.27 (t, J=7.2 Hz, 1H), 2.49 (s, 3H).

N-(3-(aminomethyl)phenyl)-3-methyl-5-oxo-1-phenyl-4,5-dihydro-1H-pyrazole-4-carboxamide Compound ID: 223

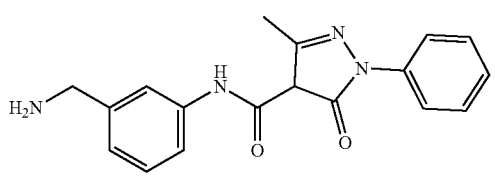 [SMILES: CC1=NN(c2ccccc2)C(=O)C1C(=O)Nc1cccc(CN)c1]

LCMS: m/z 323.2 [M+H]$^+$;
$^1$H NMR (400 MHz, DMSO-d$_6$) δ 10.81 (s, 1H), 8.35 (br s, 2H), 7.80-7.75 (m, 2H), 7.75-7.69 (m, 2H), 7.52 (t, J=8.0 Hz, 2H), 7.41-7.29 (m, 2H), 7.15 (d, J=7.6 Hz, 1H), 4.00 (d, J=5.6 Hz, 2H), 2.57 (s, 3H).

N-(4-(N,N-dimethylsulfamoyl)phenyl)-3-methyl-5-oxo-1-phenyl-4,5-dihydro-1H-pyrazole-4-carboxamide Compound ID: 105

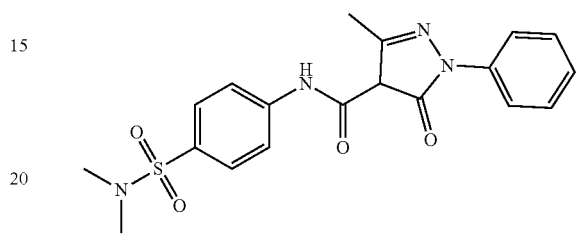

LCMS: m/z 401.2 [M+H]$^+$;
$^1$H NMR (400 MHz, METHANOL-d$_4$) δ 8.16 (s, 1H), 7.87 (d, J=8.8 Hz, 2H), 7.77 (d, J=7.8 Hz, 2H), 7.71 (d, J=8.8 Hz, 2H), 7.43 (t, J=8.0 Hz, 2H), 7.27-7.18 (m, 1H), 2.68 (s, 6H), 2.47 (s, 3H).

3-methyl-5-oxo-1-phenyl-N-(tetrahydrofuran-3-yl)-4,5-dihydro-1H-pyrazole-4-carboxamide Compound ID: 106

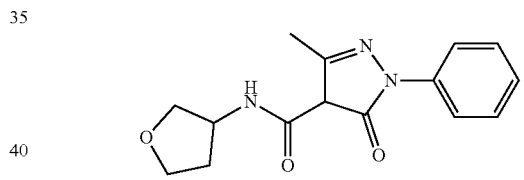

LCMS: m/z 288.1 [M+H]$^+$;
$^1$H NMR (400 MHz, DMSO-d$_6$) δ 8.62 (br s, 1H), 7.71 (d, J=7.6 Hz, 2H), 7.48 (t, J=7.6 Hz, 2H), 7.28 (t, J=7.6 Hz, 1H), 4.43 (s, 1H), 3.85-3.77 (m, 2H), 3.76-3.69 (m, 1H), 3.49 (dd, J=3.6, 8.8 Hz, 1H), 2.47 (s, 3H), 2.23-2.13 (m, 1H), 1.78-1.68 (m, 1H)

N-(3-(1H-imidazol-2-yl)phenyl)-3-methyl-5-oxo-1-phenyl-4,5-dihydro-1H-pyrazole-4-carboxamide Compound ID: 107

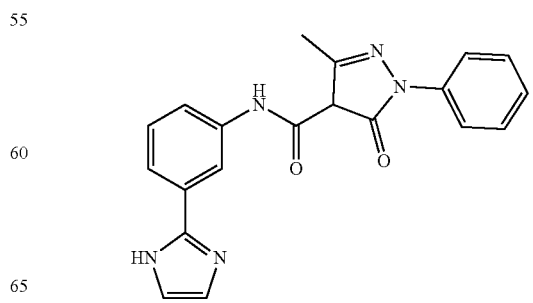

LCMS: m/z 360.1 [M+H]+;

¹H NMR (400 MHz, METHANOL-d₄) δ 8.19 (s, 1H), 7.83-7.74 (d, J=8.4 Hz, 3H), 7.57-7.49 (m, 4H), 7.43 (t, J=7.6 Hz, 2H), 7.22 (t, J=7.2 Hz, 1H), 2.47 (s, 3H)

N-(3-(furan-2-yl)phenyl)-3-methyl-5-oxo-1-phenyl-4,5-dihydro-1H-pyrazole-4-carboxamide Compound ID: 108

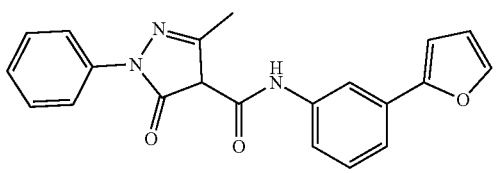 [SMILES: CC1=NN(c2ccccc2)C(=O)C1C(=O)Nc1cccc(-c2ccco2)c1]

LCMS: m/z 360.2 [M+H]+;

¹H NMR (400 MHz, DMSO-d₆) δ 10.82 (s, 1H), 8.10-7.96 (m, 1H), 7.86-7.67 (m, 3H), 7.61-7.43 (m, 3H), 7.41-7.34 (m, 2H), 7.33-7.27 (m, 1H), 6.94 (d, J=3.2 Hz, 1H), 6.60 (dd, J=1.6, 3.2 Hz, 1H), 2.54 (s, 3H)

3-methyl-5-oxo-1-phenyl-N-(3-(pyrazin-2-yl)phenyl)-4,5-dihydro-1H-pyrazole-4-carboxamide Compound ID: 109

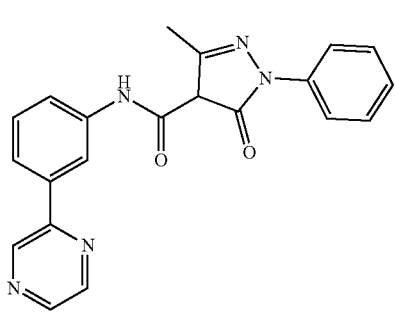 [SMILES: CC1=NN(c2ccccc2)C(=O)C1C(=O)Nc1cccc(-c2cnccn2)c1]

LCMS: m/z 372.1 [M+H]+;

¹H NMR (400 MHz, DMSO-d₆) δ 10.86 (s, 1H), 9.24 (d, J=1.6 Hz, 1H), 8.74-8.73 (m, 1H), 8.63 (d, J=2.4 Hz, 1H), 8.44 (t, J=2.0 Hz, 1H), 7.81 (d, J=7.6 Hz, 1H), 7.77-7.73 (m, 3H), 7.56-7.47 (m, 3H), 7.34 (t, J=7.6 Hz, 3H), 2.58 (s, 3H).

1-(4-(N,N-dimethylsulfamoyl)phenyl)-3-methyl-5-oxo-N-phenyl-4,5-dihydro-1H-pyrazole-4-carboxamide Compound ID: 110

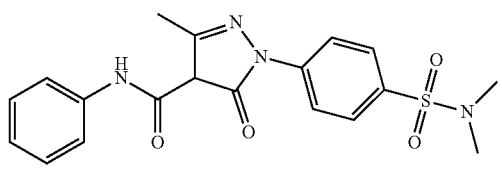 [SMILES: CC1=NN(c2ccc(S(=O)(=O)N(C)C)cc2)C(=O)C1C(=O)Nc1ccccc1]

LCMS: m/z 401.2 [M+H]+;

¹H NMR (400 MHz, DMSO-d₆) δ=11.00 (s, 1H), 8.39 (d, J=8.8 Hz, 2H), 7.66 (d, J=8.8 Hz, 2H), 7.59 (d, J=7.6 Hz, 2H), 7.23 (t, J=7.6 Hz, 2H), 6.89 (t, J=7.2 Hz, 1H), 2.58 (s, 6H), 2.27 (s, 3H).

N-(3-(hydroxymethyl)phenyl)-3-methyl-5-oxo-1-phenyl-4,5-dihydro-1H-pyrazole-4-carboxamide Compound ID: 111

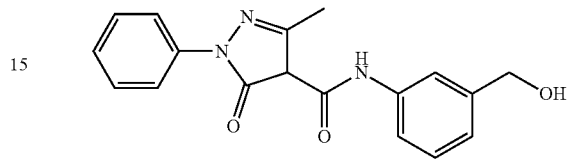

LCMS: m/z 324.1 [M+H]+;

¹H NMR (400 MHz, DMSO-d₆) δ 10.69 (s, 1H), 7.72 (d, J=7.6 Hz, 2H), 7.57-7.54 (m, 1H), 7.52-7.50 (m, 3H), 7.34-7.25 (m, 1H), 7.25-7.23 (m, 1H), 6.98 (d, J=7.6 Hz, 1H), 4.48 (s, 2H), 2.55 (s, 3H).

3-methyl-5-oxo-1-phenyl-N-(tetrahydro-2H-pyran-4-yl)-4,5-dihydro-1H-pyrazole-4-carboxamide

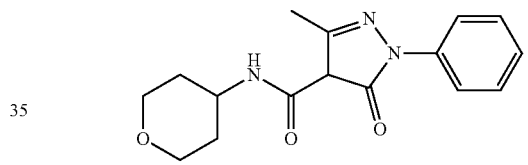

Compound ID: 112

LCMS: m/z 302.2 [M+H]+;

¹H NMR (400 MHz, DMSO-d₆) δ 8.47 (s, 1H), 7.75 (d, J=8.0 Hz, 2H), 7.44 (t, J=7.6 Hz, 2H), 7.23 (t, J=7.2 Hz, 1H), 3.96-3.92 (m, 1H), 3.83-3.80 (m, 2H), 3.41 (t, J=10.4 Hz, 2H), 2.43 (s, 3H), 1.80 (d, J=10.8 Hz, 2H), 1.45-1.37 (m, 2H).

Ethyl 3-(3-methyl-5-oxo-1-phenyl-4,5-dihydro-1H-pyrazole-4-carboxamido)benzoate

Compound ID: 113

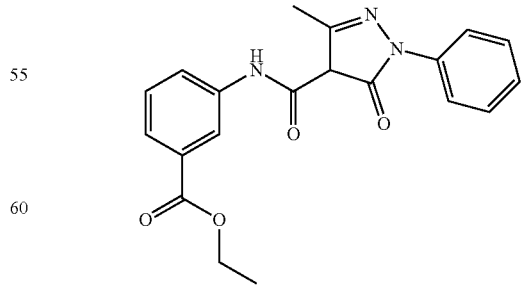

LCMS: m/z 366.2 [M+H]+;

¹H NMR (400 MHz, DMSO-d₆) δ 10.94 (s, 1H), 8.31 (t, J=2.0 Hz, 1H), 7.81-7.76 (m, 3H), 7.62 (d, J=7.6 Hz, 1H), 7.52-7.43 (m, 3H), 7.29 (t, J=7.6 Hz, 1H), 4.33 (q, J=7.2 Hz, 2H), 2.52 (s, 3H), 1.38 (t, J=7.2 Hz, 3H).

N-(3-butyrylphenyl)-3-methyl-5-oxo-1-phenyl-4,5-dihydro-1H-pyrazole-4-carboxamide Compound ID: 114

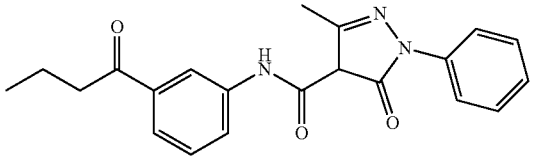 [SMILES: CCCC(=O)c1cccc(NC(=O)C2C(=O)N(c3ccccc3)N=C2C)c1]

LCMS: m/z 364.1 [M+H]⁺;

¹H NMR (400 MHz, DMSO-d₆) δ 10.93 (s, 1H), 8.25 (t, J=1.6 Hz, 1H), 7.82 (dd, J=1.2, 8.0 Hz, 3H), 7.62 (d, J=8.0 Hz, 1H), 7.51-7.44 (m, 3H), 7.32-7.26 (m, 1H), 2.99 (t, J=7.2 Hz, 2H), 2.52 (s, 3H), 1.64 (q, J=7.2 Hz, 2H), 0.94 (t, J=8.0 Hz, 3H).

N-(3-(tert-butyl)phenyl)-3-methyl-5-oxo-1-phenyl-4,5-dihydro-1H-pyrazole-4-carboxamide Compound ID: 115

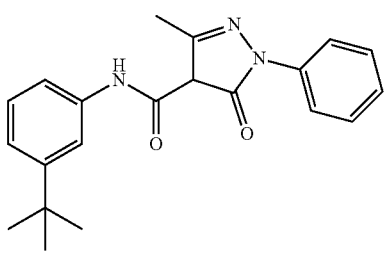 [SMILES: CC1=NN(c2ccccc2)C(=O)C1C(=O)Nc1cccc(C(C)(C)C)c1]

LCMS: m/z 350.3 [M+H]⁺;

¹H NMR (400 MHz, DMSO-d₆) δ 10.72 (s, 1H), 7.76 (d, J=7.6 Hz, 2H), 7.58 (s, 1H), 7.50-7.45 (m, 3H), 7.27-7.21 (m, 1H), 7.20 (t, J=7.6 Hz, 1H), 7.03 (d, J=7.6 Hz, 1H), 2.49 (s, 3H), 1.27 (s, 9H).

3-(3-methyl-5-oxo-1-phenyl-4,5-dihydro-1H-pyrazole-4-carboxamido)benzoic acid

Compound ID: 116

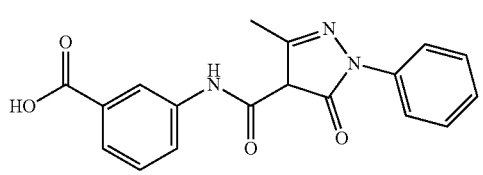 [SMILES: CC1=NN(c2ccccc2)C(=O)C1C(=O)Nc1cccc(C(=O)O)c1]

LCMS: m/z 338.2 [M+H]⁺;

¹H NMR (400 MHz, DMSO-d₆) δ 13.12 (s, 1H), 10.84 (s, 1H), 8.31 (s, 1H), 7.79-7.70 (m, 3H), 7.64-7.59 (m, 1H), 7.57-7.49 (m, 2H), 7.44 (s, 1H), 7.33 (m, 1H), 2.56 (s, 3H).

3-methyl-5-oxo-1-phenyl-N-(3-propionylphenyl)-4,5-dihydro-1H-pyrazole-4-carboxamide Compound ID: 117

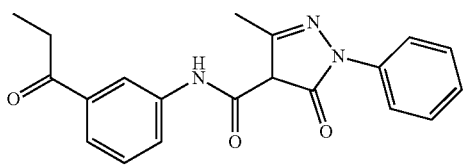 [SMILES: CCC(=O)c1cccc(NC(=O)C2C(=O)N(c3ccccc3)N=C2C)c1]

LCMS: m/z 350.2 [M+H]⁺;

¹H NMR (400 MHz, DMSO-d₆) δ 10.86 (s, 1H), 8.21 (d, J=1.6 Hz, 1H), 7.80 (d, J=7.6 Hz, 1H), 7.74 (d, J=7.6 Hz, 2H), 7.60 (d, J=8.0 Hz, 1H), 7.49 (t, J=7.6 Hz, 2H), 7.44-7.42 (d, J=8.0 Hz, 1H), 7.26 (d, J=7.6 Hz, 1H), 3.05 (q, J=7.2 Hz, 2H), 2.54 (s, 3H), 1.10 (t, J=7.2 Hz, 3H).

3-methyl-5-oxo-N-(3-pentylphenyl)-1-phenyl-4,5-dihydro-1H-pyrazole-4-carboxamide Compound ID: 118

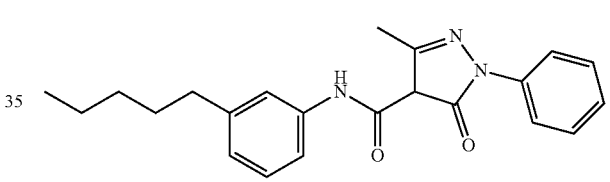

LCMS: m/z 364.3 [M+H]⁺;

¹H NMR (400 MHz, DMSO-d₆) δ=10.66 (s, 1H), 7.74 (d, J=8.0 Hz, 2H), 7.52-7.51 (m, 2H), 7.51-7.49 (m, 2H), 7.45-7.43 (m, 1H), 7.24-7.15 (t, J=6.8 Hz, 1H), 6.88-6.81 (J=7.2 Hz, 1H), 2.57-2.52 (m, 5H), 1.62-1.51 (m, 2H), 1.35-1.23 (m, 4H), 0.86 (s, 3H).

N-(3-cyclopropylphenyl)-3-methyl-5-oxo-1-phenyl-4,5-dihydro-1H-pyrazole-4-carboxamide Compound ID: 119

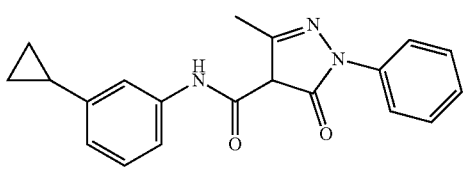 [SMILES: CC1=NN(c2ccccc2)C(=O)C1C(=O)Nc1cccc(C2CC2)c1]

LCMS: m/z 334.2 [M+H]⁺;

¹H NMR (400 MHz, DMSO-d₆) δ 10.64 (s, 1H), 7.73 (d, J=7.6 Hz, 2H), 7.54-7.49 (m, 2H), 7.36-7.32 (m, 3H), 7.17 (t, J=8.0 Hz, 1H), 6.75 (d, J=7.6 Hz, 1H), 2.54 (s, 3H), 1.90-1.89 (m, 1H), 0.95-0.92 (m, 2H), 0.66-0.64 (m, 2H).

4-(4-((3-acetylphenyl)carbamoyl)-3-methyl-5-oxo-4,5-dihydro-1H-pyrazol-1-yl)benzoic acid Compound ID: 120

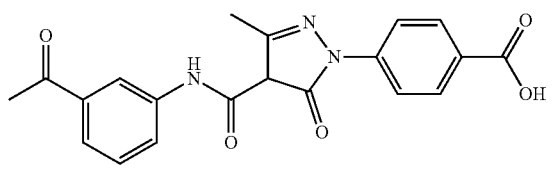 [SMILES: CC(=O)c1cccc(NC(=O)C2C(=O)N(c3ccc(C(=O)O)cc3)N=C2C)c1]

LCMS: m/z 380.2 [M+H]$^+$;

$^1$H NMR (400 MHz, METHANOL-d$_4$) δ 8.35 (s, 1H), 8.09-8.01 (m, 4H), 7.83-7.81 (m, 1H), 7.67 (d, J=4.4 Hz, 1H), 7.47-7.44 (m, 1H), 2.62 (s, 3H), 2.53 (s, 3H).

3-methyl-5-oxo-1-phenyl-N-(4-piperidyl)-4H-pyrazole-4-carboxamide

Compound ID: 121

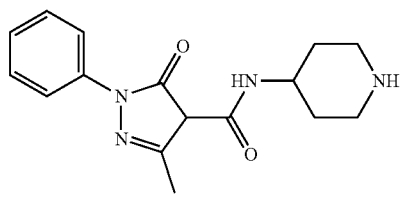 [SMILES: CC1=NN(c2ccccc2)C(=O)C1C(=O)NC1CCNCC1]

LCMS: m/z 301.2 [M+H]$^+$;

$^1$H NMR (400 MHz, METHANOL-d$_4$) δ=8.36 (s, 1H), 7.73 (d, J=8.0 Hz, 2H), 7.40 (t, J=7.6 Hz, 2H), 7.28-7.05 (m, 1H), 4.24-3.98 (m, 1H), 3.40-3.34 (m, 2H), 3.18-3.07 (m, 2H), 2.40 (s, 3H), 2.25-2.06 (m, 2H), 1.87-1.64 (m, 2H)

3-methyl-5-oxo-N-(3-oxo-1,3-dihydroisobenzofuran-5-yl)-1-phenyl-4,5-dihydro-1H-pyrazole-4-carboxamide Compound ID: 122

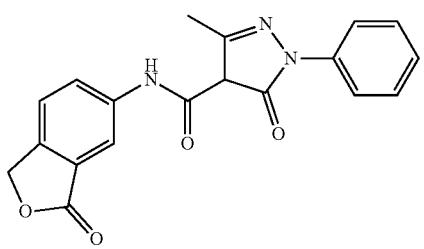 [SMILES: CC1=NN(c2ccccc2)C(=O)C1C(=O)Nc1ccc2c(c1)C(=O)OC2]

LCMS: m/z 350.0 [M+H]$^+$;

$^1$H NMR (400 MHz, DMSO-d$_6$) δ=10.99 (s, 1H), 8.37 (s, 1H), 7.80-7.77 (m, 3H), 7.75-7.69 (m, 1H), 7.54-7.49 (m, 2H), 7.38-7.31 (m, 1H), 5.36 (s, 2H), 2.54 (s, 3H).

3-(4-((3-acetylphenyl)carbamoyl)-3-methyl-5-oxo-4,5-dihydro-1H-pyrazol-1-yl)benzoic acid Compound ID: 123

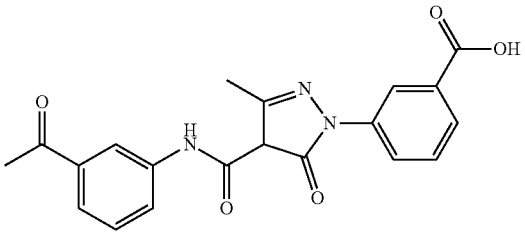 [SMILES: CC(=O)c1cccc(NC(=O)C2C(=O)N(c3cccc(C(=O)O)c3)N=C2C)c1]

LCMS: m/z 380.0 [M+H]$^+$;

$^1$H NMR (400 MHz, DMSO-d$_6$) δ 10.82 (s, 1H), 8.38 (s, 1H), 8.26 (t, J=2.0 Hz, 1H), 8.10-8.04 (m, 1H), 7.85 (d, J=8.0 Hz, 2H), 7.64-7.62 (m, 2H), 7.47 (d, J=8.0 Hz, 1H), 2.59 (s, 3H), 2.56 (s, 3H)

3-methyl-N-(3-(oxazol-2-yl)phenyl)-5-oxo-1-phenyl-4,5-dihydro-1H-pyrazole-4-carboxamide Compound ID: 124

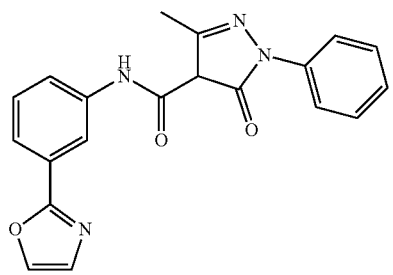 [SMILES: CC1=NN(c2ccccc2)C(=O)C1C(=O)Nc1cccc(-c2ncco2)c1]

LCMS: m/z 361.1 [M+H]$^+$;

$^1$H NMR (400 MHz, DMSO-d$_6$) δ 10.95 (s, 1H), 8.47 (s, 1H), 8.23 (s, 1H), 7.78 (d, J=8.0 Hz, 2H), 7.62 (dd, J=7.6, 18.4 Hz, 2H), 7.53-7.44 (m, 3H), 7.39 (s, 1H), 7.32-7.26 (m, 1H), 2.53 (s, 3H)

N-(3-ethylphenyl)-3-methyl-5-oxo-1-(pyridin-4-yl)-4,5-dihydro-1H-pyrazole-4-carboxamide Compound ID: 125

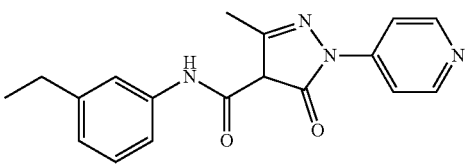 [SMILES: CCc1cccc(NC(=O)C2C(=O)N(c3ccncc3)N=C2C)c1]

LCMS: m/z 323.1 [M+H]$^+$;

$^1$H NMR (400 MHz, METHANOL-d$_4$) δ 8.46-8.60 (m, 4H), 7.47 (s, 1H), 7.41 (d, J=8.0 Hz, 1H), 7.20 (t, J=8.0 Hz, 1H), 6.89 (d, J=7.6 Hz, 1H), 2.64 (q, J=7.6 Hz, 2H), 2.44 (s, 3H), 1.25 (t, J=7.6 Hz, 3H)

217

N-(3-ethylphenyl)-5-oxo-1,3-diphenyl-4,5-dihydro-1H-pyrazole-4-carboxamide

Compound ID: 126

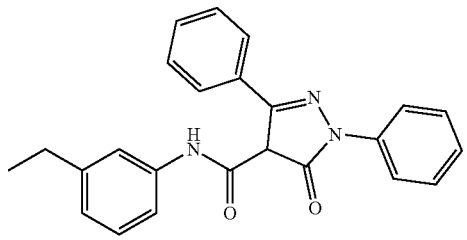 [SMILES: CCc1cccc(NC(=O)C2C(=O)N(c3ccccc3)N=C2c2ccccc2)c1]

LCMS: m/z 384.2 [M+H]$^+$;

$^1$H NMR (400 MHz, DMSO-d$_6$) δ 11.00-10.73 (s, 1H), 7.84 (d, J=7.6 Hz, 4H), 7.59-7.46 (m, 6H), 7.44-7.39 (m, 1H), 7.38-7.33 (m, 1H), 7.25-7.15 (m, 1H), 6.88 (d, J=8.0 Hz, 1H), 2.57 (d, J=7.6 Hz, 2H), 1.17 (t, J=7.6 Hz, 3H).

N-(3-ethylphenyl)-3-methyl-5-oxo-1-(4-(trifluoromethyl)phenyl)-4,5-dihydro-1H-pyrazole-4-carboxamide Compound ID: 127

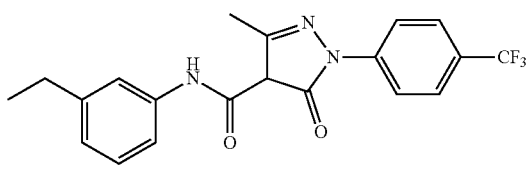

LCMS: m/z 390.2 [M+H]$^+$;

$^1$H NMR (400 MHz, CHLOROFORM-d) δ 7.83 (s, 2H), 7.65 (s, 2H), 7.39-7.29 (m, 2H), 7.22 (s, 1H), 6.98 (d, J=7.2 Hz, 1H), 2.62 (d, J=7.2 Hz, 2H), 2.54 (s, 3H), 1.22 (t, J=7.6 Hz, 3H).

N-(3-ethylphenyl)-3-isopropyl-5-oxo-1-phenyl-4,5-dihydro-1H-pyrazole-4-carboxamide Compound ID: 128

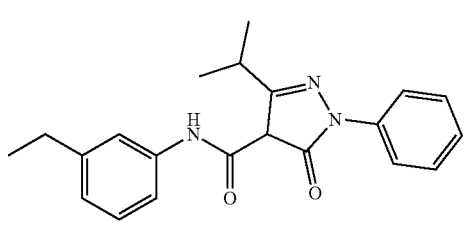 [SMILES: CCc1cccc(NC(=O)C2C(=O)N(c3ccccc3)N=C2C(C)C)c1]

LCMS: m/z 350.3 [M+H]$^+$;

$^1$H NMR (400 MHz, DMSO-d$_6$) δ 10.90 (s, 1H), 7.67 (d, J=8.0 Hz, 2H), 7.53 (t, J=8.0 Hz, 2H), 7.47 (s, 1H), 7.42 (d, J=8.0 Hz, 1H), 7.34 (d, J=8.0 Hz, 1H), 7.20 (t, J=7.6 Hz, 1H), 6.88 (d, J=8.0 Hz, 1H), 3.95-3.91 (m, 1H), 2.59-2.51 (m, 2H), 1.32 (d, J=7.2 Hz, 6H), 1.18 (t, J=7.6 Hz, 3H).

218

3-benzyl-N-(3-ethylphenyl)-5-oxo-1-phenyl-4,5-dihydro-1H-pyrazole-4-carboxamide

Compound ID: 129

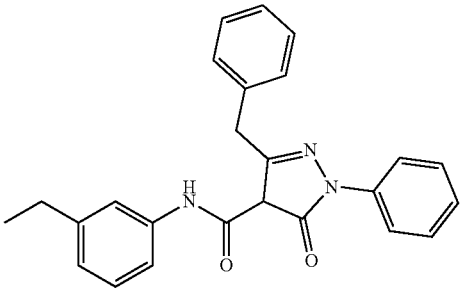 [SMILES: CCc1cccc(NC(=O)C2C(=O)N(c3ccccc3)N=C2Cc2ccccc2)c1]

LCMS: m/z 398.3 [M+H]$^+$;

$^1$H NMR (400 MHz, DMSO-d$_6$) δ 10.74 (s, 1H), 7.72 (d, J=8.0 Hz, 2H), 7.54 (t, J=8.0 Hz, 2H), 7.45-7.43 (m, 4H), 7.43-7.41 (m, 3H), 7.34-7.32 (m, 2H), 6.88 (d, J=7.8 Hz, 1H), 4.36 (s, 2H), 2.59 (q, J=7.8 Hz, 2H), 1.17 (t, J=7.5 Hz, 3H).

N-(3-ethylphenyl)-5-oxo-1-phenyl-3-(trifluoromethyl)-4,5-dihydro-1H-pyrazole-4-carboxamide Compound ID: 130

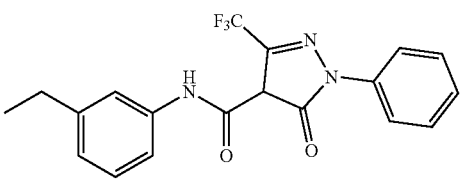 [SMILES: CCc1cccc(NC(=O)C2C(=O)N(c3ccccc3)N=C2C(F)(F)F)c1]

LCMS: m/z 376.2 [M+H]$^+$;

$^1$H NMR (400 MHz, DMSO-d$_6$) δ 11.03 (s, 1H), 8.02 (d, J=8.0 Hz, 2H), 7.49 (s, 1H), 7.42-7.40 (m, 3H), 7.24-7.13 (m, 2H), 6.81-6.79 (d, J=8.0 Hz, 1H), 2.53-2.61 (m, 2H), 1.18 (t, J=7.6 Hz, 3H).

N-(3-((dimethylamino)methyl)phenyl)-3-methyl-5-oxo-1-phenyl-4,5-dihydro-1H-pyrazole-4-carboxamide Compound ID: 131

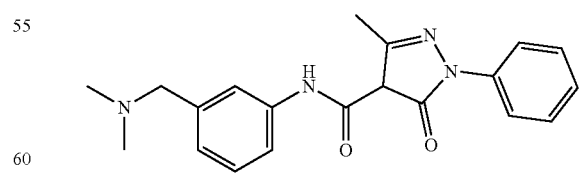

LCMS: m/z 351.2 [M+H]$^+$;

$^1$H NMR (400 MHz, METHANOL-d$_4$) δ 7.80-7.77 (m, 3H), 7.65-7.58 (m, 1H), 7.44-7.36 (m, 3H), 7.23-7.20 (m, 1H), 7.07 (d, J=7.6 Hz, 1H), 4.21 (s, 2H), 2.80 (s, 6H), 2.45 (s, 3H)

219

3-methyl-5-oxo-1-phenyl-N-(3-(pyrimidin-5-yl)phenyl)-4,5-dihydro-1H-pyrazole-4-carboxamide Compound ID: 132

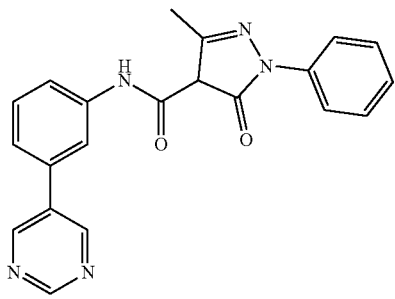 [SMILES: CC1=NN(c2ccccc2)C(=O)C1C(=O)Nc1cccc(-c2cncnc2)c1]

LCMS: m/z 372.2 [M+H]$^+$;
$^1$H NMR (400 MHz, DMSO-d$_6$) δ 10.83 (s, 1H), 9.20 (s, 1H), 9.12 (s, 2H), 8.01 (s, 1H), 7.74 (d, J=7.6 Hz, 1H), 7.74-7.72 (m, 2H), 7.55-7.51 (t, J=8.0 Hz, 2H), 7.49-7.47 (m, 2H), 7.47-7.34 (m, 1H), 2.58 (s, 3H).

N-(3-ethylphenyl)-5-oxo-1-phenyl-4,5-dihydro-1H-pyrazole-4-carboxamide

Compound ID: 133

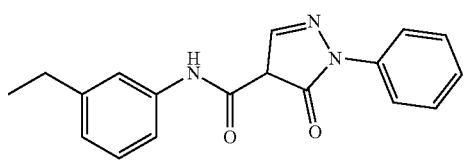 [SMILES: CCc1cccc(NC(=O)C2C=NN(c3ccccc3)C2=O)c1]

LCMS: m/z 308.0 [M+H]$^+$;
$^1$H NMR (400 MHz, DMSO-d$_6$) δ 10.31 (s, 1H), 8.28 (s, 1H), 7.78 (d, J=8.4 Hz, 2H), 7.53-7.47 (m, 4H), 7.32-7.29 (m, 1H), 7.28-7.23 (m, 1H), 6.90 (d, J=7.6 Hz, 1H), 2.57 (q, J=7.6 Hz, 2H), 1.19 (t, J=7.6 Hz, 3H)

1-(4-ethoxyphenyl)-N-(3-ethylphenyl)-3-methyl-5-oxo-4,5-dihydro-1H-pyrazole-4-carboxamide Compound ID: 134

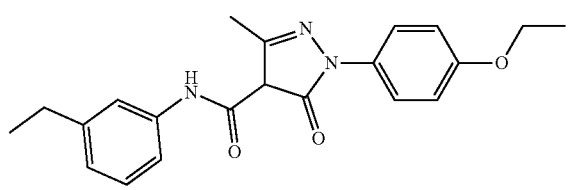 [SMILES: CCOc1ccc(N2N=C(C)C(C(=O)Nc3cccc(CC)c3)C2=O)cc1]

LCMS: m/z 285.1 [M−80];
$^1$H NMR (400 MHz, DMSO-d$_6$) δ 8.51 (s, 1H), 8.43 (s, 1H), 7.33 (d, J=8.8 Hz, 2H), 7.30 (s, 1H), 7.24-7.19 (m, 1H), 7.16 (t, J=7.6 Hz, 1H), 6.84 (d, J=7.2 Hz, 2H), 6.80 (d, J=7.6 Hz, 1H), 3.97 (q, J=6.8 Hz, 2H), 2.56 (q, J=7.6 Hz, 2H), 2.52 (s, 3H), 1.30 (t, J=6.8 Hz, 3H), 1.17 (t, J=7.6 Hz, 3H).

220 ethyl 4-(3-methyl-5-oxo-1-phenyl-4,5-dihydro-1H-pyrazole-4-carboxamido)picolinate Compound ID: 135

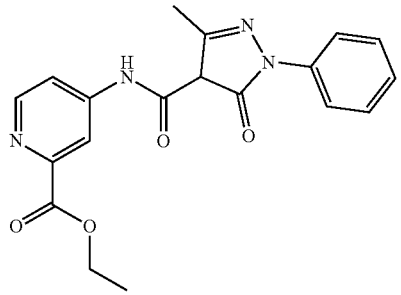 [SMILES: CCOC(=O)c1cc(NC(=O)C2C(=O)N(c3ccccc3)N=C2C)ccn1]

LCMS: m/z 367.0 [M+H]$^+$;
$^1$H NMR (400 MHz, DMSO-d$_6$) δ 11.81 (s, 1H), 8.51 (d, J=6.0 Hz, 1H), 8.44 (s, 1H), 7.87 (d, J=7.6 Hz, 3H), 7.44 (t, J=7.6 Hz, 2H), 7.20 (t, J=7.6 Hz, 1H), 4.39 (q, J=6.8 Hz, 2H), 2.43 (s, 3H), 1.36 (t, J=6.8 Hz, 3H)

3-ethyl-N-(3-ethylphenyl)-5-oxo-1-phenyl-4,5-dihydro-1H-pyrazole-4-carboxamide

Compound ID: 136

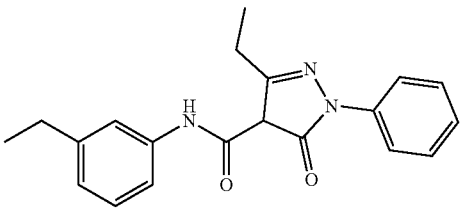 [SMILES: CCC1=NN(c2ccccc2)C(=O)C1C(=O)Nc1cccc(CC)c1]

LCMS: m/z 336.2 [M+H]$^+$;
$^1$H NMR (400 MHz, DMSO-d$_6$) δ 10.74 (s, 1H), 7.72 (d, J=8.0 Hz, 2H), 7.53 (t, J=7.6 Hz, 2H), 7.48 (s, 1H), 7.43 (d, J=7.6 Hz, 1H), 7.38-7.30 (m, 1H), 7.21 (t, J=7.6 Hz, 1H), 6.89 (d, J=7.6 Hz, 1H), 2.97 (q, J=7.6 Hz, 2H), 2.59 (q, J=7.6 Hz, 2H), 1.28 (t, J=7.6 Hz, 3H), 1.18 (t, J=7.6 Hz, 3H).

N-(3-ethylphenyl)-5-oxo-1-phenyl-3-(pyridin-4-yl)-4,5-dihydro-1H-pyrazole-4-carboxamide Compound ID: 137

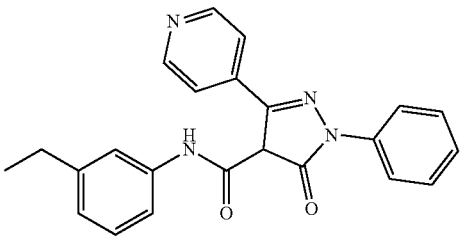 [SMILES: CCc1cccc(NC(=O)C2C(=O)N(c3ccccc3)N=C2c2ccncc2)c1]

LCMS: m/z 385.3 [M+H]$^+$;
$^1$H NMR (400 MHz, DMSO-d$_6$) δ 11.79 (s, 1H), 8.81 (q, J=6.4 Hz, 4H), 8.21 (d, J=7.6 Hz, 2H), 7.49-7.40 (m, 4H), 7.18 (t, J=7.6 Hz, 2H), 6.81 (d, J=7.6 Hz, 1H), 2.58 (q, J=7.6 Hz, 2H), 1.19 (t, J=7.6 Hz, 3H).

N-(3-ethylphenyl)-1-(4-methoxyphenyl)-3-methyl-5-oxo-4,5-dihydro-1H-pyrazole-4-carboxamide Compound ID: 138

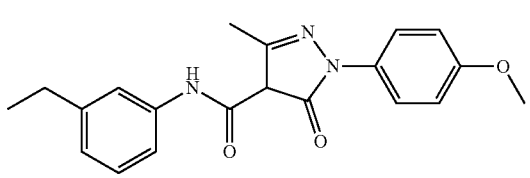 [SMILES: CCc1cccc(NC(=O)C2C(=O)N(c3ccc(OC)cc3)N=C2C)c1]

LCMS: m/z 352.0 [M+H]$^+$;
$^1$H NMR (400 MHz, CHLOROFORM-d) δ 7.39 (s, 1H), 7.31 (d, J=7.6 Hz, 3H), 7.21 (t, J=7.6 Hz, 1H), 6.94 (d, J=7.2 Hz, 1H), 6.81 (d, J=7.2 Hz, 2H), 3.74 (s, 3H), 2.62 (q, J=7.2 Hz, 2H), 2.41 (s, 3H), 1.22 (t, J=7.6 Hz, 3H).

N-(3-(N,N-dimethylsulfamoyl)phenyl)-3-methyl-5-oxo-1-phenyl-4,5-dihydro-1H-pyrazole-4-carboxamide Compound ID: 139

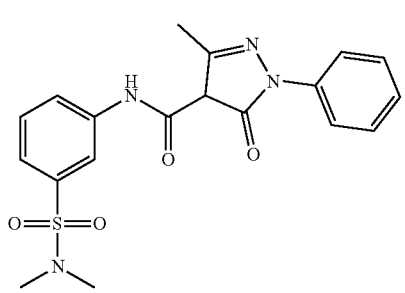 [SMILES: CC1=NN(c2ccccc2)C(=O)C1C(=O)Nc1cccc(S(=O)(=O)N(C)C)c1]

LCMS: m/z 401.0 [M+H]$^+$;
$^1$H NMR (400 MHz, DMSO-d$_6$) δ 10.98 (s, 1H), 8.26 (t, J=1.6 Hz, 1H), 7.73 (d, J=8.0 Hz, 3H), 7.58 (t, J=7.6 Hz, 1H), 7.53 (t, J=8.0 Hz, 2H), 7.39 (d, J=8.0 Hz, 1H), 7.36-7.29 (m, 1H), 2.63 (s, 6H), 2.55 (s, 3H).

3-methyl-5-oxo-1-phenyl-N-(3-propylphenyl)-4,5-dihydro-1H-pyrazole-4-carboxamide Compound ID: 140

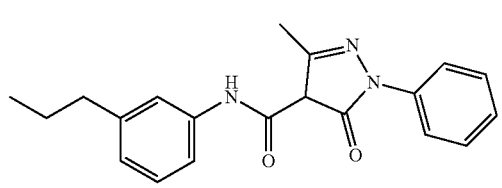 [SMILES: CCCc1cccc(NC(=O)C2C(=O)N(c3ccccc3)N=C2C)c1]

LCMS: m/z 336.1 [M+H]$^+$;
$^1$H NMR (400 MHz, DMSO-d$_6$) δ 10.70 (s, 1H), 7.76 (d, J=7.6 Hz, 2H), 7.51 (t, J=8.0 Hz, 2H), 7.46 (s, 1H), 7.43 (d, J=8.0 Hz, 1H), 7.30 (t, J=7.6 Hz, 1H), 7.20 (t, J=7.6 Hz, 1H), 6.86 (d, J=7.6 Hz, 1H), 2.55 (s, 2H), 2.53 (s, 3H), 1.64-1.54 (m, 2H), 0.90 (t, J=7.6 Hz, 3H).

N-(3-(1,1-difluoroethyl)phenyl)-3-methyl-5-oxo-1-phenyl-4,5-dihydro-1H-pyrazole-4-carboxamide Compound ID: 141

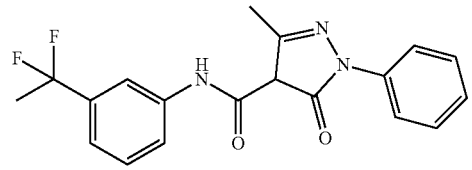 [SMILES: CC1=NN(c2ccccc2)C(=O)C1C(=O)Nc1cccc(C(C)(F)F)c1]

LCMS: m/z 358.1 [M+H]$^+$;
$^1$H NMR (400 MHz, DMSO-d$_6$) δ 10.90 (s, 1H), 7.95 (s, 1H), 7.76 (d, J=7.6 Hz, 2H), 7.62 (d, J=8.0 Hz, 1H), 7.51 (t, J=7.6 Hz, 2H), 7.42 (t, J=8.0 Hz, 1H), 7.30 (t, J=7.6 Hz, 1H), 7.21 (d, J=8.0 Hz, 1H), 2.53 (s, 3H), 1.96 (t, J=18.8 Hz, 3H)

N-(3-ethylphenyl)-1-(4-isopropoxyphenyl)-3-methyl-5-oxo-4,5-dihydro-1H-pyrazole-4-carboxamide Compound ID: 142

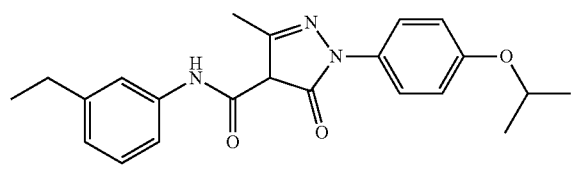 [SMILES: CCc1cccc(NC(=O)C2C(=O)N(c3ccc(OC(C)C)cc3)N=C2C)c1]

LCMS: m/z 380.3 [M+H]$^+$;
$^1$H NMR (400 MHz, DMSO-d$_6$) δ 10.88 (s, 1H), 7.69 (s, 2H), 7.45 (s, 1H), 7.41 (d, J=8.0 Hz, 1H), 7.17 (t, J=7.6 Hz, 1H), 7.01-6.94 (m, 2H), 6.82 (d, J=7.2 Hz, 1H), 4.61 (td, J=5.6, 11.2 Hz, 1H), 2.62-2.53 (q, J=7.6 Hz, 2H), 2.42 (s, 3H), 1.27 (d, J=6.0 Hz, 6H), 1.18 (t, J=7.6 Hz, 3H)

1-(4-(cyclopropylmethoxy)phenyl)-N-(3-ethylphenyl)-3-methyl-5-oxo-4,5-dihydro-1H-pyrazole-4-carboxamide Compound ID: 143

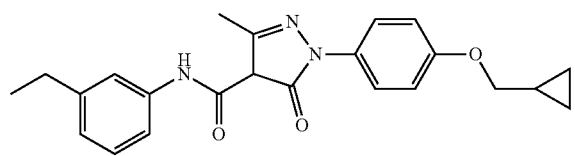 [SMILES: CCc1cccc(NC(=O)C2C(=O)N(c3ccc(OCC4CC4)cc3)N=C2C)c1]

LCMS: m/z 392.2 [M+H]$^+$;
$^1$H NMR (400 MHz, DMSO-d$_6$) δ 10.77 (s, 1H), 7.61 (d, J=9.2 Hz, 2H), 7.46 (s, 1H), 7.42 (d, J=8.0 Hz, 1H), 7.20 (t, J=8.0 Hz, 1H), 7.03 (d, J=9.2 Hz, 2H), 6.86 (d, J=7.6 Hz, 1H), 3.85 (d, J=6.8 Hz, 2H), 2.58 (q, J=7.6 Hz, 2H), 2.48 (s, 3H), 1.28-1.21 (m, 1H), 1.18 (t, J=7.6 Hz, 3H), 0.63-0.54 (m, 2H), 0.38-0.30 (m, 2H).

223

1-(4-acetamidophenyl)-N-(3-ethylphenyl)-3-methyl-5-oxo-4,5-dihydro-1H-pyrazole-4-carboxamide Compound ID: 144

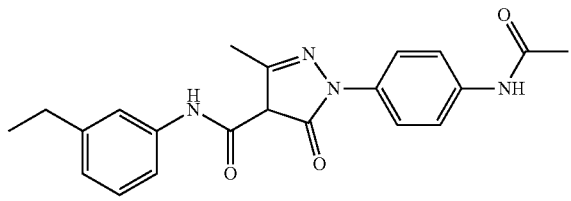 [SMILES: CCc1cccc(NC(=O)C2C(=O)N(c3ccc(NC(C)=O)cc3)N=C2C)c1]

LCMS: m/z 379.2 [M+H]$^+$;

$^1$H NMR (400 MHz, DMSO-d$_6$) δ 10.70 (s, 1H), 10.07 (s, 1H), 7.69 (d, J=8.0 Hz, 2H), 7.62 (d, J=8.8 Hz, 2H), 7.46 (s, 1H), 7.42 (d, J=8.0 Hz, 1H), 7.20 (t, J=8.0 Hz, 1H), 6.87 (d, J=7.2 Hz, 1H), 2.58 (q, J=8.0 Hz, 2H), 2.51 (s, 3H), 2.06 (s, 3H), 1.17 (t, J=7.6 Hz, 3H)

3-methyl-5-oxo-N-(3-(2-oxopropyl)phenyl)-1-phenyl-4,5-dihydro-1H-pyrazole-4-carboxamide Compound ID: 145

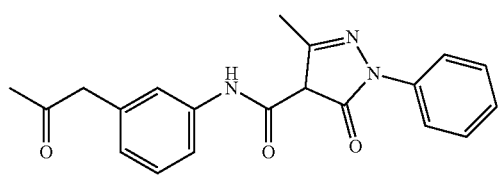 [SMILES: CC(=O)Cc1cccc(NC(=O)C2C(=O)N(c3ccccc3)N=C2C)c1]

LCMS: m/z 350.2 [M+H]$^+$;

$^1$H NMR (400 MHz, DMSO-d$_6$) δ 10.71 (s, 1H), 7.74 (d, J=8.0 Hz, 2H), 7.54-7.49 (t, J=7.2 Hz, 3H), 7.47 (s, 1H), 7.31 (t, J=7.6 Hz, 1H), 7.25 (t, J=7.6 Hz, 1H), 6.86 (d, J=7.6 Hz, 1H), 3.74 (s, 2H), 2.54 (s, 3H), 2.13 (s, 3H).

N-(3-cyclopentylphenyl)-3-methyl-5-oxo-1-phenyl-4,5-dihydro-1H-pyrazole-4-carboxamide

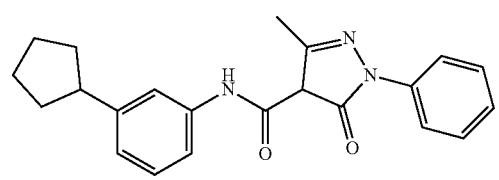 [SMILES: CC1=NN(c2ccccc2)C(=O)C1C(=O)Nc1cccc(C2CCCC2)c1]

Compound ID: 146

LCMS: m/z 362.2 [M+H]$^+$;

$^1$H NMR (400 MHz, DMSO-d$_6$) δ 10.65 (s, 1H), 7.79-7.68 (d, J=7.8 Hz, 2H), 7.55-7.51 (m, 3H), 7.40 (d, J=8.0 Hz, 1H), 7.33 (d, J=7.6 Hz, 1H), 7.21 (t, J=8.0 Hz, 1H), 6.93 (d, J=7.6 Hz, 1H), 2.99-2.90 (m, 1H), 2.55 (s, 3H), 2.04-1.97 (m, 2H), 1.82-1.71 (m, 2H), 1.69-1.59 (m, 2H), 1.58-1.48 (m, 2H).

224

N-(3-isobutylphenyl)-3-methyl-5-oxo-1-phenyl-4,5-dihydro-1H-pyrazole-4-carboxamide Compound ID: 147

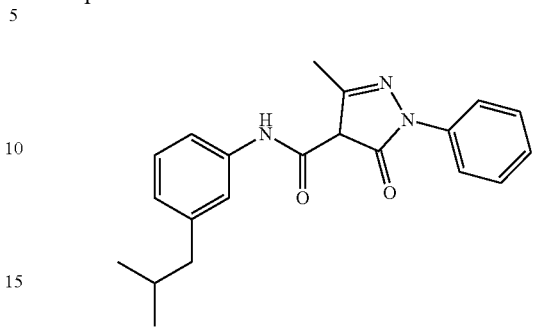

LCMS: m/z 350.1 [M+H]$^+$;

$^1$H NMR (400 MHz, DMSO-d$_6$) δ 10.70 (s, 1H), 7.76 (d, J=8.0 Hz, 2H), 7.51 (d, J=7.6 Hz, 2H), 7.49-7.42 (m, 2H), 7.30-7.25 (m, 1H), 7.22-7.20 (m, 1H), 6.83-6.80 (m, 1H), 2.67 (s, 3H), 2.42 (d, J=7.2 Hz, 2H), 1.85-1.81 (m, 1H), 0.87 (d, J=6.8 Hz, 6H)

N-(3-(1H-imidazol-2-yl)phenyl)-3-methyl-5-oxo-1-(4-(trifluoromethyl)phenyl)-4,5-dihydro-1H-pyrazole-4-carboxamide Compound ID: 148

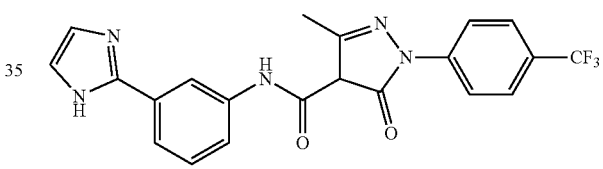

LCMS: m/z 428.2 [M+H]$^+$;

$^1$H NMR (400 MHz, DMSO-d$_6$) δ 11.09 (s, 1H), 8.26 (s, 1H), 8.18 (d, J=8.4 Hz, 2H), 8.01 (d, J=8.0 Hz, 1H), 7.81 (s, 3H), 7.80 (s, 1H), 7.67 (d, J=7.6 Hz, 1H), 7.56 (t, J=8.0 Hz, 1H), 2.48 (s, 3H).

N-(3-(1H-imidazol-2-yl)phenyl)-3-methyl-5-oxo-1-(3-(trifluoromethyl)phenyl)-4,5-dihydro-1H-pyrazole-4-carboxamide

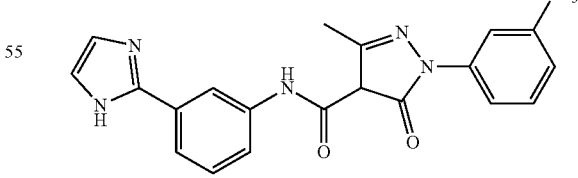

Compound ID: 149

LCMS: m/z 428.0 [M+H]$^+$;

$^1$H NMR (400 MHz, DMSO-d$_6$) δ 10.98 (s, 1H), 8.37 (s, 1H), 8.23 (s, 1H), 8.13 (d, J=8.8 Hz, 2H), 8.07 (d, J=8.0 Hz, 1H), 7.82 (s, 2H), 7.74-7.71 (m, 2H), 7.60-7.56 (m, 2H), 2.54 (s, 3H).

3-methyl-5-oxo-N-(3-(pyrazin-2-yl)phenyl)-1-(4-(trifuoromethyl)phenyl)-4,5-dihydro-1H-pyrazole-4-carboxamide Compound ID: 150

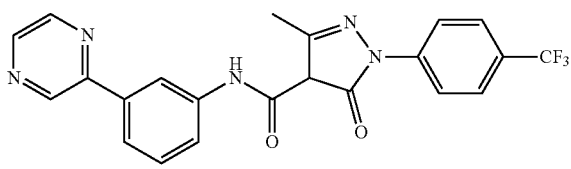 [SMILES: CC1=NN(c2ccc(C(F)(F)F)cc2)C(=O)C1C(=O)Nc1cccc(-c2cnccn2)c1]

LCMS: m/z 440.0 [M+H]$^+$;
$^1$H NMR (400 MHz, DMSO-d$_6$) δ 10.80 (s, 1H), 9.24 (d, J=1.6 Hz, 1H), 8.74 (dd, J=1.6, 2.4 Hz, 1H), 8.63 (d, J=2.4 Hz, 1H), 8.44 (s, 1H), 8.08 (d, J=8.8 Hz, 2H), 7.87 (d, J=8.8 Hz, 2H), 7.83-7.71 (m, 2H), 7.47 (t, J=7.6 Hz, 1H), 2.55 (s, 3H).

3-methyl-5-oxo-N-(3-(pyrazin-2-yl)phenyl)-1-(3-(trifuoromethyl)phenyl)-4,5-dihydro-1H-pyrazole-4-carboxamide Compound ID: 166

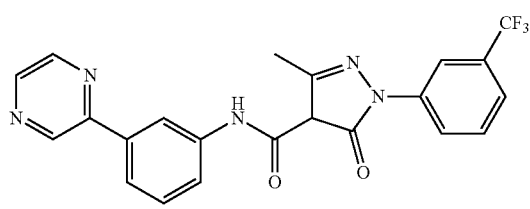 [SMILES: CC1=NN(c2cccc(C(F)(F)F)c2)C(=O)C1C(=O)Nc1cccc(-c2cnccn2)c1]

LCMS: m/z 440.2 [M+H]$^+$;
$^1$H NMR (400 MHz, DMSO-d$_6$) δ 10.81 (s, 1H), 9.25 (d, J=1.6 Hz, 1H), 8.77-8.71 (m, 1H), 8.63 (d, J=2.4 Hz, 1H), 8.44 (t, J=1.6 Hz, 1H), 8.28 (s, 1H), 8.12 (d, J=9.6 Hz, 1H), 7.80 (dd, J=2.0, 7.6 Hz, 2H), 7.74 (t, J=8.0 Hz, 1H), 7.62 (d, J=7.6 Hz, 1H), 7.48 (t, J=8.0 Hz, 1H), 2.55 (s, 3H).

4-((3-ethylphenyl)carbamoyl)-3-methyl-1-(4-(methylamino)phenyl)-1H-pyrazol-5-yl dimethylcarbamate Compound ID: 224

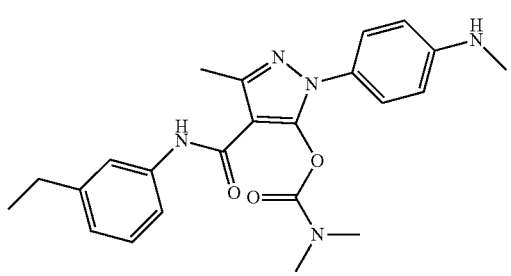 [SMILES: CCc1cccc(NC(=O)c2c(C)nn(-c3ccc(NC)cc3)c2OC(=O)N(C)C)c1]

LCMS: m/z 422.1 [M+H]$^+$;
$^1$H NMR (400 MHz, DMSO-d$_6$) δ 9.50 (s, 1H), 7.51 (s, 1H), 7.41 (d, J=8.0 Hz, 1H), 7.26-7.16 (m, 3H), 6.92 (d, J=7.6 Hz, 1H), 6.62 (d, J=8.8 Hz, 2H), 6.04-5.97 (m, 1H), 3.02 (s, 3H), 2.79 (s, 3H), 2.71 (d, J=4.8 Hz, 3H), 2.59 (q, J=7.6 Hz, 2H), 2.37 (s, 3H), 1.18 (t, J=7.6 Hz, 3H).

3-methyl-5-oxo-1-phenyl-N-(3-(2,2,2-trifluoroacetyl)phenyl)-4,5-dihydro-1H-pyrazole-4-carboxamide Compound ID: 152

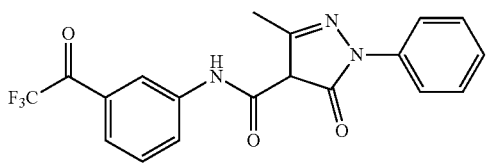 [SMILES: CC1=NN(c2ccccc2)C(=O)C1C(=O)Nc1cccc(C(=O)C(F)(F)F)c1]

LCMS: m/z 408.3 [M+H+H$_2$O]$^+$;
$^1$H NMR (400 MHz, DMSO-d$_6$) δ 10.77 (s, 1H), 7.82 (s, 1H), 7.74-7.71 (m, 2H), 7.55-7.51 (m, 3H), 7.36-7.32 (m, 3H), 2.56 (s, 3H)
$^{19}$F NMR (400 MHz, DMSO-d$_6$) δ: −82.71 (s, 3 F).

N-(3-ethylphenyl)-3-methyl-1-(4-nitrophenyl)-5-oxo-4,5-dihydro-1H-pyrazole-4-carboxamide Compound ID: 153

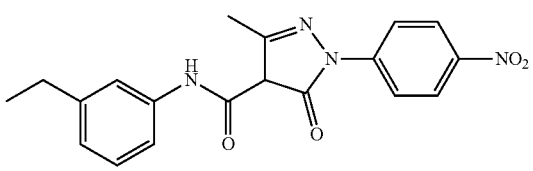 [SMILES: CCc1cccc(NC(=O)C2C(=O)N(c3ccc([N+](=O)[O-])cc3)N=C2C)c1]

LCMS: m/z 367.2 [M+H]$^+$;
$^1$H NMR (400 MHz, DMSO-d$_6$) δ 10.48 (s, 1H), 8.37 (d, J=9.2 Hz, 2H), 8.12 (d, J=9.6 Hz, 2H), 7.47 (s, 1H), 7.44 (d, J=8.0 Hz, 1H), 7.21 (t, J=8.0 Hz, 1H), 6.87 (d, J=7.6 Hz, 1H), 2.58 (q, J=7.6 Hz, 2H), 2.54 (s, 3H), 1.18 (t, J=7.6 Hz, 3H).

1-(4-aminophenyl)-N-(3-ethylphenyl)-3-methyl-5-oxo-4,5-dihydro-1H-pyrazole-4-carboxamide Compound ID: 154

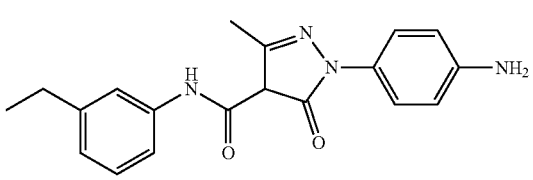 [SMILES: CCc1cccc(NC(=O)C2C(=O)N(c3ccc(N)cc3)N=C2C)c1]

LCMS: m/z 337.2 [M+H]$^+$;
$^1$H NMR (400 MHz, DMSO-d$_6$) δ 10.80 (s, 1H), 7.45 (s, 1H), 7.41 (d, J=8.4 Hz, 1H), 7.28 (d, J=6.8 Hz, 2H), 7.20 (t, J=7.6 Hz, 1H), 6.86 (d, J=7.6 Hz, 1H), 6.69 (d, J=8.4 Hz, 2H), 2.57 (q, J=7.6 Hz, 2H), 2.47 (s, 3H), 1.17 (t, J=7.6 Hz, 3H)

1-(4-(3,3-dimethylureido)phenyl)-N-(3-ethylphenyl)-3-methyl-5-oxo-4,5-dihydro-1H-pyrazole-4-carboxamide Compound ID: 155

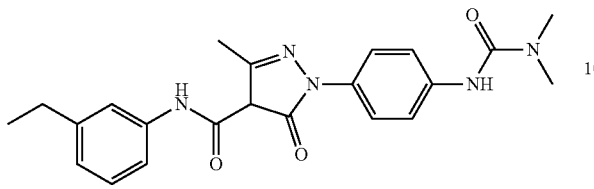

LCMS: m/z 408.3 [M+H]$^+$;
$^1$H NMR (400 MHz, DMSO-d$_6$) δ 10.90 (s, 1H), 8.32 (s, 1H), 7.67 (s, 2H), 7.50 (d, J=9.2 Hz, 2H), 7.45 (s, 1H), 7.41 (d, J=8.4 Hz, 1H), 7.16 (t, J=7.6 Hz, 1H), 6.81 (d, J=7.6 Hz, 1H), 2.93 (s, 6H), 2.56 (q, J=7.6 Hz, 2H), 2.41 (s, 3H), 1.17 (t, J=7.6 Hz, 3H).

N-(3-ethylphenyl)-5-oxo-1-phenyl-3-(pyridin-2-yl)-4,5-dihydro-1H-pyrazole-4-carboxamide Compound ID: 156

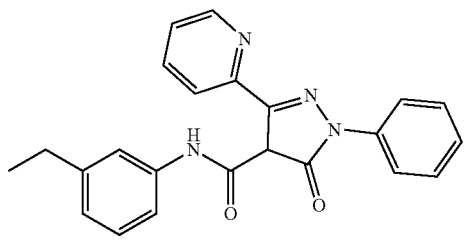 [SMILES: CCc1cccc(NC(=O)C2C(=O)N(c3ccccc3)N=C2c2ccccn2)c1]

LCMS: m/z 385.1 [M+H]$^+$;
$^1$H NMR (400 MHz, DMSO-d$_6$) δ 12.03 (s, 1H), 9.00 (s, 1H), 8.65 (d, J=7.6 Hz, 1H), 8.49 (t, J=7.6 Hz, 1H), 8.21 (d, J=8.0 Hz, 2H), 7.90 (t, J=2.4 Hz, 1H), 7.53 (d, J=8.0 Hz, 1H), 7.50-7.46 (m, 3H), 7.30 (t, J=7.6 Hz, 1H), 7.25 (t, J=7.6 Hz, 1H), 6.98 (d, J=7.6 Hz, 1H), 2.66-2.60 (q, J=7.6 Hz, 2H), 1.21 (t, J=7.6 Hz, 3H).

N-(3-ethylphenyl)-5-oxo-1-phenyl-3-(pyridin-3-yl)-4,5-dihydro-1H-pyrazole-4-carboxamide Compound ID: 157

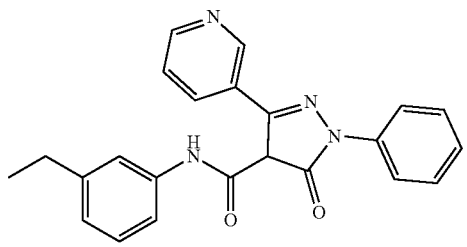 [SMILES: CCc1cccc(NC(=O)C2C(=O)N(c3ccccc3)N=C2c2cccnc2)c1]

LCMS: m/z 385.2 [M+H]$^+$;
$^1$H NMR (400 MHz, DMSO-d$_6$) δ 11.66 (s, 1H), 9.68 (s, 1H), 9.11 (d, J=8.0 Hz, 1H), 8.81 (d, J=5.2 Hz, 1H), 8.20 (d, J=7.6 Hz, 2H), 8.04 (dd, J=5.6, 8.0 Hz, 1H), 7.49 (s, 1H), 7.47-7.37 (m, 3H), 7.16 (td, J=7.6, 10.0 Hz, 2H), 6.81 (d, J=7.6 Hz, 1H), 2.58 (q, J=7.6 Hz, 2H), 1.19 (t, J=7.6 Hz, 3H).

N-(3-ethylphenyl)-3-methyl-5-oxo-1-(4-propoxyphenyl)-4,5-dihydro-1H-pyrazole-4-carboxamide Compound ID: 158

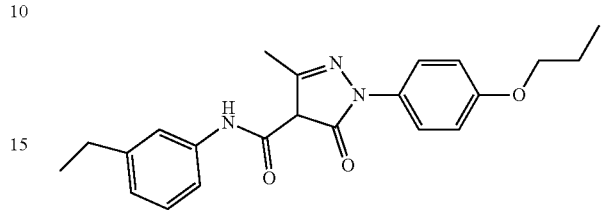

LCMS: m/z 380.1 [M+H]$^+$;
$^1$H NMR (400 MHz, DMSO-d$_6$) δ 13.24 (s, 1H), 10.71 (s, 1H), 7.56 (d, J=9.2 Hz, 2H), 7.47-7.45 (m, 1H), 7.43-7.41 (m, 1H), 7.22-7.20 (m, 1H), 7.07 (d, J=8.8 Hz, 2H), 6.88 (d, J=7.6 Hz, 1H), 3.97 (t, J=6.4 Hz, 2H), 2.61-2.58 (m, 2H), 2.57 (s, 3H), 1.76 (t, J=6.8 Hz, 2H), 1.18 (t, J=7.6 Hz, 3H), 0.99 (t, J=7.6 Hz, 3H).

3-(4-((3-(furan-2-yl)phenyl)carbamoyl)-3-methyl-5-oxo-4,5-dihydro-1H-pyrazol-1-yl)benzoic acid Compound ID: 159

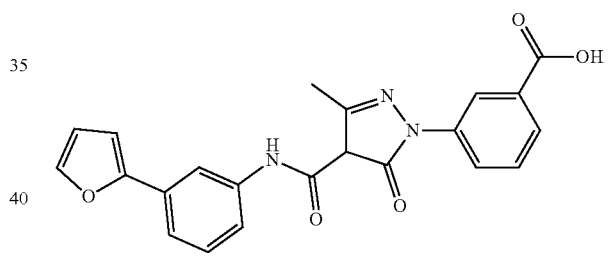

LCMS: m/z 404.0 [M+H]$^+$;
$^1$H NMR (400 MHz, METHANOL-d$_4$) δ 8.33 (s, 1H), 7.89-8.10 (m, 3H), 7.66-7.63 (m, 1H), 7.55 (d, J=1.2 Hz, 1H), 7.48-7.40 (m, 2H), 7.36-7.34 (m, 1H), 6.78 (d, J=3.2 Hz, 1H), 6.52-6.50 (m, 1H), 2.63 (s, 3H).

1-(4-(N,N-dimethylsulfamoyl)phenyl)-N-(3-(furan-2-yl)phenyl)-3-methyl-5-oxo-4,5-dihydro-1H-pyrazole-4-carboxamide Compound ID: 160

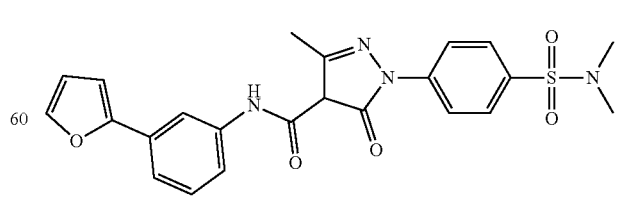

LCMS: m/z 467.1 [M+H]$^+$;
$^1$H NMR (400 MHz, METHANOL-d$_4$) δ 8.19-8.05 (m, 3H), 7.88 (d, J=8.4 Hz, 2H), 7.57 (d, J=1.2 Hz, 1H), 7.50 (d,

J=7.6 Hz, 1H), 7.45-7.39 (m, 1H), 7.38-7.31 (m, 1H), 6.80 (d, J=3.2 Hz, 1H), 6.54 (dd, J=1.6, 3.2 Hz, 1H), 2.73 (s, 6H), 2.58 (s, 3H).

3-methyl-5-oxo-1-phenyl-N-(3-(2,2,2-trifluoroethyl) phenyl)-4,5-dihydro-1H-pyrazole-4-carboxamide Compound ID: 161

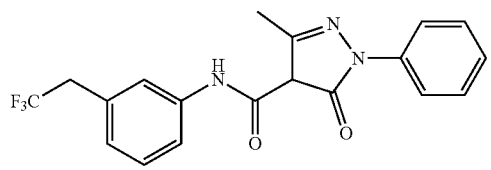 [SMILES: CC1=NN(c2ccccc2)C(=O)C1C(=O)Nc1cccc(CC(F)(F)F)c1]

LCMS: m/z 376.0 [M+H]$^+$;

$^1$H NMR (400 MHz, DMSO-d$_6$) δ 10.83 (s, 1H), 7.78 (d, J=7.6 Hz, 2H), 7.67 (s, 1H), 7.60 (d, J=8.0 Hz, 1H), 7.50 (t, J=8.0 Hz, 2H), 7.34-7.25 (m, 2H), 7.01 (d, J=7.6 Hz, 1H), 3.63 (q, J=11.6 Hz, 2H), 2.52 (s, 3H).

N-(3-(furan-2-yl)phenyl)-3-methyl-5-oxo-1-(4-(trifluoromethyl)phenyl)-4,5-dihydro-1H-pyrazole-4-carboxamide

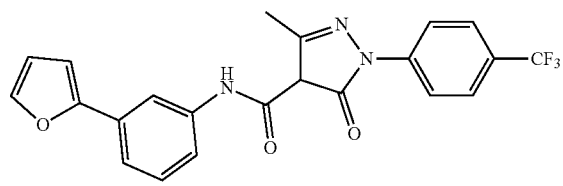 [SMILES: CC1=NN(c2ccc(C(F)(F)F)cc2)C(=O)C1C(=O)Nc1cccc(-c2ccco2)c1]

Compound ID: 162

LCMS: m/z 428.0 [M+H]$^+$;

$^1$H NMR (400 MHz, DMSO-d$_6$) δ 10.74 (s, 1H), 8.10 (d, J=8.0 Hz, 2H), 8.06 (s, 1H), 7.86 (s, 2H), 7.75 (s, 1H), 7.48 (s, 1H), 7.35 (s, 2H), 6.97-6.89 (m, 1H), 6.60 (s, 1H), 2.53 (s, 3H).

N-(3-(1H-imidazol-2-yl)phenyl)-1-(4-(N,N-dimethylsulfamoyl)phenyl)-3-methyl-5-oxo-4,5-dihydro-1H-pyrazole-4-carboxamide Compound ID: 173

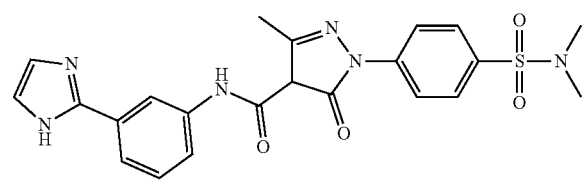 [SMILES: CC1=NN(c2ccc(S(=O)(=O)N(C)C)cc2)C(=O)C1C(=O)Nc1cccc(-c2ncc[nH]2)c1]

LCMS: m/z 467.1 [M+H]$^+$;

$^1$H NMR (400 MHz, METHANOL-d$_4$) δ 8.35 (s, 1H), 7.99 (q, J=8.8 Hz, 4H), 7.90-7.86 (m, 1H), 7.69 (s, 2H), 7.66-7.61 (m, 2H), 2.75 (s, 6H), 2.72 (s, 3H)

Example 2

Biological Activity of Compounds of the Invention

ACSS2 Cell-Free Activity Assay (Cell-Free IC$_{50}$)

The assay is based on a coupling reaction with Pyrophosphatase: ACSS2 is converting ATP+CoA+Acetate=>AMP+pyrophosphate+Acetyl-CoA (Ac-CoA). Pyrophosphatase converts pyrophosphate, a product of the ACSS2 reaction, to phosphate which can be detected by measuring the absorbance at 620 nm after incubation with the Biomol green reagent (Enzo life Science, BML-AK111).

Cell-free IC$_{50}$ Determination:

10 nM of human ACSS2 protein (OriGene Technologies, Inc) was incubated for 90 minutes at 37 C with various compounds' concentrations in a reaction containing 50 mM Hepes pH 7.5, 10 mM DTT, 90 mM KCl, 0.006% Tween-20, 0.1 mg/ml BSA, 2 mM MgCl$_2$, 10 μM CoA, 5 mM NaAc, 300 μM ATP and 0.5 U/ml Pyrophosphatase (Sigma). At the end of the reaction, Biomol Green was added for 30 minutes at RT and the activity was measured by reading the absorbance at 620 nm. IC$_{50}$ values were calculated using non-linear regression curve fit with 0% and 100% constrains (CDD Vault, Collaborative Drug Discovery, Inc.).

Results:

The results are presented in Table 2 below:

TABLE 2

ACSS2 cell-free activity assay results (Cell-free IC$_{50}$).

| ACSS2 PPase IC$_{50}$ assay: IC$_{50}$ (uM) | From 1E-5 μM to 6E-3 μM | From 6E-3 μM to 0.1 μM | From 0.1 μM to 1 μM | From 1 μM to 100 uM | Above 100 uM |
|---|---|---|---|---|---|
| Compounds number | 226 | 159 | 233 | 111 | 180 |
| | 261 | 168 | 123 | 118 | 186 |
| | 271 | 237 | 146 | 131 | 187 |
| | 242 | 142 | 125 | 122 | 190 |
| | 228 | 259 | 173 | 105 | 192 |
| | 265 | 244 | 132 | 116 | 193 |
| | 269 | 255 | 100 | 179 | 194 |
| | 250 | 263 | 135 | 126 | 195 |
| | 247 | 149 | 174 | 121 | 196 |
| | 246 | 231 | 153 | 112 | 199 |
| | 141 | 251 | 144 | 104 | 200 |
| | 230 | 257 | 155 | 128 | 202 |
| | 236 | 107 | 154 | 129 | 204 |
| | 266 | 169 | 254 | 130 | 213 |
| | 253 | 138 | 147 | 134 | 214 |
| | 229 | 240 | 110 | 136 | 217 |
| | 264 | 124 | 270 | 137 | 221 |
| | 164 | 170 | 103 | 152 | 106 |
| | 275 | 274 | 260 | 156 | |
| | 165 | 235 | 133 | 157 | |
| | 252 | 184 | 139 | 176 | |
| | 166 | 171 | 120 | 239 | |
| | 108 | 277 | 115 | 268 | |
| | 227 | 245 | 209 | | |
| | 258 | 158 | 102 | | |
| | 241 | 272 | 283 | 182 | |
| | 249 | 143 | 284 | 185 | |
| | 220 | 215 | 285 | 188 | |
| | 117 | 114 | 288 | 189 | |
| | 243 | 238 | 290 | 191 | |
| | 248 | 162 | 302 | 197 | |
| | 145 | 127 | 329 | 198 | |
| | 119 | 232 | 339 | 201 | |
| | 234 | 113 | 340 | 203 | |
| | 167 | 256 | 341 | 205 | |
| | 276 | 150 | 345 | 207 | |
| | 109 | 267 | 346 | 212 | |
| | 206 | 172 | 347 | 216 | |
| | 280 | 273 | 349 | 218 | |

TABLE 2-continued

ACSS2 cell-free activity assay results (Cell-free IC$_{50}$).

| ACSS2 PPase IC$_{50}$ assay: IC$_{50}$ (uM) | From 1E−5 μM to 6E−3 μM | From 6E−3 μM to 0.1 μM | From 0.1 μM to 1 μM | From 1 μM to 100 uM | Above 100 uM |
|---|---|---|---|---|---|
| 281 | | 262 | 350 | 222 | |
| 282 | | 148 | 358 | 223 | |
| 286 | | 101 | 373 | 224 | |
| 287 | | 160 | 391 | 278 | |
| 289 | | 103 | 392 | | |
| 291 | | 161 | 393 | | |
| 292 | | 183 | 394 | | |
| 297 | | 208 | 395 | | |
| 298 | | 210 | 397 | | |
| 300 | | 211 | 408 | | |
| 301 | | 215 | 409 | | |
| 303 | | 140 | 417 | | |
| 304 | | 279 | 418 | | |
| 305 | | 293 | 423 | | |
| 306 | | 294 | 424 | | |
| 307 | | 295 | 425 | | |
| 308 | | 296 | 427 | | |
| 309 | | 299 | 428 | | |
| 310 | | 333 | 436 | | |
| 311 | | 335 | | | |
| 312 | | 337 | | | |
| 313 | | 338 | | | |
| 314 | | 348 | | | |
| 315 | | 354 | | | |
| 316 | | 356 | | | |
| 317 | | 362 | | | |
| 318 | | 365 | | | |
| 319 | | 376 | | | |
| 320 | | 384 | | | |
| 321 | | 385 | | | |
| 322 | | 396 | | | |
| 323 | | 397 | | | |
| 324 | | 400 | | | |
| 325 | | 401 | | | |
| 326 | | 402 | | | |
| 327 | | 403 | | | |
| 328 | | 405 | | | |
| 330 | | 411 | | | |
| 331 | | 413 | | | |
| 332 | | 414 | | | |
| 334 | | 416 | | | |
| 336 | | 426 | | | |
| 342 | | 432 | | | |
| 343 | | | | | |
| 344 | | | | | |
| 351 | | | | | |
| 352 | | | | | |
| 353 | | | | | |
| 355 | | | | | |
| 357 | | | | | |
| 359 | | | | | |
| 360 | | | | | |
| 361 | | | | | |
| 363 | | | | | |
| 364 | | | | | |
| 366 | | | | | |
| 367 | | | | | |
| 368 | | | | | |
| 369 | | | | | |
| 370 | | | | | |
| 371 | | | | | |
| 372 | | | | | |
| 374 | | | | | |
| 375 | | | | | |
| 377 | | | | | |
| 378 | | | | | |
| 379 | | | | | |
| 380 | | | | | |
| 381 | | | | | |
| 382 | | | | | |
| 383 | | | | | |
| 386 | | | | | |
| 387 | | | | | |
| 388 | | | | | |
| 389 | | | | | |
| 390 | | | | | |
| 399 | | | | | |
| 404 | | | | | |
| 406 | | | | | |
| 407 | | | | | |
| 410 | | | | | |
| 412 | | | | | |
| 415 | | | | | |
| 419 | | | | | |
| 420 | | | | | |
| 421 | | | | | |
| 422 | | | | | |
| 429 | | | | | |
| 430 | | | | | |
| 431 | | | | | |
| 433 | | | | | |
| 434 | | | | | |
| 435 | | | | | |
| 437 | | | | | |
| 438 | | | | | |
| 439 | | | | | |
| 440 | | | | | |
| 441 | | | | | |
| 442 | | | | | |
| 443 | | | | | |
| 444 | | | | | |
| 445 | | | | | |
| 446 | | | | | |
| 447 | | | | | |
| 448 | | | | | |
| 449 | | | | | |
| 450 | | | | | |
| 451 | | | | | |
| 452 | | | | | |
| 453 | | | | | |
| 454 | | | | | |
| 455 | | | | | |
| 456 | | | | | |
| 457 | | | | | |
| 458 | | | | | |
| 459 | | | | | |
| 460 | | | | | |

ACSS2 Cellular Activity Assay (Cellular IC50)

The cellular activity of ACSS2 was based on tracing the incorporation of carbons from $^{13}$C-Acetate into fatty-acids.

Cell Treatment:

BT474/MDA-MB-468 cells growing in DMEM+25 mM D-glucose+1 mM sodium pyruvate+10% FBS+2 mM glutamine were plated in 12-well plates at 0.4×10$^6$ cells/well. The cells were then incubated at CO$_2$ incubator for 24 hrs at hypoxic conditions (1% O$_2$) before treated with compounds. At day 2, the medium was replaced to DMEM medium containing 15 mM Glucose, 1 mM Pyruvate, 0.65 mM Glutamine, 1% Dialyzed serum, 3.5 ug/ml Biotin, 0.2 mM $^{13}$C-Acetate and various concentrations of the compounds. The cells were incubated for 5 hours at CO$_2$ incubator in hypoxic conditions (1% O$_2$). At the end of the 5 hours' incubation, the cells were washed twice with cold PBS, harvested in 1 ml PBS and transfer into V-shaped HPLC glass vials and centrifuge for 10 min at 600 g at 4 C. The supernatant was removed, and the cells' pellets were stored at −80° C. until taken for saponification.

Saponification Assay

The cells pellets were resuspended with 0.5 ml of the 90% Methanol, 10% H$_2$O, 0.3M NaOH mixture and incubated at 80° C. for 60 min. Following the incubation, 50 μl formic acid and 0.4 ml hexane were added and the mixture was vortexed for 2 minutes. The vials were left few minutes for phases separation and then 200 μl of the top hexane phase extracted to a new glass vial. The hexane was dried under nitrogen and reconstituted in 100 μl of Methanol:Acetonitrile 5:3 mixture. The solution transferred to Eppendorf tubes, spun down at 17000 G for 20 min and transferred to LC-MS vials.

LCMS Method

The analysis was performed with Thermo Q Exactive mass spectrometer with HESI probe and Dionex Ultimate 3000 UHPLC system. The separations were performed on Phenomenex Kintex 2.6u XB-C18 100A 150×2.10 mm column by injecting 5 ul of each sample. The chromatography started with a linear gradient from 85% to 100% of organic solvent (Methanol:Acetonitrile 1:1) versus 10 mM Ammonium Acetate buffer pH 4.7 for 3.5 minutes, followed by 4.5 minutes of isocratic 100% organic solvent and then 3 minutes of isocratic initial conditions, at a flow rate of 0.3 ul/min. The MS source conditions that were used: capillary temperature 325° C., sheath flow 25, aux flow 15, spray voltage 3.8 kV, aux temperature 300° C. The data collected from Negative ion mode at resolution of 70000 at Full-MS mode in 75-1000 m/z range.

LCMS Results Analysis

The analysis of $^{13}C$ acetate incorporation into fatty acids (palmitate, myristate and stearate) performed on TraceFinder 3.2.512.0. The negative control areas and $^{13}C$ isotopic theoretical natural abundance were subtracted from the samples areas. Total $^{13}C$ incorporation for each fatty-acid (palmitate, myristate and stearate) was calculated and presented as percentage of the total amount. Cellular $EC_{50}$ values were calculated using a non-linear regression curve fit with 0% and 100% constrains (CDD Vault, Collaborative Drug Discovery, Inc.)

Results:

The results are presented in Tables 3 and 4 below:

TABLE 3

$^{13}C$ acetate incorporation into fatty acids (BT474 cells).
$IC_{50}$ (nM) BT474

| | Myristate | Palmitate | Stearate |
|---|---|---|---|
| <100 nM | 141, 108 | 141, 108, 117 | 141, 117, 108 |
| 100 nM < $IC_{50}$ < 1000 nM | 117, 138, 140, 142, | 138, 140, 142, 119, 109, 220, 206, 124 | 138, 140, 142, 119, 109, 220, 206, 124, 107, 114, 208, 215, 184 |
| ≥1000 nM | | 107, 114, 208, 215, 184, 183 | 183 |

Fatty-Acid Assay

Testing the inhibitory effect of compounds on the cellular activity of ACSS2 was done by tracing the incorporation of $^{13}C$ from $^{13}C$-acetate into fatty-acids in MDA-MB-468 cells under hypoxic conditions of 1% O2. The assay was done for 5 hours in DMEM with 5.5 mM glucose, 1 mM sodium Pyruvate, 0.65 mM Glutamine, 3.5 ug/ml Biotin, 1% dialyzed serum, 0.5 mM 13C-acetate and with different concentrations of the inhibitors. At the end of the incubation, the cells were washed with cold PBS, harvested into glass tubes and undergo saponification. The level of $^{13}C$ incorporation into Palmitate was done by LC-MS analysis and the level of inhibition was calculated with PRISM software.

TABLE 5

Fatty-acid assay: Incorporation of $^{13}C$-Acetate for compounds of the invention.

| Compound | FA IC50 MDA468 (nM) |
|---|---|
| 107 | +++ |
| 108 | +++ |
| 109 | ++ |
| 117 | +++ |
| 119 | +++ |
| 124 | + |
| 138 | +++ |
| 140 | + |
| 141 | +++ |
| 142 | + |
| 145 | + |
| 149 | + |
| 159 | + |
| 164 | + |
| 165 | +++ |
| 166 | + |
| 167 | + |
| 168 | +++ |
| 169 | + |
| 206 | ++ |
| 208 | + |
| 220 | + |
| 226 | ++ |
| 227 | ++ |
| 228 | +++ |
| 229 | + |
| 230 | +++ |
| 231 | + |
| 234 | + |
| 235 | + |
| 236 | +++ |
| 237 | + |
| 241 | ++ |
| 242 | +++ |
| 243 | + |
| 244 | + |
| 246 | +++ |
| 247 | +++ |
| 248 | + |

TABLE 4

$^{13}C$ acetate incorporation into fatty acids (BT474 cells).
$IC_{50}$ (nM) MDA-468

| | Myristate | Palmitate | Stearate |
|---|---|---|---|
| <100 nM | 141, 108, 165, 119, 117, 138, 145, 164, 109, 167 | 141, 108, 165, 119, 117, 138, 145, 164, 109, 220, 167, 166 | 141, 108, 165, 119, 117, 138, 145, 164, 109, 220, 167, 166, 140 |
| 100 nM < $IC_{50}$ < 1000 nM | 220, 166, 140, 107, 142, 124, 168, 208 | 140, 107, 142, 124, 168, 208 | 107, 142, 124, 168, 208 |
| ≥1000 nM | 159, 169 | 159, 169 | 159, 169 |

TABLE 5-continued

Fatty-acid assay: Incorporation of $^{13}$C-Acetate for compounds of the invention.

| Compound | FA IC50 MDA468 (nM) |
|---|---|
| 249 | +++ |
| 250 | +++ |
| 251 | ++ |
| 252 | ++ |
| 253 | +++ |
| 255 | + |
| 257 | + |
| 258 | + |
| 259 | + |
| 261 | +++ |
| 263 | +++ |
| 264 | +++ |
| 265 | +++ |
| 266 | +++ |
| 269 | +++ |
| 271 | +++ |
| 279 | + |
| 280 | +++ |
| 282 | +++ |
| 286 | +++ |
| 287 | +++ |
| 289 | +++ |
| 291 | +++ |
| 292 | +++ |
| 297 | + |
| 298 | +++ |
| 300 | +++ |
| 301 | +++ |
| 303 | +++ |
| 304 | +++ |
| 305 | + |
| 306 | +++ |
| 307 | + |
| 308 | +++ |
| 309 | +++ |
| 310 | +++ |
| 311 | +++ |
| 312 | ++ |
| 313 | +++ |
| 314 | +++ |
| 315 | +++ |
| 316 | +++ |
| 317 | +++ |
| 318 | +++ |
| 319 | +++ |
| 320 | +++ |
| 321 | +++ |
| 322 | +++ |
| 323 | +++ |
| 324 | +++ |
| 325 | +++ |
| 326 | +++ |
| 327 | +++ |
| 328 | +++ |
| 330 | +++ |
| 331 | +++ |
| 332 | +++ |

+++ 0.5 nM to 50 nM
++ 50 nM to 100 nm
+ >100 nM

Example 3

In-Vivo Efficacy Study of Compound 265 in MDA-MB-468 Breast Cancer Cells Xenograft An in-vivo efficacy study was carried out by Charles-River Laboratories at the Freiburg, Germany site.

Tumor pieces from Breast cancer cell line MDA-MB-468 passaged as subcutaneous xenograft were subcutaneously implanted into female NMRI nude mice (Crl:NMRI-Foxn-lnu). The animals were randomized into groups when tumors volume reached 50 to 250 mm³. Vehicle control or compound 265 at 100 mg/kg were dosed orally once daily. Body weights and tumor volume [mm3] by caliper were measured twice weekly.

Figure 4:
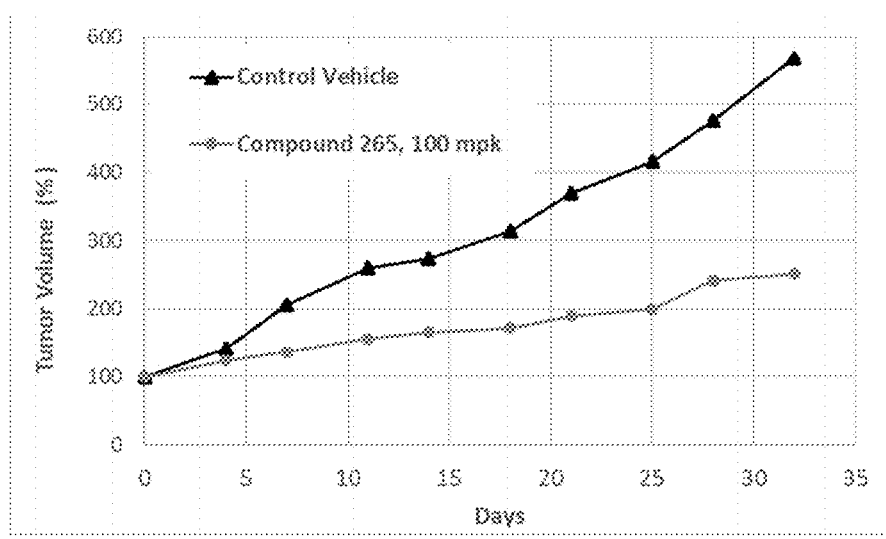
FIG. 4 depicts an in-vivo efficacy study of compound 265 in MDA-MB-468 breast cancer cells xenograft mouse model.

The results show a significant tumor growth delay in the group that was treated with 100 mg/kg of compound-265 (FIG. 4).

What is claimed is:

1. An Acyl-CoA Synthetase Short-Chain Family Member 2 (ACSS2) inhibitor compound represented by the structure of formula (I):

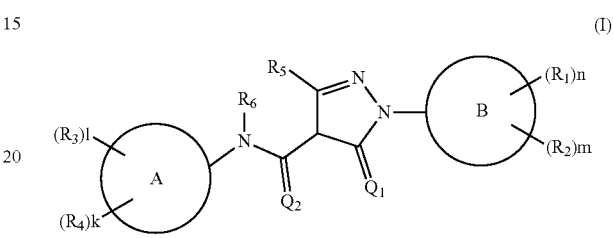

(I)

wherein A and B rings are each independently a single or fused aromatic or heteroaromatic ring system, or a single or fused $C_3$-$C_{10}$ cycloalkyl or a single or fused $C_3$-$C_{10}$ heterocyclic ring;

$R_1$ and $R_2$ are each independently H, F, Cl, Br, I, OH, SH, $R_8$—OH, $CH_2$—OH, $R_8$—SH, —$R_8$—O—$R_{10}$, —$CH_2$—O—$CH_3$, $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$, $CH_2$—$NH_2$, $CH_2$—$N(CH_3)_2$, $R_9$—$R_8$—$N(R_{10})(R_{11})$, C≡C—$CH_2$—$NH_2$, $B(OH)_2$, —$OC(O)CF_3$, —$OCH_2Ph$, NHC(O)—$R_{10}$, NHC(O)$CH_3$, NHCO—N$(R_{10})(R_{11})$, NHC(O)N$(CH_3)_2$, COOH, —C(O)Ph, C(O)O—$R_{10}$, C(O)O—$CH_3$, C(O)O—$CH(CH_3)_2$, C(O)O—$CH_2CH_3$, $R_8$—C(O)—$R_{10}$, $CH_2C(O)CH_3$, C(O)H, C(O)—$R_{10}$, C(O)—$CH_3$, C(O)—$CH_2CH_3$, C(O)—$CH_2CH_2CH_3$, $C_1$-$C_5$ linear or branched C(O)-haloalkyl, C(O)—$CF_3$, —C(O)$NH_2$, C(O)NHR, C(O)N$(R_{10})(R_{11})$, C(O)N$(CH_3)_2$, $SO_2R$, $SO_2N(R_{10})(R_{11})$, $SO_2N(CH_3)_2$, $SO_2NHC(O)CH_3$, $C_1$-$C_5$ linear or branched, substituted or unsubstituted alkyl, methyl, 2, 3, or 4-$CH_2$—$C_6H_4$—Cl, ethyl, propyl, iso-propyl, t-Bu, iso-butyl, pentyl, benzyl, $C(CH_3)(OH)Ph$, $C_1$-$C_5$ linear or branched haloalkyl, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $C_1$-$C_5$ linear, branched or cyclic alkoxy optionally wherein at least one methylene group ($CH_2$) in the alkoxy is replaced with an oxygen atom, methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu, O-1-oxacyclobutyl, O-2-oxacyclobutyl, $C_1$-$C_5$ linear or branched thioalkoxy, $C_1$-$C_5$ linear or branched haloalkoxy, $OCF_3$, $OCHF_2$, $C_1$-$C_5$ linear or branched alkoxyalkyl, substituted or unsubstituted $C_3$—$C_8$cycloalkyl, cyclopropyl, cyclopentyl, substituted or unsubstituted $C_3$-$C_8$ heterocyclic ring, 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide, substituted or unsubstituted aryl, phenyl, or $CH(CF_3)(NH$—$R_{10})$; wherein substitutions include: F, Cl, Br, I, $C_1$-$C_5$ linear or branched alkyl, methyl, ethyl, OH, alkoxy, N(R)$_2$, CF$_3$, aryl, phenyl, halophenyl, (benzyloxy)phenyl, CN, NO$_2$ or any combination thereof;

or R$_2$ and R$_1$ are joint together to form a 5 or 6 membered substituted or unsubstituted, aliphatic or aromatic, carbocyclic or heterocyclic ring;

R$_3$ and R$_4$ are each independently H, F, Cl, Br, I, OH, SH, R$_8$—OH, CH$_2$—OH, R$_8$—SH, —R$_8$—O—R$_{10}$, CH$_2$—O—CH$_3$, CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$), CH$_2$—NH$_2$, CH$_2$—N(CH$_3$)$_2$, R$_9$—R$_8$—N(R$_{10}$)(R$_{11}$), B(OH)$_2$, —OC(O)CF$_3$, —OCH$_2$Ph, —NHCO—R$_{10}$, NHC(O)CH$_3$, NHCO—N(R$_{10}$)(R$_{11}$), NHC(O)N(CH$_3$)$_2$, COOH, —C(O)Ph, C(O)O—R$_{10}$, C(O)O—CH$_3$, C(O)O—CH$_2$CH$_3$, R$_8$—C(O)—R$_{10}$, CH$_2$C(O)CH$_3$, C(O)H, C(O)—R$_{10}$, C(O)—CH$_3$, C(O)—CH$_2$CH$_3$, C(O)—CH$_2$CH$_2$CH$_3$, C$_1$-C$_5$ linear or branched C(O)-haloalkyl, C(O)—CF$_3$, —C(O)NH$_2$, C(O)NHR, C(O)N(R$_{10}$)(R$_{11}$), C(O)N(CH$_3$)$_2$, SO$_2$R, SO$_2$N(R$_{10}$)(R$_{11}$), SO$_2$N(CH$_3$)$_2$, C$_1$-C$_5$ linear or branched, substituted or unsubstituted alkyl, methyl, C(OH)(CH$_3$)(Ph), ethyl, propyl, iso-propyl, t-Bu, iso-butyl, pentyl, C(CH$_3$)(OH)Ph, C$_1$-C$_5$ linear or branched haloalkyl, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, C$_1$-C$_5$ linear, branched or cyclic alkoxy, methoxy, ethoxy, propoxy, iso-propoxy, O—CH$_2$-cyclopropyl, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl, cyclopropyl, cyclopentyl, substituted or unsubstituted C$_3$-C$_8$ heterocyclic ring, 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl, phenyl, or CH(CF$_3$)(NH—R$_{10}$); wherein substitutions include: F, Cl, Br, I, C$_1$-C$_5$ linear or branched alkyl, OH, alkoxy, N(R)$_2$, CF$_3$, aryl, phenyl, halophenyl, (benzyloxy)phenyl, CN, NO$_2$ or any combination thereof;

or R$_3$ and R$_4$ are joint together to form a 5 or 6 membered substituted or unsubstituted, aliphatic or aromatic, carbocyclic or heterocyclic ring;

R$_5$ is H, C$_1$-C$_5$ linear or branched, substituted or unsubstituted alkyl, methyl, CH$_2$SH, ethyl, iso-propyl, C$_1$-C$_5$ linear or branched haloalkyl, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, R$_8$-aryl, CH$_2$—Ph, substituted or unsubstituted aryl, phenyl, substituted or unsubstituted heteroaryl, pyridine (2, 3, and 4-pyridine); wherein substitutions include: F, Cl, Br, I, C$_1$-C$_5$ linear or branched alkyl, OH, alkoxy, N(R)$_2$, CF$_3$, phenyl, halophenyl, (benzyloxy)phenyl, CN, NO$_2$ or any combination thereof;

R$_6$ is H, C$_1$-C$_5$ linear or branched alkyl, methyl, C(O)R, or S(O)$_2$R;

R$_8$ is [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ linear or branched alkyl, methyl, ethyl, C(O)R, or S(O)$_2$R;

R is H, C$_1$-C$_5$ linear or branched alkyl, methyl, ethyl, C$_1$-C$_5$ linear or branched alkoxy, phenyl, aryl or heteroaryl, or two gem R substituents are joint together to form a 5 or 6 membered heterocyclic ring;

m, n, l and k are each independently an integer between 0 and 4;

Q$_1$ and Q$_2$ are each independently S, O, N—OH, CH$_2$, C(R)$_2$ or N—OMe;

or its pharmaceutically acceptable salt, optical isomer, tautomer, hydrate, N-oxide, prodrug, isotopic variant (e.g., deuterated analog), PROTAC, pharmaceutical product or any combination thereof.

2. An Acyl-CoA Synthetase Short-Chain Family Member 2 (ACSS2) inhibitor compound represented by the structure of formula (I):

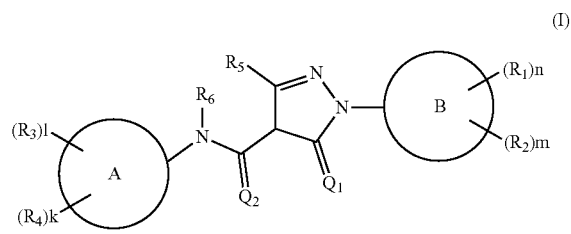

(I)

wherein

A and B rings are each independently a single or fused aromatic or heteroaromatic ring system, or a single or fused C$_3$-C$_{10}$ cycloalkyl or a single or fused C$_3$-C$_{10}$ heterocyclic ring;

R$_1$ and R$_2$ are each independently H, F, Cl, Br, I, OH, SH, R$_8$—OH, R$_8$—SH, —R$_8$—O—R$_{10}$, CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$), CH$_2$—NH$_2$, R$_9$—R$_8$—N(R$_{10}$)(R$_{11}$)C≡C—CH$_2$—NH$_2$, B(OH)$_2$, —OC(O)CF$_3$, —OCH$_2$Ph, NHC(O)—R$_{10}$, NHCO—N(R$_{10}$)(R$_{11}$), COOH, —C(O)Ph, C(O)O—R$_{10}$, R$_8$—C(O)—R$_{10}$, C(O)H, C(O)—R$_{10}$, C(O)—CH$_3$, C(O)—CH$_2$CH$_3$, C(O)—CH$_2$CH$_2$CH$_3$), C$_1$-C$_5$ linear or branched C(O)-haloalkyl, —C(O)NH$_2$, C(O)NHR, C(O)N(R$_{10}$)(R$_{11}$), SO$_2$R, SO$_2$N(R$_{10}$)(R$_{11}$), C$_1$-C$_5$ linear or branched, substituted or unsubstituted alkyl, 4-CH$_2$—C$_6$H$_4$—Cl, benzyl, C(CH$_3$)(OH)Ph, C$_1$-C$_5$ linear or branched haloalkyl, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, C$_1$-C$_5$ linear, branched or cyclic alkoxy, optionally wherein at least one methylene group (CH$_2$) in the alkoxy is replaced with an oxygen atom, O-1-oxacyclobutyl, O-2-oxacyclobutyl, O-cyclobutyl, O-cyclopentyl, O-cyclohexyl, C$_1$-C$_5$ linear or branched thioalkoxy, C$_1$-C$_5$ linear or branched haloalkoxy, OCHF$_2$, CH(CF$_3$)(NH—R$_{10}$), C$_1$-C$_5$ linear or branched alkoxyalkyl, substituted or unsubstituted C$_3$-C$_5$ cycloalkyl, substituted or unsubstituted C$_3$-C$_8$ heterocyclic ring, substituted or unsubstituted aryl, phenyl, wherein substitutions include: F, Cl, Br, I, C$_1$-C$_5$ linear or branched alkyl, OH, alkoxy, N(R)$_2$, CF$_3$, aryl, phenyl, halophenyl, (benzyloxy)phenyl, CN, NO$_2$ or any combination thereof;

or R$_2$ and R$_1$ are joint together to form a 5 or 6 membered substituted or unsubstituted, aliphatic or aromatic, carbocyclic or heterocyclic ring;

R$_3$ is C$_2$—C linear or branched haloalkyl, CF$_2$CH$_3$, CH$_2$CF$_3$, CF$_2$CH$_2$CH$_3$, CH$_2$CH$_2$CF$_3$, CF$_2$CH(CH$_3$)$_2$, or CF(CH$_3$)—CH(CH$_3$)$_2$);

R$_4$ is H, F, Cl, Br, I, OH, SH, R$_8$—OH, CH$_2$—OH, R$_8$—SH, —R$_8$—O—R$_{10}$, CH$_2$—O—CH$_3$, CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$), CH$_2$—NH$_2$, CH$_2$—N(CH$_3$)$_2$,

R$_9$—R$_8$—N(R$_{10}$)(R$_{11}$), B(OH)$_2$, —OC(O)CF$_3$, —OCH$_2$Ph, —NHCO—R$_{10}$, NHC(O)CH$_3$, NHCO—N(R$_{10}$)(R$_{11}$), NHC(O)N(CH$_3$)$_2$, COOH, —C(O)Ph, C(O)O—R$_{10}$, C(O)O—CH$_3$, C(O)O—CH$_2$CH$_3$, R$_8$—C(O)—R$_{10}$, CH$_2$C(O)CH$_3$, C(O)H, C(O)—R$_{10}$, C(O)—CH$_3$, C(O)—CH$_2$CH$_3$, C(O)—CH$_2$CH$_2$CH$_3$, C$_1$-C$_5$ linear or branched C(O)-haloalkyl, C(O)—CF$_3$, —C(O)NH$_2$, C(O)NHR, C( )N(R$_{10}$)(R$_{11}$), C(O)N(CH$_3$)$_2$, SO$_2$R, SO$_2$N(R$_{10}$)(R$_{11}$), SO$_2$N(CH$_3$)$_2$, C$_1$-C$_5$ linear or branched, substituted or unsubstituted alkyl, methyl, C(OH)(CH$_3$)(Ph), ethyl, propyl, iso-propyl, t-Bu, iso-butyl, pentyl, C(CH$_3$)(OH)Ph, C$_1$-C$_5$ linear or branched haloalkyl, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, C$_1$-C$_5$ linear, branched or cyclic alkoxy, methoxy, ethoxy, propoxy, isopropoxy, O—CH$_2$-cyclopropyl, C$_1$-C$_5$ linear or branched thio-alkoxy, C$_1$-C$_5$ linear or branched haloalkoxy, C$_1$-C$_5$ linear or branched alkoxyalkyl, substituted or unsubstituted C$_3$-C$_8$ cycloalkyl, cyclopropyl, cyclopentyl, substituted or unsubstituted C$_3$-C$_8$ heterocyclic ring, 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl, phenyl, or CH(CF$_3$)(NH—R$_{10}$); wherein substitutions include: F, Cl, Br, I, C$_1$-C$_5$ linear or branched alkyl, OH, alkoxy, N(R)$_2$, CF$_3$, aryl, phenyl, halophenyl, (benzyloxy)phenyl, CN, NO$_2$ or any combination thereof;

or R$_3$ and R$_4$ are joint together to form a 5 or 6 membered substituted or unsubstituted, aliphatic or aromatic, carbocyclic or heterocyclic ring;

R$_5$ is H, C$_1$-C$_5$ linear or branched, substituted or unsubstituted alkyl, methyl, CH$_2$SH, ethyl, iso-propyl, C$_1$-C$_5$ linear or branched haloalkyl, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, R$_8$-aryl, CH$_2$—Ph, substituted or unsubstituted aryl, phenyl, substituted or unsubstituted heteroaryl, pyridine (2, 3, and 4-pyridine); wherein substitutions include: F, Cl, Br, I, C$_1$-C$_5$ linear or branched alkyl, OH, alkoxy, N(R)$_2$, CF$_3$, phenyl, halophenyl, (benzyloxy)phenyl, CN, NO$_2$ or any combination thereof;

R$_6$ is H, C$_1$-C$_5$ linear or branched alkyl, methyl, C(O)R, or S(O)$_2$R;

R$_8$ is [CH$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ linear or branched alkyl, methyl, ethyl, C(O)R, or S(O)$_2$R;

R is H, C$_1$-C$_5$ linear or branched alkyl, methyl, ethyl, C$_1$-C$_5$ linear or branched alkoxy, phenyl, aryl or heteroaryl, or two gem R substituents are joint together to form a 5 or 6 membered heterocyclic ring;

m, n, l and k are each independently an integer between 0 and 4;

Q$_1$ and Q$_2$ are each independently S, 0, N—OH, CH$_2$, C(R)$_2$ or N—OMe;

or its pharmaceutically acceptable salt, optical isomer, tautomer, hydrate, N-oxide, prodrug, isotopic variant, PROTAC, pharmaceutical product or any combination thereof.

3. The Acyl-CoA Synthetase Short-Chain Family Member 2 (ACSS2) inhibitor compound of claim 1, represented by the structure of formula (II):

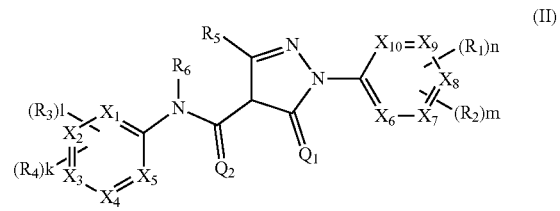

wherein

X$_1$, X$_2$, X$_3$, X$_4$, X$_5$, X$_6$, X$_7$, X$_8$, X$_9$ or X$_{10}$ are each independently C or N;

or its pharmaceutically acceptable salt, optical isomer, tautomer, hydrate, N-oxide, prodrug, isotopic variant, PROTAC, pharmaceutical product or any combination thereof.

4. The Acyl-CoA Synthetase Short-Chain Family Member 2 (ACSS2) inhibitor compound of claim 3, represented by the structure of formula (IV):

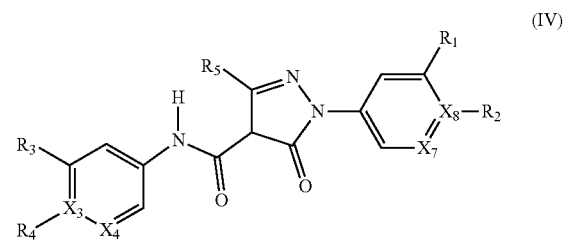

wherein if X$_3$ is N, then R$_4$ is absent; and if X$_8$ is N, then R$_2$ is absent;

or its pharmaceutically acceptable salt, optical isomer, tautomer, hydrate, N-oxide, prodrug, isotopic variant, PROTAC, pharmaceutical product or any combination thereof.

5. The Acyl-CoA Synthetase Short-Chain Family Member 2 (ACSS2) inhibitor compound of claim 4, represented by the structure of formula (V):

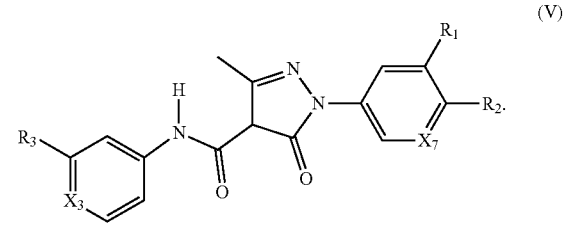

6. The Acyl-CoA Synthetase Short-Chain Family Member 2 (ACSS2) inhibitor compound of claim 2, wherein R$_3$ is CF$_2$CH$_2$CH$_3$, R$_2$ is OCH$_3$, R$_5$ is CH$_3$ or any combination thereof.

7. An Acyl-CoA Synthetase Short-Chain Family Member 2 (ACSS2) inhibitor compound, represented by the following structures:

| Compound name | Structure |
|---|---|
| 100 | 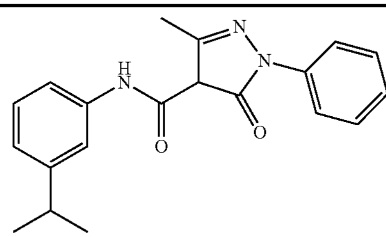 |
| 101 | 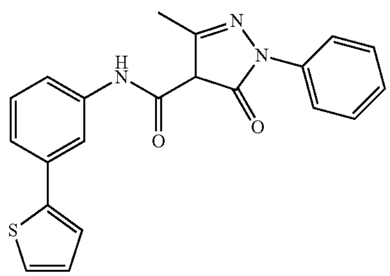 [SMILES: CC1=NN(c2ccccc2)C(=O)C1C(=O)Nc1cccc(-c2cccs2)c1] |
| 102 | 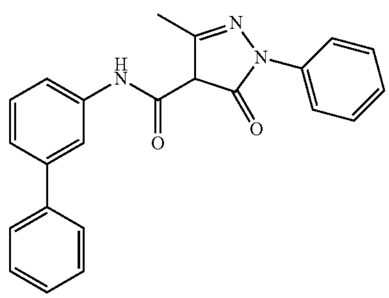 [SMILES: CC1=NN(c2ccccc2)C(=O)C1C(=O)Nc1cccc(-c2ccccc2)c1] |
| 103 | 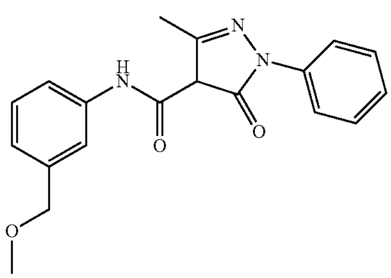 [SMILES: COCc1cccc(NC(=O)C2C(=O)N(c3ccccc3)N=C2C)c1] |
| 104 | 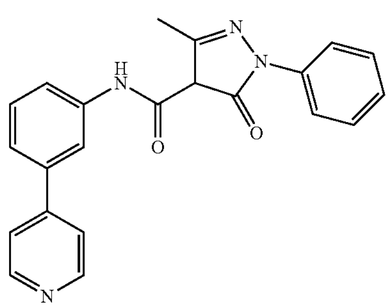 [SMILES: CC1=NN(c2ccccc2)C(=O)C1C(=O)Nc1cccc(-c2ccncc2)c1] |
| 105 | 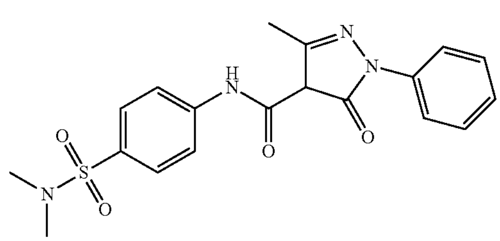 [SMILES: CC1=NN(c2ccccc2)C(=O)C1C(=O)Nc1ccc(S(=O)(=O)N(C)C)cc1] |

| Compound name | Structure |
|---|---|
| 106 | 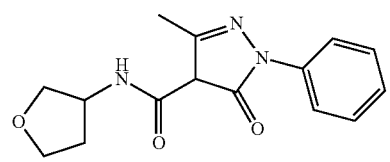 [SMILES: CC1=NN(c2ccccc2)C(=O)C1C(=O)NC1CCOC1] |
| 107 | 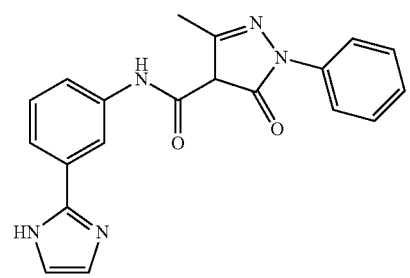 [SMILES: CC1=NN(c2ccccc2)C(=O)C1C(=O)Nc1cccc(-c2ncc[nH]2)c1] |
| 108 | 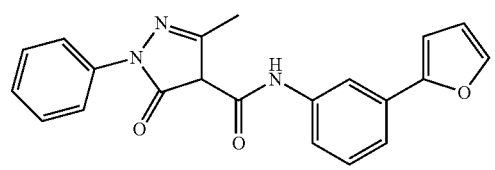 [SMILES: CC1=NN(c2ccccc2)C(=O)C1C(=O)Nc1cccc(-c2ccco2)c1] |
| 109 | 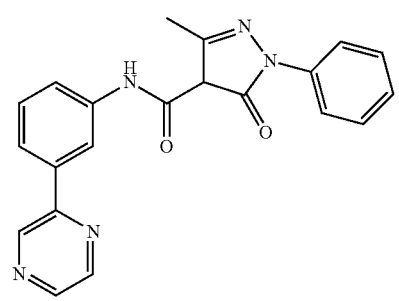 [SMILES: CC1=NN(c2ccccc2)C(=O)C1C(=O)Nc1cccc(-c2cnccn2)c1] |
| 110 | 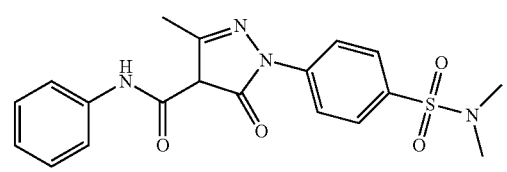 [SMILES: CC1=NN(c2ccc(S(=O)(=O)N(C)C)cc2)C(=O)C1C(=O)Nc1ccccc1] |
| 111 | 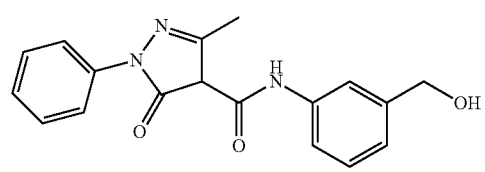 [SMILES: CC1=NN(c2ccccc2)C(=O)C1C(=O)Nc1cccc(CO)c1] |
| 112 | 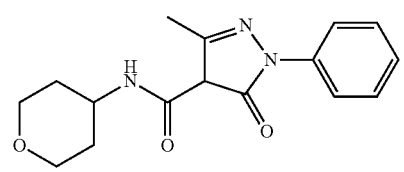 [SMILES: CC1=NN(c2ccccc2)C(=O)C1C(=O)NC1CCOCC1] |

| Compound name | Structure |
|---|---|
| 113 | 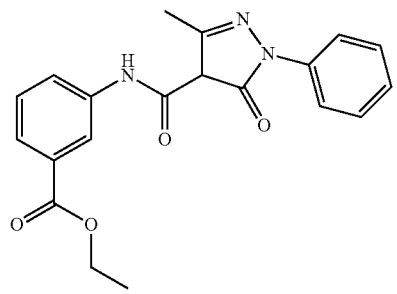 [SMILES: CCOC(=O)c1cccc(NC(=O)C2C(=O)N(c3ccccc3)N=C2C)c1] |
| 114 | 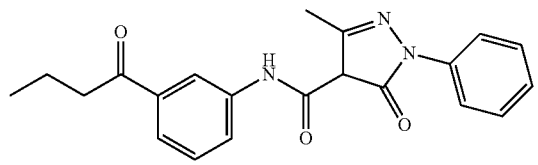 [SMILES: CCCC(=O)c1cccc(NC(=O)C2C(=O)N(c3ccccc3)N=C2C)c1] |
| 115 | 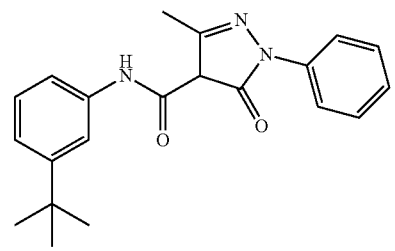 [SMILES: CC1=NN(c2ccccc2)C(=O)C1C(=O)Nc1cccc(C(C)(C)C)c1] |
| 116 | 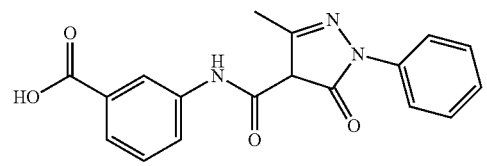 [SMILES: CC1=NN(c2ccccc2)C(=O)C1C(=O)Nc1cccc(C(=O)O)c1] |
| 117 | 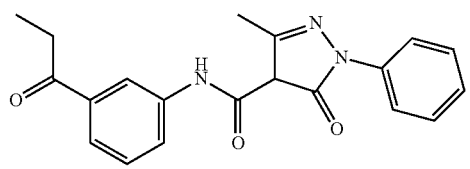 [SMILES: CCC(=O)c1cccc(NC(=O)C2C(=O)N(c3ccccc3)N=C2C)c1] |
| 118 | 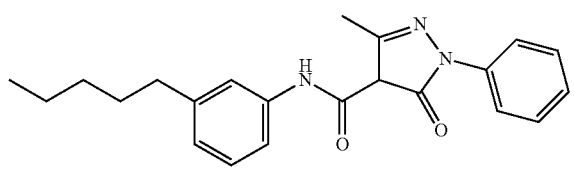 [SMILES: CCCCCc1cccc(NC(=O)C2C(=O)N(c3ccccc3)N=C2C)c1] |
| 119 | 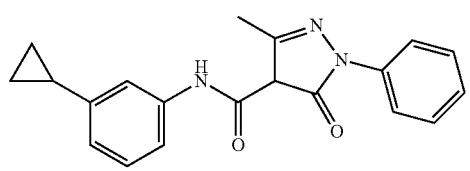 [SMILES: CC1=NN(c2ccccc2)C(=O)C1C(=O)Nc1cccc(C2CC2)c1] |

-continued

| Compound name | Structure |
|---|---|
| 120 | 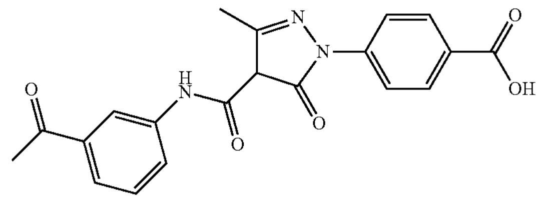 [SMILES: CC(=O)c1cccc(NC(=O)C2C(=O)N(c3ccc(C(=O)O)cc3)N=C2C)c1] |
| 121 | 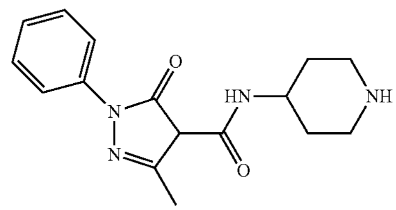 [SMILES: CC1=NN(c2ccccc2)C(=O)C1C(=O)NC1CCNCC1] |
| 122 | 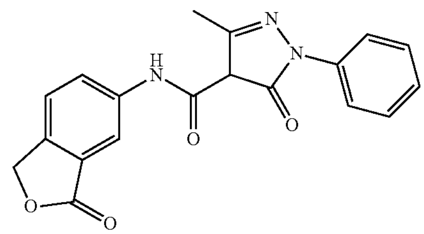 [SMILES: CC1=NN(c2ccccc2)C(=O)C1C(=O)Nc1ccc2c(c1)C(=O)OC2] |
| 123 | 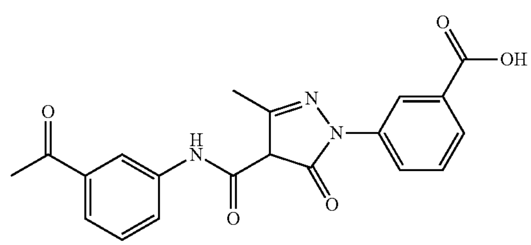 [SMILES: CC(=O)c1cccc(NC(=O)C2C(=O)N(c3cccc(C(=O)O)c3)N=C2C)c1] |
| 124 | 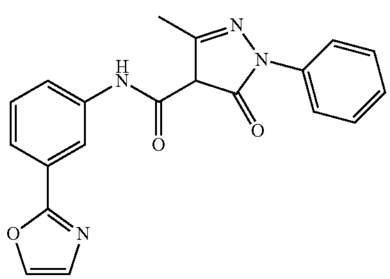 [SMILES: CC1=NN(c2ccccc2)C(=O)C1C(=O)Nc1cccc(-c2ncco2)c1] |
| 125 | 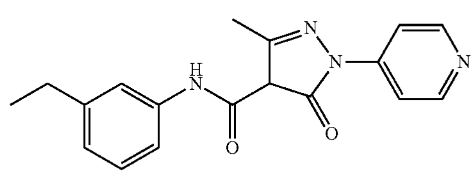 [SMILES: CCc1cccc(NC(=O)C2C(=O)N(c3ccncc3)N=C2C)c1] |

| Compound name | Structure |
|---|---|
| 126 | 3-ethyl-N-phenyl, 5-phenyl-pyrazolone carboxamide (1,3-diphenyl-5-oxo-pyrazoline-4-carboxamide with 3-ethylphenyl on amide N) |
| 127 | 3-methyl-1-(4-trifluoromethylphenyl)-5-oxo-pyrazoline-4-carboxamide with N-(3-ethylphenyl) |
| 128 | 3-isopropyl-1-phenyl-5-oxo-pyrazoline-4-carboxamide with N-(3-ethylphenyl) |
| 129 | 3-benzyl-1-phenyl-5-oxo-pyrazoline-4-carboxamide with N-(3-ethylphenyl) |
| 130 | 3-trifluoromethyl-1-phenyl-5-oxo-pyrazoline-4-carboxamide with N-(3-ethylphenyl) |
| 131 | 3-methyl-1-phenyl-5-oxo-pyrazoline-4-carboxamide with N-[3-(dimethylaminomethyl)phenyl] |
| 132 | 3-methyl-1-phenyl-5-oxo-pyrazoline-4-carboxamide with N-[3-(pyrimidin-5-yl)phenyl] |

-continued

| Compound name | Structure |
|---|---|
| 133 | N-(3-ethylphenyl)-5-oxo-1-phenyl-4,5-dihydro-1H-pyrazole-4-carboxamide |
| 134 | N-(3-ethylphenyl)-1-(4-ethoxyphenyl)-3-methyl-5-oxo-4,5-dihydro-1H-pyrazole-4-carboxamide |
| 135 | ethyl 4-(3-methyl-5-oxo-1-phenyl-4,5-dihydro-1H-pyrazole-4-carboxamido)picolinate |
| 136 | N-(3-ethylphenyl)-3-ethyl-5-oxo-1-phenyl-4,5-dihydro-1H-pyrazole-4-carboxamide |
| 137 | N-(3-ethylphenyl)-5-oxo-1-phenyl-3-(pyridin-4-yl)-4,5-dihydro-1H-pyrazole-4-carboxamide |
| 138 | N-(3-ethylphenyl)-1-(4-methoxyphenyl)-3-methyl-5-oxo-4,5-dihydro-1H-pyrazole-4-carboxamide |

-continued

| Compound name | Structure |
|---|---|
| 139 | 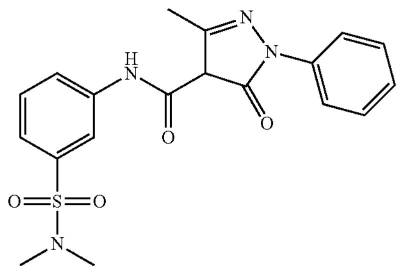 [SMILES: CC1=NN(c2ccccc2)C(=O)C1C(=O)Nc1cccc(S(=O)(=O)N(C)C)c1] |
| 140 | 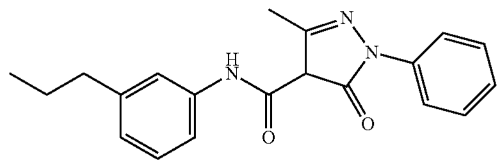 [SMILES: CCCc1cccc(NC(=O)C2C(=O)N(c3ccccc3)N=C2C)c1] |
| 141 | 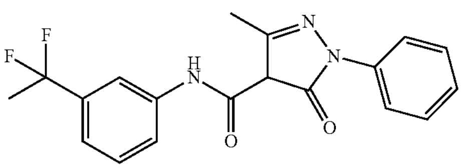 [SMILES: CC1=NN(c2ccccc2)C(=O)C1C(=O)Nc1cccc(C(C)(F)F)c1] |
| 142 | 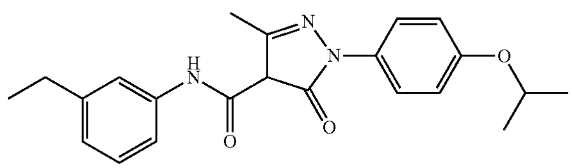 [SMILES: CCc1cccc(NC(=O)C2C(=O)N(c3ccc(OC(C)C)cc3)N=C2C)c1] |
| 143 | 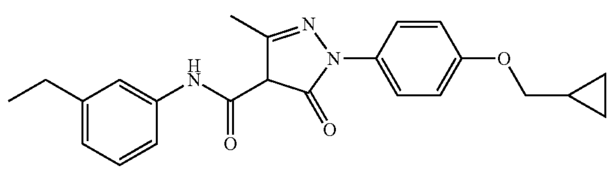 [SMILES: CCc1cccc(NC(=O)C2C(=O)N(c3ccc(OCC4CC4)cc3)N=C2C)c1] |
| 144 | 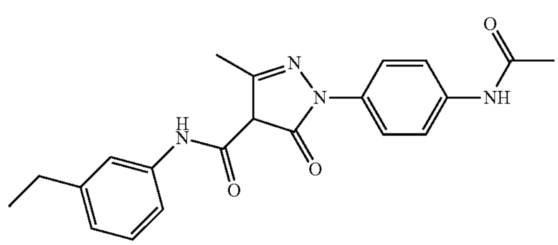 [SMILES: CCc1cccc(NC(=O)C2C(=O)N(c3ccc(NC(C)=O)cc3)N=C2C)c1] |
| 145 | 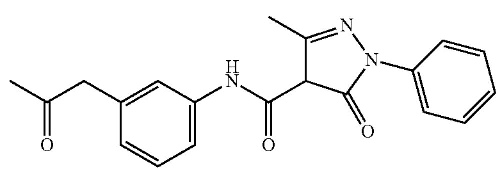 [SMILES: CC(=O)Cc1cccc(NC(=O)C2C(=O)N(c3ccccc3)N=C2C)c1] |
| 146 | 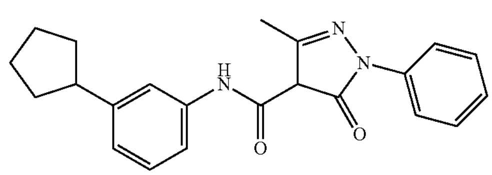 [SMILES: CC1=NN(c2ccccc2)C(=O)C1C(=O)Nc1cccc(C2CCCC2)c1] |

-continued

| Compound name | Structure |
|---|---|
| 147 | 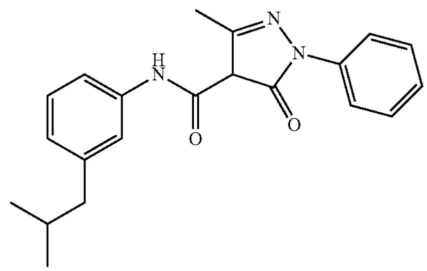 [SMILES: CC1=NN(c2ccccc2)C(=O)C1C(=O)Nc1cccc(CC(C)C)c1] |
| 148 | 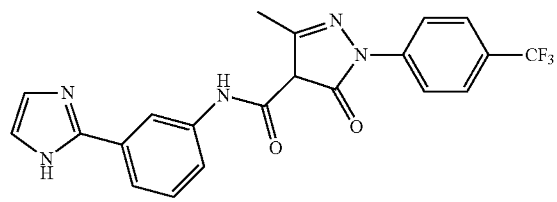 [SMILES: CC1=NN(c2ccc(C(F)(F)F)cc2)C(=O)C1C(=O)Nc1cccc(-c2ncc[nH]2)c1] |
| 149 | 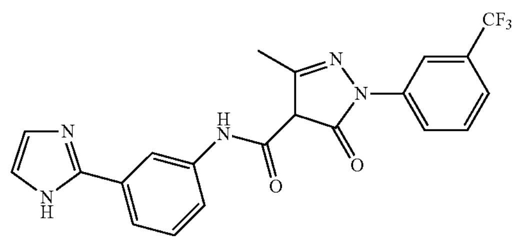 [SMILES: CC1=NN(c2cccc(C(F)(F)F)c2)C(=O)C1C(=O)Nc1cccc(-c2ncc[nH]2)c1] |
| 150 | 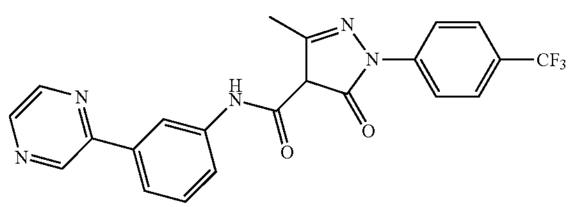 [SMILES: CC1=NN(c2ccc(C(F)(F)F)cc2)C(=O)C1C(=O)Nc1cccc(-c2cnccn2)c1] |
| 152 | 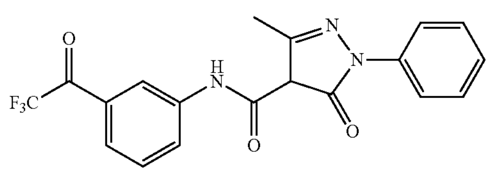 [SMILES: CC1=NN(c2ccccc2)C(=O)C1C(=O)Nc1cccc(C(=O)C(F)(F)F)c1] |
| 153 | 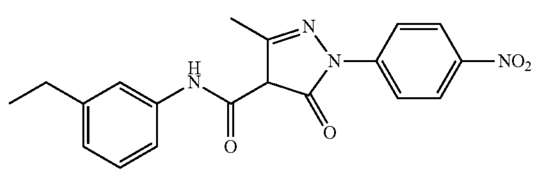 |
| 154 | 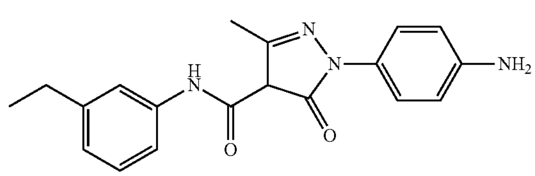 |

-continued

| Compound name | Structure |
|---|---|
| 155 | 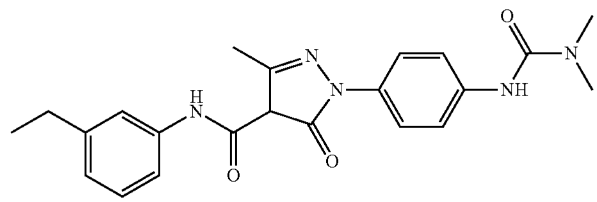 [SMILES: CCc1cccc(NC(=O)C2C(=O)N(c3ccc(NC(=O)N(C)C)cc3)N=C2C)c1] |
| 156 | 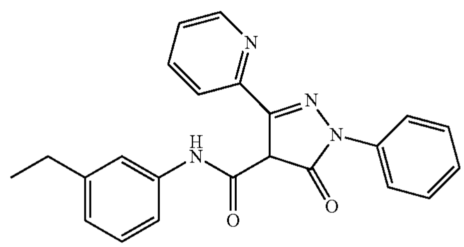 [SMILES: CCc1cccc(NC(=O)C2C(=O)N(c3ccccc3)N=C2c2ccccn2)c1] |
| 157 | 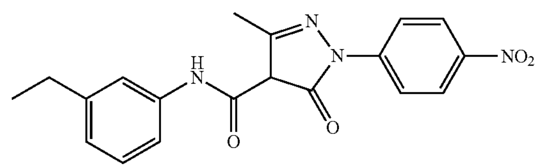 |
| 158 | 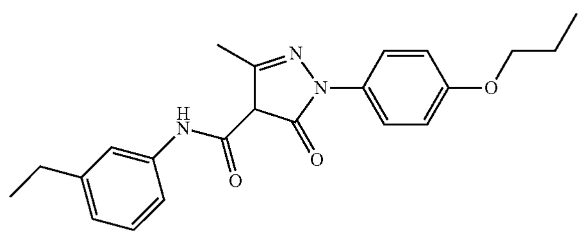 [SMILES: CCCOc1ccc(N2N=C(C)C(C(=O)Nc3cccc(CC)c3)C2=O)cc1] |
| 159 | 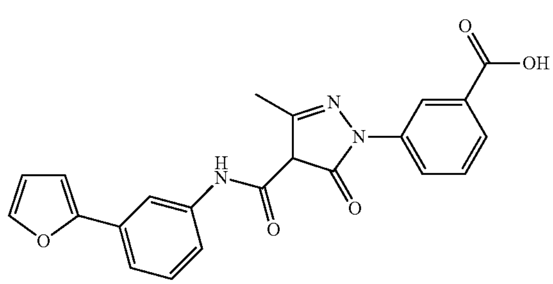 [SMILES: CC1=NN(c2cccc(C(=O)O)c2)C(=O)C1C(=O)Nc1cccc(-c2ccco2)c1] |
| 160 | 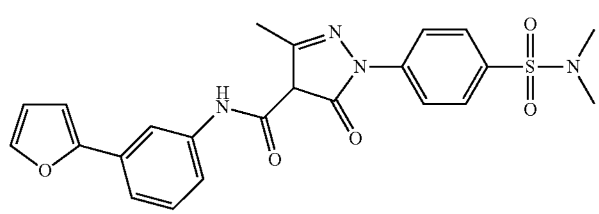 [SMILES: CC1=NN(c2ccc(S(=O)(=O)N(C)C)cc2)C(=O)C1C(=O)Nc1cccc(-c2ccco2)c1] |
| 161 | 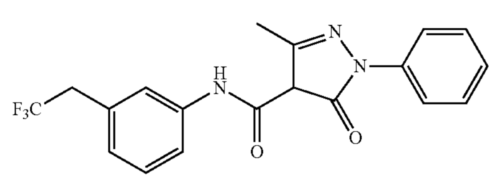 [SMILES: CC1=NN(c2ccccc2)C(=O)C1C(=O)Nc1cccc(CC(F)(F)F)c1] |

| Compound name | Structure |
|---|---|
| 162 | 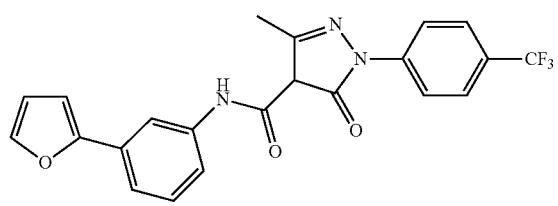 [SMILES: CC1=NN(c2ccc(C(F)(F)F)cc2)C(=O)C1C(=O)Nc1cccc(-c2ccco2)c1] |
| 164 | 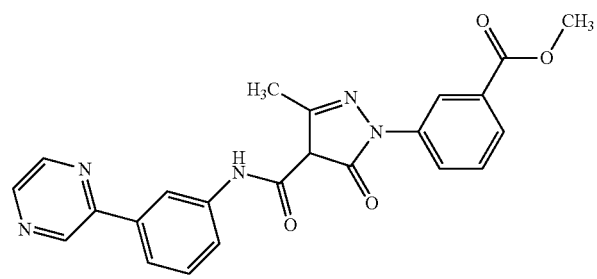 [SMILES: COC(=O)c1cccc(N2N=C(C)C(C(=O)Nc3cccc(-c4cnccn4)c3)C2=O)c1] |
| 165 | 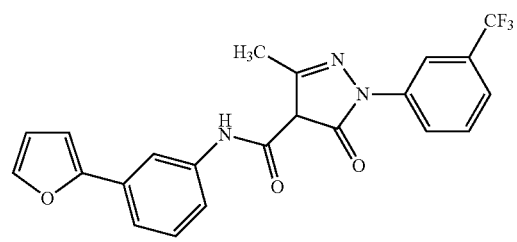 [SMILES: CC1=NN(c2cccc(C(F)(F)F)c2)C(=O)C1C(=O)Nc1cccc(-c2ccco2)c1] |
| 166 | 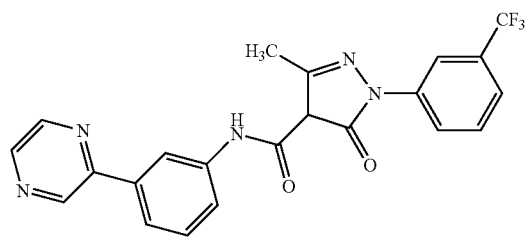 [SMILES: CC1=NN(c2cccc(C(F)(F)F)c2)C(=O)C1C(=O)Nc1cccc(-c2cnccn2)c1] |
| 167 | 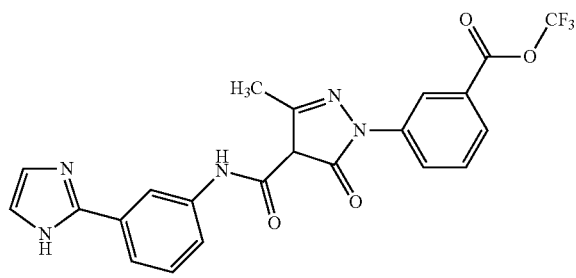 [SMILES: CC1=NN(c2cccc(C(=O)OC(F)(F)F)c2)C(=O)C1C(=O)Nc1cccc(-c2ncc[nH]2)c1] |
| 168 | 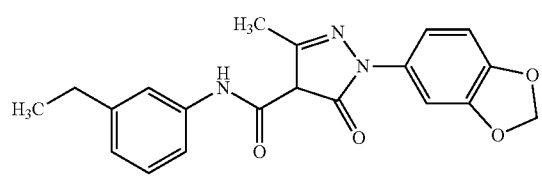 [SMILES: CCc1cccc(NC(=O)C2C(=O)N(c3ccc4c(c3)OCO4)N=C2C)c1] |

-continued

| Compound name | Structure |
|---|---|
| 169 | 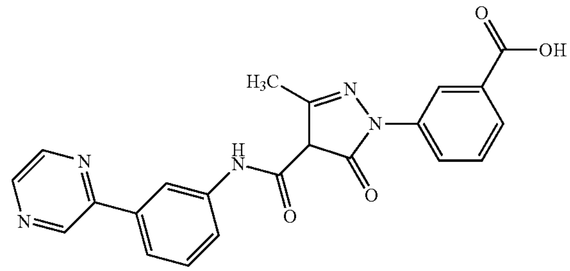 [SMILES: CC1=NN(c2cccc(C(=O)O)c2)C(=O)C1C(=O)Nc1cccc(-c2cnccn2)c1] |
| 170 | 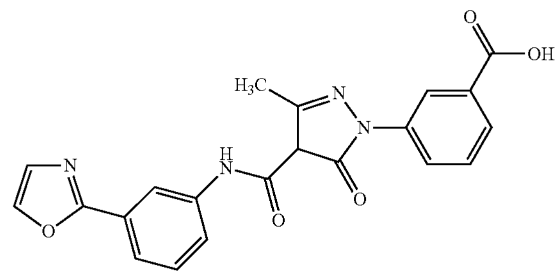 [SMILES: CC1=NN(c2cccc(C(=O)O)c2)C(=O)C1C(=O)Nc1cccc(-c2ncco2)c1] |
| 171 | 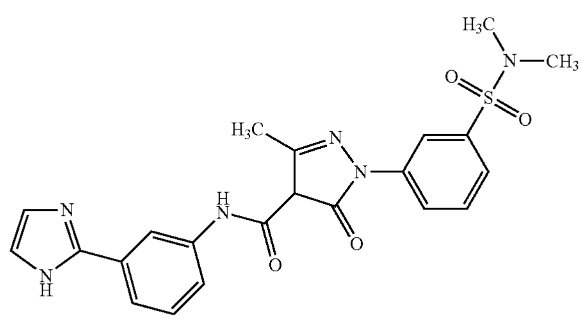 |
| 172 | 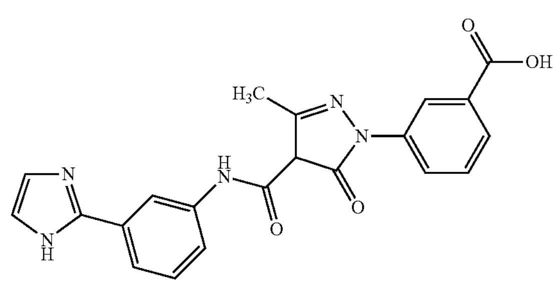 |
| 173 | 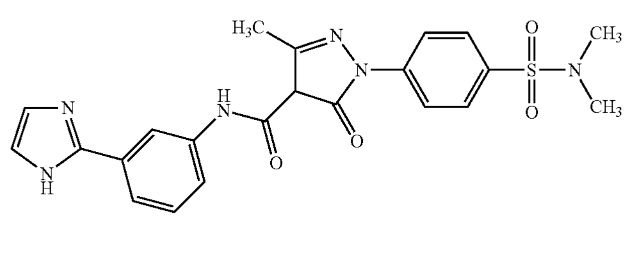 [SMILES: CC1=NN(c2ccc(S(=O)(=O)N(C)C)cc2)C(=O)C1C(=O)Nc1cccc(-c2ncc[nH]2)c1] |

-continued

| Compound name | Structure |
|---|---|
| 174 | 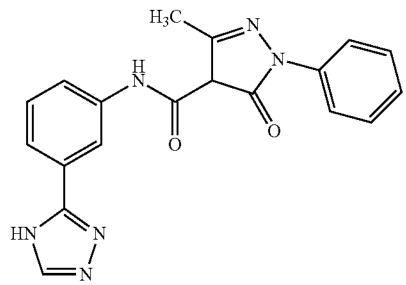 [SMILES: CC1=NN(c2ccccc2)C(=O)C1C(=O)Nc1cccc(-c2nnc[nH]2)c1] |
| 176 | 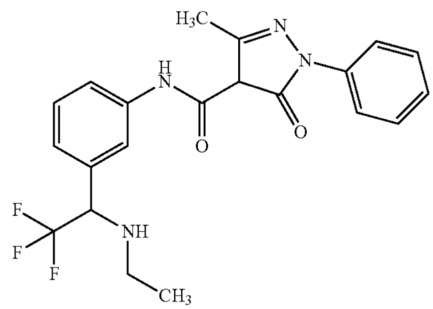 [SMILES: CCNC(c1cccc(NC(=O)C2C(=O)N(c3ccccc3)N=C2C)c1)C(F)(F)F] |
| 179 | 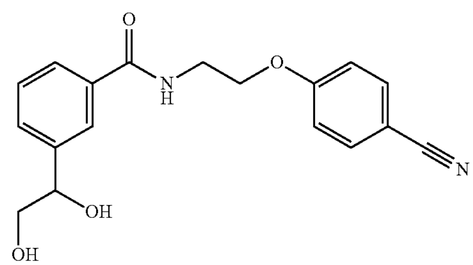 [SMILES: N#Cc1ccc(OCCNC(=O)c2cccc(C(O)CO)c2)cc1] |
| 180 | 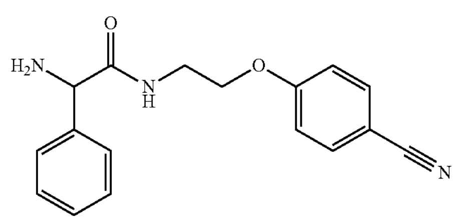 [SMILES: N#Cc1ccc(OCCNC(=O)C(N)c2ccccc2)cc1] |
| 183 | 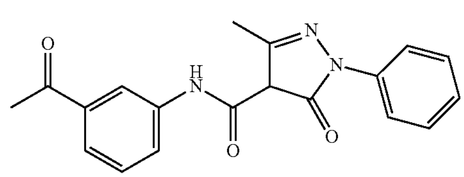 [SMILES: CC(=O)c1cccc(NC(=O)C2C(=O)N(c3ccccc3)N=C2C)c1] |
| 184 | 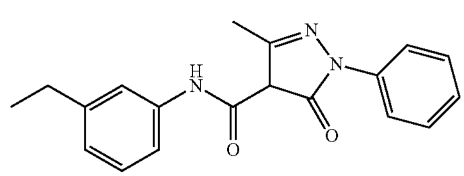 [SMILES: CCc1cccc(NC(=O)C2C(=O)N(c3ccccc3)N=C2C)c1] |

-continued

| Compound name | Structure |
|---|---|
| 185 | N-(naphthalen-1-yl)-3-methyl-5-oxo-1-phenyl-4,5-dihydro-1H-pyrazole-4-carboxamide |
| 186 | N-benzyl-3-methyl-5-oxo-1-phenyl-4,5-dihydro-1H-pyrazole-4-carboxamide |
| 187 | 1-isopropyl-3-methyl-5-oxo-N-phenyl-4,5-dihydro-1H-pyrazole-4-carboxamide |
| 188 | N-(4-methoxyphenyl)-3-methyl-5-oxo-1-phenyl-4,5-dihydro-1H-pyrazole-4-carboxamide |
| 189 | N-(4-fluorophenyl)-3-methyl-5-oxo-1-phenyl-4,5-dihydro-1H-pyrazole-4-carboxamide |
| 190 | 1,3-dimethyl-5-oxo-N,1-diphenyl-4,5-dihydro-1H-pyrazole-4-carboxamide |
| 191 | 3-methyl-5-oxo-1-phenyl-N-(pyridin-3-yl)-4,5-dihydro-1H-pyrazole-4-carboxamide |

-continued

| Compound name | Structure |
|---|---|
| 192 | 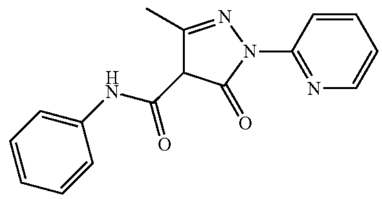 [SMILES: CC1=NN(c2ccccn2)C(=O)C1C(=O)Nc1ccccc1] |
| 193 | 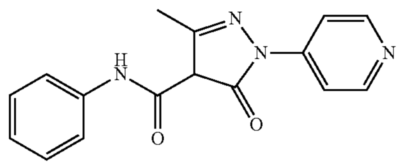 [SMILES: CC1=NN(c2ccncc2)C(=O)C1C(=O)Nc1ccccc1] |
| 194 | 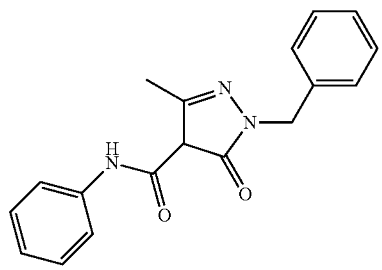 [SMILES: CC1=NN(Cc2ccccc2)C(=O)C1C(=O)Nc1ccccc1] |
| 195 | 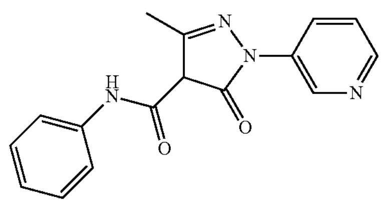 |
| 196 | 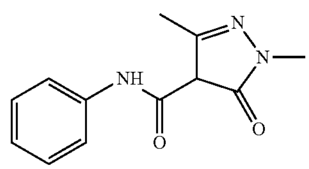 [SMILES: CC1=NN(C)C(=O)C1C(=O)Nc1ccccc1] |
| 198 | 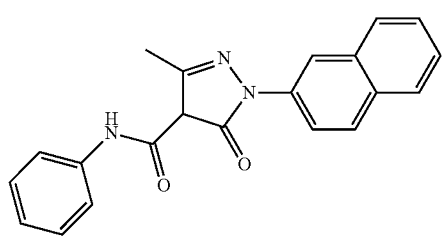 [SMILES: CC1=NN(c2ccc3ccccc3c2)C(=O)C1C(=O)Nc1ccccc1] |
| 199 | 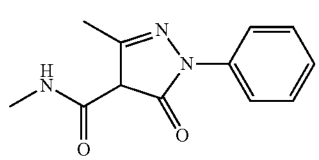 [SMILES: CNC(=O)C1C(=O)N(c2ccccc2)N=C1C] |
| 200 | 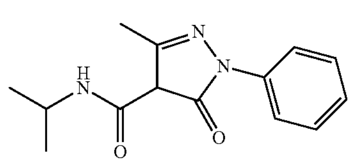 [SMILES: CC1=NN(c2ccccc2)C(=O)C1C(=O)NC(C)C] |

-continued
| Compound name | Structure |
|---|---|
| 201 | 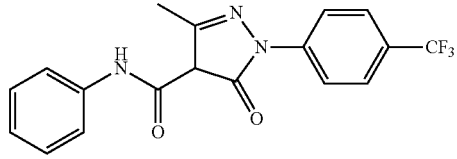 [SMILES: CC1=NN(c2ccc(C(F)(F)F)cc2)C(=O)C1C(=O)Nc1ccccc1] |
| 202 | 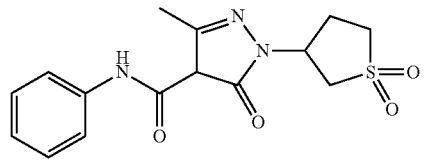 [SMILES: CC1=NN(C2CCS(=O)(=O)C2)C(=O)C1C(=O)Nc1ccccc1] |
| 203 | 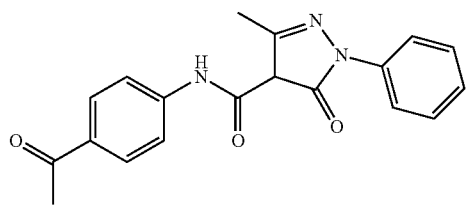 [SMILES: CC(=O)c1ccc(NC(=O)C2C(=O)N(c3ccccc3)N=C2C)cc1] |
| 204 | 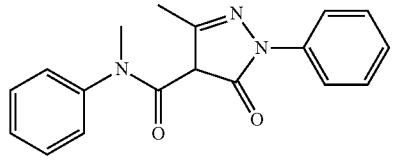 |
| 205 | 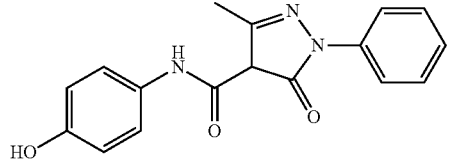 [SMILES: CC1=NN(c2ccccc2)C(=O)C1C(=O)Nc1ccc(O)cc1] |
| 206 | 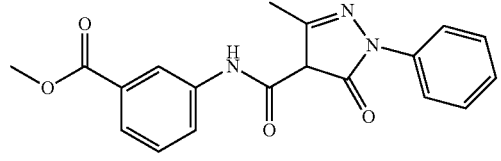 [SMILES: COC(=O)c1cccc(NC(=O)C2C(=O)N(c3ccccc3)N=C2C)c1] |
| 207 | 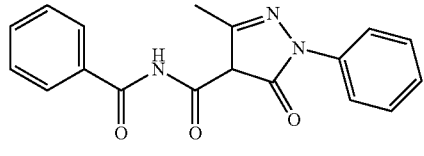 [SMILES: CC1=NN(c2ccccc2)C(=O)C1C(=O)NC(=O)c1ccccc1] |
| 208 | 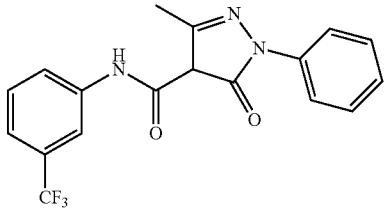 [SMILES: CC1=NN(c2ccccc2)C(=O)C1C(=O)Nc1cccc(C(F)(F)F)c1] |

-continued
| Compound name | Structure |
|---|---|
| 209 | 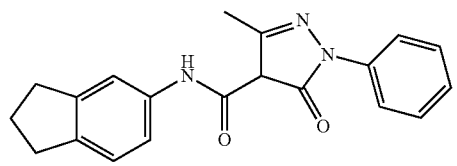 [SMILES: CC1=NN(c2ccccc2)C(=O)C1C(=O)Nc1ccc2c(c1)CCC2] |
| 211 | 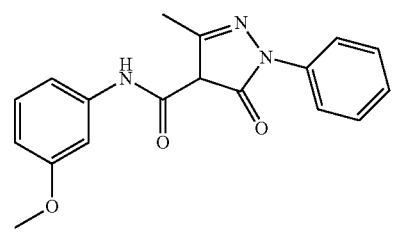 [SMILES: COc1cccc(NC(=O)C2C(=O)N(c3ccccc3)N=C2C)c1] |
| 213 | 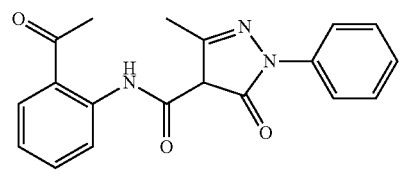 [SMILES: CC(=O)c1ccccc1NC(=O)C1C(=O)N(c2ccccc2)N=C1C] |
| 214 | 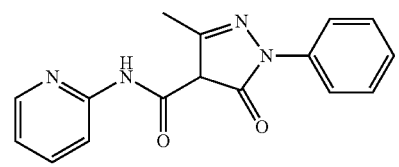 [SMILES: CC1=NN(c2ccccc2)C(=O)C1C(=O)Nc1ccccn1] |
| 215 | 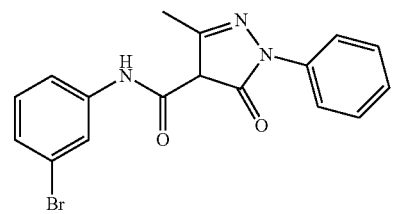 [SMILES: CC1=NN(c2ccccc2)C(=O)C1C(=O)Nc1cccc(Br)c1] |
| 216 | 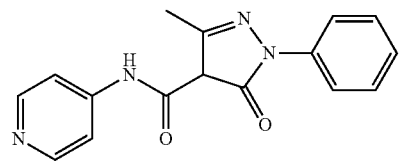 [SMILES: CC1=NN(c2ccccc2)C(=O)C1C(=O)Nc1ccncc1] |
| 217 | 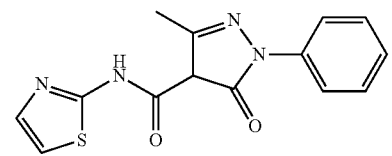 [SMILES: CC1=NN(c2ccccc2)C(=O)C1C(=O)Nc1nccs1] |
| 218 | 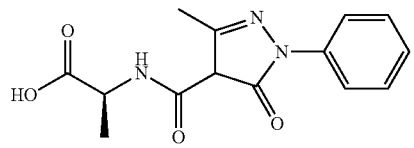 [SMILES: CC1=NN(c2ccccc2)C(=O)C1C(=O)N[C@@H](C)C(=O)O] |

-continued

| Compound name | Structure |
|---|---|
| 219 | 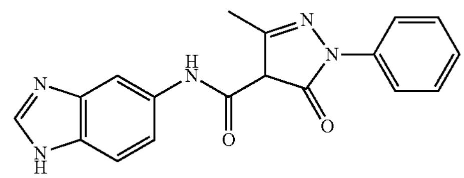 [SMILES: CC1=NN(c2ccccc2)C(=O)C1C(=O)Nc1ccc2[nH]cnc2c1] |
| 220 | 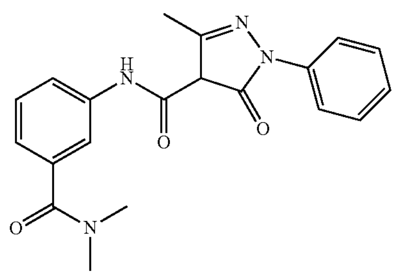 [SMILES: CC1=NN(c2ccccc2)C(=O)C1C(=O)Nc1cccc(C(=O)N(C)C)c1] |
| 221 | 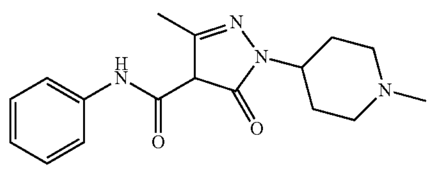 [SMILES: CC1=NN(C2CCN(C)CC2)C(=O)C1C(=O)Nc1ccccc1] |
| 222 | 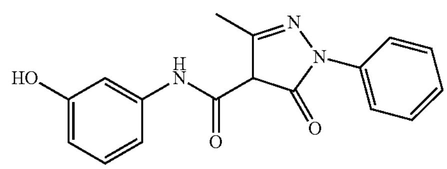 [SMILES: CC1=NN(c2ccccc2)C(=O)C1C(=O)Nc1cccc(O)c1] |
| 223 | 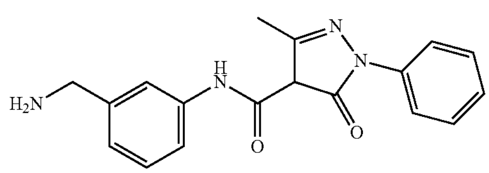 [SMILES: CC1=NN(c2ccccc2)C(=O)C1C(=O)Nc1cccc(CN)c1] |
| 224 | 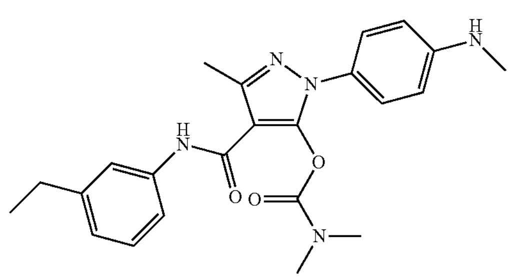 [SMILES: CCc1cccc(NC(=O)c2c(C)nn(-c3ccc(NC)cc3)c2OC(=O)N(C)C)c1] |
| 226 | 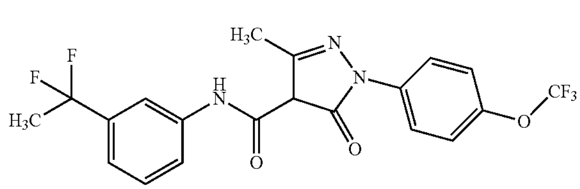 [SMILES: CC1=NN(c2ccc(OC(F)(F)F)cc2)C(=O)C1C(=O)Nc1cccc(C(C)(F)F)c1] |

-continued

| Compound name | Structure |
|---|---|
| 227 | 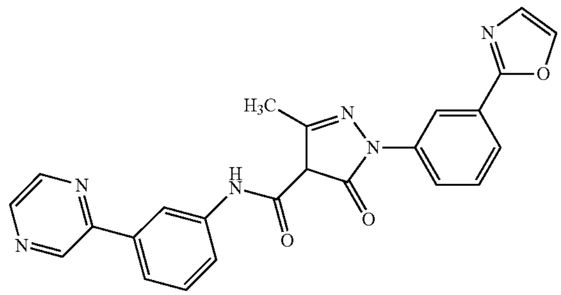 [SMILES: CC1=NN(c2cccc(-c3ncco3)c2)C(=O)C1C(=O)Nc1cccc(-c2cnccn2)c1] |
| 228 | 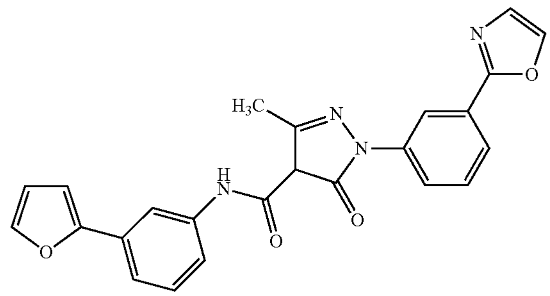 [SMILES: CC1=NN(c2cccc(-c3ncco3)c2)C(=O)C1C(=O)Nc1cccc(-c2ccco2)c1] |
| 229 | 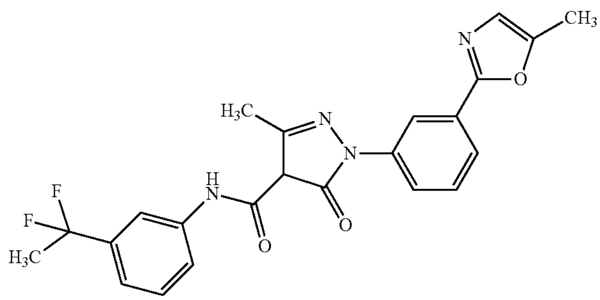 [SMILES: CC1=NN(c2cccc(-c3ncc(C)o3)c2)C(=O)C1C(=O)Nc1cccc(C(C)(F)F)c1] |
| 230 | 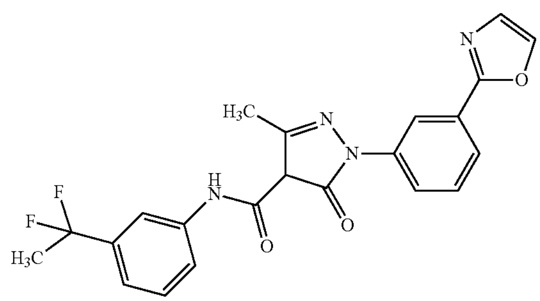 [SMILES: CC1=NN(c2cccc(-c3ncco3)c2)C(=O)C1C(=O)Nc1cccc(C(C)(F)F)c1] |
| 231 | 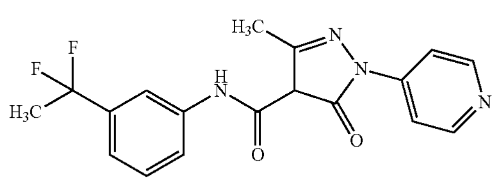 [SMILES: CC1=NN(c2ccncc2)C(=O)C1C(=O)Nc1cccc(C(C)(F)F)c1] |
| 232 | 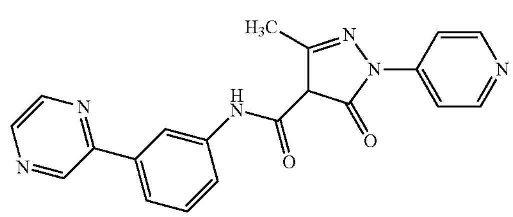 [SMILES: CC1=NN(c2ccncc2)C(=O)C1C(=O)Nc1cccc(-c2cnccn2)c1] |

-continued

| Compound name | Structure |
|---|---|
| 233 | 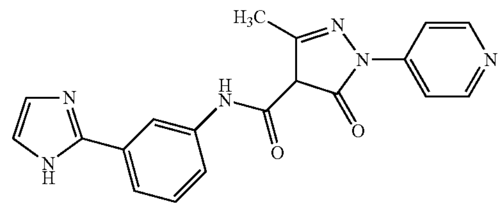 [SMILES: CC1=NN(c2ccncc2)C(=O)C1C(=O)Nc1cccc(-c2ncc[nH]2)c1] |
| 234 | 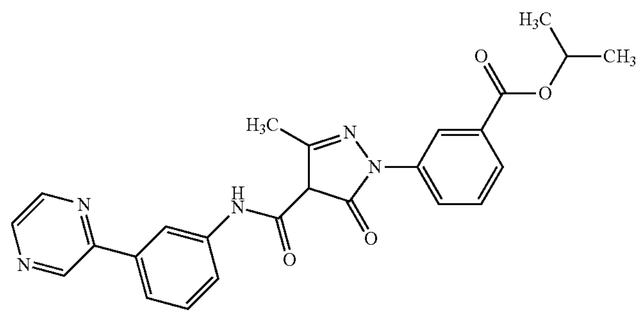 [SMILES: CC1=NN(c2cccc(C(=O)OC(C)C)c2)C(=O)C1C(=O)Nc1cccc(-c2cnccn2)c1] |
| 235 | 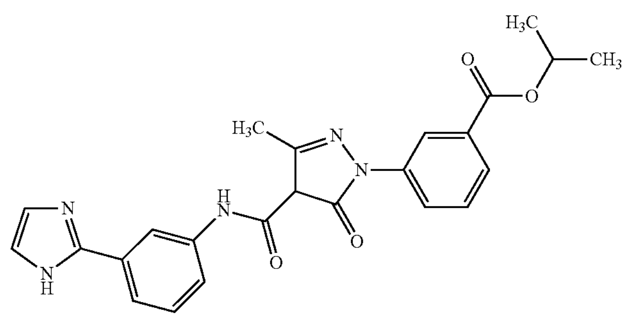 [SMILES: CC1=NN(c2cccc(C(=O)OC(C)C)c2)C(=O)C1C(=O)Nc1cccc(-c2ncc[nH]2)c1] |
| 236 | 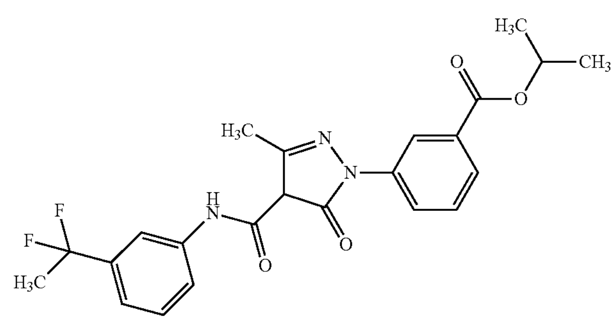 [SMILES: CC1=NN(c2cccc(C(=O)OC(C)C)c2)C(=O)C1C(=O)Nc1cccc(C(C)(F)F)c1] |
| 237 | 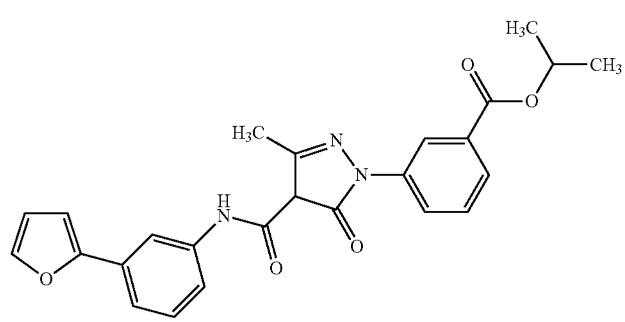 [SMILES: CC1=NN(c2cccc(C(=O)OC(C)C)c2)C(=O)C1C(=O)Nc1cccc(-c2ccco2)c1] |

| Compound name | Structure |
|---|---|
| 238 | 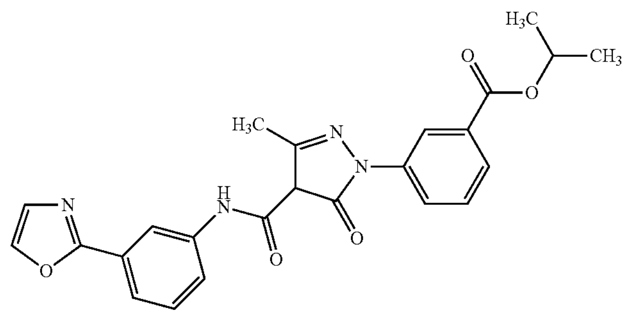 [SMILES: CC1=NN(c2cccc(C(=O)OC(C)C)c2)C(=O)C1C(=O)Nc1cccc(-c2ncco2)c1] |
| 239 | 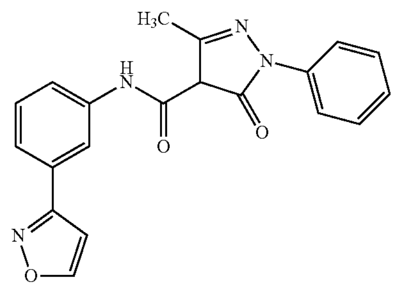 [SMILES: CC1=NN(c2ccccc2)C(=O)C1C(=O)Nc1cccc(-c2ccon2)c1] |
| 240 | 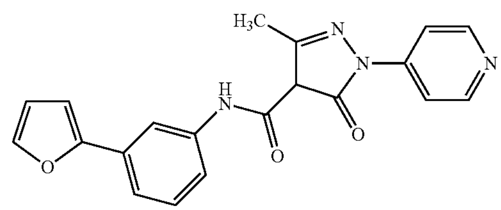 [SMILES: CC1=NN(c2ccncc2)C(=O)C1C(=O)Nc1cccc(-c2ccco2)c1] |
| 241 | 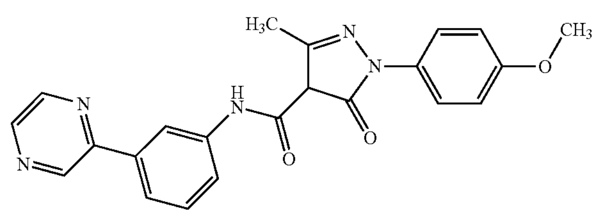 [SMILES: COc1ccc(N2N=C(C)C(C(=O)Nc3cccc(-c4cnccn4)c3)C2=O)cc1] |
| 242 | 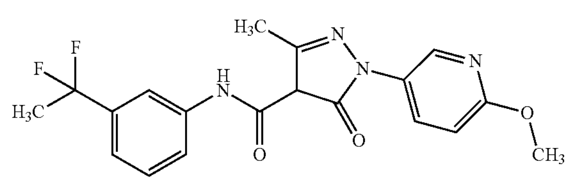 [SMILES: COc1ccc(N2N=C(C)C(C(=O)Nc3cccc(C(C)(F)F)c3)C2=O)cn1] |
| 243 | 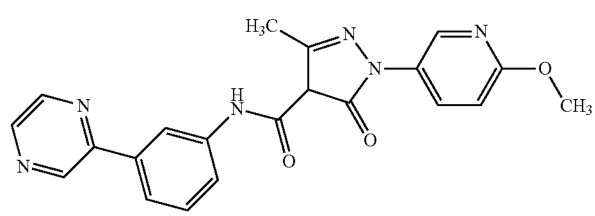 [SMILES: COc1ccc(N2N=C(C)C(C(=O)Nc3cccc(-c4cnccn4)c3)C2=O)cn1] |

-continued

| Compound name | Structure |
|---|---|
| 244 | 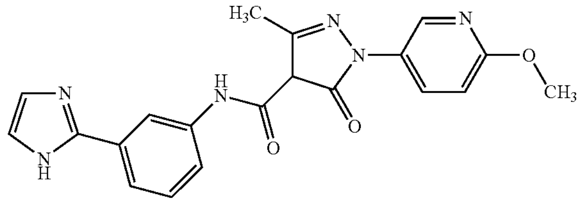 [SMILES: COc1ccc(N2N=C(C)C(C(=O)Nc3cccc(-c4ncc[nH]4)c3)C2=O)cn1] |
| 245 | 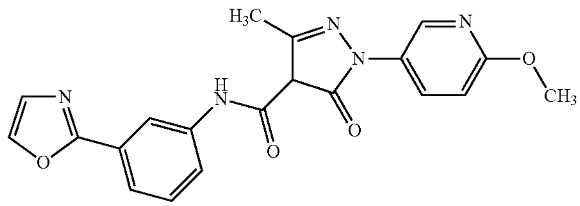 |
| 246 | 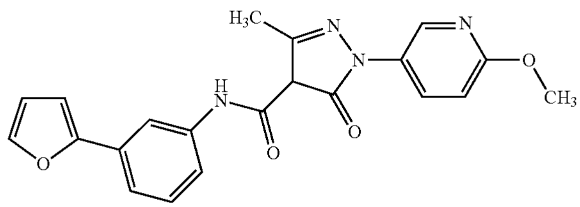 [SMILES: COc1ccc(N2N=C(C)C(C(=O)Nc3cccc(-c4ccco4)c3)C2=O)cn1] |
| 247 | 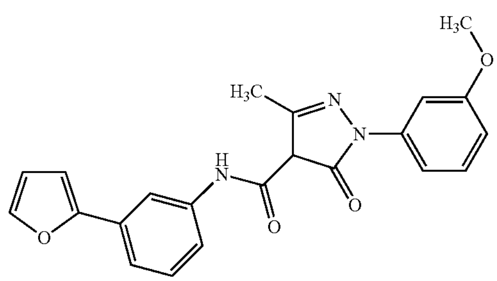 [SMILES: COc1cccc(N2N=C(C)C(C(=O)Nc3cccc(-c4ccco4)c3)C2=O)c1] |
| 248 | 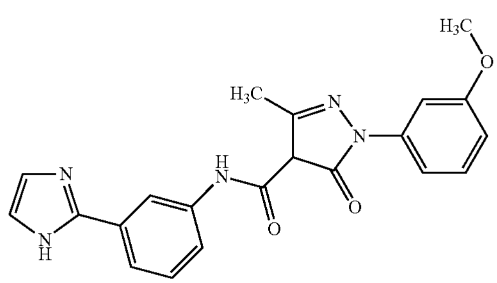 [SMILES: COc1cccc(N2N=C(C)C(C(=O)Nc3cccc(-c4ncc[nH]4)c3)C2=O)c1] |
| 249 | 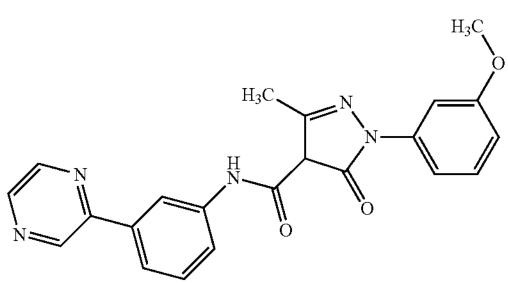 [SMILES: COc1cccc(N2N=C(C)C(C(=O)Nc3cccc(-c4cnccn4)c3)C2=O)c1] |

-continued

| Compound name | Structure |
|---|---|
| 250 | 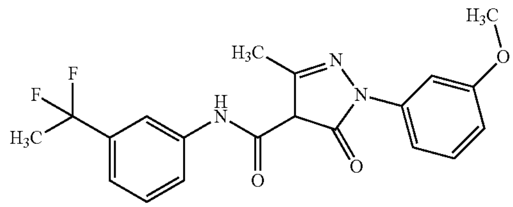 [SMILES: COc1cccc(N2N=C(C)C(C(=O)Nc3cccc(C(C)(F)F)c3)C2=O)c1] |
| 251 | 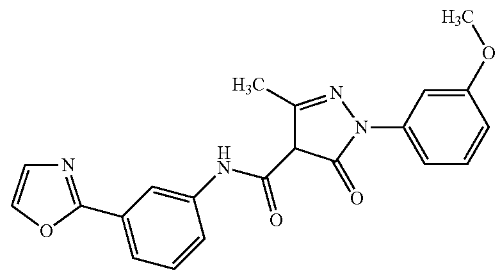 [SMILES: COc1cccc(N2N=C(C)C(C(=O)Nc3cccc(-c4ncco4)c3)C2=O)c1] |
| 252 | 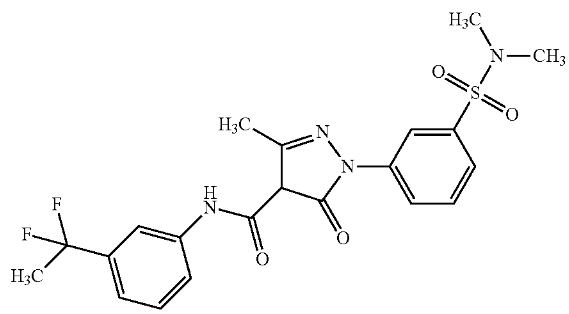 [SMILES: CC1=NN(c2cccc(S(=O)(=O)N(C)C)c2)C(=O)C1C(=O)Nc1cccc(C(C)(F)F)c1] |
| 253 | 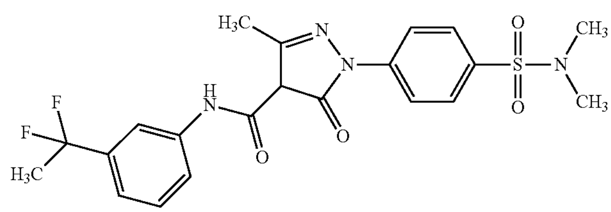 [SMILES: CC1=NN(c2ccc(S(=O)(=O)N(C)C)cc2)C(=O)C1C(=O)Nc1cccc(C(C)(F)F)c1] |
| 254 | 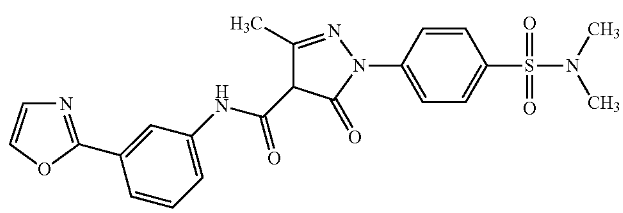 [SMILES: CC1=NN(c2ccc(S(=O)(=O)N(C)C)cc2)C(=O)C1C(=O)Nc1cccc(-c2ncco2)c1] |
| 255 | 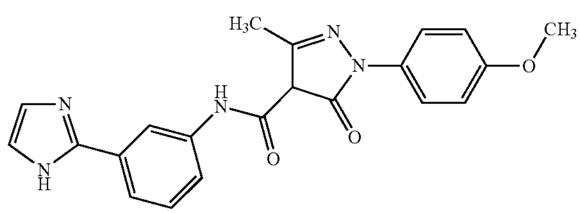 [SMILES: COc1ccc(N2N=C(C)C(C(=O)Nc3cccc(-c4ncc[nH]4)c3)C2=O)cc1] |

| Compound name | Structure |
|---|---|
| 256 | 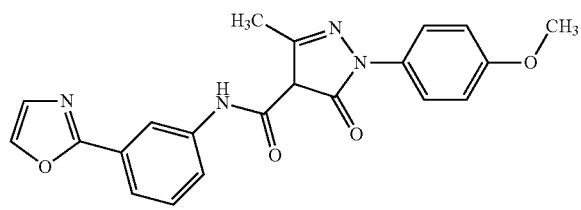 |
| 257 | 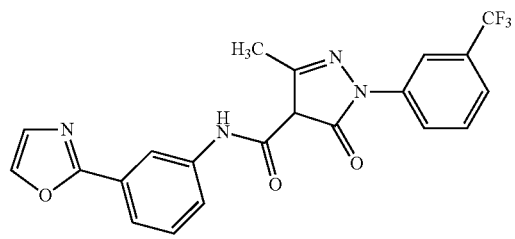 |
| 258 | 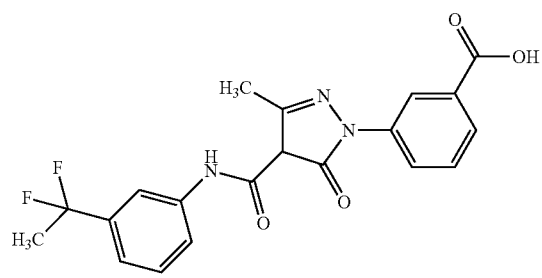 [SMILES: CC1=NN(c2cccc(C(=O)O)c2)C(=O)C1C(=O)Nc1cccc(C(C)(F)F)c1] |
| 259 | 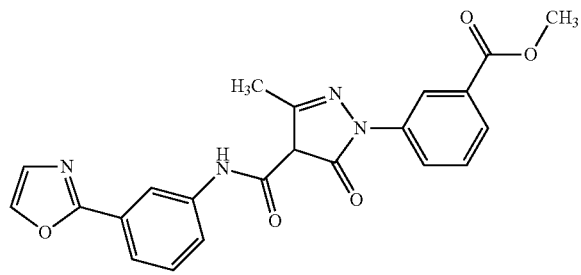 [SMILES: COC(=O)c1cccc(N2N=C(C)C(C(=O)Nc3cccc(-c4ncco4)c3)C2=O)c1] |
| 260 | 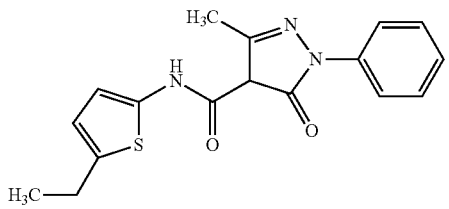 [SMILES: CCc1ccc(NC(=O)C2C(=O)N(c3ccccc3)N=C2C)s1] |
| 261 | 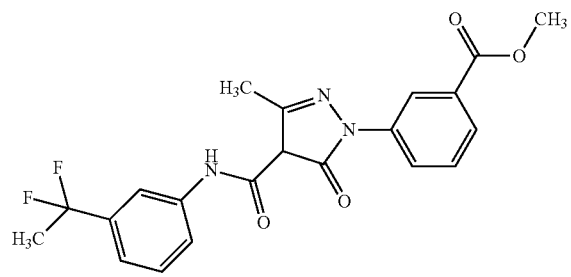 [SMILES: COC(=O)c1cccc(N2N=C(C)C(C(=O)Nc3cccc(C(C)(F)F)c3)C2=O)c1] |

-continued

| Compound name | Structure |
|---|---|
| 262 | 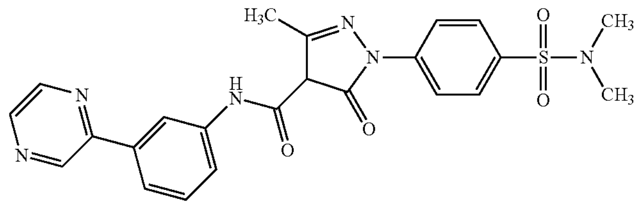 [SMILES: CC1=NN(c2ccc(S(=O)(=O)N(C)C)cc2)C(=O)C1C(=O)Nc1cccc(-c2cnccn2)c1] |
| 263 | 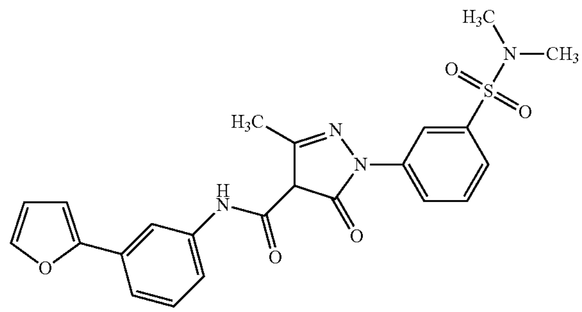 [SMILES: CC1=NN(c2cccc(S(=O)(=O)N(C)C)c2)C(=O)C1C(=O)Nc1cccc(-c2ccco2)c1] |
| 264 | 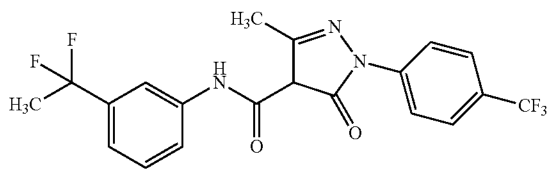 [SMILES: CC1=NN(c2ccc(C(F)(F)F)cc2)C(=O)C1C(=O)Nc1cccc(C(C)(F)F)c1] |
| 265 | 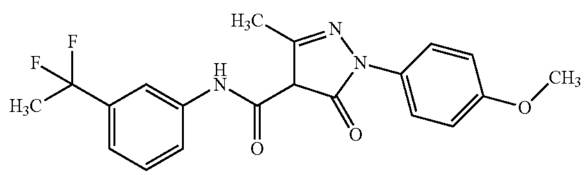 [SMILES: COc1ccc(N2N=C(C)C(C(=O)Nc3cccc(C(C)(F)F)c3)C2=O)cc1] |
| 266 | 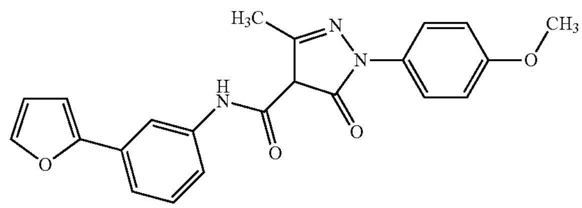 |
| 267 | 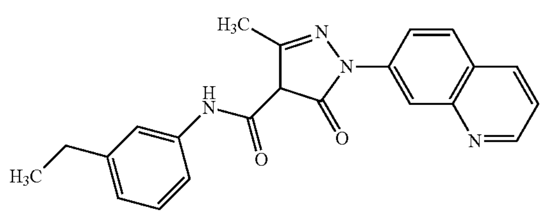 [SMILES: CCc1cccc(NC(=O)C2C(=O)N(c3ccc4cccnc4c3)N=C2C)c1] |
| 268 | 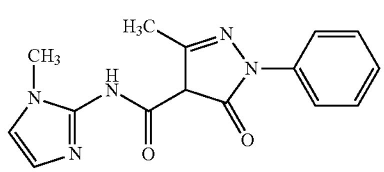 [SMILES: CC1=NN(c2ccccc2)C(=O)C1C(=O)Nc1nccn1C] |

| Compound name | Structure |
|---|---|
| 269 | 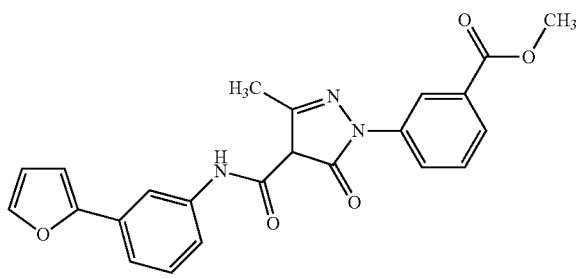 [SMILES: COC(=O)c1cccc(N2N=C(C)C(C(=O)Nc3cccc(-c4ccco4)c3)C2=O)c1] |
| 270 | 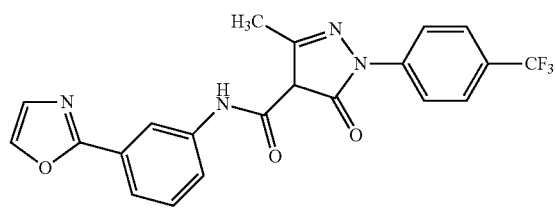 [SMILES: CC1=NN(c2ccc(C(F)(F)F)cc2)C(=O)C1C(=O)Nc1cccc(-c2ncco2)c1] |
| 271 | 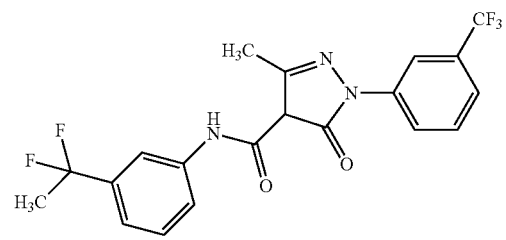 [SMILES: CC1=NN(c2cccc(C(F)(F)F)c2)C(=O)C1C(=O)Nc1cccc(C(C)(F)F)c1] |
| 272 | 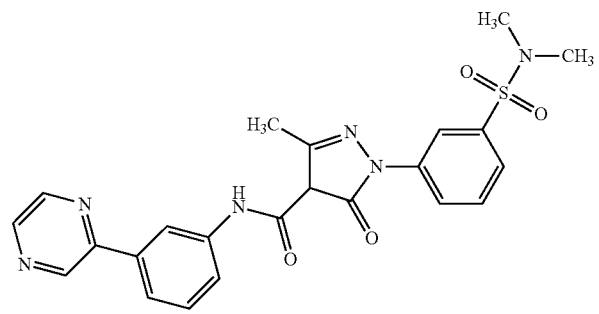 [SMILES: CC1=NN(c2cccc(S(=O)(=O)N(C)C)c2)C(=O)C1C(=O)Nc1cccc(-c2cnccn2)c1] |
| 273 | 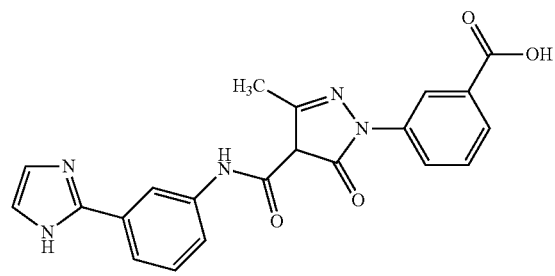 |

-continued
| Compound name | Structure |
|---|---|
| 274 | 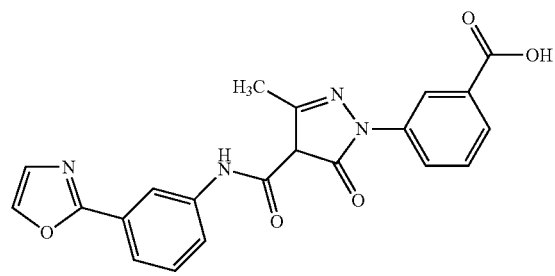 [SMILES: CC1=NN(c2cccc(C(=O)O)c2)C(=O)C1C(=O)Nc1cccc(-c2ncco2)c1] |
| 275 | 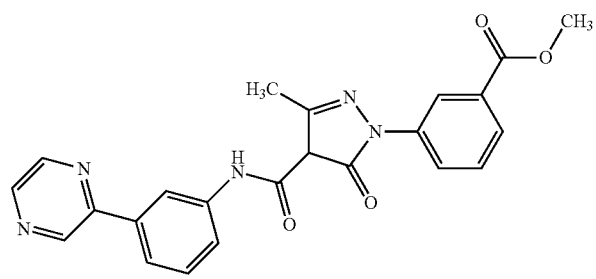 [SMILES: COC(=O)c1cccc(N2N=C(C)C(C(=O)Nc3cccc(-c4cnccn4)c3)C2=O)c1] |
| 276 | 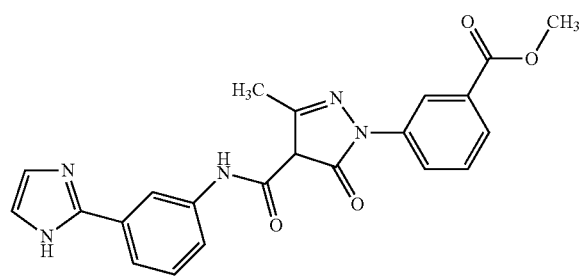 [SMILES: COC(=O)c1cccc(N2N=C(C)C(C(=O)Nc3cccc(-c4ncc[nH]4)c3)C2=O)c1] |
| 277 | 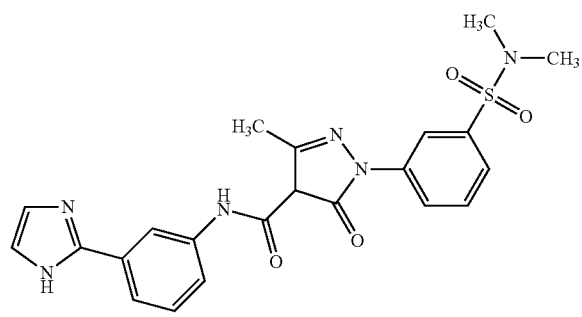 |
| 278 | 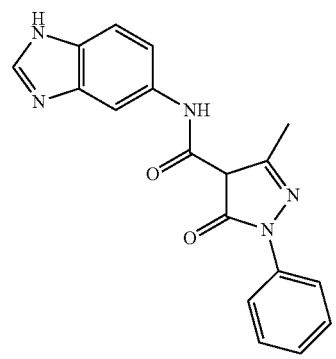 [SMILES: CC1=NN(c2ccccc2)C(=O)C1C(=O)Nc1ccc2[nH]cnc2c1] |

-continued
| Compound name | Structure |
|---|---|
| 279 | 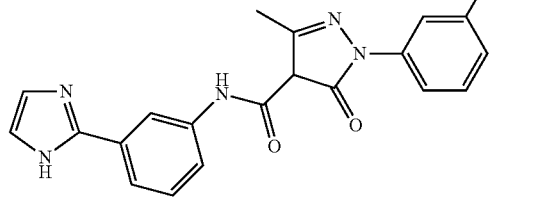 |
| 280 | 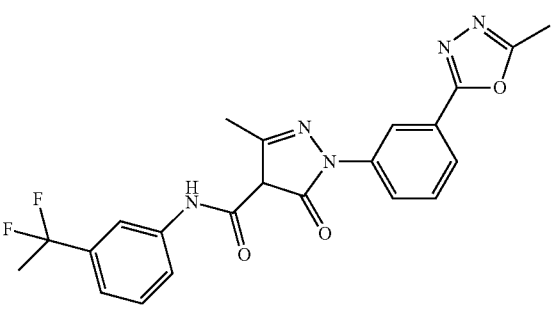 [SMILES: CC1=NN(c2cccc(-c3nnc(C)o3)c2)C(=O)C1C(=O)Nc1cccc(C(C)(F)F)c1] |
| 281 | 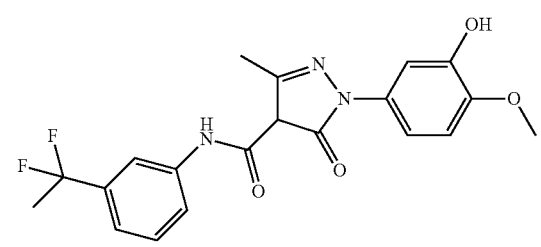 [SMILES: COc1ccc(N2N=C(C)C(C(=O)Nc3cccc(C(C)(F)F)c3)C2=O)cc1O] |
| 282 | 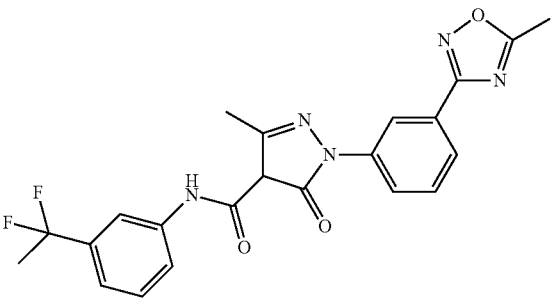 [SMILES: CC1=NN(c2cccc(-c3noc(C)n3)c2)C(=O)C1C(=O)Nc1cccc(C(C)(F)F)c1] |
| 283 | 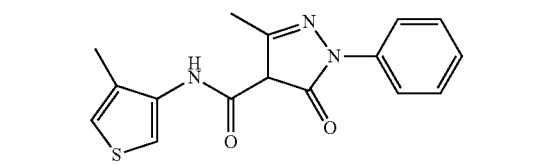 [SMILES: CC1=NN(c2ccccc2)C(=O)C1C(=O)Nc1cscc1C] |
| 284 | 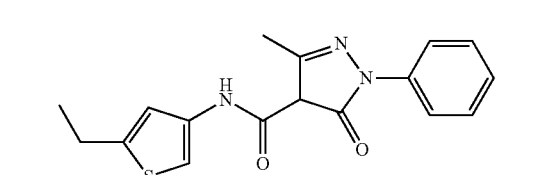 |

295 296
-continued

| Compound name | Structure |
|---|---|
| 285 | 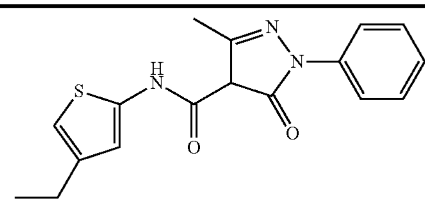 |
| 286 | 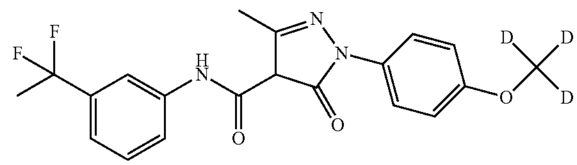 [SMILES: [2H]C([2H])([2H])Oc1ccc(N2N=C(C)C(C(=O)Nc3cccc(C(C)(F)F)c3)C2=O)cc1] |
| 287 | 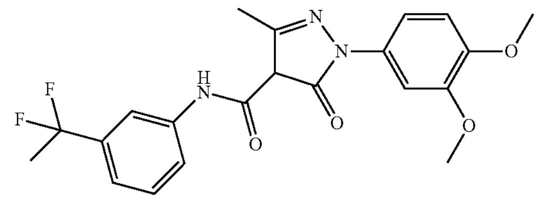 [SMILES: COc1ccc(N2N=C(C)C(C(=O)Nc3cccc(C(C)(F)F)c3)C2=O)cc1OC] |
| 288 | 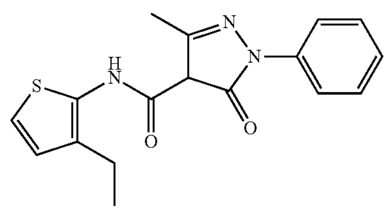 [SMILES: CCc1ccsc1NC(=O)C1C(=O)N(c2ccccc2)N=C1C] |
| 289 | 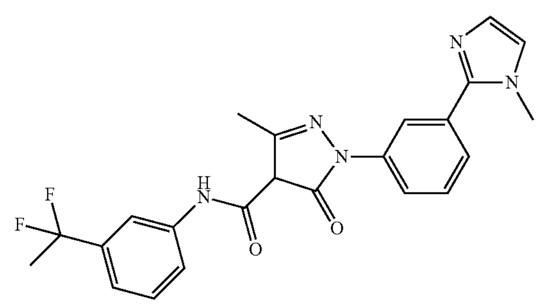 [SMILES: CC1=NN(c2cccc(-c3nccn3C)c2)C(=O)C1C(=O)Nc1cccc(C(C)(F)F)c1] |
| 290 | 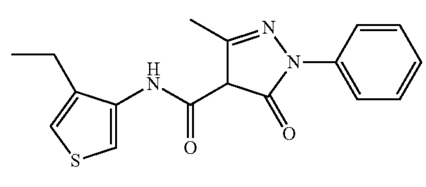 [SMILES: CCc1cscc1NC(=O)C1C(=O)N(c2ccccc2)N=C1C] |
| 291 | 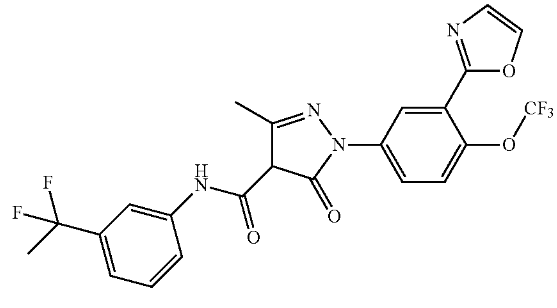 [SMILES: CC1=NN(c2ccc(OC(F)(F)F)c(-c3ncco3)c2)C(=O)C1C(=O)Nc1cccc(C(C)(F)F)c1] |

-continued
| Compound name | Structure |
|---|---|
| 292 | 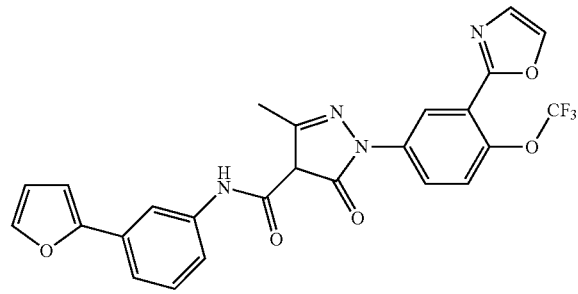 [SMILES: CC1=NN(c2ccc(OC(F)(F)F)c(-c3ncco3)c2)C(=O)C1C(=O)Nc1cccc(-c2ccco2)c1] |
| 293 | 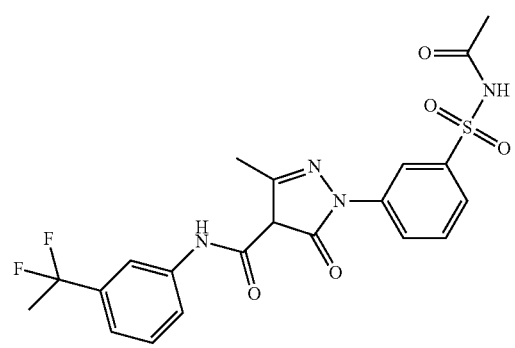 [SMILES: CC(=O)NS(=O)(=O)c1cccc(N2N=C(C)C(C(=O)Nc3cccc(C(C)(F)F)c3)C2=O)c1] |
| 294 | 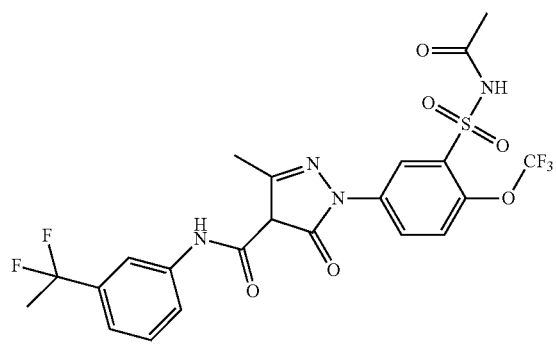 [SMILES: CC(=O)NS(=O)(=O)c1cc(N2N=C(C)C(C(=O)Nc3cccc(C(C)(F)F)c3)C2=O)ccc1OC(F)(F)F] |
| 295 | 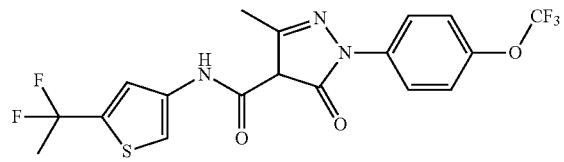 [SMILES: CC1=NN(c2ccc(OC(F)(F)F)cc2)C(=O)C1C(=O)Nc1csc(C(C)(F)F)c1] |
| 296 | 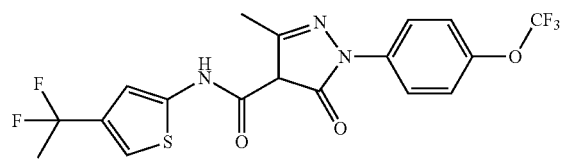 [SMILES: CC1=NN(c2ccc(OC(F)(F)F)cc2)C(=O)C1C(=O)Nc1cc(C(C)(F)F)cs1] |
| 297 | 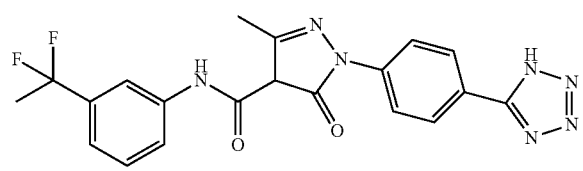 [SMILES: CC1=NN(c2ccc(-c3nnn[nH]3)cc2)C(=O)C1C(=O)Nc1cccc(C(C)(F)F)c1] |

| Compound name | Structure |
|---|---|
| 298 | 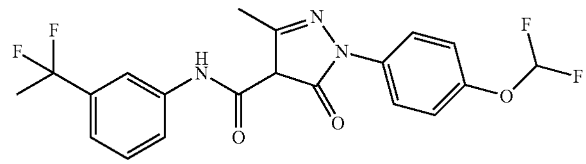 [SMILES: CC1=NN(c2ccc(OC(F)F)cc2)C(=O)C1C(=O)Nc1cccc(C(C)(F)F)c1] |
| 299 | 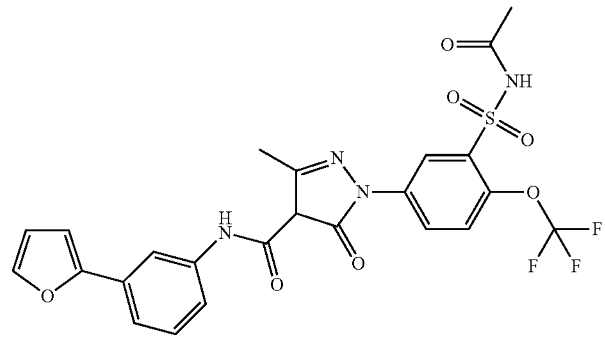 [SMILES: CC(=O)NS(=O)(=O)c1cc(N2N=C(C)C(C(=O)Nc3cccc(-c4ccco4)c3)C2=O)ccc1OC(F)(F)F] |
| 300 | 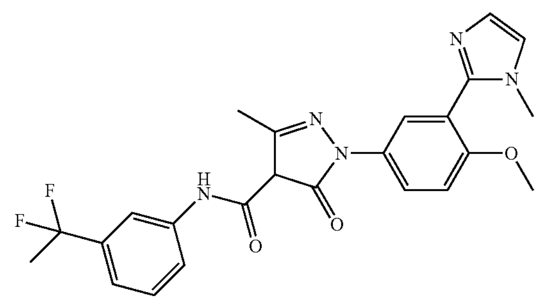 [SMILES: COc1ccc(N2N=C(C)C(C(=O)Nc3cccc(C(C)(F)F)c3)C2=O)cc1-c1nccn1C] |
| 301 | 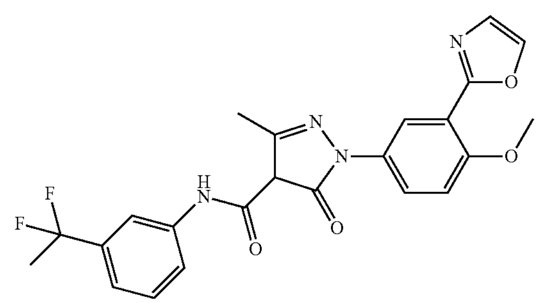 [SMILES: COc1ccc(N2N=C(C)C(C(=O)Nc3cccc(C(C)(F)F)c3)C2=O)cc1-c1ncco1] |
| 302 | 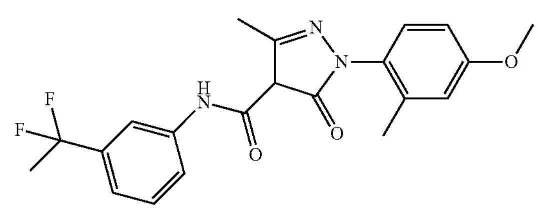 |
| 303 | 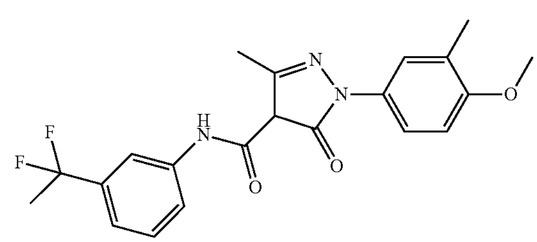 [SMILES: COc1ccc(N2N=C(C)C(C(=O)Nc3cccc(C(C)(F)F)c3)C2=O)cc1C] |

-continued

| Compound name | Structure |
|---|---|
| 304 | 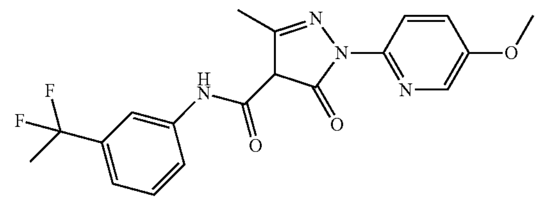 [SMILES: COc1ccc(N2N=C(C)C(C(=O)Nc3cccc(C(C)(F)F)c3)C2=O)nc1] |
| 305 | 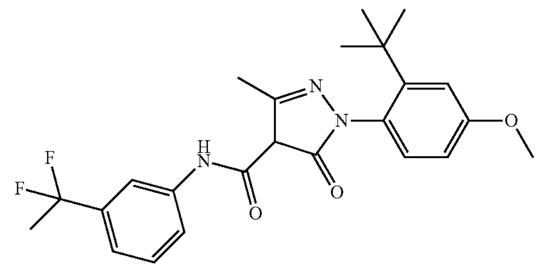 [SMILES: COc1ccc(N2N=C(C)C(C(=O)Nc3cccc(C(C)(F)F)c3)C2=O)c(C(C)(C)C)c1] |
| 306 | 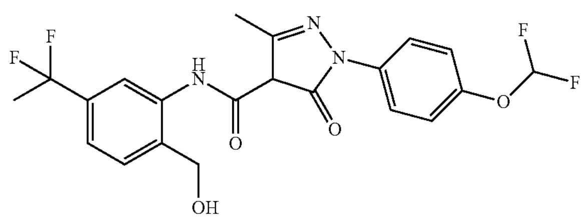 [SMILES: CC1=NN(c2ccc(OC(F)F)cc2)C(=O)C1C(=O)Nc1cc(C(C)(F)F)ccc1CO] |
| 307 | 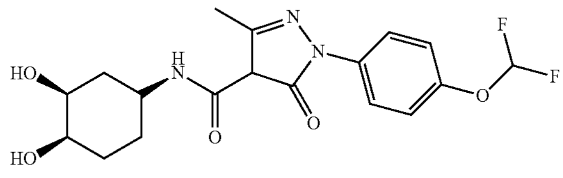 |
| 308 | 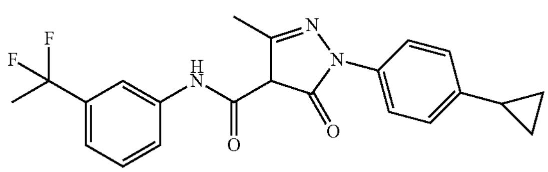 [SMILES: CC1=NN(c2ccc(C3CC3)cc2)C(=O)C1C(=O)Nc1cccc(C(C)(F)F)c1] |
| 309 | 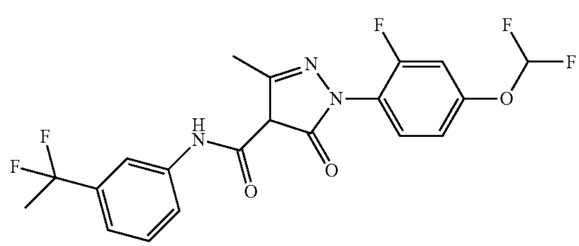 [SMILES: CC1=NN(c2ccc(OC(F)F)cc2F)C(=O)C1C(=O)Nc1cccc(C(C)(F)F)c1] |

| Compound name | Structure |
|---|---|
| 310 | 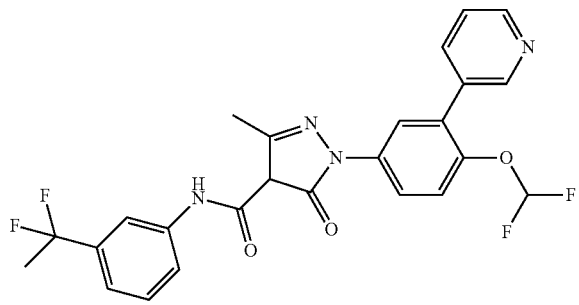 |
| 311 | 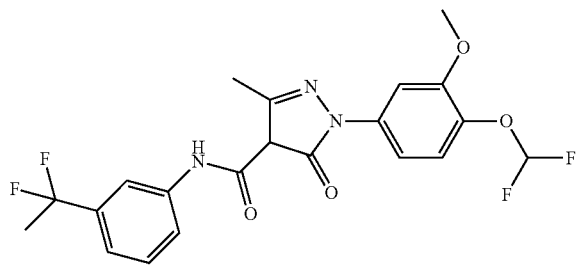 [SMILES: COc1cc(N2N=C(C)C(C(=O)Nc3cccc(C(C)(F)F)c3)C2=O)ccc1OC(F)F] |
| 312 | 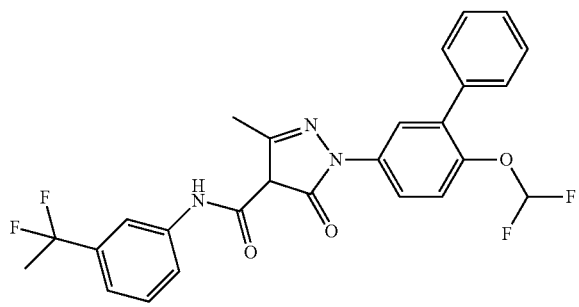 |
| 313 | 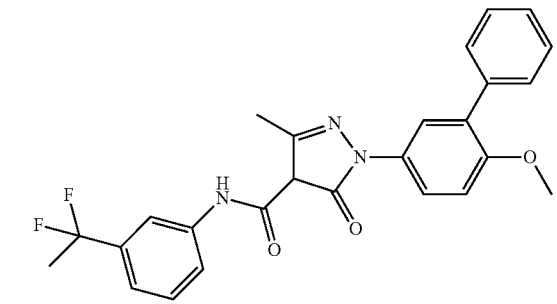 |
| 314 | 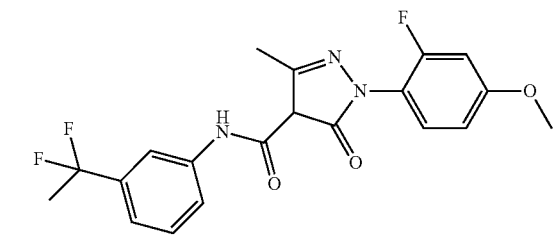 [SMILES: COc1ccc(N2N=C(C)C(C(=O)Nc3cccc(C(C)(F)F)c3)C2=O)c(F)c1] |

-continued

| Compound name | Structure |
|---|---|
| 315 | 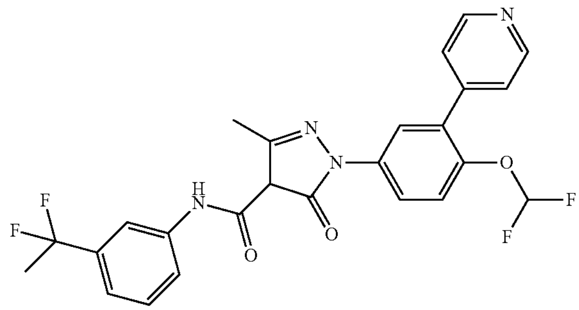 |
| 316 | 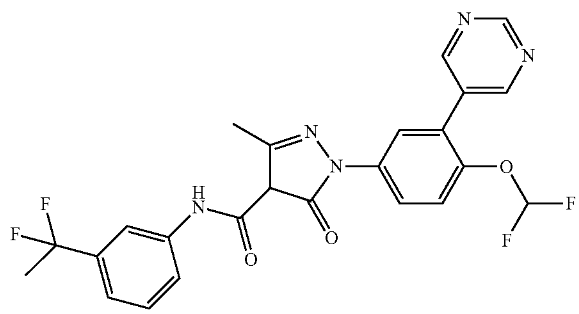 |
| 317 | 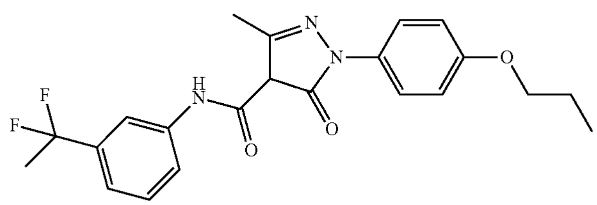 [SMILES: CCCOc1ccc(N2N=C(C)C(C(=O)Nc3cccc(C(C)(F)F)c3)C2=O)cc1] |
| 318 | 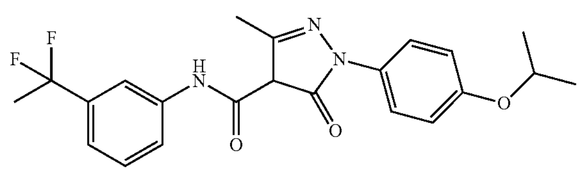 [SMILES: CC1=NN(c2ccc(OC(C)C)cc2)C(=O)C1C(=O)Nc1cccc(C(C)(F)F)c1] |
| 319 | 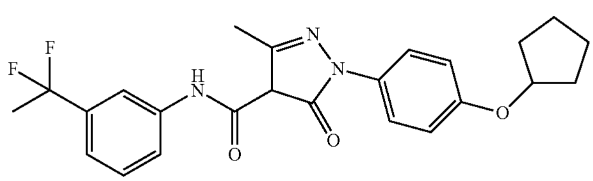 [SMILES: CC1=NN(c2ccc(OC3CCCC3)cc2)C(=O)C1C(=O)Nc1cccc(C(C)(F)F)c1] |
| 320 | 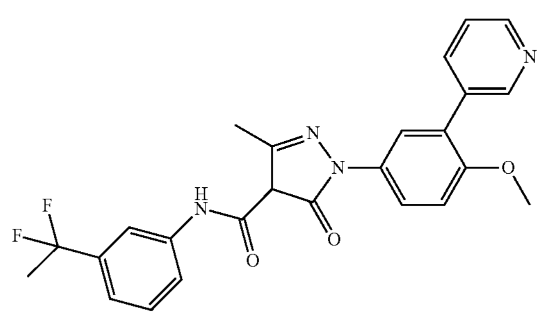 [SMILES: COc1ccc(N2N=C(C)C(C(=O)Nc3cccc(C(C)(F)F)c3)C2=O)cc1-c1cccnc1] |

| Compound name | Structure |
|---|---|
| 321 | 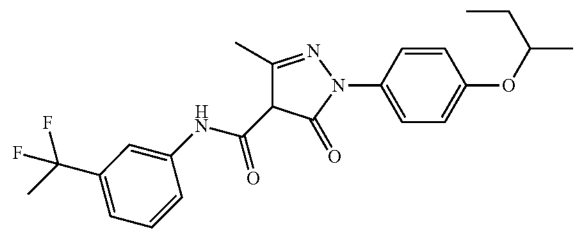 [SMILES: CCC(C)Oc1ccc(N2N=C(C)C(C(=O)Nc3cccc(C(C)(F)F)c3)C2=O)cc1] |
| 322 | 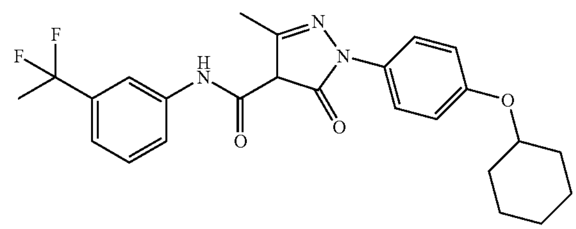 [SMILES: CC1=NN(c2ccc(OC3CCCCC3)cc2)C(=O)C1C(=O)Nc1cccc(C(C)(F)F)c1] |
| 323 | 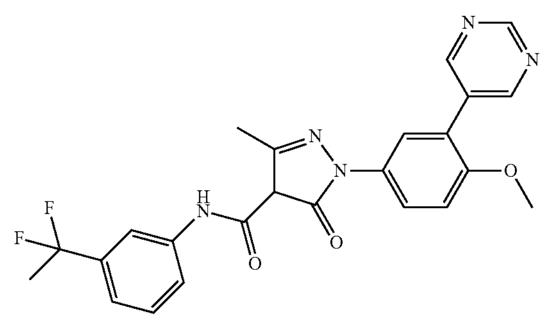 [SMILES: COc1ccc(N2N=C(C)C(C(=O)Nc3cccc(C(C)(F)F)c3)C2=O)cc1-c1cncnc1] |
| 324 | 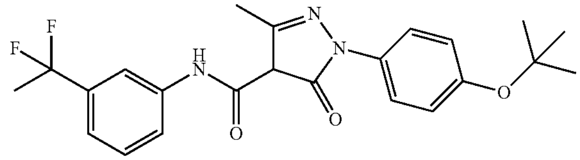 [SMILES: CC1=NN(c2ccc(OC(C)(C)C)cc2)C(=O)C1C(=O)Nc1cccc(C(C)(F)F)c1] |
| 325 | 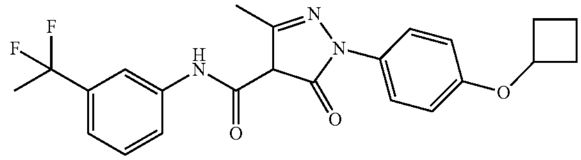 [SMILES: CC1=NN(c2ccc(OC3CCC3)cc2)C(=O)C1C(=O)Nc1cccc(C(C)(F)F)c1] |
| 326 | 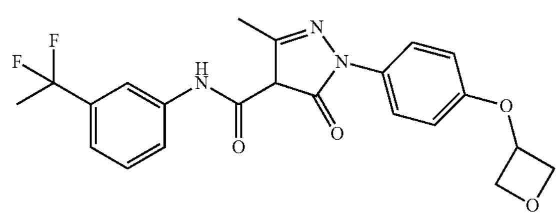 [SMILES: CC1=NN(c2ccc(OC3COC3)cc2)C(=O)C1C(=O)Nc1cccc(C(C)(F)F)c1] |

-continued
| Compound name | Structure |
|---|---|
| 327 | 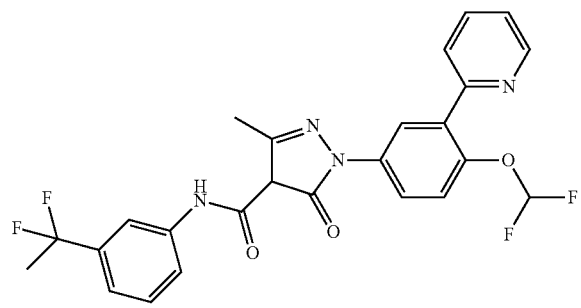 [SMILES: CC1=NN(c2ccc(OC(F)F)c(-c3ccccn3)c2)C(=O)C1C(=O)Nc1cccc(C(C)(F)F)c1] |
| 328 | 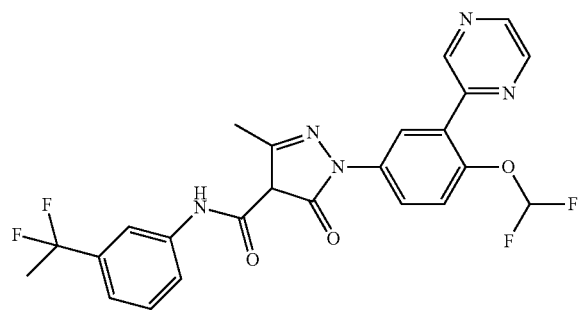 [SMILES: CC1=NN(c2ccc(OC(F)F)c(-c3cnccn3)c2)C(=O)C1C(=O)Nc1cccc(C(C)(F)F)c1] |
| 329 | 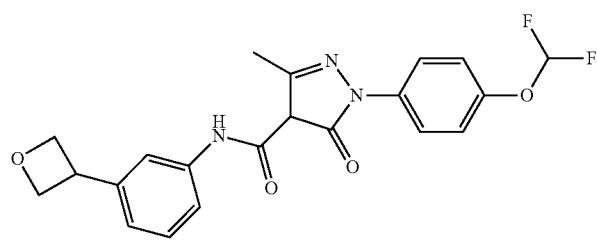 [SMILES: CC1=NN(c2ccc(OC(F)F)cc2)C(=O)C1C(=O)Nc1cccc(C2COC2)c1] |
| 330 | 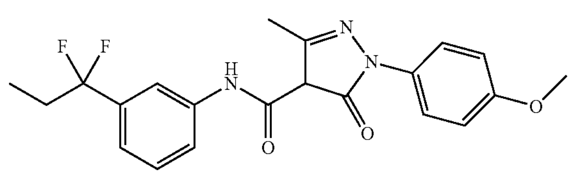 [SMILES: CCC(F)(F)c1cccc(NC(=O)C2C(=O)N(c3ccc(OC)cc3)N=C2C)c1] |
| 331 | 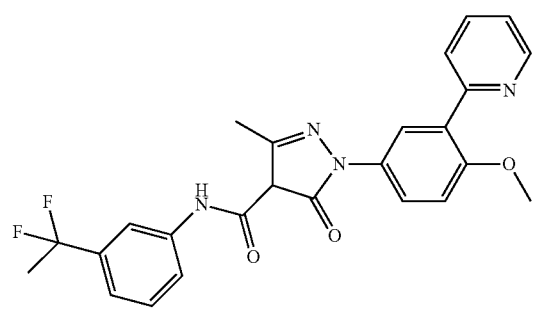 [SMILES: COc1ccc(N2N=C(C)C(C(=O)Nc3cccc(C(C)(F)F)c3)C2=O)cc1-c1ccccn1] |

| Compound name | Structure |
|---|---|
| 332 | 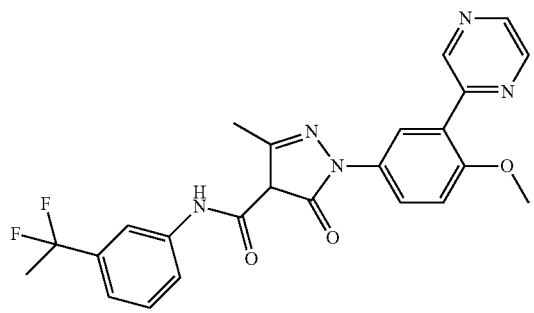 [SMILES: COc1ccc(N2N=C(C)C(C(=O)Nc3cccc(C(C)(F)F)c3)C2=O)cc1-c1cnccn1] |
| 333 | 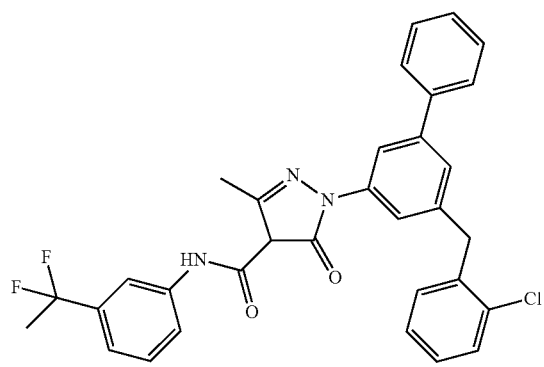 [SMILES: CC1=NN(c2cc(Cc3ccccc3Cl)cc(-c3ccccc3)c2)C(=O)C1C(=O)Nc1cccc(C(C)(F)F)c1] |
| 334 | 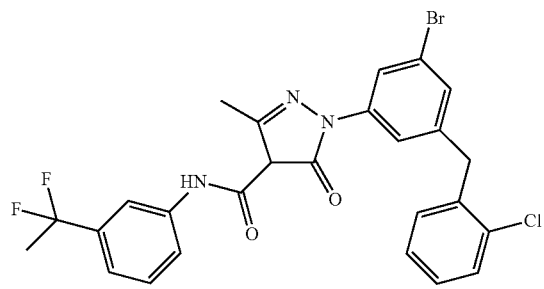 [SMILES: CC1=NN(c2cc(Br)cc(Cc3ccccc3Cl)c2)C(=O)C1C(=O)Nc1cccc(C(C)(F)F)c1] |
| 335 | 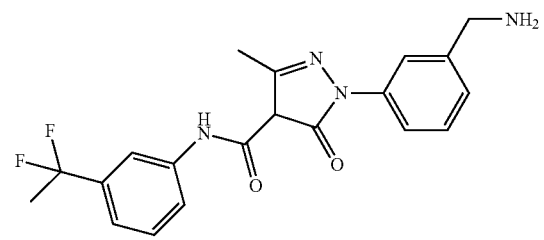 [SMILES: CC1=NN(c2cccc(CN)c2)C(=O)C1C(=O)Nc1cccc(C(C)(F)F)c1] |
| 336 | 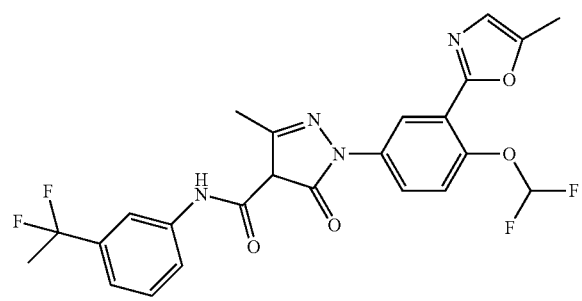 [SMILES: CC1=NN(c2ccc(OC(F)F)c(-c3ncc(C)o3)c2)C(=O)C1C(=O)Nc1cccc(C(C)(F)F)c1] |

-continued
| Compound name | Structure |
|---|---|
| 337 | 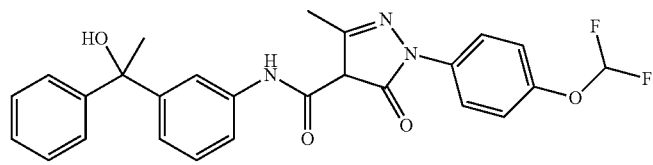 [SMILES: CC1=NN(c2ccc(OC(F)F)cc2)C(=O)C1C(=O)Nc1cccc(C(C)(O)c2ccccc2)c1] |
| 338 | 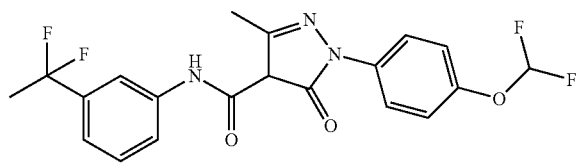 |
| 339 | 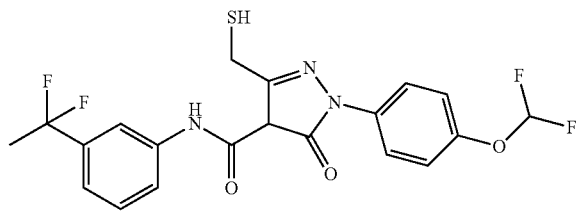 [SMILES: CC(F)(F)c1cccc(NC(=O)C2C(=O)N(c3ccc(OC(F)F)cc3)N=C2CS)c1] |
| 340 | 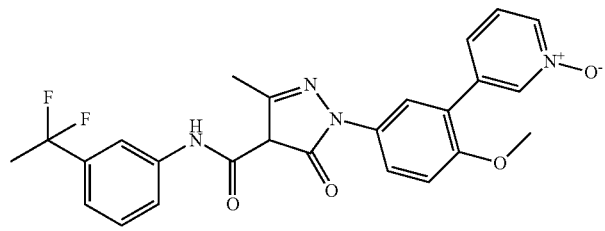 [SMILES: COc1ccc(N2N=C(C)C(C(=O)Nc3cccc(C(C)(F)F)c3)C2=O)cc1-c1ccc[n+]([O-])c1] |
| 341 | 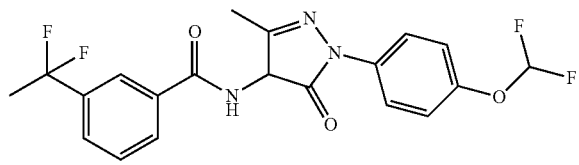 [SMILES: CC1=NN(c2ccc(OC(F)F)cc2)C(=O)C1NC(=O)c1cccc(C(C)(F)F)c1] |
| 342 | 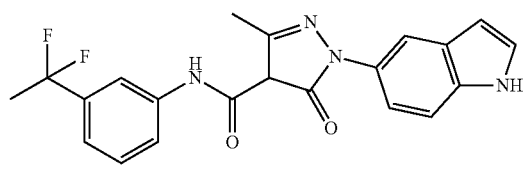 [SMILES: CC1=NN(c2ccc3[nH]ccc3c2)C(=O)C1C(=O)Nc1cccc(C(C)(F)F)c1] |
| 343 | 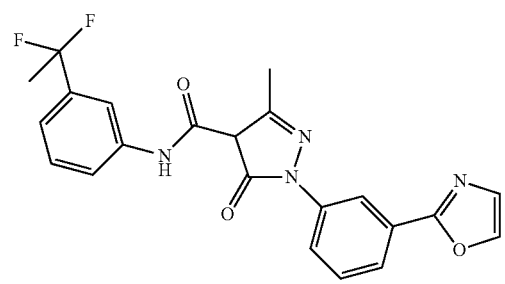 [SMILES: CC1=NN(c2cccc(-c3ncco3)c2)C(=O)C1C(=O)Nc1cccc(C(C)(F)F)c1] |

| Compound name | Structure |
|---|---|
| 344 | 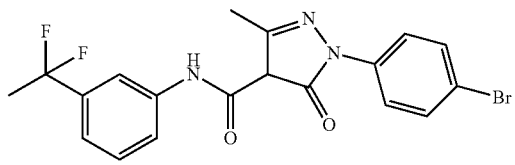 [SMILES: CC1=NN(c2ccc(Br)cc2)C(=O)C1C(=O)Nc1cccc(C(C)(F)F)c1] |
| 345 | 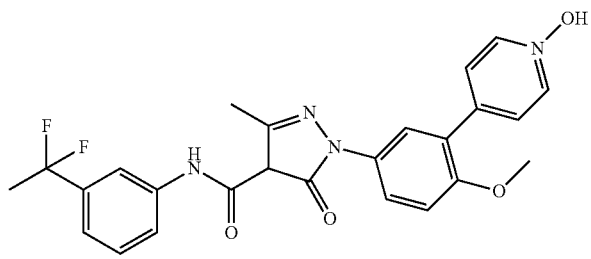 |
| 346 | 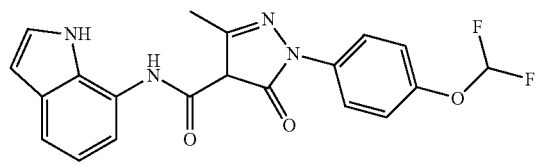 [SMILES: CC1=NN(c2ccc(OC(F)F)cc2)C(=O)C1C(=O)Nc1cccc2cc[nH]c12] |
| 347 | 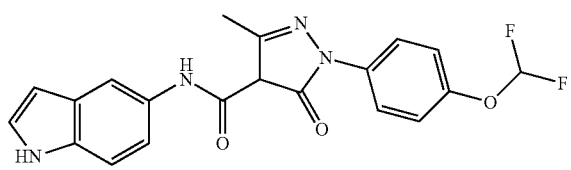 [SMILES: CC1=NN(c2ccc(OC(F)F)cc2)C(=O)C1C(=O)Nc1ccc2[nH]ccc2c1] |
| 348 | 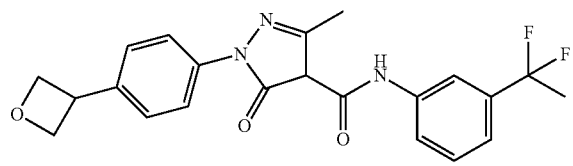 [SMILES: CC1=NN(c2ccc(C3COC3)cc2)C(=O)C1C(=O)Nc1cccc(C(C)(F)F)c1] |
| 349 | 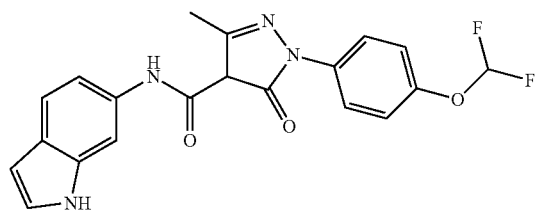 [SMILES: CC1=NN(c2ccc(OC(F)F)cc2)C(=O)C1C(=O)Nc1ccc2cc[nH]c2c1] |
| 350 | 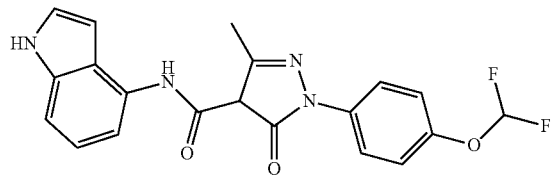 [SMILES: CC1=NN(c2ccc(OC(F)F)cc2)C(=O)C1C(=O)Nc1cccc2[nH]ccc12] |

| Compound name | Structure |
|---|---|
| 351 | 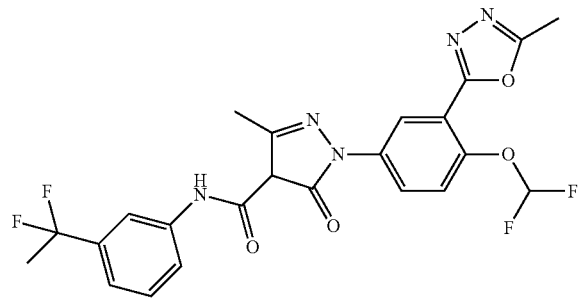 [SMILES: CC1=NN(c2ccc(OC(F)F)c(-c3nnc(C)o3)c2)C(=O)C1C(=O)Nc1cccc(C(C)(F)F)c1] |
| 352 | 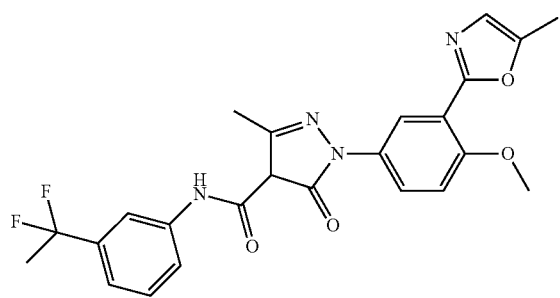 [SMILES: COc1ccc(N2N=C(C)C(C(=O)Nc3cccc(C(C)(F)F)c3)C2=O)cc1-c1ncc(C)o1] |
| 353 | 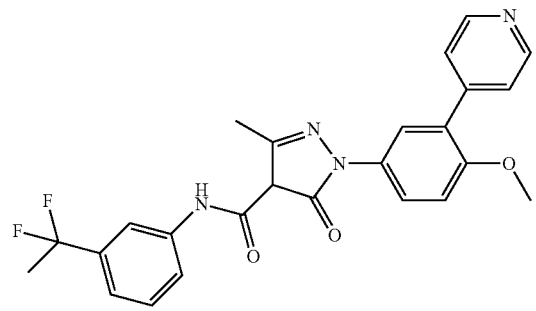 [SMILES: COc1ccc(N2N=C(C)C(C(=O)Nc3cccc(C(C)(F)F)c3)C2=O)cc1-c1ccncc1] |
| 354 | 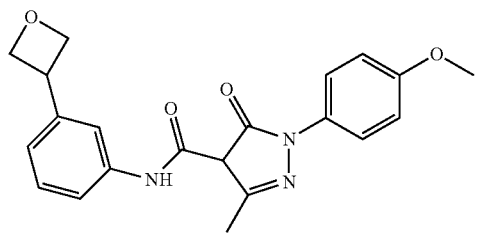 [SMILES: COc1ccc(N2N=C(C)C(C(=O)Nc3cccc(C4COC4)c3)C2=O)cc1] |
| 355 | 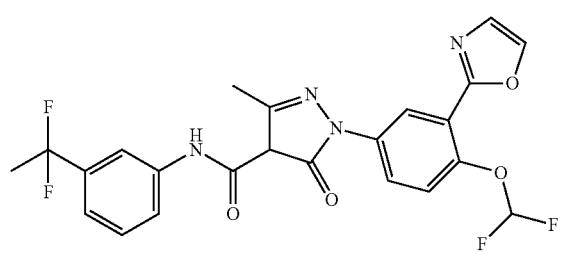 [SMILES: CC1=NN(c2ccc(OC(F)F)c(-c3ncco3)c2)C(=O)C1C(=O)Nc1cccc(C(C)(F)F)c1] |

| Compound name | Structure |
|---|---|
| 356 | *(structure shown)* |
| 357 | *(structure shown)* |
| 359 | *(structure shown)* |
| 360 | *(structure shown)* |
| 361 | *(structure shown)* |
| 362 | *(structure shown)* |
| 363 | *(structure shown)* |

| Compound name | Structure |
|---|---|
| 364 | 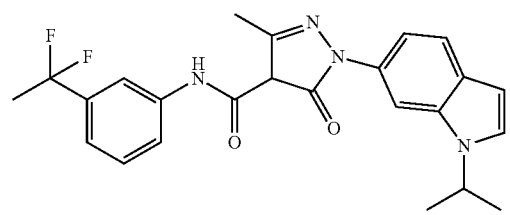 [SMILES: CC1=NN(c2ccc3ccn(C(C)C)c3c2)C(=O)C1C(=O)Nc1cccc(C(C)(F)F)c1] |
| 365 | 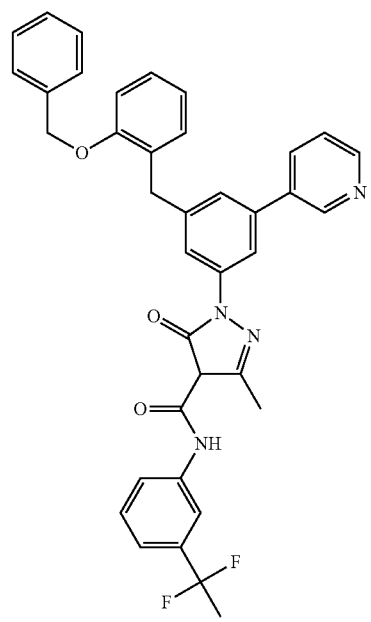 [SMILES: CC1=NN(c2cc(Cc3ccccc3OCc3ccccc3)cc(-c3cccnc3)c2)C(=O)C1C(=O)Nc1cccc(C(C)(F)F)c1] |
| 366 | 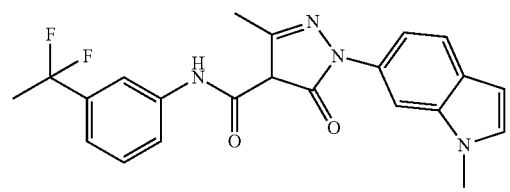 [SMILES: CC1=NN(c2ccc3ccn(C)c3c2)C(=O)C1C(=O)Nc1cccc(C(C)(F)F)c1] |
| 367 | 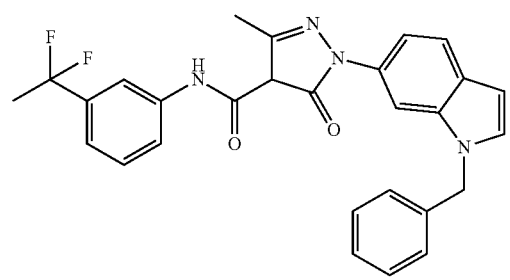 [SMILES: CC1=NN(c2ccc3ccn(Cc4ccccc4)c3c2)C(=O)C1C(=O)Nc1cccc(C(C)(F)F)c1] |

-continued
| Compound name | Structure |
|---|---|
| 368 | 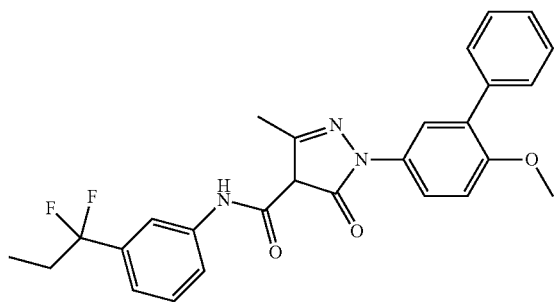 [SMILES: CCC(F)(F)c1cccc(NC(=O)C2C(=O)N(c3ccc(OC)c(-c4ccccc4)c3)N=C2C)c1] |
| 369 | 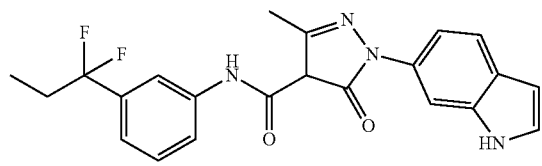 [SMILES: CCC(F)(F)c1cccc(NC(=O)C2C(=O)N(c3ccc4cc[nH]c4c3)N=C2C)c1] |
| 370 | 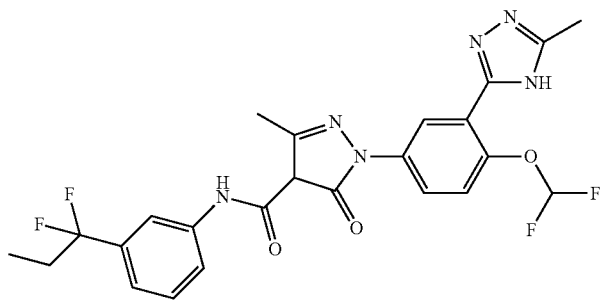 [SMILES: CCC(F)(F)c1cccc(NC(=O)C2C(=O)N(c3ccc(OC(F)F)c(-c4nnc(C)[nH]4)c3)N=C2C)c1] |
| 371 | 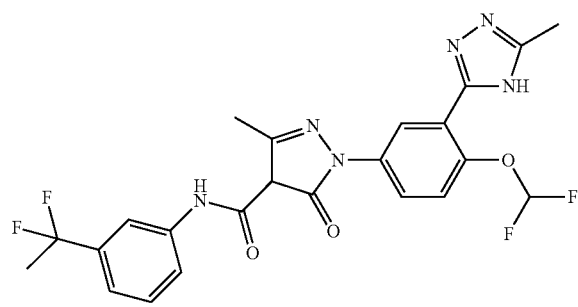 |
| 372 | 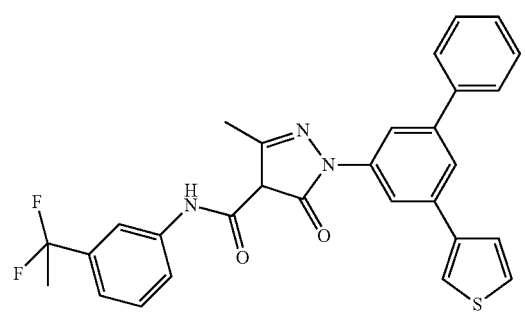 [SMILES: CC1=NN(c2cc(-c3ccccc3)cc(-c3ccsc3)c2)C(=O)C1C(=O)Nc1cccc(C(C)(F)F)c1] |

-continued
| Compound name | Structure |
|---|---|
| 373 | 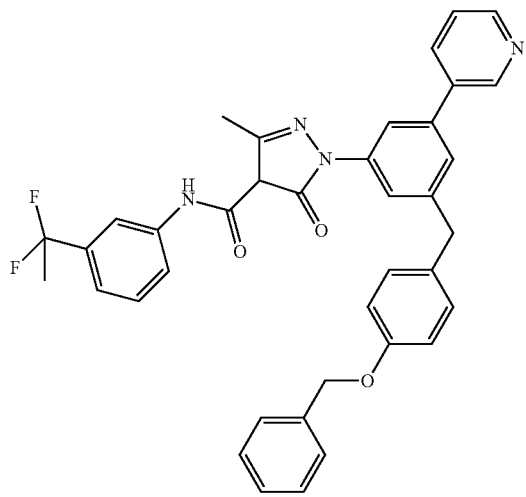 [SMILES: CC1=NN(c2cc(Cc3ccc(OCc4ccccc4)cc3)cc(-c3cccnc3)c2)C(=O)C1C(=O)Nc1cccc(C(C)(F)F)c1] |
| 374 | 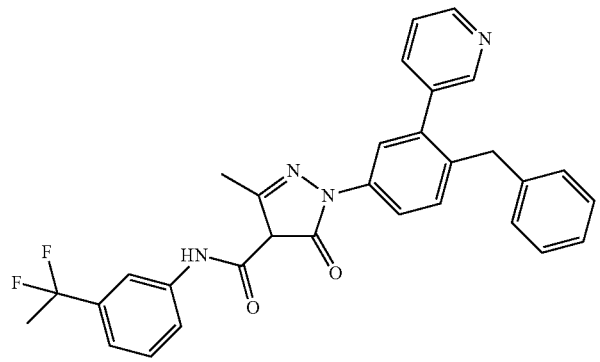 |
| 375 | 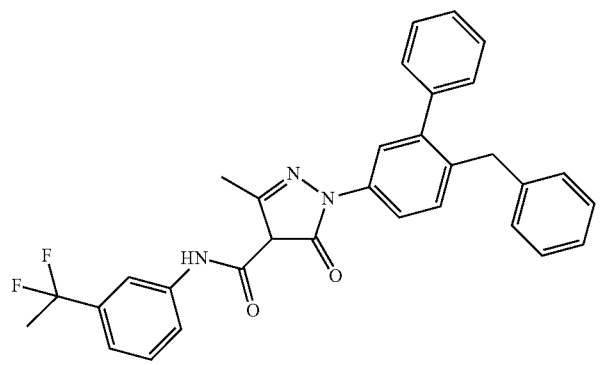 [SMILES: CC1=NN(c2ccc(Cc3ccccc3)c(-c3ccccc3)c2)C(=O)C1C(=O)Nc1cccc(C(C)(F)F)c1] |

| Compound name | Structure |
|---|---|
| 376 | 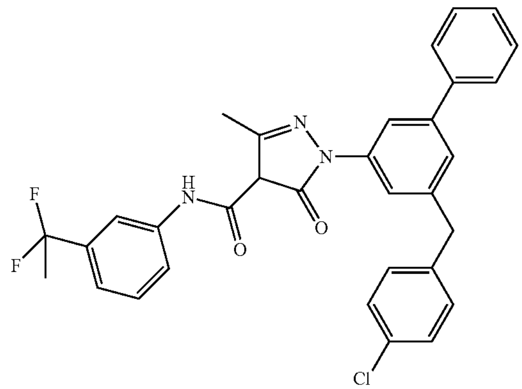 [SMILES: CC1=NN(c2cc(Cc3ccc(Cl)cc3)cc(-c3ccccc3)c2)C(=O)C1C(=O)Nc1cccc(C(C)(F)F)c1] |
| 377 | 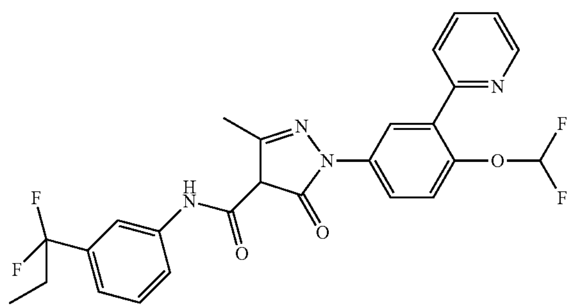 [SMILES: CCC(F)(F)c1cccc(NC(=O)C2C(=O)N(c3ccc(OC(F)F)c(-c4ccccn4)c3)N=C2C)c1] |
| 378 | 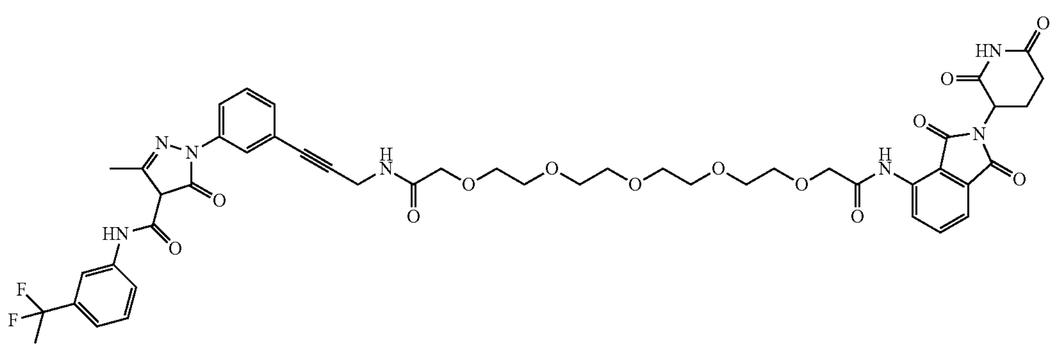 [SMILES: CC1=NN(c2cccc(C#CCNC(=O)COCCOCCOCCOCCOCC(=O)Nc3cccc4c3C(=O)N(C3CCC(=O)NC3=O)C4=O)c2)C(=O)C1C(=O)Nc1cccc(C(C)(F)F)c1] |
| 379 | 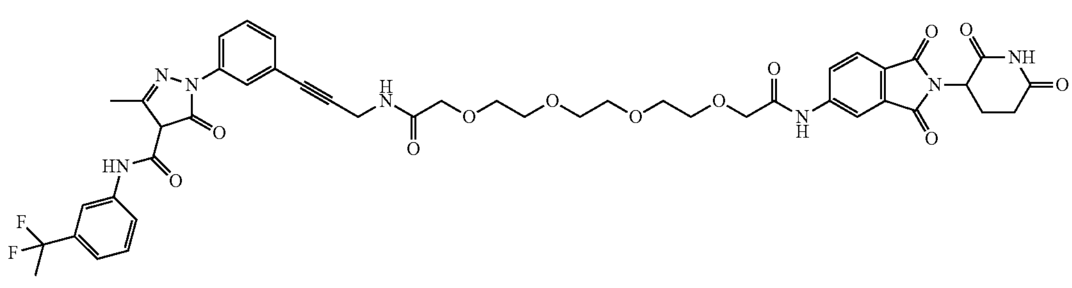 [SMILES: CC1=NN(c2cccc(C#CCNC(=O)COCCOCCOCCOCC(=O)Nc3ccc4c(c3)C(=O)N(C3CCC(=O)NC3=O)C4=O)c2)C(=O)C1C(=O)Nc1cccc(C(C)(F)F)c1] |

-continued

| Compound name | Structure |
|---|---|
| 380 | 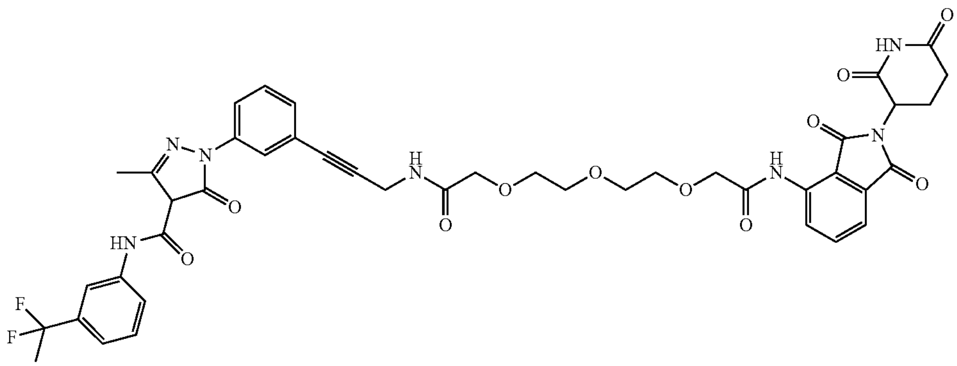 [SMILES: CC1=NN(c2cccc(C#CCNC(=O)COCCOCCOCC(=O)Nc3cccc4c3C(=O)N(C3CCC(=O)NC3=O)C4=O)c2)C(=O)C1C(=O)Nc1cccc(C(C)(F)F)c1] |
| 381 | 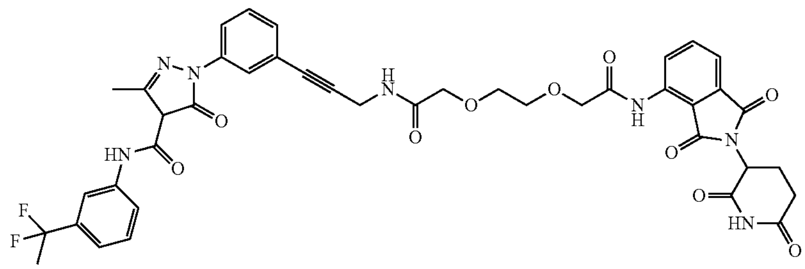 [SMILES: CC1=NN(c2cccc(C#CCNC(=O)COCCOCC(=O)Nc3cccc4c3C(=O)N(C3CCC(=O)NC3=O)C4=O)c2)C(=O)C1C(=O)Nc1cccc(C(C)(F)F)c1] |
| 382 | 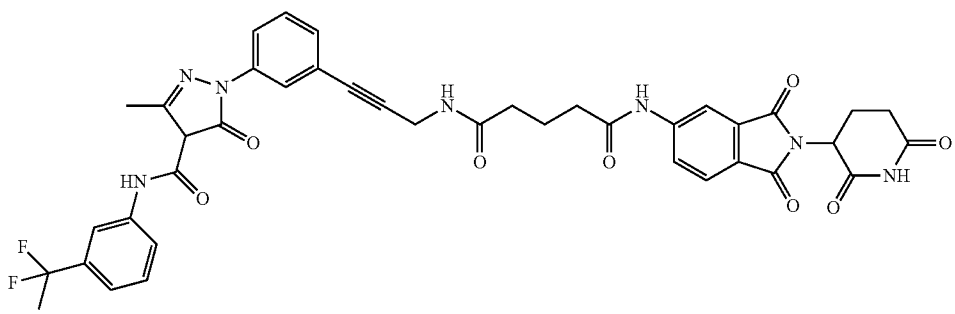 [SMILES: CC1=NN(c2cccc(C#CCNC(=O)CCCC(=O)Nc3ccc4c(c3)C(=O)N(C3CCC(=O)NC3=O)C4=O)c2)C(=O)C1C(=O)Nc1cccc(C(C)(F)F)c1] |
| 383 | 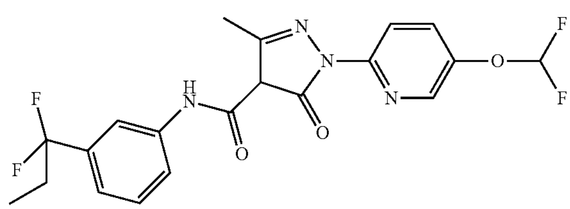 [SMILES: CCC(F)(F)c1cccc(NC(=O)C2C(=O)N(c3ccc(OC(F)F)cn3)N=C2C)c1] |
| 384 | 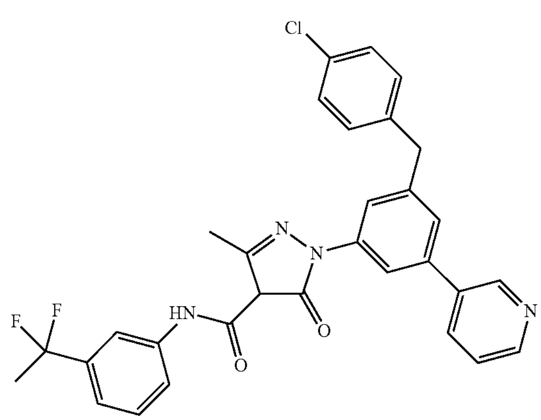 [SMILES: CC1=NN(c2cc(Cc3ccc(Cl)cc3)cc(-c3cccnc3)c2)C(=O)C1C(=O)Nc1cccc(C(C)(F)F)c1] |

| Compound name | Structure |
|---|---|
| 385 | 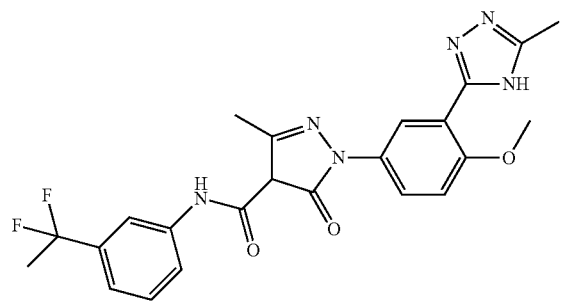 [SMILES: COc1ccc(N2N=C(C)C(C(=O)Nc3cccc(C(C)(F)F)c3)C2=O)cc1-c1nnc(C)[nH]1] |
| 386 | 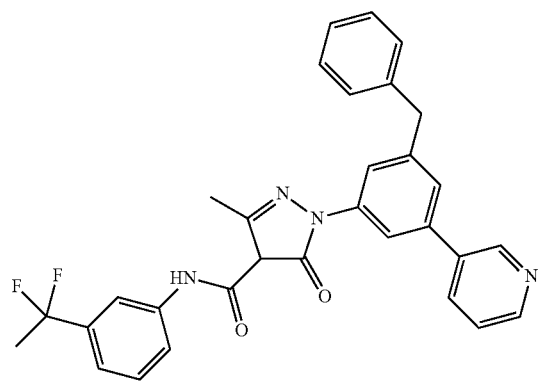 [SMILES: CC1=NN(c2cc(Cc3ccccc3)cc(-c3cccnc3)c2)C(=O)C1C(=O)Nc1cccc(C(C)(F)F)c1] |
| 387 | 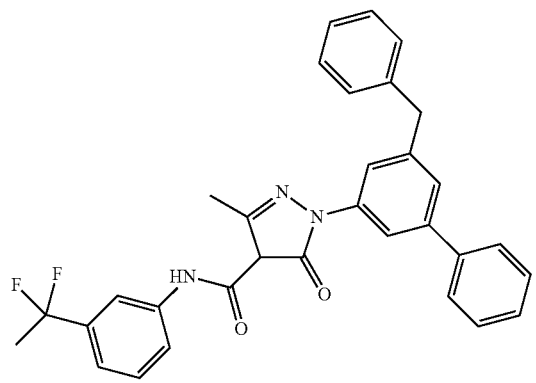 [SMILES: CC1=NN(c2cc(Cc3ccccc3)cc(-c3ccccc3)c2)C(=O)C1C(=O)Nc1cccc(C(C)(F)F)c1] |
| 388 | 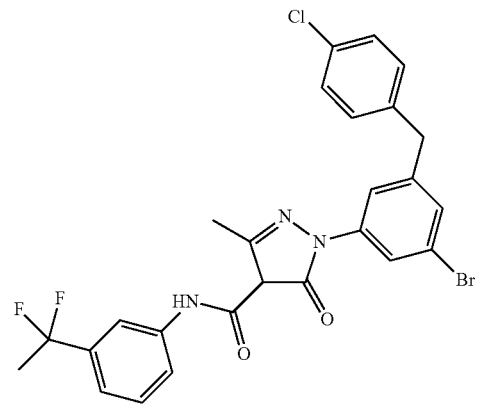 [SMILES: CC1=NN(c2cc(Br)cc(Cc3ccc(Cl)cc3)c2)C(=O)C1C(=O)Nc1cccc(C(C)(F)F)c1] |

| Compound name | Structure |
|---|---|
| 389 | 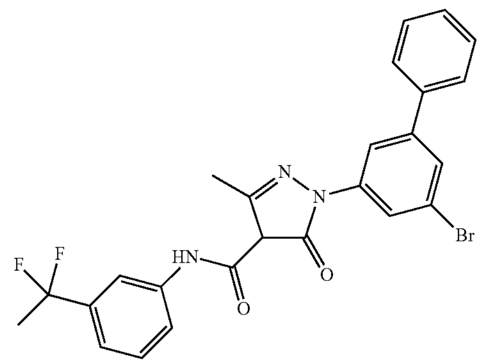 [SMILES: CC1=NN(c2cc(Br)cc(-c3ccccc3)c2)C(=O)C1C(=O)Nc1cccc(C(C)(F)F)c1] |
| 390 | 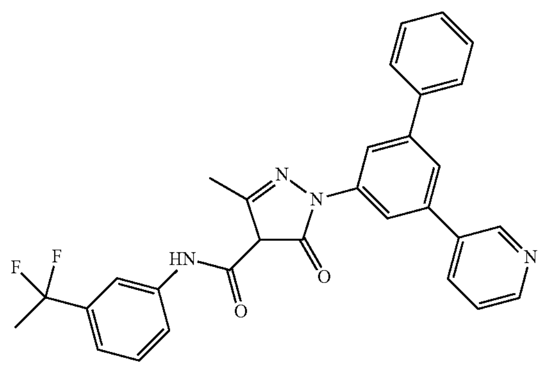 [SMILES: CC1=NN(c2cc(-c3ccccc3)cc(-c3cccnc3)c2)C(=O)C1C(=O)Nc1cccc(C(C)(F)F)c1] |
| 391 | 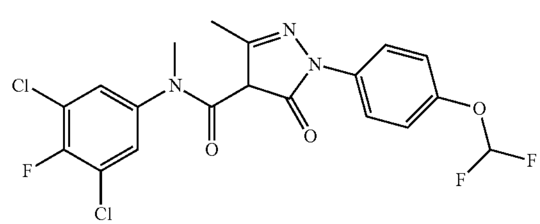 [SMILES: CC1=NN(c2ccc(OC(F)F)cc2)C(=O)C1C(=O)N(C)c1cc(Cl)c(F)c(Cl)c1] |
| 392 | 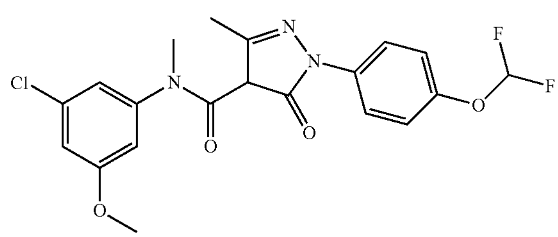 [SMILES: COc1cc(Cl)cc(N(C)C(=O)C2C(=O)N(c3ccc(OC(F)F)cc3)N=C2C)c1] |
| 393 | 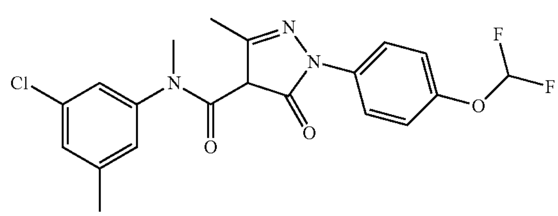 [SMILES: CC1=NN(c2ccc(OC(F)F)cc2)C(=O)C1C(=O)N(C)c1cc(C)cc(Cl)c1] |

| Compound name | Structure |
|---|---|
| 394 | 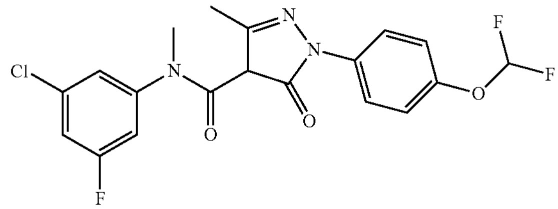 [SMILES: CC1=NN(c2ccc(OC(F)F)cc2)C(=O)C1C(=O)N(C)c1cc(F)cc(Cl)c1] |
| 395 | 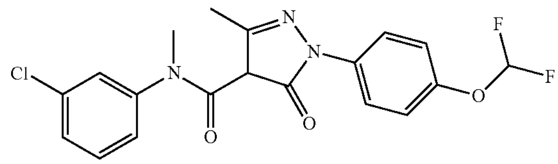 [SMILES: CC1=NN(c2ccc(OC(F)F)cc2)C(=O)C1C(=O)N(C)c1cccc(Cl)c1] |
| 396 | 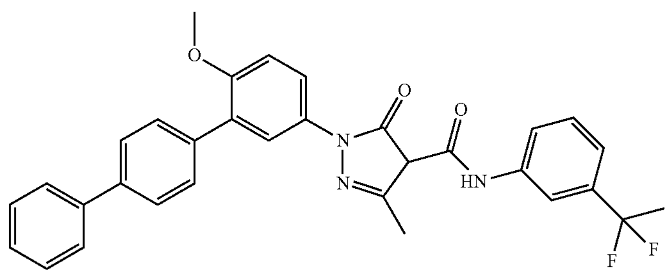 [SMILES: COc1ccc(N2N=C(C)C(C(=O)Nc3cccc(C(C)(F)F)c3)C2=O)cc1-c1ccc(-c2ccccc2)cc1] |
| 397 | 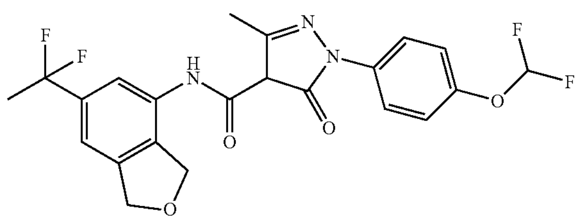 [SMILES: CC1=NN(c2ccc(OC(F)F)cc2)C(=O)C1C(=O)Nc1cc(C(C)(F)F)cc2c1COC2] |
| 398 | 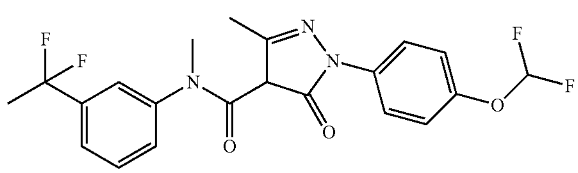 [SMILES: CC1=NN(c2ccc(OC(F)F)cc2)C(=O)C1C(=O)N(C)c1cccc(C(C)(F)F)c1] |
| 399 | 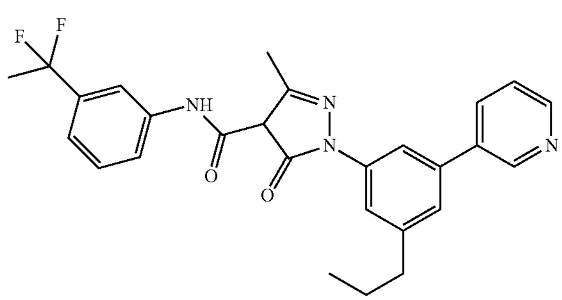 [SMILES: CCCc1cc(-c2cccnc2)cc(N2N=C(C)C(C(=O)Nc3cccc(C(C)(F)F)c3)C2=O)c1] |

| Compound name | Structure |
|---|---|
| 400 | 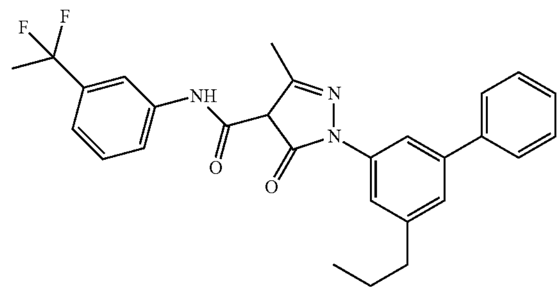 [SMILES: CCCc1cc(-c2ccccc2)cc(N2N=C(C)C(C(=O)Nc3cccc(C(C)(F)F)c3)C2=O)c1] |
| 401 | 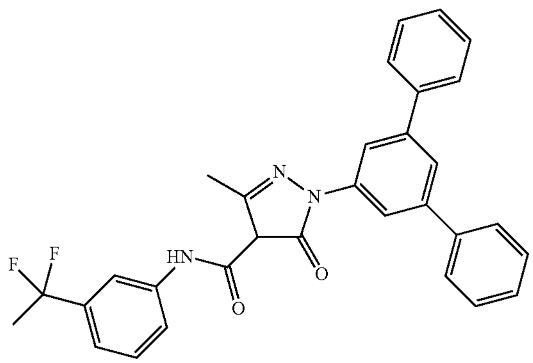 [SMILES: CC1=NN(c2cc(-c3ccccc3)cc(-c3ccccc3)c2)C(=O)C1C(=O)Nc1cccc(C(C)(F)F)c1] |
| 402 | 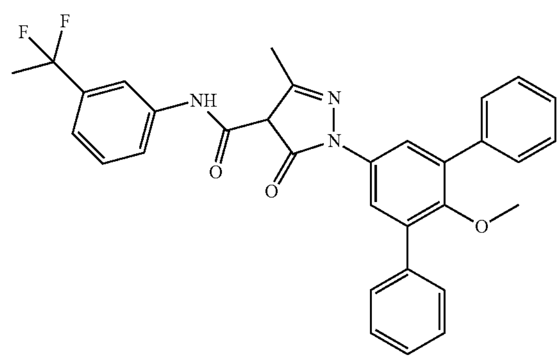 [SMILES: COc1c(-c2ccccc2)cc(N2N=C(C)C(C(=O)Nc3cccc(C(C)(F)F)c3)C2=O)cc1-c1ccccc1] |
| 403 | 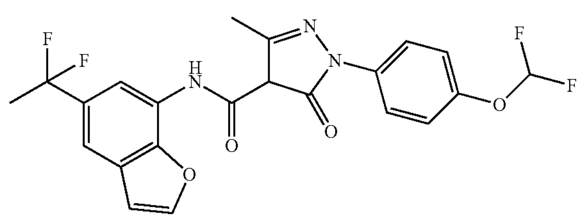 [SMILES: CC1=NN(c2ccc(OC(F)F)cc2)C(=O)C1C(=O)Nc1cc(C(C)(F)F)cc2ccoc12] |
| 404 | 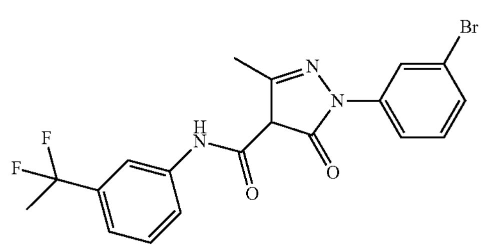 [SMILES: CC1=NN(c2cccc(Br)c2)C(=O)C1C(=O)Nc1cccc(C(C)(F)F)c1] |

| Compound name | Structure |
|---|---|
| 405 | 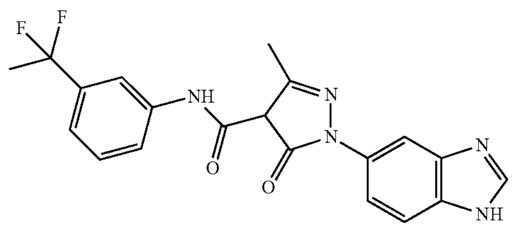 [SMILES: CC1=NN(c2ccc3[nH]cnc3c2)C(=O)C1C(=O)Nc1cccc(C(C)(F)F)c1] |
| 406 | 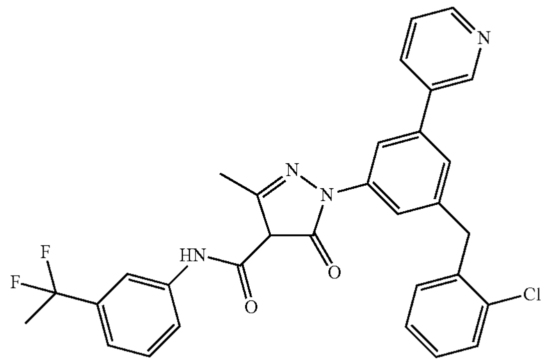 [SMILES: CC1=NN(c2cc(Cc3ccccc3Cl)cc(-c3cccnc3)c2)C(=O)C1C(=O)Nc1cccc(C(C)(F)F)c1] |
| 407 | 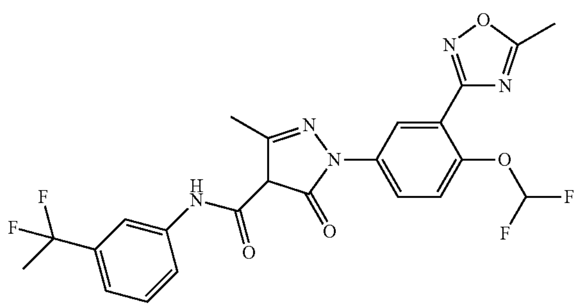 [SMILES: CC1=NN(c2ccc(OC(F)F)c(-c3noc(C)n3)c2)C(=O)C1C(=O)Nc1cccc(C(C)(F)F)c1] |
| 408 | 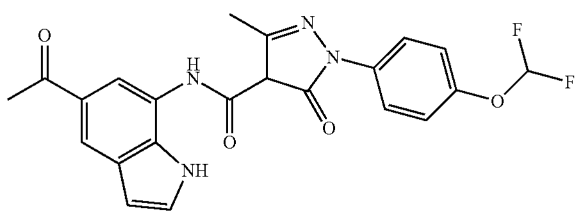 [SMILES: CC(=O)c1cc(NC(=O)C2C(=O)N(c3ccc(OC(F)F)cc3)N=C2C)c2[nH]ccc2c1] |
| 409 | 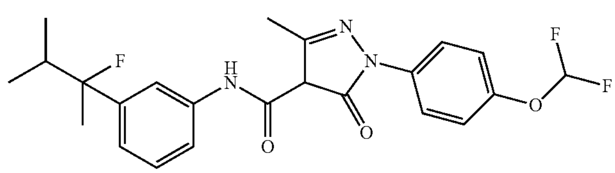 [SMILES: CC1=NN(c2ccc(OC(F)F)cc2)C(=O)C1C(=O)Nc1cccc(C(C)(F)C(C)C)c1] |
| 410 | 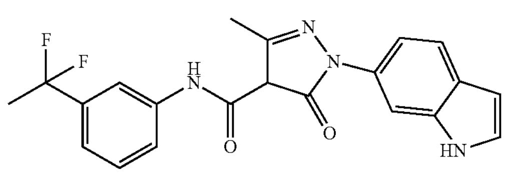 [SMILES: CC1=NN(c2ccc3cc[nH]c3c2)C(=O)C1C(=O)Nc1cccc(C(C)(F)F)c1] |

| Compound name | Structure |
|---|---|
| 411 | 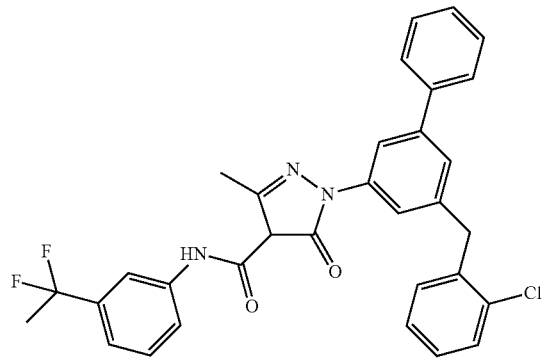 [SMILES: CC1=NN(c2cc(Cc3ccccc3Cl)cc(-c3ccccc3)c2)C(=O)C1C(=O)Nc1cccc(C(C)(F)F)c1] |
| 412 | 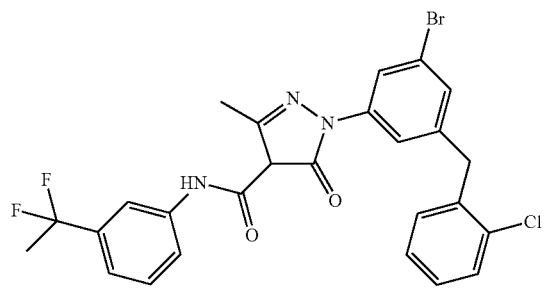 [SMILES: CC1=NN(c2cc(Br)cc(Cc3ccccc3Cl)c2)C(=O)C1C(=O)Nc1cccc(C(C)(F)F)c1] |
| 413 | 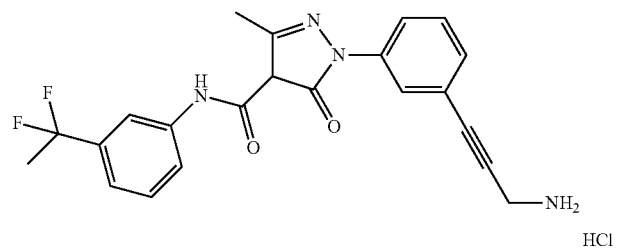 [SMILES: CC1=NN(c2cccc(C#CCN)c2)C(=O)C1C(=O)Nc1cccc(C(C)(F)F)c1 ; Cl] |
| 414 | 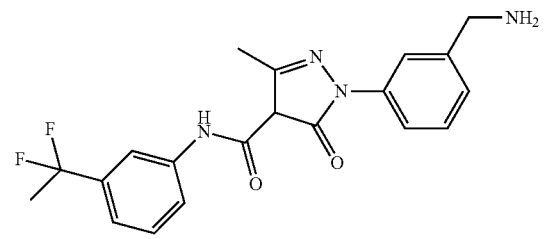 [SMILES: CC1=NN(c2cccc(CN)c2)C(=O)C1C(=O)Nc1cccc(C(C)(F)F)c1] |
| 415 | 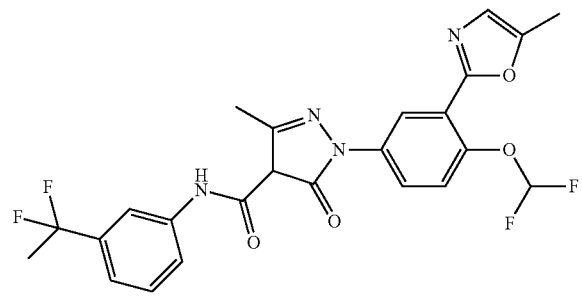 [SMILES: CC1=NN(c2ccc(OC(F)F)c(-c3ncc(C)o3)c2)C(=O)C1C(=O)Nc1cccc(C(C)(F)F)c1] |

| Compound name | Structure |
|---|---|
| 416 | 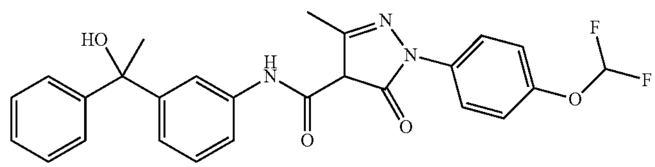 [SMILES: CC1=NN(c2ccc(OC(F)F)cc2)C(=O)C1C(=O)Nc1cccc(C(C)(O)c2ccccc2)c1] |
| 417 | 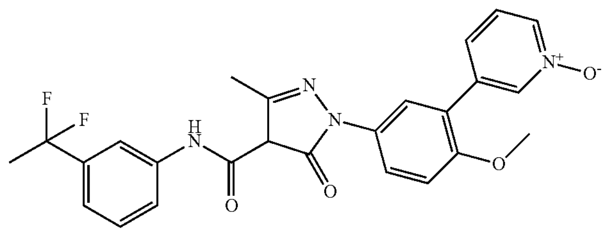 [SMILES: COc1ccc(N2N=C(C)C(C(=O)Nc3cccc(C(C)(F)F)c3)C2=O)cc1-c1ccc[n+]([O-])c1] |
| 418 | 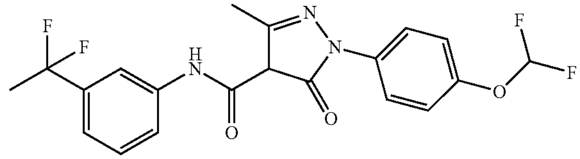 [SMILES: CC1=NN(c2ccc(OC(F)F)cc2)C(=O)C1C(=O)Nc1cccc(C(C)(F)F)c1] |
| 419 | 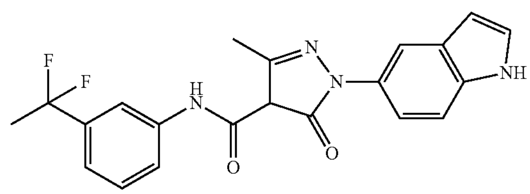 [SMILES: CC1=NN(c2ccc3[nH]ccc3c2)C(=O)C1C(=O)Nc1cccc(C(C)(F)F)c1] |
| 420 | 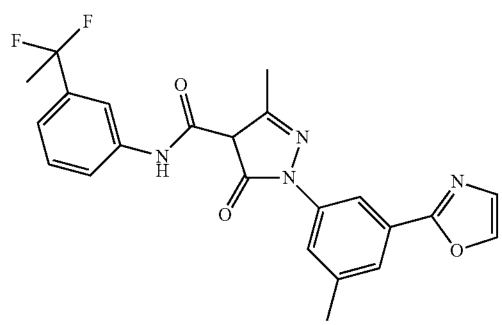 [SMILES: CC1=NN(c2cc(C)cc(-c3ncco3)c2)C(=O)C1C(=O)Nc1cccc(C(C)(F)F)c1] |
| 421 | 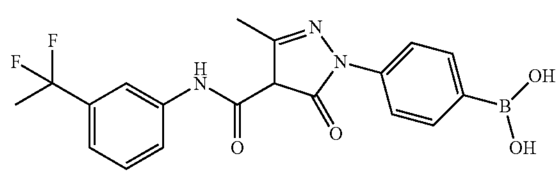 [SMILES: CC1=NN(c2ccc(B(O)O)cc2)C(=O)C1C(=O)Nc1cccc(C(C)(F)F)c1] |
| 422 | 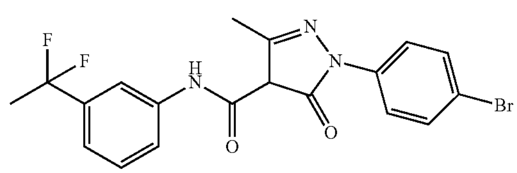 [SMILES: CC1=NN(c2ccc(Br)cc2)C(=O)C1C(=O)Nc1cccc(C(C)(F)F)c1] |

| Compound name | Structure |
|---|---|
| 423 | 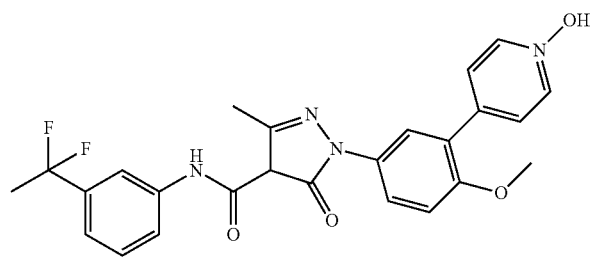 |
| 424 | 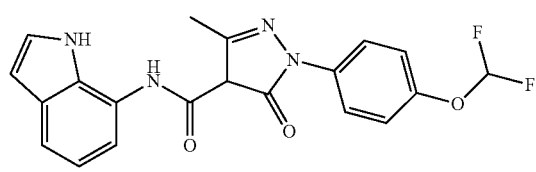 [SMILES: CC1=NN(c2ccc(OC(F)F)cc2)C(=O)C1C(=O)Nc1cccc2cc[nH]c12] |
| 425 | 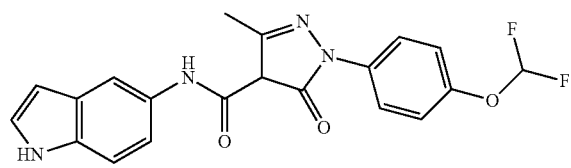 [SMILES: CC1=NN(c2ccc(OC(F)F)cc2)C(=O)C1C(=O)Nc1ccc2[nH]ccc2c1] |
| 426 | 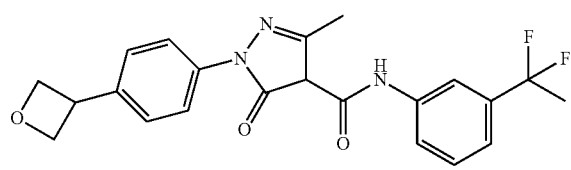 [SMILES: CC1=NN(c2ccc(C3COC3)cc2)C(=O)C1C(=O)Nc1cccc(C(C)(F)F)c1] |
| 427 | 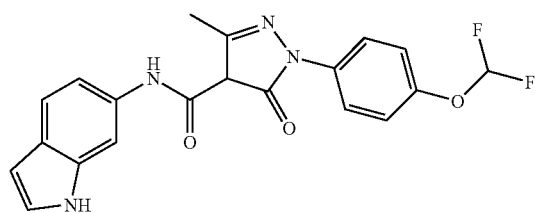 [SMILES: CC1=NN(c2ccc(OC(F)F)cc2)C(=O)C1C(=O)Nc1ccc2cc[nH]c2c1] |
| 428 | 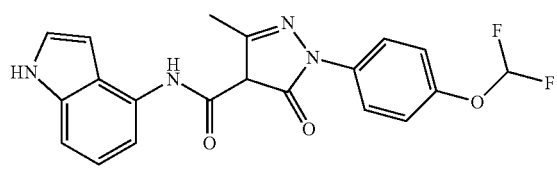 [SMILES: CC1=NN(c2ccc(OC(F)F)cc2)C(=O)C1C(=O)Nc1cccc2[nH]ccc12] |
| 429 | 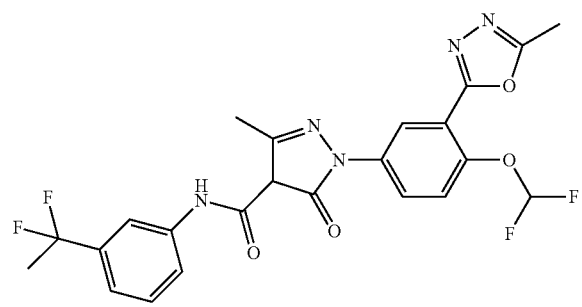 [SMILES: CC1=NN(c2ccc(OC(F)F)c(-c3nnc(C)o3)c2)C(=O)C1C(=O)Nc1cccc(C(C)(F)F)c1] |

-continued

| Compound name | Structure |
|---|---|
| 430 | 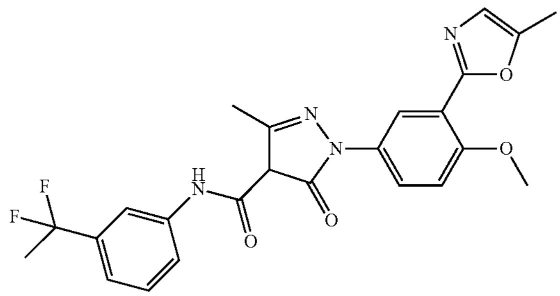 [SMILES: COc1ccc(N2N=C(C)C(C(=O)Nc3cccc(C(C)(F)F)c3)C2=O)cc1-c1ncc(C)o1] |
| 431 | 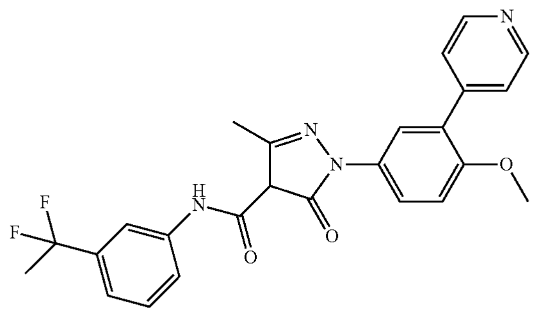 [SMILES: COc1ccc(N2N=C(C)C(C(=O)Nc3cccc(C(C)(F)F)c3)C2=O)cc1-c1ccncc1] |
| 432 | 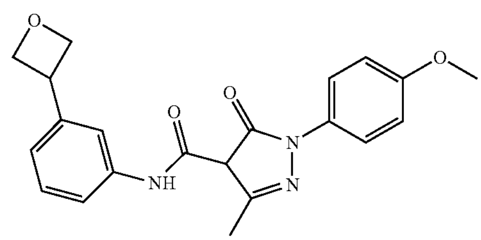 [SMILES: COc1ccc(N2N=C(C)C(C(=O)Nc3cccc(C4COC4)c3)C2=O)cc1] |
| 433 | 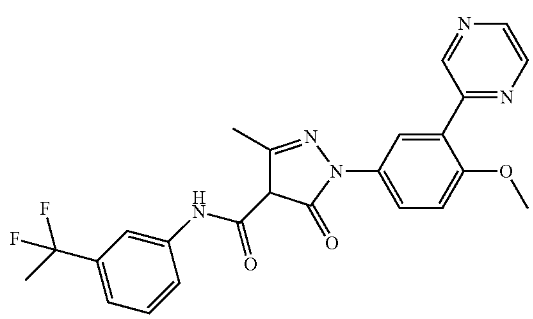 [SMILES: COc1ccc(N2N=C(C)C(C(=O)Nc3cccc(C(C)(F)F)c3)C2=O)cc1-c1cnccn1] |
| 434 | 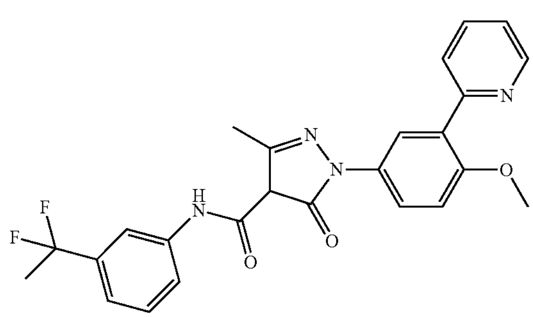 [SMILES: COc1ccc(N2N=C(C)C(C(=O)Nc3cccc(C(C)(F)F)c3)C2=O)cc1-c1ccccn1] |

-continued

| Compound name | Structure |
|---|---|
| 435 | 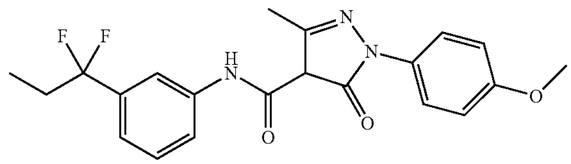 [SMILES: CCC(F)(F)c1cccc(NC(=O)C2C(=O)N(c3ccc(OC)cc3)N=C2C)c1] |
| 436 | 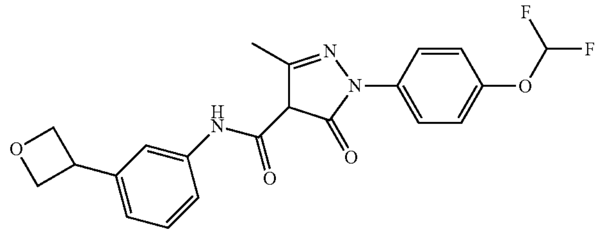 [SMILES: CC1=NN(c2ccc(OC(F)F)cc2)C(=O)C1C(=O)Nc1cccc(C2COC2)c1] |
| 437 | 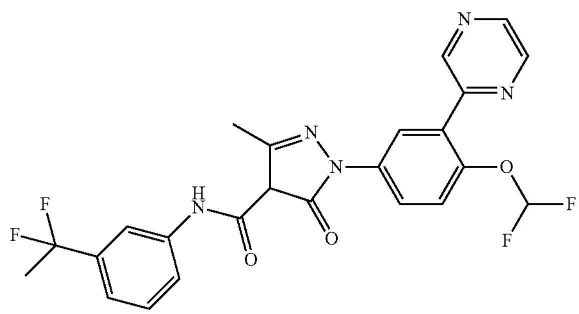 [SMILES: CC1=NN(c2ccc(OC(F)F)c(-c3cnccn3)c2)C(=O)C1C(=O)Nc1cccc(C(C)(F)F)c1] |
| 438 | 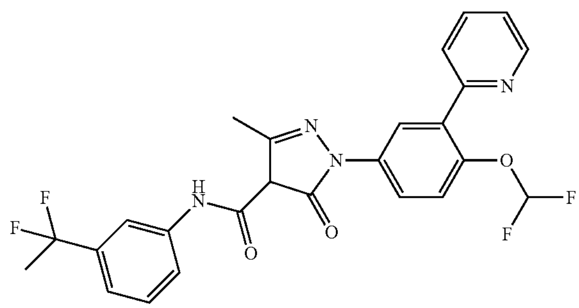 [SMILES: CC1=NN(c2ccc(OC(F)F)c(-c3ccccn3)c2)C(=O)C1C(=O)Nc1cccc(C(C)(F)F)c1] |
| 439 | 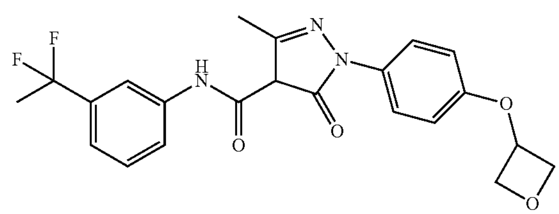 [SMILES: CC1=NN(c2ccc(OC3COC3)cc2)C(=O)C1C(=O)Nc1cccc(C(C)(F)F)c1] |
| 440 | 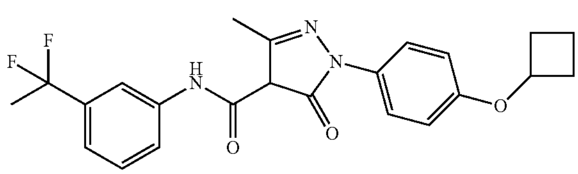 [SMILES: CC1=NN(c2ccc(OC3CCC3)cc2)C(=O)C1C(=O)Nc1cccc(C(C)(F)F)c1] |
| 441 | 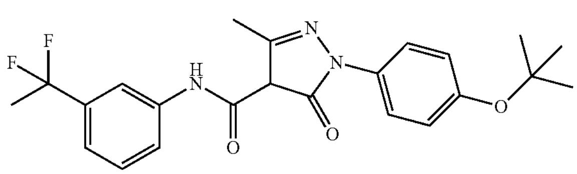 [SMILES: CC1=NN(c2ccc(OC(C)(C)C)cc2)C(=O)C1C(=O)Nc1cccc(C(C)(F)F)c1] |

| Compound name | Structure |
|---|---|
| 442 | 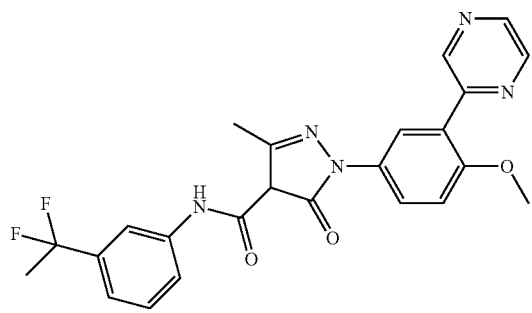 [SMILES: COc1ccc(N2N=C(C)C(C(=O)Nc3cccc(C(C)(F)F)c3)C2=O)cc1-c1cnccn1] |
| 443 | 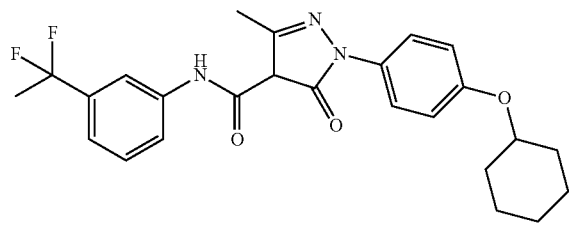 [SMILES: CC1=NN(c2ccc(OC3CCCCC3)cc2)C(=O)C1C(=O)Nc1cccc(C(C)(F)F)c1] |
| 444 | 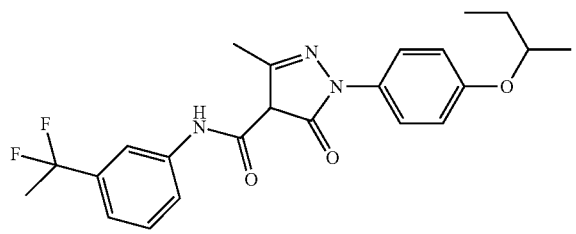 [SMILES: CCC(C)Oc1ccc(N2N=C(C)C(C(=O)Nc3cccc(C(C)(F)F)c3)C2=O)cc1] |
| 445 | 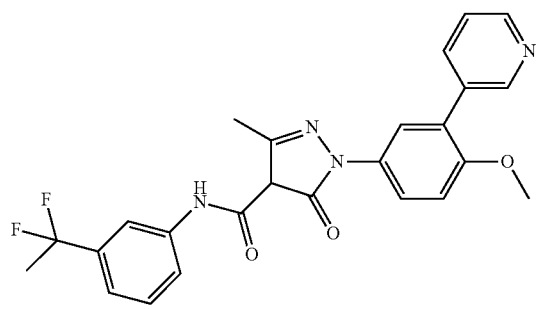 [SMILES: COc1ccc(N2N=C(C)C(C(=O)Nc3cccc(C(C)(F)F)c3)C2=O)cc1-c1cccnc1] |
| 446 | 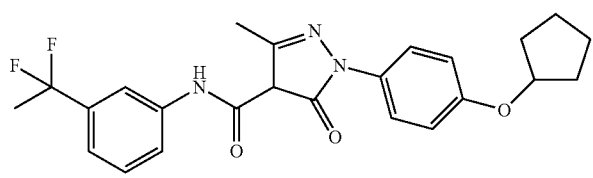 [SMILES: CC1=NN(c2ccc(OC3CCCC3)cc2)C(=O)C1C(=O)Nc1cccc(C(C)(F)F)c1] |
| 447 | 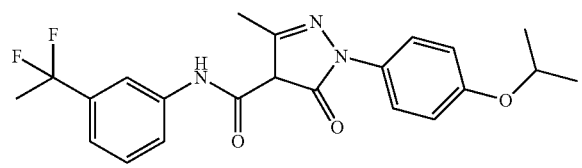 [SMILES: CC1=NN(c2ccc(OC(C)C)cc2)C(=O)C1C(=O)Nc1cccc(C(C)(F)F)c1] |

| Compound name | Structure |
|---|---|
| 448 | 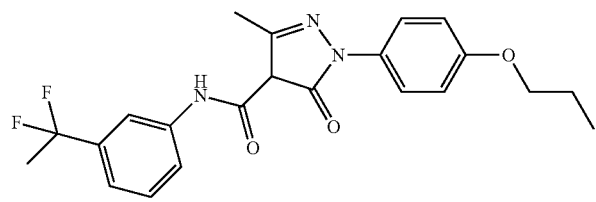 [SMILES: CCCOc1ccc(N2N=C(C)C(C(=O)Nc3cccc(C(C)(F)F)c3)C2=O)cc1] |
| 449 | 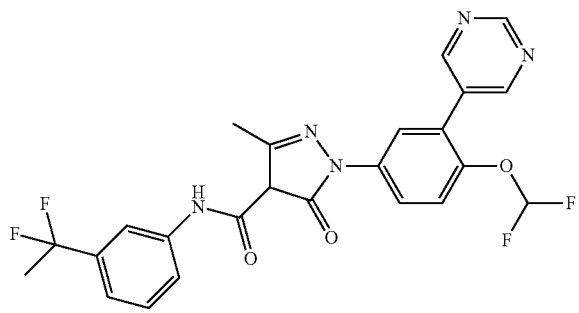 [SMILES: CC1=NN(c2ccc(OC(F)F)c(-c3cncnc3)c2)C(=O)C1C(=O)Nc1cccc(C(C)(F)F)c1] |
| 450 | 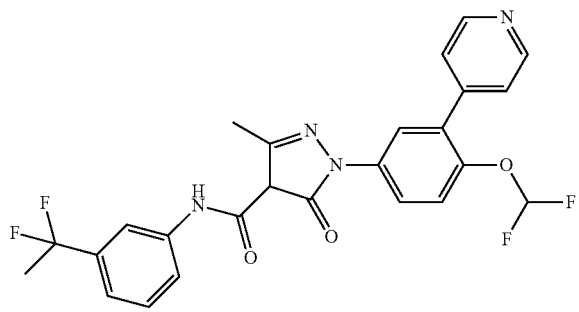 [SMILES: CC1=NN(c2ccc(OC(F)F)c(-c3ccncc3)c2)C(=O)C1C(=O)Nc1cccc(C(C)(F)F)c1] |
| 451 | 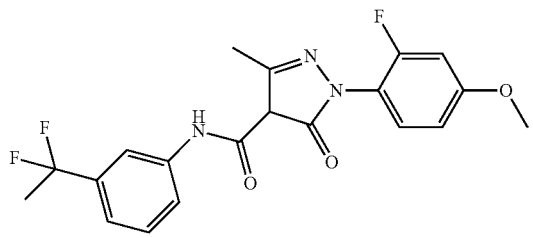 [SMILES: COc1ccc(N2N=C(C)C(C(=O)Nc3cccc(C(C)(F)F)c3)C2=O)c(F)c1] |
| 452 | 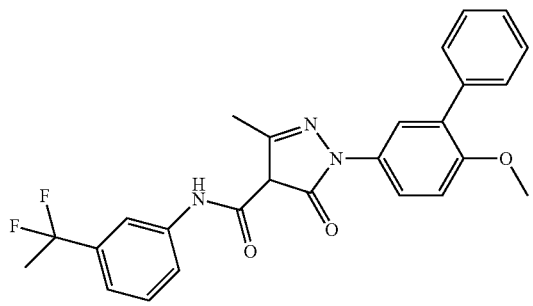 |

-continued
| Compound name | Structure |
|---|---|
| 453 | 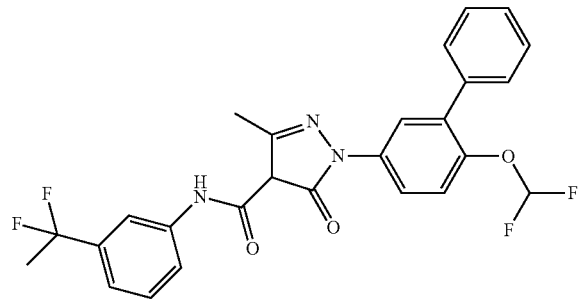 |
| 454 | 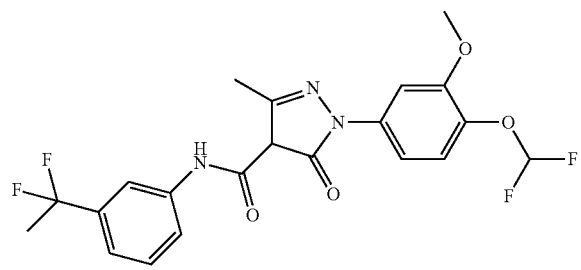 [SMILES: COc1cc(N2N=C(C)C(C(=O)Nc3cccc(C(C)(F)F)c3)C2=O)ccc1OC(F)F] |
| 455 | 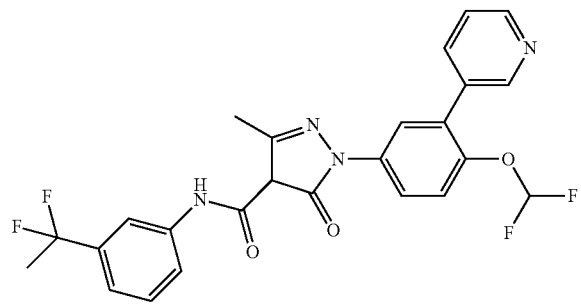 |
| 456 | 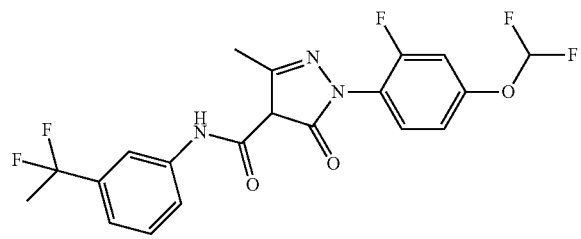 [SMILES: CC1=NN(c2ccc(OC(F)F)cc2F)C(=O)C1C(=O)Nc1cccc(C(C)(F)F)c1] |
| 457 | 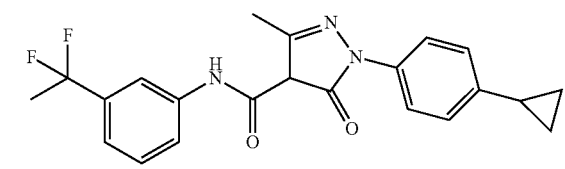 [SMILES: CC1=NN(c2ccc(C3CC3)cc2)C(=O)C1C(=O)Nc1cccc(C(C)(F)F)c1] |
| 458 | 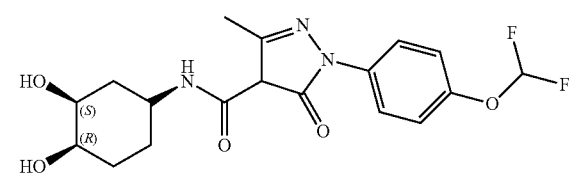 |

-continued

| Compound name | Structure |
|---|---|
| 459 | 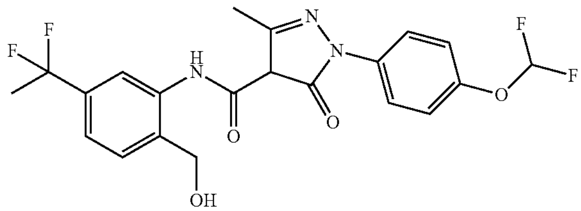 [SMILES: CC1=NN(c2ccc(OC(F)F)cc2)C(=O)C1C(=O)Nc1cc(C(C)(F)F)ccc1CO] |
| 460 | 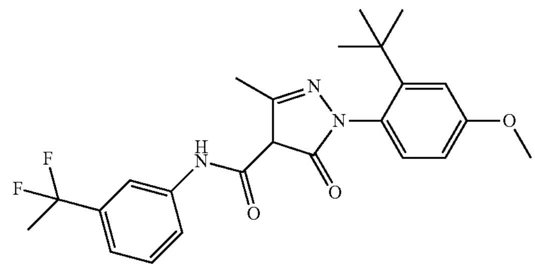 |

8. A pharmaceutical composition comprising a compound according to claim 1 and a pharmaceutically acceptable carrier.

* * * * *